(12) United States Patent
Setoi et al.

(10) Patent No.: US 6,211,242 B1
(45) Date of Patent: *Apr. 3, 2001

(54) BENZAMIDE DERIVATIVES AS VASOPRESSIN ANTAGONISTS

(75) Inventors: Hiroyuki Setoi, Tsukuba; Takehiko Ohkawa, Yuki-gun; Tatsuya Zenkoh, Kitasouma-gun; Keiji Hemmi, deceased, late of Tsukuba, by Mitsue Hemmi, Keiichiro Hemmi, Yusuke Hemmi, heirs; Hirokazu Tanaka, Takarazuka, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/722,243

(22) PCT Filed: Apr. 21, 1995

(86) PCT No.: PCT/JP95/00788

§ 371 Date: Jan. 30, 1998

§ 102(e) Date: Jan. 30, 1998

(87) PCT Pub. No.: WO95/29152

PCT Pub. Date: Nov. 2, 1995

(30) Foreign Application Priority Data

Apr. 25, 1994 (GB) ................................. 9408185

(51) Int. Cl.[7] ...................... A61K 31/165; A61K 31/167; C07C 237/42

(52) U.S. Cl. ............... 514/616; 514/253.13; 514/255.01; 514/332; 514/333; 514/336; 514/346; 514/352; 514/353; 514/354; 514/355; 544/364; 544/365; 544/390; 546/256; 546/260; 546/261; 546/280.4; 546/281.4; 546/297; 546/305; 546/309; 546/316; 546/323

(58) Field of Search ................................... 564/154, 155, 564/157, 617; 546/309; 549/69; 514/617, 255.01, 352.447, 616; 544/390

(56) References Cited

U.S. PATENT DOCUMENTS

| 5,110,348 | * | 5/1992 | Hopwood | 504/307 |
| 5,159,114 | * | 10/1992 | Bridge | 564/154 |
| 5,521,170 |   | 5/1996 | Setoi et al. | 514/183 |
| 6,054,457 | * | 4/2000 | Setoi et al. | 54/255 |

FOREIGN PATENT DOCUMENTS 0 620 216    10/1994 (EP).
WO 91 05549   5/1991 (WO).

* cited by examiner

*Primary Examiner*—Richard L. Raymond
(74) *Attorney, Agent, or Firm*—Oblon, Spivak, McClelland, Maier & Neustadt, P.C.

(57) ABSTRACT

This invention relates to new benzamide derivatives having a vasopressin antagonistic activity, etc. and represented by the general formula (I):

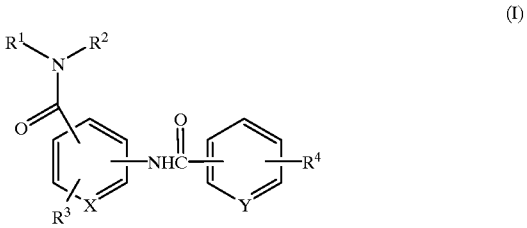

wherein $R^1$ is aryl optionally substituted with lower alkyl, etc., $R^2$ is lower alkyl, etc., $R^3$ is hydrogen, etc., $R^4$ is aryl, etc., X is CH or N, and Y is CH or N, and pharmaceutically acceptable salts thereof, to processes for the preparation thereof and to a pharmaceutical composition comprising the same.

8 Claims, No Drawings

BENZAMIDE DERIVATIVES AS VASOPRESSIN ANTAGONISTS

This application is a 371 of PCT/JP95/00788, filed Apr. 21, 1995.

TECHNICAL FIELD

This invention relates to new benzamide derivatives and pharmaceutically acceptable salts thereof which are useful as a medicament.

BACKGROUND ART

Some benzamide derivatives have been known as vasopressin antagonist, for example, in PCT International Publication No. WO 91/05549 and EP Application Publication No. 0620216.

DISCLOSURE OF INVENTION

This invention relates to new benzamide derivatives and pharmaceutically acceptable salts thereof.

More particularly, it relates to new benzamide derivatives and pharmaceutically acceptable salts thereof which possess activities as vasopressin antagonistic activity, vasodilating activity, hypotensive activity, activity for inhibiting saccharide release in liver, activity for inhibiting growth of mesangium cells, water diuretic activity, platelet agglutination inhibitory activity, oxytocin antagonistic activity and the like, to a pharmaceutical composition comprising the same and to a method for the treatment and/or prevention of hypertension, heart failure, renal insufficiency, edema, ascites, vasopressin parasecretion syndrome, hepatocirrhosis, hyponatremia, hypokalemia, diabetic, circulation disorder, cerebrovascular disease (e.g. cerebral edema, cerebral infarction, etc.), Meniere's syndrome (e.g. Meniere's disease, etc.), motion sickness and the like in human beings or animals.

One object of this invention is to provide new and useful benzamide derivatives which possess aforesaid activities.

Another object of this invention is to provide processes for the preparation of said benzamide derivatives and salts thereof.

A further object of this invention is to provide a pharmaceutical composition comprising, as an active ingredient, said benzamide derivatives and pharmaceutically acceptable salts thereof.

Still further object of this invention is to provide a therapeutical method for the treatment and/or prevention of aforesaid diseases in human beings or animals, using said benzamide derivatives and pharmaceutically acceptable salts thereof.

The object benzamide derivatives of this invention are new and can be represented by the following general formula (I):

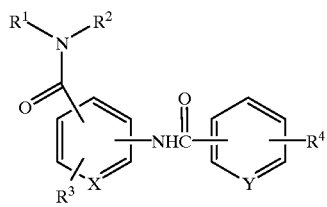

wherein $R^1$ is lower alkyl, aryl, cyclo(lower)alkyl or a heterocyclic group, each of which may be substituted with substituent(s) selected from the group consisting of halogen; hydroxy; nitro; amino; acyl; substituted acyl; acyl(lower)alkylsulfinyl; acyl(lower)alkylsulfonyl; acyloxy; lower alkylamino(lower)alkylcarbamoyloxy; aryl; cyano; a heterocyclic group; lower alkenyl optionally substituted with acyl or substituted acyl; lower alkynyl optionally substituted with amino, acylamino or substituted acylamino; lower alkyl optionally substituted with halogen, amino, lower alkylamino, acylamino, substituted acylamino, hydroxy, acyloxy, acyl(lower)alkanoyloxy, acyl, substituted acyl or acyl(lower)alkoxyimino; lower alkylthio optionally substituted with acyl or substituted acyl; alkoxy optionally substituted with aryl, substituted aryl, hydroxy, acyloxy, amino, lower alkylamino, protected amino, a heterocyclic group, acyl-substituted pyridyl, substituted acyl-substituted pyridyl, halogen, acyl(lower)alkylamino, N-protected-acyl(lower)alkylamino, N-acyl(lower)alkyl-N-lower alkylamino, acyl, substituted acyl, acylamino, substituted acylamino, lower alkylhydrazinocarbonylamino, hydroxyimino, acyl(lower)alkoxyimino or substituted acyl(lower)alkoxyimino; and lower alkenyloxy optionally substituted with acyl or substituted acyl;

$R^2$ is lower alkyl optionally substituted with hydroxy, aryl or acyl; or cyclo(lower)alkyl;

$R^3$ is hydrogen, halogen, lower alkyl, lower alkoxy, nitro or amino;

$R^4$ is lower alkyl; aryl; or substituted aryl;

X is CH or N, and

Y is CH or N, and pharmaceutically acceptable salts thereof.

The object compound (I) for its salt can be prepared by the processes as illustrated in the following reaction schemes.

Process 1

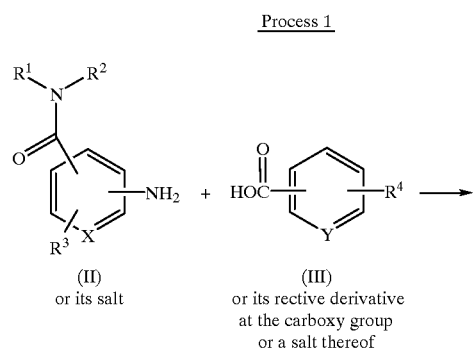

(II)
or its salt (III)
or its rective derivative
at the carboxy group
or a salt thereof -continued
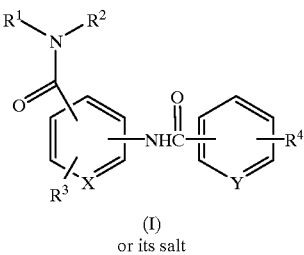
(I) or its salt
Process 2
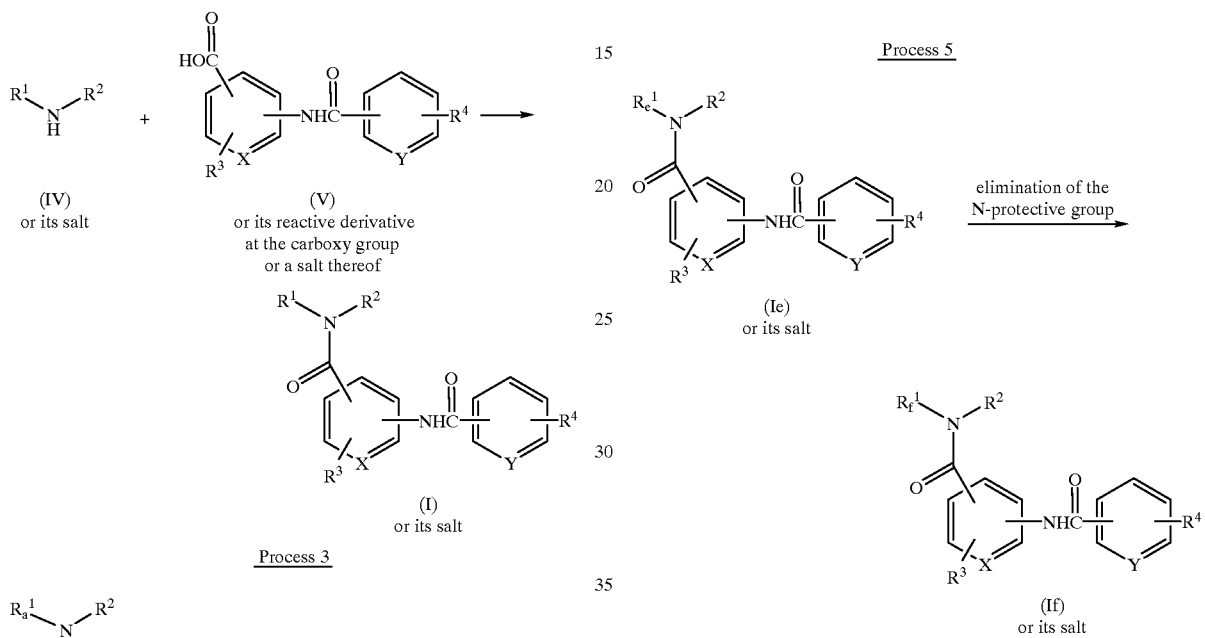
Process 3
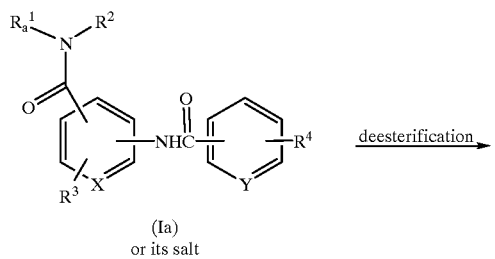
Process 4
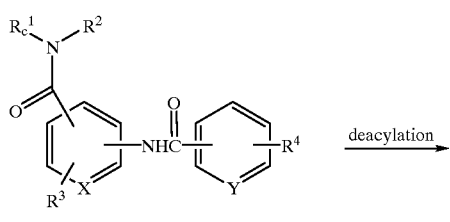
-continued
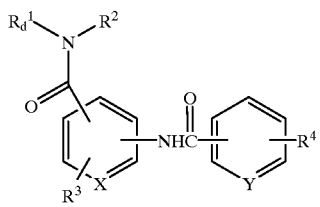
(Id) or its salt
Process 5
elimination of the N-protective group
Process 6
amidation
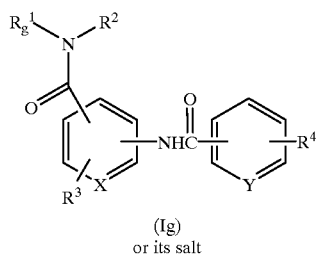

Process 7
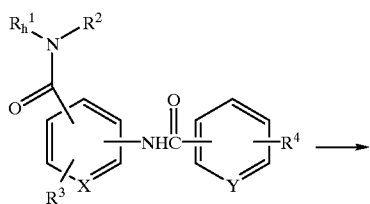
(Ih)
or its reactive derivative
at the carboxy group
or a salt thereof
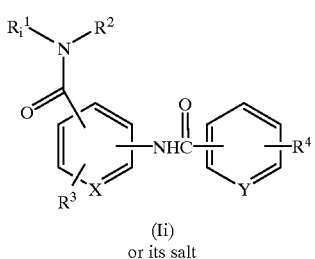
(Ii)
or its salt
Process 8
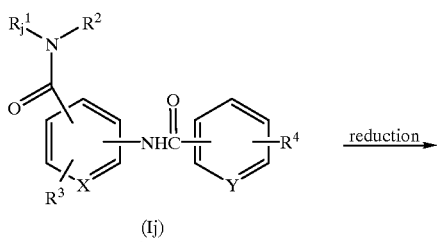
(Ij)
or its salt
reduction
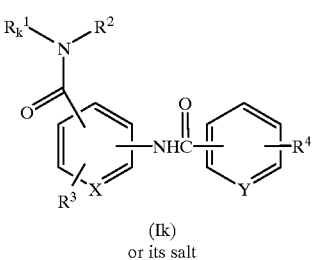
(Ik)
or its salt
Process 9
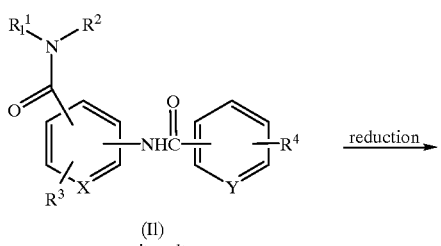
(Il)
or its salt
reduction
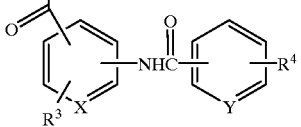
(Im)
or its salt
Process 10
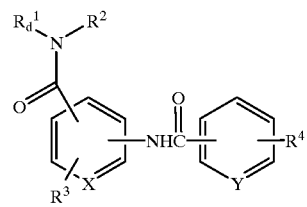
(Id)
or its salt
acylation
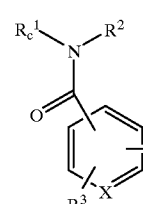
(Ic)
or its salt
Process 11
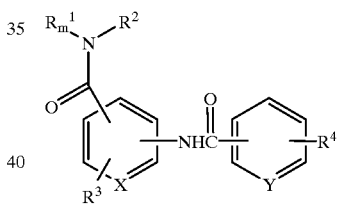
(Im)
or its salt
oxidation
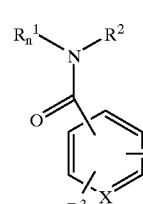
(In)
or its salt
Process 12
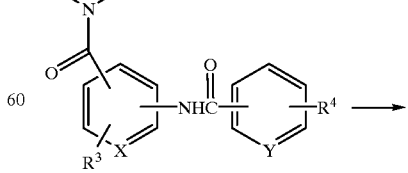
(In)
or its salt

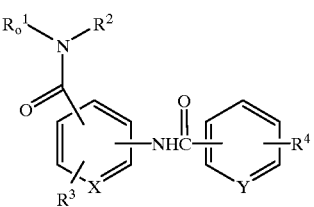
(Io) or its salt
Process 13
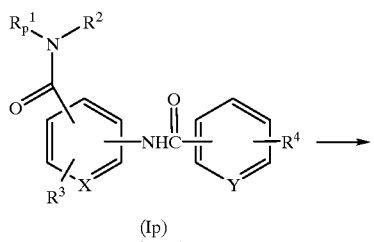
(Ip) or its salt
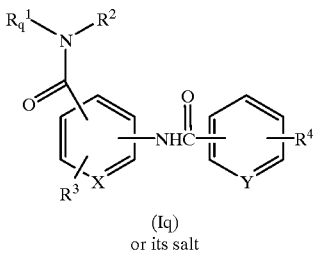
(Iq) or its salt
Process 14
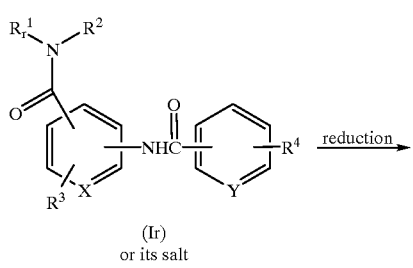
(Ir) or its salt
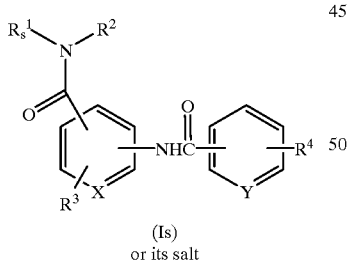
(Is) or its salt
Process 15
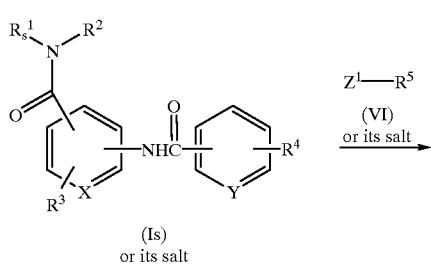
(Is) or its salt
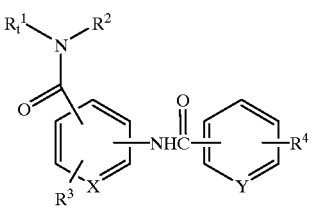
(It) or its salt
Process 16
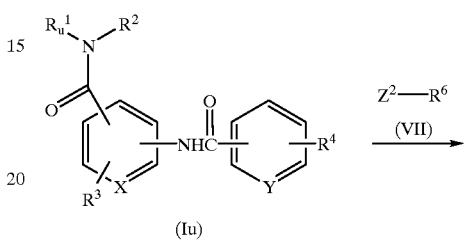
(Iu) or its salt
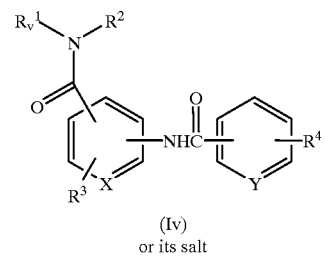
(Iv) or its salt
Process 17
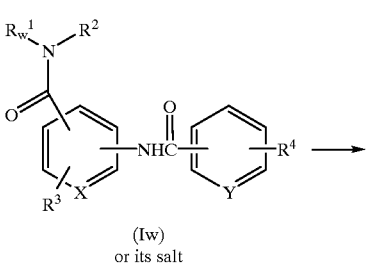
(Iw) or its salt
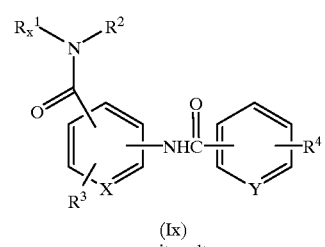
(Ix) or its salt
Process 18
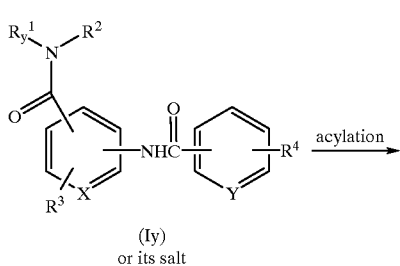
(Iy) or its salt -continued
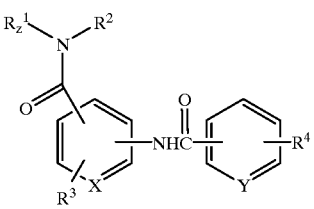
(Iz)
or its salt
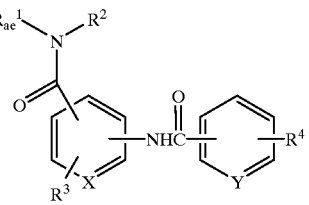
(I-5)
or its salt
Process 19
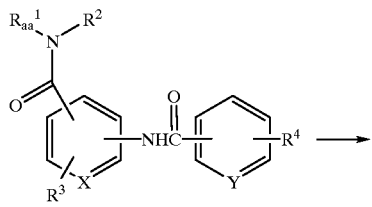
(I-1)
or its salt
Process 22
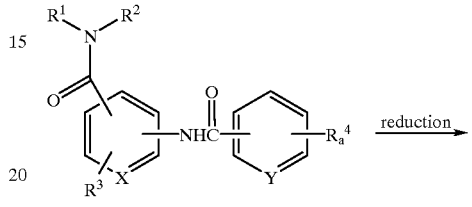 reduction
(I-6)
or its salt
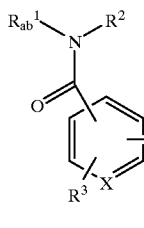
(I-2)
or its salt
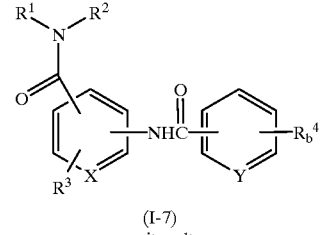
(I-7)
or its salt
Process 20
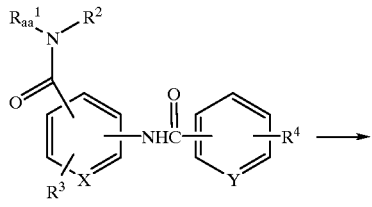
(I-1)
or its salt
Process 23
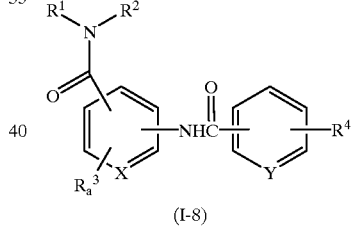 reduction
(I-8)
or its salt
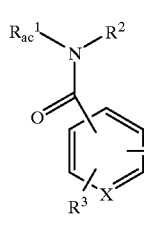
(I-3)
or its salt
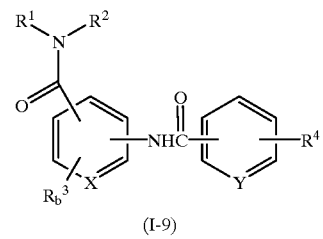
(I-9)
or its salt
Process 21
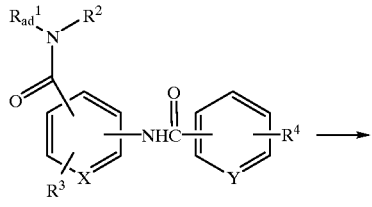
(I-4)
or its salt
Process 24
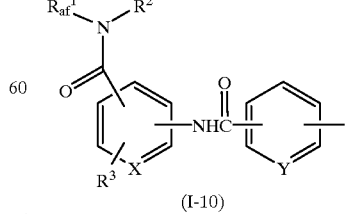
(I-10)
or its salt
B—CH$_2$—R$^7$
(VIII)
or its reactive derivative

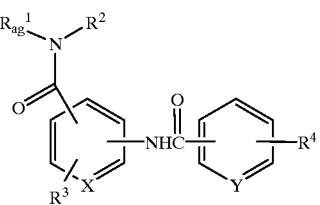
(I-11)
or its salt
Process 25
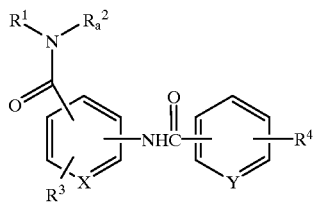
(I-12)
or its salt
→ reduction →
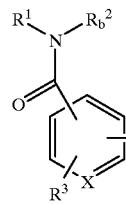
(I-13)
or its salt
Process 26
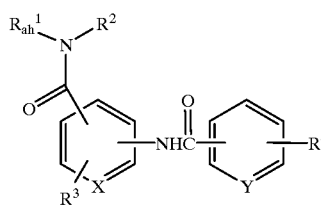
(I-14)
or its salt
→ reduction →
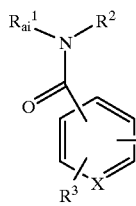
(I-15)
or its salt
Process 27
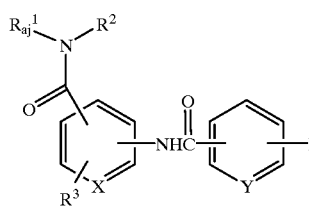
(I-16)
or its salt
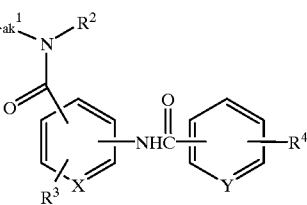
(I-17)
or its salt
Process 28
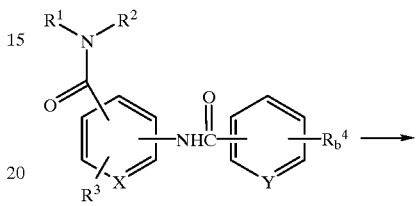
(I-7)
or its salt
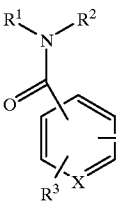
(I-18)
or its salt
Process 29
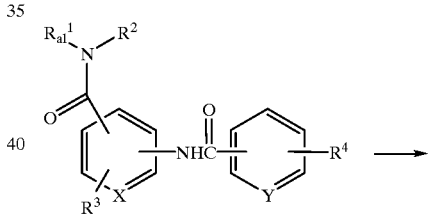
(I-19)
or its salt
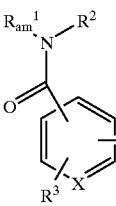
(I-20)
or its salt
Process 30
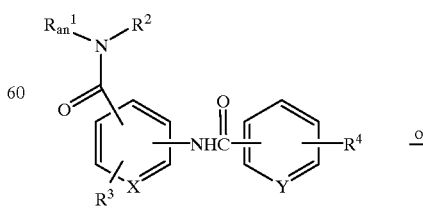
(I-21)
or its salt
→ oxidation →

-continued

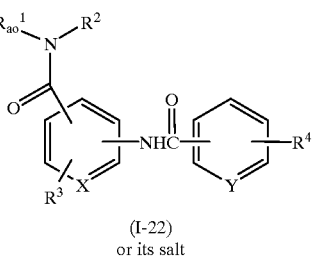

(I-22) or its salt

Process 31

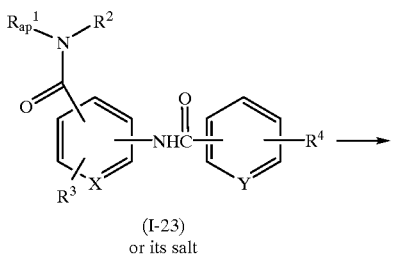

(I-23) or its salt

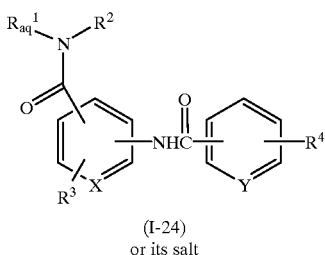

(I-24) or its salt

Process 32

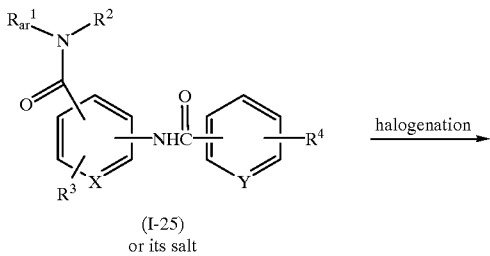

(I-25) or its salt halogenation →

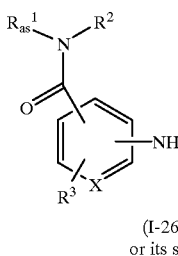

(I-26) or its salt

Process 33

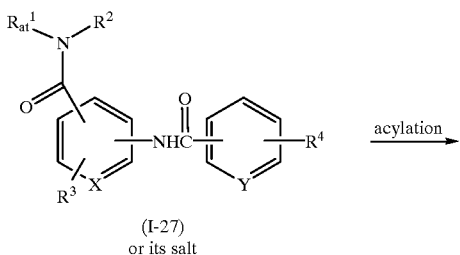

(I-27) or its salt acylation →

-continued

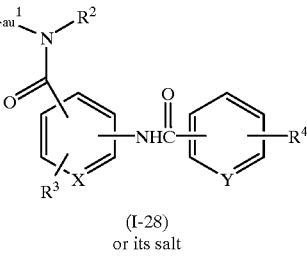

(I-28) or its salt

Process 34

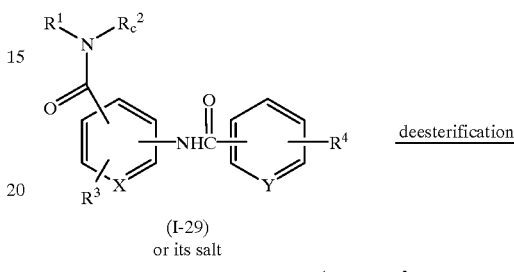

(I-29) or its salt deesterification →

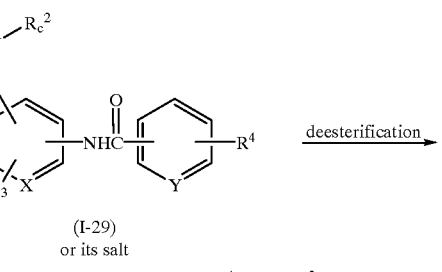

(I-30) or its salt

Process 35

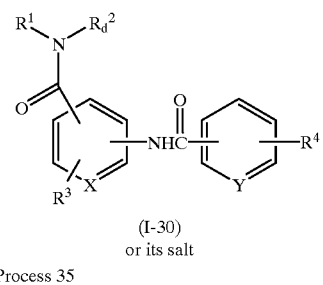

(I-30) or its reactive derivative at the carboxy group or a salt thereof amidation →

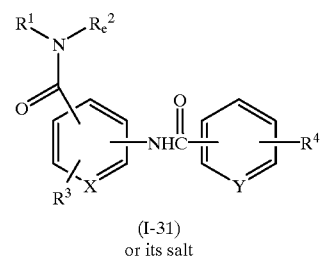

(I-31) or its salt wherein $R^1$, $R^2$, $R^3$, $R^4$, X and Y are each as defined above, $R_a^1$ is lower alkyl, aryl, haloaryl, cyclo(lower)alkyl or a heterocyclic group, each of which is substituted with esterified carboxy; lower alkenyl substituted with esterified carboxy; lower alkyl substituted with esterified carboxy, esterified carboxy(lower)alkanoyloxy or esterified carboxy(lower)alkoxyimino; lower alkylthio substituted with esterified carboxy; alkoxy substituted with esterified carboxy-substituted aryl, esterified carboxy-substituted pyridyl, esterified carboxy(lower)

alkylamino, N-protected-esterified carboxy(lower)
alkylamino, N-esterified carboxy(lower)alkyl-N-lower
alkylamino, esterified carboxy or esterified carboxy
(lower)alkoxyimino; or lower alkenyloxy substituted
with esterfied carboxy;

$R_b^1$ is lower alkyl, aryl, haloaryl, cyclo(lower)alkyl or a
heterocyclic group, each of which is substituted with
carboxy; lower alkenyl substituted with carboxy; lower
alkyl substituted with carboxy, carboxy(lower)
alkanoyloxy or carboxy(lower)alkoxyimino; lower
alkylthio substituted with carboxy; alkoxy substituted
with carboxy-substituted aryl, carboxy-substituted
pyridyl, carboxy(lower)alkylamino, N-protected-
carboxy(lower)alkylamino, N-carboxy(lower)alkyl-N-
lower alkylamino, carboxy or carboxy(lower)
alkoxyimino; or lower alkenyloxy substituted with
carboxy;

$R_c^1$ is lower alkyl, aryl, haloaryl, cyclo(lower)alkyl or a
heterocyclic group, each of which is substituted with
acyloxy; lower alkyl substituted with acyloxy or acyl
(lower)alkanoyloxy; or alkoxy substituted with acy-
loxy;

$R_d^1$ is lower alkyl, aryl, haloaryl, cyclo(lower)alkyl or a
heterocyclic group, each of which is substituted with
hydroxy; lower alkyl substituted with hydroxy;
or alkoxy substituted with hydroxy;

$R_e^1$ is lower alkyl, aryl, haloaryl, cyclo(lower)alkyl or a
heterocyclic group, each of which is substituted with
alkoxy substituted with protected amino, N-protected-
acyl(lower)alkylamino, N-protected-N-containing het-
erocycliccarbonylamino or N-protected-N-containing
heterocyclicsulfonyl-substituted aryl;

$R_f^1$ is lower alkyl, aryl, haloaryl, cyclo(lower)alkyl or a
heterocyclic group, each of which is substituted with
alkoxy substituted with amino, acyl(lower)alkylamino,
N-containing heterocycliccarbonylamino or
N-containing heterocyclicsulfonyl-substituted aryl;

$R_g^1$ is lower alkyl, aryl, haloaryl, cyclo(lower)alkyl or a
heterocyclic group, each of which is substituted with
substituted or unsubstituted N-containing heterocyclic-
carbonyl; carbamoyl; substituted or unsubstituted
lower alkylcarbamoyl; lower alkenyl substituted with
substituted or unsubstituted N-containing
heterocycliccarbonyl, carbamoyl or substituted or
unsubstituted lower alkylcarbamoyl; lower alkyl sub-
stituted with substituted or unsubstituted N-containing
heterocycliccarbonyl, carbamoyl, substituted or unsub-
stituted lower alkylcarbamoyl, substituted or unsubsti-
tuted N-containing heterocycliccarbonyl(lower)
alkanoyloxy, carbamoyl(lower)alkanoyloxy,
substituted or unsubstituted lower alkylcarbamoyl
(lower)alkanoyloxy, substituted or unsubstituted
N-containing heterocycliccarbonyl(lower)
alkoxyimino, carbamoyl-(lower)alkoxyimino or substi-
tuted or unsubstituted lower alkylcarbamoyl(lower)
alkoxyimino; lower alkylthio substituted with
substituted or unsubstituted N-containing
heterocycliccarbonyl, carbamoyl or substituted or
unsubstituted lower alkylcarbamoyl; alkoxy substituted
with substituted or unsubstituted N-containing
heterocycliccarbonyl-substituted aryl, carbamoyl-
substituted aryl, substituted or unsubstituted lower
alkylcarbamoyl-substituted aryl, substituted or unsub-
stituted N-containing heterocycliccarbonyl-substituted
pyridyl, carbamoyl-substituted pyridyl, substituted or
unsubstituted lower alkylcarbamoyl-substituted
pyridyl, substituted or unsubstituted N-containing
heterocycliccarbonyl(lower)alkylamino, carbamoyl
(lower)alkylamino, substituted or unsubstituted lower
alkylcarbamoyl(lower)alkylamino, N-protected-
(substituted or unsubstituted N-containing
heterocyclic)carbonyl(lower)alkylamino, N-protected-
carbamoyl(lower)alkylamino, N-protected substituted
or unsubstituted lower alkylcarbamoyl-(lower)
alkylamino, N-(substituted or unsubstituted
N-containing heterocyclic)carbonyl(lower)alkyl-N-
lower alkylamino, N-carbamoyl (lower)alkyl-N-lower
alkylamino, substituted or unsubstituted N-lower
alkylcarbamoyl-N-lower alkylamino, substituted or
unsubstituted N-containing heterocycliccarbonyl,
carbamoyl, substituted or unsubstituted lower
alkylcarbamoyl, substituted or unsubstituted
N-containing heterocycliccarbonyl(lower)
alkoxyimino, carbamoyl(lower)alkoxyimino or substi-
tuted or unsubstituted lower alkylcarbamoyl(lower)
alkoxyimino; or lower alkenyloxy substituted with
substituted or unsubstituted N-containing
heterocycliccarbonyl, carbamoyl or substituted or
unsubstituted lower alkylcarbamoyl;

$R_h^1$ is lower alkyl, aryl, haloaryl, cyclo(lower)alkyl or a
heterocyclic group, each of which is substituted with
carboxy;

$R_i^1$ is lower alkyl, aryl, haloaryl, cyclo(lower)alkyl or a
heterocyclic group, each of which is substituted with
amino;

$R_j^1$ is lower alkyl, aryl, haloaryl, cyclo(lower)alkyl or a
heterocyclic group, each of which is substituted with
lower alkenyl optionally substituted with acyl; lower
alkynyl optionally substituted with acylamino; or lower
alkenyloxy optionally substituted with acyl;

$R_k^1$ is lower alkyl, aryl, haloaryl, cyclo(lower)alkyl or a
heterocyclic group, each of which is substituted with
lower alkyl optionally substituted with aryl or acy-
lamino; or lower alkyloxy optionally substituted with
acyl;

$R_l^1$ is lower alkyl, aryl, haloaryl, cyclo(lower)alkyl or a
heterocyclic group, each of which is substituted with
lower alkanoyl; carboxy; esterified carboxy; or alkoxy
substituted with esterified carboxy or esterified
carboxy-substituted aryl;

$R_m^1$ is lower alkyl, aryl, haloaryl, cyclo(lower)alkyl or a
heterocyclic group, each of which is substituted with
1-hydroxy(lower)alkyl; or alkoxy substituted with
hydroxy or hydroxymethyl-substituted aryl;

$R_n^1$ is lower alkyl, aryl, haloaryl, cyclo(lower)alkyl or a
heterocyclic group, each of which is substituted with
lower alkanoyl; or alkoxy substituted with lower
alkanoyl or formyl-substituted aryl;

$R_o^1$ is lower alkyl, aryl, haloaryl, cyclo(lower)alkyl or a
heterocyclic group, each of which is substituted with
1-(lower alkyl)amino(lower)alkyl; or alkoxy substi-
tuted with N-acyl(lower)alkyl-N-lower alkylamino,
acyl(lower)alkylamino or N-containing heterocyclic
group-substituted methyl;

$R_p^1$ is lower alkyl, aryl, haloaryl, cyclo(lower)alkyl or a
heterocyclic group, each of which is substituted with
lower alkyl substituted with mono(lower)alkylamino;
or alkoxy substituted with amino optionally substituted
with acyl(lower)alkyl or piperazinylsulfonyl-
substituted aryl;

$R_q^1$ is lower alkyl, aryl, haloaryl, cyclo(lower)alkyl or a
heterocyclic group, each of which is substituted with lower alkyl substituted with di(lower)alkylamino; or alkoxy substituted with lower alkylamino, N-acyl(lower)alkyl-N-lower alkylamino or N-lower alkylpiperazinylsulfonyl-substituted aryl;

$R_r^1$ is lower alkyl, aryl, haloaryl, cyclo(lower)alkyl or a heterocyclic group, each of which is substituted with methoxy substituted with aryl or substituted aryl;

$R_s^1$ is lower alkyl, aryl, haloaryl, cyclo(lower)alkyl or a heterocyclic group, each of which is substituted with hydroxy;

$R^5$ is alkyl optionally substituted with aryl, substituted aryl, hydroxy, acyloxy, amino, lower alkylamino, protected amino, a heterocyclic group, acyl-substituted pyridyl, halogen, acyl(lower)alkylamino, N-protected-acyl(lower) alkylamino, N-acyl(lower)alkyl-N-lower alkylamino, acyl, substituted acyl, acylamino, substituted acylamino or lower alkylhydrazinocarbonylamino;

$Z^1$ is acid residue;

$R_t^1$ is lower alkyl, aryl, haloaryl, cyclo(lower)alkyl or a heterocyclic group, each of which is substituted with alkoxy optionally substituted with aryl, substituted aryl, hydroxy, acyloxy, amino, lower alkylamino, protected amino, a heterocyclic group, acyl-substituted pyridyl, halogen, acyl(lower)alkylamino, N-protected-acyl(lower)alkylamino, N-acyl(lower)alkyl-N-lower alkylamino, acyl, substituted acyl, acylamino, substituted acylamino or lower alkylhydrazinocarbonylamino;

$R_u^1$ is lower alkyl, aryl, haloaryl, cyclo(lower)alkyl or a heterocyclic group, each of which is substituted with alkoxy substituted with hydroxyimino;

$R^6$ is lower alkyl substituted with acyl;

$Z^2$ is acid residue;

$R_v^1$ is lower alkyl, aryl, haloaryl, cyclo(lower)alkyl or a heterocyclic group, each of which is substituted with alkoxy substituted with acyl(lower)alkyloxyimino;

$R_w^1$ is lower alkyl, aryl, haloaryl, cyclo(lower)alkyl or a heterocyclic group, each of which is substituted with alkoxy substituted with halogen;

$R_x^1$ is lower alkyl, aryl, haloaryl, cyclo(lower)alkyl or a heterocyclic group, each of which is substituted with alkoxy substituted with amino, lower alkylamino, phthalimido or N-containing heterocyclic group;

$R_y^1$ is lower alkyl, aryl, haloaryl, cyclo(lower)alkyl or a heterocyclic group, each of which is substituted with lower alkyl substituted with amino; lower alkynyl substituted with amino; or alkoxy substituted with amino;

$R_z^1$ is lower alkyl, aryl, haloaryl, cyclo(lower)alkyl or a heterocyclic group, each of which is substituted with lower alkyl substituted with substituted or unsubstituted acylamino; lower alkynyl substituted with substituted or unsubstituted acylamino; or alkoxy substituted with substituted or unsubstituted acylamino;

$R_{aa}^1$ is lower alkyl, aryl, haloaryl, cyclo(lower)alkyl or aa a heterocyclic group, each of which is substituted with lower alkyl substituted with substituted or unsubstituted aryloxycarbonylamino; lower alkynyl substituted with substituted or unsubstituted aryloxycarbonylamino; or alkoxy substituted with substituted or unsubstituted aryloxycarbonylamino;

$R_{ab}^1$ is lower alkyl, aryl, haloaryl, cyclo(lower)alkyl or a heterocyclic group, each of which is substituted with lower alkyl substituted with substituted or unsubstituted N-containing heterocycliccarbonylamino or lower alkylhydrazinocarbonylamino; lower alkynyl substituted with substituted or unsubstituted N-containing heterocycliccarbonylamino or lower alkylhydrazinocarbonylamino; or alkoxy substituted with substituted or unsubstituted N-containing heterocycliccarbonylamino or lower alkylhydrazinocarbonylamino;

$R_{ac}^1$ is lower alkyl, aryl, haloaryl, cyclo(lower)alkyl or a heterocyclic group, each of which is unsubstituted with lower alkyl substituted with heterocyclicoxycarbonylamino; or alkoxy substituted with heterocyclicoxycarbonylamino;

$R_{ad}^1$ is lower alkyl, aryl, haloaryl, cyclo(lower)alkyl or a heterocyclic group, each of which is substituted with substituted or unsubstituted aryloxycarbonyloxy; lower alkyl substituted with substituted or unsubstituted aryloxycarbonyloxy; or alkoxy substituted with substituted or unsubstituted aryloxycarbonyloxy;

$R_{ae}^1$ is lower alkyl, aryl, haloaryl, cyclo(lower)alkyl or a heterocyclic group, each of which is substituted with N-containing heterocycliccarbonyloxy; lower alkylamino(lower)alkylcarbamoyloxy; lower alkyl substituted with N-containing heterocycliccarbonyloxy or lower alkylamino(lower)alkylcarbamoyloxy; or alkoxy substituted with N-containing heterocycliccarbonyloxy or lower alkylamino(lower)alkylcarbamoyloxy;

$R_a^4$ is aryl substituted with nitro;

$R_b^4$ is aryl substituted with amino;

$R_a^3$ is nitro;

$R_b^3$ is amino;

$R_{af}^1$ is lower alkyl, aryl, haloaryl, cyclo(lower)alkyl or a heterocyclic group, each of which is substituted with formyl; lower alkyl substituted with formyl; or lower alkoxy substituted with formyl;

B is carboxy, esterified carboxy, di-esterified phosphono or triphenylphosphonium salt;

$R^7$ is lower alkyl optionally substituted with acyl;

$R_{ag}^1$ is lower alkyl, aryl, haloaryl, cyclo(lower)alkyl or a heterocyclic group, each of which is substituted with lower alkenyl optionally substituted with acyl; lower alkenyloxy optionally substituted with acyl;

$R_a^2$ is lower alkyl substituted with carboxy or esterified carboxy;

$R_b^2$ is lower alkyl substituted with hydroxy;

$R_{ah}^1$ is lower alkyl, aryl, haloaryl, cyclo(lower)alkyl or a heterocyclic group, each of which is substituted with lower alkyl substituted with esterified carboxy; or alkoxy substituted with esterified carboxy;

$R_{ai}^1$ is lower alkyl, aryl, haloaryl, cyclo(lower)alkyl or a heterocyclic group, each of which is substituted with lower alkyl substituted with formyl; or alkoxy substituted with formyl;

$R_{aj}^1$ is lower alkyl, aryl, haloaryl, cyclo(lower)alkyl or a heterocyclic group, each of which is substituted with alkoxy substituted with formyl;

$R_{ak}^1$ is lower alkyl, aryl, haloaryl, cyclo(lower)alkyl or a heterocyclic group, each of which is substituted with alkoxy substituted with hydroxyimino;

$R_c^4$ is aryl substituted with lower alkylamino;

$R_{al}^1$ is lower alkyl, aryl, haloaryl, cyclo(lower)alkyl or a heterocyclic group, each of which is substituted with cyano;

$R_{am}^1$ is lower alkyl, aryl, haloaryl, cyclo(lower)alkyl or a heterocyclic group, each of which is substituted with tetrazolyl;

$R_{an}^1$ is lower alkyl, aryl, haloaryl, cyclo(lower)alkyl or a heterocyclic group, each of which is substituted with lower alkylthio substituted with acyl;

$R_{ao}^1$ is lower alkyl, aryl, haloaryl, cyclo(lower)alkyl or a heterocyclic group, each of which is substituted with lower alkylsulfinyl substituted with acyl; or lower alkylsulfonyl substituted with acyl;

$R_{ap}^1$ is lower alkyl, aryl, haloaryl, cyclo(lower)alkyl or a heterocyclic group, each of which is substituted with alkoxy substituted with acyl(lower)alkylamino;

$R_{aq}^1$ is lower alkyl, aryl, haloaryl, cyclo(lower)alkyl or a heterocyclic group, each of which is substituted with alkoxy substituted with N-protected-acyl(lower)alkylamino;

$R_{ar}^1$ is lower alkyl, aryl, haloaryl, cyclo(lower)alkyl or a heterocyclic group, each of which is substituted with lower alkyl substituted with hydroxy; or alkoxy substituted with hydroxy;

$R_{as}^1$ is lower alkyl, aryl, haloaryl, cyclo(lower)alkyl or a heterocyclic group, each of which is substituted with lower alkyl substituted with halogen; or alkoxy substituted with halogen;

$R_{at}^1$ is lower alkyl, aryl, haloaryl, cyclo(lower)alkyl or a heterocyclic group, each of which is substituted with alkoxy substituted with piperazinylcarbonyl;

$R_{au}^1$ is lower alkyl, aryl, haloaryl, cyclo(lower)alkyl or a heterocyclic group, each of which is substituted with alkoxy substituted with acylpiperazinylcarbonyl;

$R_c^2$ is lower alkyl substituted with esterified carboxy;

$R_d^2$ is lower alkyl substituted with carboxy; and $R_e^2$ is lower alkyl substituted with substituted or unsubstituted N-containing heterocycliccarbonyl; carbamoyl; or substituted or unsubstituted lower alkylcarbamoyl.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

The "higher" is intended to mean 7 to 20 carbon atoms, unless otherwise provided.

The lower moiety in the term "cyclo(lower)alkyl is intended to mean a group having 3 to 6 carbon atoms.

The lower moiety in the terms "lower alkenyl", "lower alkenyloxy" and "lower alkynyl" is intended to mean a group having 2 to 6 carbon atoms.

The term "alkoxy" may included lower alkoxy and higher alkoxy.

Suitable "lower alkoxy" and lower alkoxy moiety in the terms "acyl(lower)alkoxy", acyl(lower)alkoxyimino", "esterified carboxy(lower)alkoxyimino", "carboxy(lower)alkoxyimino", "N-containing heterocycliccarbonyl(lower)alkoxyimino", "carbamoyl(lower)alkoxyimino", "lower alkylcarbamoyl(lower)alkoxyimino" and "lower alkoxycarbonyl" may be straight or branched $C_1$–$C_6$ alkoxy such as methoxy, ethoxy, propoxy, isopropoxy, butoxy, isobutoxy, tert-butoxy, pentyloxy, hexyloxy or the like.

Suitable "higher alkoxy" may be straight or branched $C_7$–$C_{20}$ alkoxy such as heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosyloxy, methylheptyloxy, methyloctyloxy, methylnonyloxy, methyldecyloxy, ethylheptyloxy, ethyloctyloxy, ethylnonyloxy, ethyldecyloxy or the like, in which preferable one is heptyloxy.

Suitable "lower alkyl" and lower alkyl moiety in the terms "acyl(lower)alkylsulfinyl", "acyl(lower)alkylsulfonyl", "lower alkylamino(lower)alkylcarbamoyloxy", "acyl(lower)alkylamino", "N-protected-acyl(lower)alkylamino", "N-acyl(lower)alkyl-N-lower alkylamino", "lower alkylhydrazinocarbonylamino", "esterified carboxy(lower)alkylamino", "N-protected-esterified carboxy(lower)alkylamino", "N-esterified carboxy(lower)alkyl-N-lower alkylamino", "carboxy(lower)alkylamino", "N-protected-carboxy(lower)alkylamino", "N-carboxy(lower)alkyl-N-lower alkylamino", "lower alkylcarbamoyl", "lower alkylcarbamoyl(lower)alkanoyloxy", "lower alkylcarbamoyl(lower)alkoxyimino", "lower alkylthio", "N-protected-(substituted or unsubstituted N-containing heterocyclic)carbonyl(lower)alkylamino", "N-protected-carbamoyl(lower)alkylamino", "N-protected-substituted or unsubstituted lower alkylcarbamoyl(lower)alkylamino", "N-(substituted or unsubstituted N-containing heterocyclic)carbonyl(lower)alkyl-N-lower alkylamino", "N-carbamoyl(lower)alkyl-N-lower alkylamino", "N-lower alkylcarbamoyl-N-lower alkylamino", "lower alkylcarbamoyl-(lower)alkoxyimino", "1-hydroxy(lower)alkyl", "1-(lower alkyl)amino(lower)alkyl", "mono(lower)alkylamino", "acyl(lower)alkyl", "di(lower)alkylamino", "lower alkylsulfinyl" and "lower alkylsulfonyl" may be straight or branched $C_1$–$C_6$ alkyl such as methyl, ethyl, propyl, isopropyl, butyl, isobutyl, tert-butyl, pentyl, ethylpropyl, hexyl or the like.

Suitable "cyclo(lower)alkyl" may be cyclo($C_3$–$C_6$)alkyl such as cyclopropyl, cyclobutyl, cyclopentyl or cyclohexyl, in which preferable one is cyclopentyl or cyclohexyl.

Suitable "lower alkenyl" and lower alkenyl moiety in the term "lower alkenyloxy" may be straight and branched $C_2$–$C_6$ alkenyl such as ethenyl, propenyl, pentenyl, isopropenyl, butenyl, hexenyl or the like, in which preferable one is propenyl, pentenyl or hexenyl.

Suitable "aryl" and aryl moiety in the term "haloaryl" may be phenyl, naphthyl, phenyl substituted with lower alkyl [e.g. tolyl, xylyl, mesityl, cumenyl, di(tert-butyl) phenyl, etc.] and the like, in which preferable one is phenyl, tolyl or xylyl.

Suitable "substituted aryl" may be aryl substituted with suitable substituent(s) such as acyl, N-protected piperazinylsulfonyl, piperazinylsulfonyl, N-lower alkylpiperazinylsulfonyl, hydroxy(lower)alkyl, a heterocyclic(lower)alkyl, halogen, nitro, amino, lower alkylamino or the like, in which preferable one for the substituent of alkoxy for $R^1$ is aryl substituted with N-methylpiperazinylsulfonyl, N-t-butoxycarbonyl-piperazinylsulfonyl, piperazinylsulfonyl, carboxy, esterified carboxy, N-lower alkylpiperazinylcarbonyl, lower alkanoyl, hydroxy(lower)alkyl or N-lower alkyl-piperazinyl(lower)alkyl, and preferable one for $R^4$ is aryl substituted with halogen, nitro, amino or lower alkylamino.

Suitable "halogen" and halo moiety in the term "haloaryl" may be fluorine, chlorine, bromine and iodine, in which preferable one is chlorine or bromine.

Suitable "lower alkylamino" and lower alkylamino moiety in the terms "lower alkylamino(lower) alkylcarbamoyloxy", "acyl(lower)alkylamino", "esterified carboxy(lower)alkylamino", "carboxy(lower)alkylamino", "N-containing heterocycliccarbonyl(lower)alkylamino", "carbamoyl(lower)alkylamino" and "lower alkylcarbamoyl-(lower)alkylamino" may be mono or di(lower alkyl)amino such as methylamino, ethylamino, propylamino, isopropylamino, butylamino, tert-butylamino, isobutylamino, pentylamino, hexylamino, dimethylamino, diethylamino, dipropylamino, dibutylamino, diisopropylamino, dipentylamino, dihexylamino, N-methylethylamino or the like, in which preferable one is methylamino, dimethylamino or diethylamino.

Suitable "1-hydroxy(lower)alkyl" may be 1-hydroxy-($C_1$–$C_6$)alkyl such as hydroxymethyl, 1-hydroxyethyl, 1-hydroxypropyl, 1-hydroxybutyl, 1-hydroxy-3-methylpropyl or the like, in which preferable one is hydroxymethyl or 1-hydroxyethyl.

Suitable "1-(lower alkyl)amino(lower)alkyl" may be 1-mono or di($C_1$–$C_6$ alkyl)amino($C_1$–$C_6$)alkyl such as methylaminomethyl, dimethylaminomethyl, 1-methylaminoethyl, 1-dimethylaminoethyl, ethylaminomethyl, 1-ethylaminoethyl or the like, in which preferable one is methylaminomethyl, dimethylaminomethyl, 1-methylaminoethyl or 1-dimethylaminoethyl.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.;

saturated 3 to 7-membered heteromonocyclic group containing 1 to 4 nitrogen atoms [e.g. pyrrolidinyl, imidazolidinyl, piperidyl, piperazinyl, homopiperazinyl, etc.];

unsaturated condensed heterocyclic group containing 1 to 5 nitrogen atoms, for example, indolyl, isoindolyl, indolizinyl, benzimidazolyl, quinolyl, isoquinolyl, imidazopyridyl, indazolyl, benzotriazolyl, tetrazolopyridazinyl [e.g. tetrazolo[1,5-b]pyridazinyl, etc.], etc.;

unsaturated 3 to 6-membered heteromonocyclic group containing an oxygen atom, for example, pyranyl, furyl, etc.;

saturated 3 to 6-membered heteromonocyclic group containing an oxygen atom, for example, 1H-tetrahydropyranyl, tetrahydrofuran, etc.;

unsaturated, 3 to 6-membered heteromonocyclic group containing 1 to 2 sulfur atoms, for example, thienyl, etc.;

unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], etc.;

saturated 3 to 6-membered heteromonocyclic group containing 1 to 2 oxygen atoms and 1 to 3 nitrogen atoms [e.g. morpholinyl, etc.];

unsaturated condensed heterocyclic group containing 1 to 2 oxygen atoms and 1 to 3 nitrogen atoms [e.g. benzofurazanyl, benzoxazolyl, benzoxadiazolyl, etc.];

unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.;

saturated 3 to 6-membered heteromonocyclic group containing 1 to 2 sulfur atoms and 1 to 3 nitrogen atoms [e.g., thiazolidinyl, etc.];

unsaturated condensed heterocyclic group containing 1 to 2 sulfur atoms and 1 to 3 nitrogen atoms [e.g., benzothiazolyl, benzothiadiazolyl, etc.];

unsaturated condensed heterocyclic group containing 1 to 2 oxygen atoms [e.g. benzofuranyl, benzodioxolyl, etc.] and the like.

Said "heterocyclic group" may be substituted with lower alkyl as exemplified above, in which preferable one is N-methylpiperazinyl, tetrazolyl, morpholinyl, pyrrolidinyl, N-methylpiperidyl, N-methylhomopiperazinyl, 1H-tetrahydropyranyl, thienyl, pyridyl or piperidyl.

Suitable acyl and acyl moiety in the terms "acyl(lower)alkylsulfinyl", "acyl(lower)alkylsulfonyl", "acyloxy", "acylamino", "acyl(lower)alkanoyloxy", "acyl(lower)alkoxyimino", "acyl(lower)alkylamino", "N-protected-acyl(lower)alkylamino" and "N-acyl(lower)alkyl-N-lower alkylamino" may be carboxy, esterified carboxy, carbamoyl, lower alkylcarbamoyl, lower alkanoyl, aroyl, a heterocycliccarbonyl and the like.

The esterified carboxy may be substituted or unsubstituted lower alkoxycarbonyl [e.g. methoxycarbonyl, ethoxycarbonyl, propoxycarbonyl, butoxycarbonyl, tert-butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, 3-methoxy-4-nitrobenzyloxy-carbonyl, etc.], N-containing heterocyclicoxycarbonyl [e.g. N-methylpiperidyloxycarbonyl, etc.] and the like, in which preferable one is lower alkoxycarbonyl or N-methylpiperidyloxycarbonyl.

The lower alkylcarbamoyl may be mono or di(lower alkyl)carbamoyl such as methylcarbamoyl, ethylcarbamoyl, propylcarbamoyl, dimethylcarbamoyl, diethylcarbamoyl, N-methyl-N-ethylcarbamoyl or the like.

The lower alkanoyl may be substituted or unsubstituted $C_1$–$C_6$ alkanoyl such as formyl, acetyl, propionyl, butyryl, isobutyryl, valeryl, isovaleryl, pivaloyl, hexanoyl, trifluoroacetyl or the like, in which preferable one is formyl, acetyl or butyryl.

The aroyl may be benzoyl, naphthoyl, toluoyl, di(tert-butyl)benzoyl and the like, in which preferable one is benzoyl.

The heterocyclic moiety in the terms "a heterocycliccarbonyl" "heterocyclicoxycarbonylamino" and "heterocyclicsulfonyl" may be one mentioned above as a heterocyclic group.

The "N-containing heterocycliccarbonyl" may be one containing at least one nitrogen atom in heterocyclic group mentioned above, in which preferable one is N-(lower)alkyl)piperazinylcarbonyl (e.g. N-methyl-piperazinylcarbonyl, etc.), N-(lower alkyl)-homopiperazinylcarbonyl (e.g. N-methylhomopiperazinylcarbonyl, etc.), piperazinylcarbonyl, pyrrodinylcarbonyl or piperidylcarbonyl.

Suitable "substituted acyl" may be substituted lower alkylcarbamoyl [e.g. N-lower alkylamino-N-lower alkylcarbamoyl, pyridyl(lower)alkylcarbamoyl, morpholino(lower)alkylcarbamoyl, etc.], substituted N-containing heterocycliccarbonyl [e.g. trifluoroacetylpiperazinylcarbonyl, pyridylpiperazinylcarbonyl, dimethylaminopiperazinylcarbonyl, hydroxyethoxyethylpiperazinylcarbonyl, pyrrolidinylcarbonylmethylpiperazinylcarbonyl, etc.], n-protected-N-containing heterocycliccarbonyl [e.g. N-t-butoxycarbonylpiperidylcarbonyl, etc.], and the like.

"N-Protective group" in "protected amino" may be common N-protective group such as substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, aralkyl [e.g. trityl, benzyl, etc.] or the like, in which preferable one is phthaloyl or tert-butoxycarbonyl.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

The substituent(s) on aryl for $R^1$ may be plural and in such case the substituents may be the same or different.

Preferred "lower alkyl" for $R^1$ may be ethylpropyl.

Preferred "aryl" for $R^1$ may be phenyl or phenyl substituted with lower alkyl.

Preferred "cyclo(lower)alkyl" for $R^1$ may be cyclopentyl.

Preferred "a heterocyclic group" for $R^1$ may be pyridyl or thienyl.

Preferred compound (I) is one which has aryl, cyclo(lower)alkyl or a heterocyclic group, each of which may be substituted with substituent(s) selected from the group consisting of halogen; hydroxy; nitro; amino; acyl; acyloxy; aryl; lower alkenyl; acyl(lower)alkenyl; lower alkoxy optionally substituted with amino, lower alkylamino, protected amino or acyl; and lower alkyl optionally substituted with hydroxy, lower alkylamino, acyl, acyloxy or acyl(lower)alkanoyloxy for $R^1$, lower alkyl or cyclo(lower)alkyl for $R^2$, hydrogen, halogen or lower alkoxy for $R^3$, lower alkyl or aryl optionally substituted with amino for $R^4$, CH or N for X and CH for Y.

More preferred compound (I) is one which has pyridyl, thienyl substituted with esterified carboxy, cyclo(lower) alkyl, or aryl which may be substituted with substituent(s) selected from the group consisting of halogen; hydroxy; nitro; amino; acyl; acyloxy; aryl; lower alkenyl; acyl(lower) alkenyl; lower alkoxy optionally substituted with amino, lower alkylamino or protected amino; and lower alkyl substituted with hydroxy, lower alkylamino, acyl, acyloxy or acyl(lower)alkanoyloxy for $R^1$, lower alkyl or cyclo(lower) alkyl for $R^2$, hydrogen or halogen for $R^3$, lower alkyl or aryl for $R^4$, CH for X and CH for Y; aryl for $R^1$, lower alkyl for $R^2$, hydrogen for $R^3$, aryl for $R^4$, N for X and CH for Y; or aryl or haloaryl (more preferably phenyl, tolyl or chlophenyl), each of which is substituted with alkoxy substituted with acyl for $R^1$, lower alkyl for $R^2$, hydrogen or lower alkoxy for $R^3$, aryl (more preferably phenyl or tolyl) substituted with amino for $R^4$, CH for X and CH for Y.

Most preferred compound (I) is one which has aryl or haloaryl (more preferably tolyl or chlorophenyl), each of which is substituted with lower alkoxy substituted with N-(lower alkyl)piperazinylcarbonyl, esterified carboxy or carboxy for $R^1$, lower alkyl for $R^2$, hydrogen or lower alkoxy for $R^3$, aryl (more preferably phenyl or tolyl) optionally substituted with amino for $R^4$, CH for X and CH for Y.

Suitable pharmaceutically acceptable salts of the object compound (I) are conventional non-toxic salts and include an acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a metal salt such as an alkali metal salt [e.g. sodium salt, potassium salt, etc.] and an alkaline earth metal salt [e.g. calcium salt, magnesium salt, etc.] and the like.

The processes for preparing the object compound (I) are explained in detail in the following.

Process 1

The object compound (I) or its salt can be prepared by reacting a compound (II) or its salt with a compound (III) or its reactive derivative at the carboxy group or a salt thereof.

Suitable salt of the compound (II) may be the same as those exemplified for the compound (I).

Suitable salts of the compound (III) and its reactive derivative at the carboxy group may be base salts as exemplified for the compound (I).

Suitable reactive derivative at the carboxy group of the compound (III) may include an acid halide, an acid anhydride containing intramolecular, intermolecular and a mixed ones, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.] or an ester with an N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine;

ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenylphosphoryl azide; diphenyl chlorophosphate; diphenylphosphinic chloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, 4-dimethylaminopyridine, N-(lower) alkylmorpholine, N,N-di(lower)alkylbenzylamine, or the like.

The reaction temperature is not critical, and the reaction is usually carried out under cooling to heating.

Process 2

The object compound (I) or its salt can be prepared by reacting a compound (IV) or its salt with a compound (V) or its reactive derivative at the carboxy group or a salt thereof.

Suitable salts of the compounds (IV) and (V) and its reactive derivative at the carboxy group may be the same as those exemplified for the compound (I).

This reaction can be carried out in substantially the same manner as Process 1, and therefore the reaction mode and reaction condition (e.g. solvent, reaction temperature, etc.) of this reaction are to be referred to those as explained in Process 1.

Process 3

The object compound (Ib) or its salt can be prepared by subjecting a compound (Ia) or its salt to deesterification reaction.

Suitable salt of the compound (Ib) may be the same as those exemplified for the compound (I).

Suitable salt of the compound (Ia) may be an acid addition salt as exemplified for the compound (I).

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2] octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], xylene, diethylene glycol monomethyl ethyl, methylene chloride, tetrahydrofuran, a mixture thereof or any other solvent which does not adversely influence the reaction. A liquid base or acid can be also used as the solvent.

The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalitic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

In this reaction, in case that the compound (Ia) having lower alkyl substituted with esterified carboxy for $R^2$ is used as a starting compound, the compound (Ib) having lower alkyl substituted with carboxy for $R^2$ may be obtained according to reaction condition. This case is included within the scope of this reaction.

Process 4

The object compound (Id) or its salt can be prepared by subjecting a compound (Ic) or its salt to deacylation reaction.

Suitable salt of the compound (Ic) may be an acid addition salt as exemplified for the compound (I).

Suitable salt of the compound (Id) may be the same as those exemplified for the compound (I).

This reaction can be carried out in substantially the same manner as hydrolysis in Process 3, and therefore the reaction mode and reaction condition (e.g. solvent, reaction temperature, etc.) of this reaction are to be referred to those as explained in hydrolysis in Process 3.

Process 5

The object compound (If) or its salt can be prepared by subjecting a compound (Ie) or its salt to elimination reaction of the N-protective group.

Suitable salts of the compounds (Ie) and (If) may be acid addition salts as exemplified for the compound (I).

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

In case that the N-protective group is benzyl, the reduction is preferably carried out in the presence of a combination of palladium catalysts [e.g. palladium black, palladium on carbon, etc.] and formic acid or its salt [e.g. ammonium formate, etc.].

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc. or a mixture thereof.

The reaction temperature of this reduction is not critical and the reaction is usually carried out under cooling to heating.

Process 6

The object compound (Ig) or its salt can be prepared by reacting a compound (Ib) or its reactive derivative at the carboxy group or a salt thereof with an amine or its salt.

Suitable salt of amine may be an acid addition salt as exemplified for the compound (I).

Suitable salts of the compounds (Ig) and (Ib) and its reactive derivative at the carboxy group may be the same as those exemplified for the compound (I).

Suitable "amine" may be ammonia, substituted or unsubstituted lower alkylamine, substituted or unsubstituted N-containing heterocyclic compound and the like.

The substituted or unsubstituted lower alkylamine may be mono or di(lower)alkylamine (e.g. methylamine, ethylamine, propylamine, isopropylamine, butylamine, isobutylamine, pentylamine, hexylamine, dimethylamine, diethylamine, dipropylamine, dibutylamine, di-isopropylamine, dipentylamine, dihexylamine, etc.), pyridyl(lower)alkylamine, (e.g. pyridylmethylamine, etc.), lower alkylamino(lower)alkylamine (e.g. N-diethylaminoethyl-N-methylamine, etc.), morpholino(lower)alkylamine (e.g. morpholinoethylamine, etc.) or the like.

The substituted or unsubstituted N-containing heterocyclic compound may be saturated 5 or 6-membered N-, or N- and S-, or N- and O-containing heterocyclic compound such as pyrrolidine, imidazolidine, piperidine, piperazine, lower alkylaminopiperidine (e.g. dimethylaminopiperidine, etc.), N-(lower) alkylhomopiperazine (e.g. N-methylhomopiperazine, etc.), N-(lower)alkylpiperazine (e.g. N-methylpiperazine, N-ethylpiperazine, etc.), morpholine, thiomorpholine, N-pyridylpiperazine, N-hydroxy(lower)alkoxy(lower)alkylpiperazine (e.g. N-hydroxyethoxyethylpiperazine, etc.), N-pyrrolidinylcarbonyl(lower)alkylpiperazine (e.g. N-pyrrodidinylcarbonylmethylpiperazine, etc.), or the like, in which preferable one is N-methylpiperazine.

This reaction can be carried out in substantially the same manner as Process 1, and therefore the reaction mode and reaction condition (e.g. solvent, reaction temperature, etc.) of this reaction are to be referred to those as explained in Process 1.

Process 7

The object compound (Ii) or its salt can be prepared by the following method.

Namely, 1) the compound (Ih) or its reactive derivative at the carboxy group or its salt thereof is firstly reacted with an azide compound, and then 2) reacting the resultant product with an acid.

Suitable salts of the compound (Ih) and its reactive derivative at the carboxy group may be the same as those exemplified for the compound (I).

Suitable salt of the compound (Ii) may be an acid addition salt as exemplified for the compound (I).

Suitable reaction derivative at the carboxy group of the compound (Ih) is to be referred to those as explained in Process 1.

Suitable azide compound may be alkali metal azide [e.g. sodium azide, potassium azide, etc.], alkaline earth metal azide [e.g. calcium azide, etc.], hydrogen azide, diphenylphosphoryl azide and the like.

In the first step, the reaction is preferably carried out in the presence of a base such as trialkylamine [e.g. triethylamine, etc.] or the like.

The reaction is usually carried out in a solvent which does not adversely influence the reaction such as tetrahydrofuran, dioxane, benzene or the like.

The reaction temperature is not critical and the reaction can be carried out under cooling to heating.

Additionally, in case that the above-mentioned azide compounds are alkali metal azide, alkaline earth metal azide and hydrogen azide, its reactive derivative at the carboxy group of the compound (Ih) is preferably used.

The resultant is further reacted with an acid to give the object compound (Ii) or its salt.

Suitable acid may include an organic acid [e.g. formic acid, acetic acid, trifluoroacetic acid, etc.] and an inorganic acid [e.g. hydrochloric acid, hydrobromic acid, etc.].

The reaction is usually carried out in a solvent which does not influence the reaction such as tetrahydrofuran, dioxane, benzene, water, a mixture thereof or the like.

The reaction temperature is not critical and the reaction is usually carried out under warming to heating.

Process 8

The object compound (Ik) or its salt can be prepared by subjecting a compound (Ij) or its salt to reduction.

Suitable salts of the compounds (Ij) and (Ik) may be the same as those exemplified for the compound (I).

This reduction is carried out by catalytic reduction or a mixture of nickel chloride and sodium borohydride.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc], iron catalyst [e.g. reduced iron, Raney iron, etc.], copper catalyst [e.g. reduced copper, Raney copper, Ullman copper, etc.] or the like.

The reduction is usually carried out in a solvent. A suitable solvent to be used may be water, an alcohol [e.g. methanol, ethanol, propanol, etc.], acetonitrile or any other conventional organic solvent such as diethyl ether, dioxane, tetrahydrofuran, etc. or a mixture thereof.

The reaction temperature is not critical, and the reaction is preferably carried out under cooling to heating.

Process 9

The object compound (Im) or its salt can be prepared by reacting a compound (Il) or its salt with a reducing agent.

Suitable salts of the compound (Il) or (Im) may be the same as those exemplified for the compound (I).

Suitable reducing agent may be diborane, lithium aluminum hydride, sodium borohydride and the like.

The reaction is usually carried out in a solvent which does not adversely influence the reaction such as diethyl ether, tetrahydrofuran, alcohol [e.g. methanol, ethanol, etc.] or the like.

In case that the compound (Il) having aryl, cyclo(lower)alkyl or a heterocyclic group, each of which is substituted with carboxy or esterified carboxy for $R_t^1$ is used as a starting compound, diborane or lithium aluminum hydride is used as a reducing agent.

Additionally, in case that diborane or lithium aluminum hydride is used as a reduced agent, alcohol can not be used as a solvent.

The reaction temperature is not critical and the reaction can be carried out under cooling to heating.

Process 10

The object compound (Ic) or its salt can be prepared by reacting a compound (Id) or its salt with an acylating agent.

Suitable salts of the compounds (Ic) and (Id) may be the same as those exemplified for the compound (I).

The acylating agent may include an organic acid represented by the formula: $R^8$—OH, in which $R^8$ is acyl or acyl(lower)alkanoyl, acyl in which is illustrated above, or a reactive derivative thereof.

The suitable reactive derivative of organic acid may be a conventional one such as an acid halide [e.g. acid chloride, acid bromide, etc.], an acid azide, an acid anhydride containing intramolecular and intermolecular ones, an activated amide, an activated ester or the like.

When free acid is used as an acylating agent, the acylation reaction may preferably be conducted in the presence of a conventional condensing agent such as N,N'-dicyclohexylcarbodiimide or the like.

The reaction is usually carried out in a conventional solvent such as water, pyridine, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction is also preferably carried out in the presence of a conventional base such as triethylamine, pyridine, sodium hydroxide or the like.

The reaction temperature is not critical, and the reaction can be carried out under cooling to heating.

Process 11

The object compound (In) or its salt can be prepared by subjecting a compound (Im) or its salt to oxidation reaction.

Suitable salts of the compounds (Im) and (In) may be the same as those exemplified for the compound (I).

Suitable oxidizing agent used in this reaction may be manganese dioxide, dimethyl sulfoxide, a mixture of dimethyl sulfoxide and oxalyl chloride and the like.

The reaction is usually carried out in a conventional solvent such as pentane, hexane, benzene, diethyl ether, dimethoxyethane, acetone, chloroform, dichloromethane or any other solvent which does not adversely influence the reaction.

Additionally in case that the above-mentioned oxidizing agent is liquid, it can be used as a solvent.

In this reaction, in case that dimethyl sulfoxide or a mixture of dimethyl sulfoxide and oxalyl chloride is used as an oxidizing agent, the reaction is preferably carried out in the presence of alkali metal iodide (e.g. sodium iodide, etc.) and alkali metal carbonate (e.g. sodium carbonate) or tri(lower)alkylamine (e.g. triethylamine, etc.).

The reaction temperature is not critical, and the reaction is usually carried out under cooling to heating.

Process 12

The object compound (Io) or its salt can be prepared by reacting a compound (In) or its salt with mono or di(lower)alkylamine, N-acyl(lower)alkyl-N-lower alkylamine, N-containing heterocyclic compound, or a salt thereof in the presence of a reducing agent.

Suitable salts of the compounds (In) and (Io), mono or di(lower)alkylamine, N-acyl(lower)alkyl-N-lower alkylamine and N-containing heterocyclic compound may be acid addition salts as exemplified for the compound (I).

Suitable mono or di(lower)alkylamine may be mono or di($C_1$–$C_6$)alkylamine such as methylamine, ethylamine, dimethylamine, N-methyl-N-isopropylamine or the like, in which preferable one is methylamine.

Suitable "N-acyl(lower)alkyl-N-lower alkylamine" may be N-methylpiperazinylcarbonylmethyl-N-methylamine and the like.

Suitable "N-containing heterocyclic compound" may be the same as aforementioned, in which preferable one is N-methylpiperazine.

Suitable reducing agent may be diborane, borane-organic amine complex [e.g. borane-pyridine complex, etc.], alkali metal cyanoborohydride [e.g. sodium cyanoborohydride, lithium cyanoborohydride, etc.] and the like.

The reaction is preferably carried out in the presence of molecular sieves.

The reaction is usually carried out in a conventional solvent such as water, an alcohol [e.g. methanol, ethanol, etc.], dioxane, tetrahydrofuran, a mixture thereof or any other organic solvent which does not adversely influence the reaction.

The reaction may also be carried out in an acidic condition [e.g. presence of acetic acid, etc.] and the reaction temperature is not critical, and the reaction is usually carried out under cooling to warming.

Process 13

The object compound (Iq) or its salt can be prepared by reacting a compound (Ip) or its salt with lower alkanal.

Suitable salts of the compounds (Ip) and (Iq) may be acid addition salts as exemplified for the compound (I).

Suitable lower alkanal may be $C_1$–$C_6$ alkanal such as formaldehyde, ethanal, propanal or the like, in which preferable one is formaldehyde.

This reaction can be carried out in substantially the same manner as Process 12, and therefore the reaction mode and reaction condition (e.g. solvent, reaction temperature, etc.) of this reaction are to be referred to those as explained in Process 12.

Process 14

The object compound (Is) or its salt can be prepared by subjecting a compound (Ir) or its salt to catalytic reduction.

Suitable salts of the compounds (Ir) and (Is) may be the same as those exemplified for the compound (I).

This reaction can be carried out in substantially the same manner as catalytic reaction in Process 5, and therefore the reaction mode and reaction condition (e.g. solvent, reaction temperature, etc.) of this reaction are to be referred to those as explained in catalytic reaction in Process 5.

Process 15

The object compound (It) or its salt can be prepared by reacting a compound (Is) or its salt with a compound (VI) or its salt.

Suitable salts of the compounds (Is), (It) and (VI) may be the same as those exemplified for the compound (I).

When the compound (VII) having halogen for $Z^1$ is used in this reaction, the reaction is preferably carried out in the presence of a base such as an alkali metal (e.g. sodium, potassium, etc.), an alkaline earth metal (e.g. magnesium, calcium, etc.), the hydride or hydroxide or carbonate or bicarbonate thereof.

The reaction is usually carried out in a conventional solvent which does not adversely influence the reaction such as water, dioxane, alcohol (e.g. methanol, ethanol, etc.), acetonitrile, tetrahydrofuran, acetic acid, N,N-dimethylformamide, or a mixture thereof.

The reaction temperature is not critical and the reaction can be carried out under cooling to heating.

Process 16

The object compound (Iv) or its salt can be prepared by reacting a compound (Iu) or its salt with a compound (VII).

Suitable salts of the compounds (Iu) and (Iv) may be the same as those exemplified for the compound (I).

This reaction can be carried out in substantially the same manner as Process 15, and therefore the reaction mode and reaction condition (e.g. solvent, reaction temperature, etc.) of this reaction are to be referred those as explained in Process 15.

Process 17

The object compound (Ix) or its salt can be prepared by reacting a compound (Iw) or its salt with an amine or potassium phthalimide.

Suitable salts of the compounds (Ix) and (Iw) may be the same as those exemplified for the compound (I).

Suitable "amine" may be ammonia, lower alkylamine, N-containing heterocyclic compound and the like.

The lower alkylamine may be mono or di(lower)alkylamine such as methylamine, ethylamine, propylamine, isopropylamine, butylamine, isobutylamine, pentylamine, hexylamine, dimethylamine, diethylamine, dipropylamine, dibutylamine, di-isopropylamine, dipentylamine, dihexylamine or the like.

The N-containing heterocyclic compound may be saturated 5 or 6-membered N-, or N- and S-, or N- and O-containing heterocyclic compound such as pyrrolidine, imidazolidine, piperidine, piperazine, N-(lower)alkylpiperazine [e.g. N-methylpiperazine, N-ethylpiperazine, etc.], morpholine, thiomorpholine or the like, in which preferable one is N-methylpiperazine.

This reaction is preferably carried out in the presence of alkali metal carbonate or bicarbonate (e.g. potassium carbonate, potassium bicarbonate, etc.), alkali metal iodide [e.g. sodium iodide, potassium iodide, etc.] and the like.

This reaction is usually carried out in a conventional solvent such as tetrahydrofuran, dioxane, aromatic hydrocarbon [e.g. benzene, toluene, xylene, etc.], N,N-dimethylformamide, acetone, a mixture thereof, or any other solvent which does not adversely influence the reaction.

The reaction temperature is not critical, and the reaction is usually carried out under cooling to heating.

Process 18

The object compound (Iz) or its salt can be prepared by reacting a compound (Iy) or its salt with an acylating agent.

Suitable salts of the compounds (Iy) and (Iz) may be the same as those exemplified for the compound (I).

The acylating agent may include an organic acid represented by the formula : $R^9$—OH, in which $R^9$ is acyl or substituted acyl as illustrated above, or its reactive derivative.

This reaction can be carried out in substantially the same manner as Process 10, and therefore the reaction mode and reaction condition (e.g. solvent, reaction temperature, etc.) of this reaction are to be referred to those as explained in Process 10.

Process 19

The object compound (I-2) or its salt can be prepared by reacting a compound (I-1) or its salt with substituted or unsubstituted N-containing heterocyclic compound or lower alkylhydrazine.

Suitable salts of the compounds (I-1) or (I-2) may be the same as exemplified for the compound (I).

Suitable "substituted or unsubstituted N-containing heterocyclic compound" may be the same as those exemplified in Process 6.

Suitable "lower alkylhydrazine" may be mono or di(lower)alkylhydrazine such as methylhydrazine, dimethylhydrazine, ethylhydrazine, diethylhydrazine or the like, in which preferable one is dimethylhydrazine.

This reaction is usually carried out in a conventional solvent which does not adversely influence the reaction such as diethyl ether, tetrahydrofuran, dioxane, N,N-dimethylformamide or the like.

The reaction temperature of this reaction is not critical and the reaction is usually carried out under cooling to heating.

Process 20

The object compound (I-3) or its salt can be prepared by reacting a compound (I-1) or its salt with heterocyclic compound substituted with hydroxy.

Suitable salts of the compound (I-1) and (I-3) may be the same as those exemplified for the compound (I).

Suitable "heterocyclic compound substituted with hydroxy" may be N-containing heterocyclic compound aforementioned substituted with hydroxy and the like, in which preferable one is N-lower alkylpiperidine substituted with hydroxy.

This reaction is usually carried out in a conventional solvent which does not adversely influence the reaction such as diethyl ether, tetrahydrofuran, dioxane, N,N-dimethylformamide or the like.

The reaction temperature of this reaction is not critical and the reaction is usually carried out under cooling to heating.

Process 21

The object compound (I-5) or its salt can be prepared by reacting a compound (I-4) or its salt with N-containing heterocyclic compound or lower alkylamino(lower) alkylamine.

Suitable salts of the compounds (I-4) and (I-5) may be the same as those exemplified for the compound (I).

Suitable "N-containing heterocyclic compound" may be the same as those exemplified in Process 17.

Suitable "lower alkylamino(lower)alkylamine" may be mono or di(lower)alkylamino(lower)alkylamine such as methylaminomethylamine, dimethylaminomethylamine, dimethylaminoethylamine or the like, in which preferable one is dimethylethylamine.

This reaction is usually carried out in a conventional solvent which does not influence the reaction such as diethyl ether, tetrahydrofuran, dioxane, N,N-dimethylformamide or the like.

The reaction temperature of this reaction is not critical and the reaction is usually carried out under cooling to heating.

Process 22

The object compound (I-7) or its salt can be prepared by subjecting a compound (I-6) or its salt to reduction.

Suitable salts of the compounds (I-6) and (I-7) may be the same as those exemplified for the compound (I).

The reduction may include chemical reduction and catalytic reduction, which are carried out in a conventional manner.

Suitable reducing agents to be used in chemical reduction are a metal [e.g. tin, zinc, iron, etc.], a combination of such metal and/or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tibromide, triphenylphosphine, triethylphosphine, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, an alcohol [e.g. methanol, ethanol, propanol, etc.], acetonitrile or any other conventional organic solvent such as diethyl ether, dioxane, tetrahydrofuran, etc. or a mixture thereof.

The reaction temperature is not critical, and the reacting is preferably carried out under cooling to heating.

In this reaction, in case that the compound (I-6) having lower alkyl, aryl, chloroaryl, cyclo(lower)alkyl, each of which is substituted with benzyloxy for $R^1$ and/or nitro for $R^3$ is used as a starting compound, the compound (I-6) having lower alkyl, aryl, chloroaryl, cyclo(lower)alkyl, each of which is substituted with hydroxy for $R^1$ and/or amino for $R^3$ may be obtained according to reaction condition. This case is included within the scope of this reaction.

Process 23

The object compound (I-9) or its salt can be prepared by subjecting a compound (I-8) or its salt to reduction.

Suitable salts of the compounds (I-8) and (I-9) may be the same as those exemplified for the compound (I).

This reaction can be carried out in substantially the same manner as Process 22, and therefore the reaction mode and reaction condition (e.g. solvent, reaction temperature, etc.) of this reaction are to be referred to those as explained in Process 22.

In this reaction, in case that the compound (I-8) having aryl substituted with nitro for $R^4$ is used as a starting compound, the compound (I-9) having aryl substituted with amino may be obtained according to reaction condition. This case is included within the scope of this reaction.

Process 24

The object compound (I-11) or its salt can be prepared by reacting a compound (I-10) or its salt with a compound (VIII) or its reactive derivative.

Suitable salts of the compounds (I-10) and (I-11) may be the same as those exemplified for the compound (I).

Suitable reactive derivative of the compound (VIII) may be phosphorane derivative and the like.

This reaction is preferably carried out in the presence of an inorganic or organic base such as an alkali metal [e.g. sodium, potassium, etc.], an alkaline earth metal [e.g. magnesium, calcium, etc.], the hydroxide or carbonate thereof, alkali metal hydride [e.g. sodium hydride, etc.], alkali metal amide [e.g. sodium amide etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.], lower alkyl alkali metal [e.g. n-butyl lithium, etc.], trialkylamine [e.g. trimethylamine, triethylamine, etc.], pyridine, piperidine, picoline, 1,5-diazabicyclo[4.3.0]non-5-ene, 1,4-diazabicyclo[2.2.0]octane, 1,8-diazabicyclo[5.4.0]undec-7-ene, or the like.

The reaction is usually carried out in a solvent such as water, an alcohol [e.g. methanol, ethanol, etc.], acetonitrile, chloroform, methylene chloride, nitromethane, benzene, tetrahydrofuran, diethyl ether, dimethylacetamide, N,N-dimethylformamide, dimethyl sulfoxide or any other organic solvent which does not adversely influence the reaction.

The reaction temperature is not critical, and the reaction can be carried out under cooling to heating.

Process 25

The object compound (I-13) or its salt can be prepared by reacting a compound (I-12) or its salt with a reducing agent.

Suitable salts of the compounds (I-12) and (I-13) may be the same as those exemplified for the compound (I).

This reaction can be carried out in substantially the same manner as Process 9, and therefore the reaction mode and reaction condition (e.g. solvent, reaction temperature, etc.) of this reaction are to be referred to those as explained in Process 9.

Process 26

The object compound (I-15) or its salt can be prepared by reacting a compound (I-14) or its salt with a reducing agent.

Suitable salts of the compounds (I-14) and (I-15) may be the same as those exemplified for the compound (I).

Suitable reducing agent may be diisobutylaluminum hydride, sodium diisobutylaluminum dihydride, sodium aluminum hydride, lithium tri-t-butoxyaluminohydride, and the like.

The reaction is usually carried out in a conventional solvent such as dichloromethane, toluene, tetrahydrofuran, diethyl ether or the like.

The reaction temperature is not critical, and the reaction is usually carried out under cooling to warming.

Process 27

The object compound (I-17) or its salt can be prepared by reacting a compound (I-16) or its salt with hydroxylamine or its salt.

Suitable salts of the compounds (I-16) and (I-17) may be the same as those exemplified for the compound (I).

Suitable salt of hydroxylamine may be an acid addition salt as exemplified for the compound (I).

The reaction is preferably carried out in the presence of alkali metal salt of acetic acid (e.g. sodium acetate, etc.) or alkali metal carbonate (e.g. sodium carbonate etc.).

The reaction is usually carried out in a solvent which does not adversely influence the reaction such as water, alcohol (e.g. methanol, ethanol, etc.), tetrahydrofuran, dioxane, acetic acid or the like, or a mixture thereof.

The reaction temperature is not critical and the reaction can be carried out under cooling to heating.

Process 28

The object compound (I-18) or its salt can be prepared by reacting a compound (I-7) or its salt with lower alkanal.

Suitable salts of the compounds (I-7) and (I-18) may be acid addition salts as exemplified for the compound (I).

This reaction can be carried out in substantially the same manner as Process 13, and therefore the reaction, mode and reaction condition (e.g. solvent, reaction temperature, etc.) of this reaction are to be referred to those explained in Process 13.

Process 29

The object compound (I-20) or its salt can be prepared by reacting a compound (I-19) or its salt with an azide compound.

Suitable salts of the compounds (I-19) and (I-20) may be the same as those exemplified for the compound (I).

Suitable azide compound may be alkali metal azide [e.g. sodium azide, potassium azide, etc.], alkaline earth metal azide [e.g. calcium azide, etc.], hydrogen azide, trimethyltin azide and the like.

The reaction is usually carried out in a conventional solvent such as tetrahydrofuran, dioxane, toluene, xylene, N,N-dimethylformamide or any other organic solvent which does not adversely influence the reaction.

The reaction temperature is not critical, and the reaction can be carried out warming to heating.

Process 30

The object compound (I-22) or its salt can be prepared by subjecting a compound (I-21) or its salt with an oxidizing agent.

Suitable salts of the compounds (I-21) and (I-22) may be the same as those exemplified for the compound (I).

The suitable oxidizing agent may be hydrogen peroxide, Jones reagent, peracid [e.g. peracetic acid, perbenzoic acid, m-chloroperbenzoic acid, elc.], chromic acid, potassium permanganate, alkali metal periodate [e.g. sodium periodate, etc.] and the like.

This reaction is usually carried out in a solvent which does not adversely influence the reaction such as acetic acid, dichloromethane, acetone, ethyl acetate, chloroform, water, an alcohol [e.g. methanol, ethanol, etc.], a mixture thereoL or the like.

The reaction temperature is not critical, and the reaction is usually carried out under cooling to warming.

Process 31

The object compound (I-24) or its salt can be prepared by subjecting a compound (I-23) or its salt to introduction reaction of N-protective group.

Suitable salts of the compounds (I-23) and (I-24) may be the same as those exemplified for the compound (I).

Suitable N-protective group introducing agent in introduction reaction of N-protective group may be a halogen compound of N-protective group aforementioned such as acetyl chloride, tert-butoxycarbonyl chloride, benzyl chloride, benzyl bromide or the like, di-tert-butyl dicarbonate, or the like.

The reaction is preferably carried out in the presence of a base such as trilower alkylamine (e.g. triethylamine) or the like.

The reaction is usually carried out in a conventional solvent such as water, an alcohol [e.g. methanol, ethanol, etc.], tetrahydrofuran, dioxane, pyridine, dichloromethane or any other organic solvent which does not adversely influence the reaction, or a mixture thereof.

The reaction temperature is not critical, and the reaction can be carried out under cooling to heating.

Process 32

The object compound (I-26) or its salt can be prepared by reacting a compound (I-25) or its salt with a halogenating agent.

Suitable salts of the compounds (I-25) and (I-26) may be the same as those exemplified for the compound (I).

Suitable halogenating agent may be hydrogen halide, a mixture of triphenylphosphine and carbon tetrahalide, and the like.

The reaction is usually carried out in a conventional solvent such as chloroform, dichloromethane, tetrahydrofuran or any other organic solvent which does not influence the reaction.

The reaction temperature is not critical, and the reaction is usually carried out under cooling to heating.

Process 33

The object compound (I-28) or its salt can be prepared by reacting a compound (I-27) or its salt with an acylating agent.

Suitable salts of the compounds (I-27) and (I-28) may be the same as those exemplified for the compound (I).

This reaction can be carried out in substantially the same manner as Process 18, and therefore the reaction mode and reaction condition (e.g. solvent, reaction temperature, etc.) of this reaction are to be referred to those explained in Process 18.

Process 34

The object compound (I-30) or its salt can be prepared by subjecting a compound (I-29) or its salt to deesterification reaction.

Suitable salts of the compounds (I-29) and (I-30) may be the same as those exemplified for the compound (I).

This reaction can be carried out in substantially the same manner as Process 3, and therefore the reaction mode and reaction condition (e.g. solvent, reaction temperature, etc.) of this reaction are to be referred to those explained in Process 3.

In this reaction, in case that the compound (I-29) having lower alkyl, aryl, haloaryl, cyclo(lower)alkyl or a heterocyclic group, each of which is substituted with esterified carboxy; lower alkenyl substituted with esterified carboxy; lower alkyl substituted with esterified carboxy, esterified carboxy(lower)alkanoyloxy or esterified carboxy(lower)alkoxyimino; lower alkylthio substituted with esterified carboxy; alkoxy substituted with esterified carboxy-substituted aryl, esterified carboxy-substituted pyridyl, esterified carboxy(lower)alkylamino, N-protected-esterified carboxy(lower)alkylamino, N-esterified carboxy(lower)alkyl-N-lower alkylamino, esterified carboxy or esterified carboxy(lower)alkoxyimino; or lower alkenyloxy substituted with esterfied carboxy for $R^1$ is used as a starting compound, the compound (I-30) having lower alkyl, aryl, haloaryl, cyclo(lower)alkyl or a heterocyclic group, each of which is substituted with carboxy; lower alkenyl substituted with carboxy; lower alkyl substituted with carboxy, carboxy(lower)alkanoyloxy or carboxy(lower)alkoxyimino; lower alkylthio substituted with carboxy; alkoxy substituted with carboxy-substituted aryl, carboxy-substituted pyridyl, carboxy(lower)alkylamino, N-protected-carboxy(lower)alkylamino, N-carboxy(lower)alkyl-N-lower alkylamino, carboxy or carboxy(lower)alkoxyimino; or lower alkenyloxy substituted with carboxy for $R^1$ may be obtained according to reaction condition. This case is included within the scope of the present reaction.

Process 35

The object compound (I-31) or its salt can be prepared by reacting a compound (I-30) or its reactive derivative at the carboxy group or a salt thereof with an amine or its salt.

Suitable salts of the compounds (I-31) and (I-30) and its reactive derivative at the carboxy group may be the same as those exemplified for the compound (I).

This reaction can be carried out in substantially the same manner as Process 6, and therefore the reaction mode and reaction condition (e.g. solvent, reaction temperature, etc.) of this reaction are to be referred to those as explained in Process 6.

The starting compound (II) or a salt thereof can be prepared by the following processes.

Process A

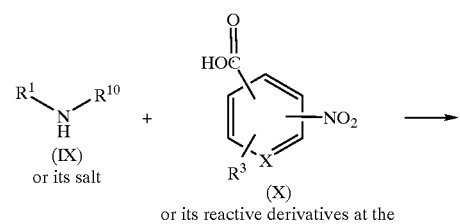

or its reactive derivatives at the carboxy group or a salt thereof

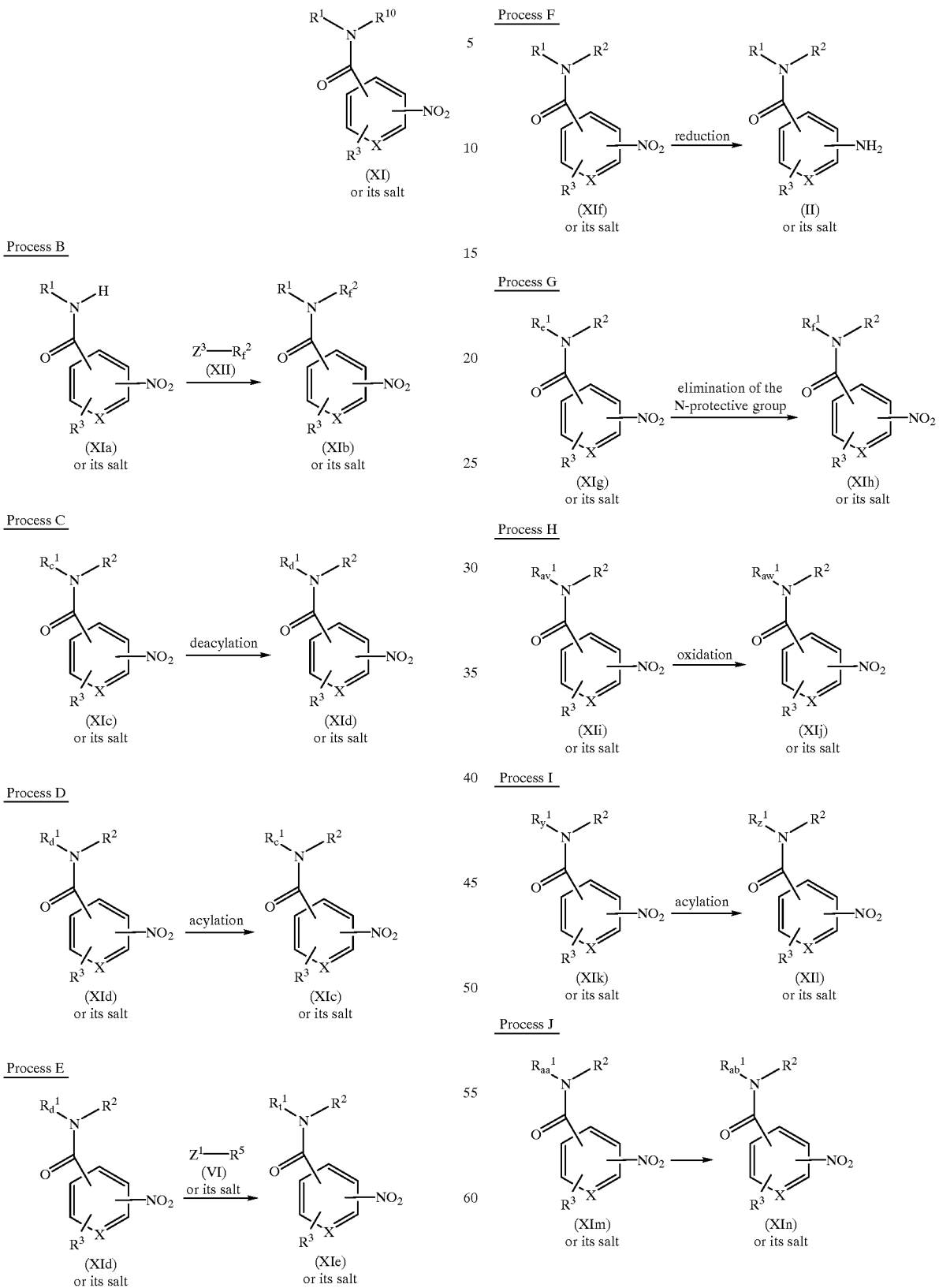

Process K

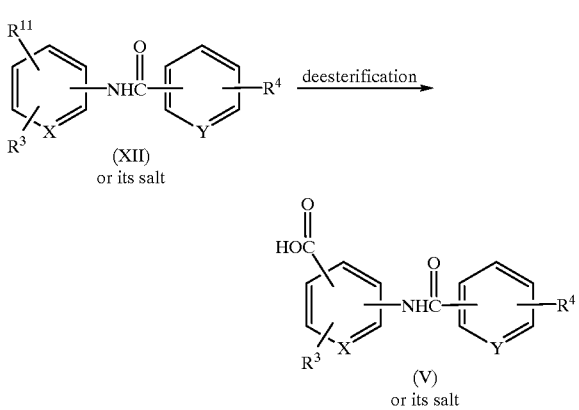

wherein $R^1$, $R_c^1$, $R_d^1$, $R_e^1$, $R_f^1$, $R_t^1$, $R_y^1$, $R_z^1$, $R_{aa}^1$, $R_{ab}^1$, $R^2$, $R_c^2$, $R^3$, $R^5$, X and $Z^1$ are each as defined above, $R^{10}$ is hydrogen; lower alkyl optionally substituted with aryl or acyl; or cyclo(lower)alkyl;

$R_j^2$ is lower alkyl optionally substituted with acyl, $Z^3$ is acid residue, $R_{av}^1$ is lower alkyl, aryl, haloaryl, cyclo(lower)alkyl or a heterocyclic group, each of which is substituted with lower alkyl substituted with hydroxymethyl, $R_{aw}^1$ is lower alkyl, aryl, haloaryl, cyclo(lower)alkyl or a heterocyclic group, each of which is substituted with lower alkyl substituted with lower alkoxycarbonyl, and $R^{11}$ is esterified carboxy.

The above-mentioned processes for preparing starting compound are explained in detail in the following.

Process A

The compound (XI) or its salt can be prepared by reacting a compound (IX) or its salt with a compound (X) or its reactive derivative at the carboxy group or a salt thereof.

Suitable salts of the compounds (IX), (XI) and (X) and its reactive derivative at the carboxy group may be the same as those exemplified for the compound (I).

This reaction can be carried out in substantially the same manner as Process 1, and therefore the reaction mode and reaction condition (e.g. solvent, reaction temperature, etc.) of this reaction are to be referred to those as explained in Process 1.

In this reaction, in case that the compound (IX) having lower alkyl, aryl, haloaryl, cyclo(lower)alkyl or a heterocyclic group, each of which is substituted with hydroxy for $R^1$ is used as a starting compound, the compound (XI) having lower alkyl, aryl, haloaryl, cyclo(lower)alkyl or a heterocyclic group, each of which is substituted with the formula

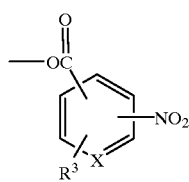

wherein $R^3$ and X are each as defined above for $R^1$ may be obtained according to reaction condition. This case is included within the scope of this reaction.

Process B

The compound (XIb) or its salt can be prepared by reacting a compound (XIa) or its salt with a compound (XII).

Suitable salts of the compounds (XIa) and (XIb) may be the same as those exemplified for the compound (I).

When the compound (XII) having halogen for $Z^3$ is used in this reaction, the reaction is preferably carried out in the presence of a base such as an alkali metal [e.g. sodium, potassium, etc.] or the hydride thereof.

The reaction is usually carried out in a conventional solvent which does not adversely influence the reaction such as dioxane, tetrahydrofuran, N,N-dimethylformamide, a mixture thereof or the like.

The reaction temperature is not critical and the reaction can be carried out under cooling to heating.

Process C

The compound (XId) or its salt can be prepared by subjecting a compound (XIc) or its salt to deacylation reaction.

Suitable salts of the compounds (XIc) and (XId) may be the same as those exemplified for the compound (I).

This reaction can be carried out in substantially the same manner as hydrolysis in Process 3, and therefore the reaction mode and reaction condition (e.g. solvent, reaction temperature, etc.) of this reaction are to be referred to those as explained in hydrolysis in Process 3.

Process D

The compound (XIc) or its salt can be prepared by subjecting a compound (XId) or its salt with an acylating agent.

Suitable salts of the compounds (XIc) or (XId) may be the same as those exemplified for the compound (I).

This reaction can be carried out in substantially the same manner as Proceed 10, and therefore the reaction mode and reaction condition (e.g. solvent, reaction temperature, etc.) of this reaction are to be referred to those as explained in Process 10.

Process E

The compound (XIe) or its salt can be prepared by reacting a compound (XId) or its salt with a compound (VI) or its salt.

Suitable salts of the compounds (XId) and (VI) may be the same as those exemplified for the compound (I).

Suitable salt of the compound (XIe) may be an acid addition salt as exemplified for the compound (I).

When the compound (VI) having halogen for $Z^1$ is used in this reaction, the reaction is preferably carried out in the presence of a base such as an alkali metal [e.g. sodium, potassium, etc.], an alkaline earth metal [e.g. magnesium, calcium, etc.], the hydride or hydroxide or carbonate or bicarbonate thereof.

The reaction is usually carried out in a conventional solvent which does not adversely influence the reaction such as water, dioxane, alcohol [e.g. methanol, ethanol, etc.], acetonitrile, tetrahydrofuran, acetic acid, N,N-dimethylformamide, or a mixture thereof.

The reaction temperature is not critical and the reaction can be carried out under cooling to heating.

Process F

The compound (II) or its salt can be prepared by subjecting a compound (XIf) or its salt to reduction.

Suitable salts of the compounds (II) or (XIf) may be the same as those exemplified for the compound (I).

The reduction may include chemical reduction and catalytic reduction, which are carried out in a conventional manner.

Suitable reducing agents to be used in chemical reduction are a metal [e.g. thin, zinc, iron, nickel, etc.], a combination of such metal and/or metallic compound [e.g. nickel chloride, chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalysts [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, an alcohol [e.g. methanol, ethanol, propanol, etc.], acetonitrile or any other conventional organic solvent such as diethyl ether, dioxane, tetrahydrofuran, etc. or a mixture thereof.

The reaction temperature is not critical, and the reaction is preferably carried out under cooling to heating.

In this reaction, in case that the compound (XIf) having lower alkyl, aryl, haloaryl, cyclo(lower)alkyl or a heterocyclic group each of which is substituted with lower alkenyl optionally substituted with acyl or substituted acyl for $R^1$ is used as a starting compound, the compound (II) having lower alkyl, aryl, haloaryl, cyclo(lower)alkyl or a heterocyclic group, each of which is substituted with lower alkyl optionally substituted with acyl for $R^1$ may be obtained according to reaction condition. This case is included within the scope of the present reaction.

Process G

The compound (XIh) or its salt can be prepared by subjecting a compound (XIg) or its salt to elimination reaction of N-protective group.

Suitable salts of the compounds (XIg) and (XIh) may be acid addition salts as exemplified for the compound (I).

This reaction can be carried out in substantially the same manner as Process 5, and therefore the reaction mode and reaction condition (e.g. solvent, reaction temperature, etc.) of this reaction are to be referred to those as explained in Process 5.

Process H

The compound (XIj) or its salt can be prepared by subjecting the compound, which is prepared by reacting a compound (XIi) or its salt with an oxidizing, to esterification reaction.

Suitable salts of the compounds (XIi) and (XIj) may be acid addition salts as exemplified for the compound (I).

Suitable oxidizing agent may be Jones reagent, pyridinium dichromate, potassium permanganate and the like.

Suitable agent used in esterification reaction may be diazo compound such as diazomethane, trimethylsilyl diazomethane or the like.

The oxidation reaction is usually carried out in a solvent which does not adversely influence the reaction such as N,N-dimethylformamide, water or the like.

This oxidation reaction temperature is not critical, and the reaction is usually carried out under cooling to heating.

The esterification reaction is usually carried out in a solvent which does not adversely influence the reaction such as an alcohol (e.g. methanol, ethanol, etc.), aromatic hydrocarbon (e.g. benzene, etc.), diethyl ether, or a mixture thereof.

This esterification reaction temperature is not critical, and the reaction is usually carried out under cooling to warming.

Process I

The object compound (XIl) or its salt can be prepared by reacting a compound (XIk) or its salt with an acylating agent.

Suitable salts of the compounds (XIk) and (XIl) may be acid addition salts as exemplified for the compound (I).

This reaction can be carried out in substantially the same manner as Process 18, and therefore the reaction mode and reaction condition (e.g. solvent, reaction temperature, etc.) of this reaction are to be referred to those as explained in Process 18.

Process J

The compound (XIn) or its salt can be prepared reacting a compound (XIm) or its salt with substituted or unsubstituted N-containing heterocyclic compound or lower alkylhydrazine.

Suitable salts of the compounds (XIm) and (XIn) may be acid addition salts as exemplified for the compound (I).

This reaction can be carried out in substantially the same manner as Process 19, and therefore the reaction mode and reaction condition (e.g. solvent, reaction temperature, etc.) of this reaction are to be referred to those as explained in Process 19.

Process K

The compound (V) or its salt can be prepared by subjecting a compound (XII) or its salt to deesterification reaction.

Suitable salts of the compounds (V) and (XII) may be the same as those exemplified for the compound (I).

This reaction can be carried out in substantially the same manner as Process 3, and therefore the reaction mode and reaction condition (e.g. solvent, reaction temperature, etc.) of this reaction are to be referred to those as explained in Process 3.

The compounds obtained by the above processes can be isolated and purified by a conventional method such as pulverization, recrystallization, column chromatography, reprecipitation, or the like.

It is to be noted that the compound (I) and the other compounds may include one or more stereoisomer(s) such as optical isomer(s) or geometrical isomer(s) due to asymmetric carbon atom(s) and double bond(s), and all of such isomers and mixture thereof are included within the scope of this invention.

The object compound (I) and pharmaceutically acceptable salts thereof possess activities as vasopressin antagonistic activity, vasodilating activity, hypotensive activity, activity for inhibiting saccharide release in liver, activity for inhibiting growth of mesangial cells, water diuretic activity, platelet agglutination inhibitory activity, oxytocin antagonistic activity and the like, and are useful for the treatment and/or prevention of hypertension, heart failure, renal insufficiency, edema, ascites, vasopressin parasecretion syndrome, hepatocirrhosis, hyponatremia, hypokalemia, diabetic, circulation disorder, cerebrovascular disease (e.g. cerebral edema, cerebral infarction, etc.), Meniere's syndrome (e.g. Meniere's disease, et.), motion sickness and the like in human beings and animals.

In order to illustrate the usefulness of the object compound (I), the pharmacological data of the compound (I) are shown in the following.

Test 1

Vasopressin 1 (V1) receptor binding
(i) Test Method:
Blood was obtained by venipuncture from normal subjects. Platelet-rich plasma (PRP) was prepared by centrifugation of whole blood at 200×g for 10 minutes. PRP was centrifuged at 45,000×g for 30 minutes. The remaining pellet was resuspended in 10 volume of ice cold 100 mM Tris-HCl (pH 7.4) buffer (containing 5 mM $MgCl_2$, 0.1% bovine serum albumin and 1 mM EGTA), and centrifuged at 45,000×g for 30 minutes again. The final pellet was resuspended in 100 mM Tris-HCl buffer. The resulting membrane preparation was used immediately for the binding assay.

Competition assays were conducted at equilibrium (15 minutes at 30° C.) by using 1.5 nM $^3$H-vasopressin (40–87 Ci/mmol; New England Nuclear) in 100 mM Tris-HCl (pH 7.4) buffer. Nonspecific binding was determined by using 1 μM vasopressin. After incubation, reaction was terminated by adding 5 ml of ice-cold 100 mM Tris-HCl (pH 7.4) buffer, and then filtered rapidly through Whatman glass filter (GF/C). The filter was washed twice with the same buffer. The glass filter was mixed with liquid scintillation cocktail, and radioactivity was counted in a liquid scintillation counter. Competition activity of the test compound was represented by $IC_{50}$ values.
(ii) Test Result:

| Test Compound (Example No.) | $IC_{50}$ (M) |
|---|---|
| 27–58) | $4.4 \times 10^{-9}$ |

Test 2

Vasopressin 2 (V2) receptor binding
(i) Test Method:
For binding assays, the receptor cDNA was permanently expressed in Chinese hamster ovary (CHO) cells. CHO cells were transfected with a vector directing expression of the cDNA for the human V2 receptor and the clonal cell lines expressing human V2 receptor was established essentially as described previously (Nakajima, Y., et. al. J. Biol. Chem., 1992, 267, 2437).

DNA-transfected cells were harvested and homogenized in ice cold 250 mM sucrose buffer containing 25 mM Tris-HCl (pH 7.4), 10 mM $MgCl_2$, 1 mM EDTA and 5 μg/ml p-amidinophenylmethylsulfonyl fluoride (A-PMSF). The homogenate was centrifuged at 500×g for 10 minutes. The supernatant was centrifuged at 100,000×g for 1 hour. The final pellet was suspended in 25 mM Tris-HCl (pH 7.4) buffer (containing 10 mM $MgCl_1$, 1 mM EDTA and 5 μg/ml A-PMSF), and stored in small aliquots at −80° C.

Competition assays were conducted at equilibrium (2 hours at 22° C.) by using 0.5 nM $^3$H-vasopressin (40–87 Ci/mmol, New England Nuclear) in 100 mM Tris-HCl (pH 7.4) buffer (containing 5 mM $MgCl_2$, 5 μg/ml A-PMSF, 4 μg/ml leupeptin, 40 μg/ml bacitracin, 20 μg/ml chymostatin and 0.1% bovine serum albumin). Nonspecific binding was determined by using 1 μM vasopressin. After incubation, reaction mixture was rapidly filtered through Whatman glass filter (GF/C). The filter was washed twice with the same buffer. The radioactivity was counted in a liquid scintillation counter. Competition activity of the test compound was represented by $IC_{50}$ values.
(ii) Test Result:

| Test Compound (Example No.) | $IC_{50}$ (M) |
|---|---|
| 27–36) | $3.0 \times 10^{-9}$ |
| 71–1) | $4.4 \times 10^{-9}$ |

For therapeutic purpose, the compound (I) of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical) administration. The pharmaceutical preparations may be capsules, tablets, dragees, granules, suppositories, solution, lotion, suspension, emulsion, ointment, gel, or the like. If desires, there may be included in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating the above-mentioned diseases. In general, amounts between 0.1 mg/body and about 1,000 mg/body may be administered per day.

The following Preparations and Examples are given for the purpose of illustrating this invention.

Preparation 1

To an ice bath cooled solution of N-methylaniline (536 mg) in dichloromethane (30 ml) were added triethylamine (0.837 ml) and p-nitrobenzoyl chloride (982 mg) and the mixture was stirred at ambient temperature for 3 hours. The solution was washed successively in 1N hydrogen chloride, saturated aqueous sodium hydrogen carbonate solution and brine, and dried over magnesium sulfate. The solvent was evaporated in vacuo to give an oil and the oil was solidified with diethyl ether to give N-methyl-N-(4-nitrobenzoyl) aniline (1.11 g) as a pale yellow solid.

NMR ($CDCl_3$, δ): 3.53 (3H, s), 6.98–7.05 (2H, m), 7.14–7.30 (3H, m), 7.44 (2H, d, J=8.5 Hz), 8.01 (2H, d, J=8.5 Hz).

Preparation 2

The following compounds were obtained according to a similar manner to that of Preparation 1.

1) N-Ethyl-N-(4-nitrobenzoyl)aniline
   NMR (CDCl$_3$, δ): 1.25 (3H, t, J=7 Hz), 4.00 (2H, q, J=7 Hz), 6.98–7.05 (2H, m), 7.14–7.30 (3H, m), 7.42 (2H, d, J=8.5 Hz), 8.01 (2H, d, J=8.5 Hz).
2) 2-Ethoxycarbonyl-N-(4-nitrobenzoyl)aniline
   NMR (CDCl$_3$, δ): 1.44 (3H, t, J=7 Hz), 4.44 (2H, q, J=7 Hz), 7.17 (1H, dt, J=1, 8 Hz), 7.63 (1H, dt, J=1.5, 8 Hz), 8.13 (1H, dd, J=1.5, 8 Hz), 8.21 (2H, d, J=8.5 Hz), 8.38 (2H, d, J=8.5 Hz), 8.90 (1H, dd, J=1, 8 Hz).
3) 2-[N-(4-Nitrobenzoyl)aminopyridine
   NMR (CDCl$_3$, δ): 7.13–7.39 (2H, m), 7.84 (1H, m), 7.93 (2H, d, J=8.5 Hz), 8.14–8.38 (4H, m).
4) 2-Chloro-N-(4-nitrobenzoyl)aniline
   NMR (CDCl$_3$, δ): 7.14 (1H, dt, J=1.5, 8 Hz), 7.36 (1H, dt, J=1, 8 Hz), 7.46 (1H, dd, J=1.5, 8 Hz), 8.09 (2H, d, J=8.5 Hz), 8.38 (2H, d, J=8.5 Hz), 8.42 (1H, br), 8.55 (1H, dd, J=1, 8 Hz).
5) N-Methyl-N-(4-nitrobenzoyl)-p-toluidine
   NMR (CDCl$_3$, δ): 2.28 (3H, s), 3.48 (3H, s), 6.89 (2H, d, J=8.5 Hz), 7.50 (2H, d, J=8.5 Hz), 7.45 (2H, d, J=8.5 Hz), 8.03 (2H, d, J=8.5 Hz).
6) N-Methyl-N-(2-chloro-4-nitrobenzoyl)aniline
   NMR (CDCl$_3$, δ): 3.51 (3H, s), 7.08–7.26 (5H, m), 7.31 (1H, d, J=8 Hz), 7.93 (1H, d, J=8 Hz), 8.07 (1H, m).
7) N-Methyl-N-(4-nitrobenzoyl)-o-toluidine
   NMR (CDCl$_3$, δ): 2.21 (3H, s), 3.40 (3H, s), 6.98–7.18 (4H, m), 7.42 (2H, d, J=8.5 Hz), 7.99 (2H, d, J=8.5 Hz).
8) 2-Isopropyl-N-(4-nitrobenzoyl)aniline
   NMR (CDCl$_3$, δ): 1.30 (6H, d, J=7 Hz), 3.10 (1H, qq, J=7, 7 Hz), 7.22–7.40 (4H, m), 7.75 (1H, br), 8.05 (2H, d, J=8.5 Hz), 8.34 (2H, d, J=8.5 Hz).
9) N-(4-Nitrobenzoyl)-o-anisidine
   NMR (CDCl$_3$, δ): 3.95 (3H, s), 6.94 (1H, dd, J=1, 8 Hz), 7.03 (1H, ddd, J=1, 8, 8 Hz), 7.14 (1H, ddd, J=1, 8, 8 Hz), 8.04 (2H, d, J=8.5 Hz), 8.35 (1H, d, J=8.5 Hz), 8.50 (1H, dd, J=1, 8 Hz), 8.58 (1H, br).
10) 3-(4-Nitrobenzoyl)aminopyridine
    NMR (CDCl$_3$+CD$_3$OD, δ): 7.39 (1H, dd, J=6, 9 Hz), 8.16 (2H, d, J=8.5 Hz), 8.31–8.39 (3H, m), 8.45 (1H, m), 8.63 (1H, d, J=3 Hz).
11) 2-Methoxycarbonyl-3-(4-nitrobenzoyl)aminothiophene
    NMR (DMSO-d$_6$, δ): 3.88 (3H, s), 8.01–8.08 (2H, m), 8.19 (2H, d, J=8.5 Hz), 8.46 (2H, d, J=8.5 Hz).
12) N-Methyl-N-(4-nitrobenzoyl)-m-toluidine
    NMR (CDCl$_3$, δ): 2.27 (3H, s), 3.49 (3H, s), 6.78 (1H, d, J=8 Hz), 6.86 (1H, s), 6.99 (1H, d, J=8 Hz), 7.10 (1H, dd, J=8, 8 Hz), 7.45 (2H, d, J=8.5 Hz), 8.02 (2H, d, J=8.5 Hz).
13) N-(4-Nitrobenzoyl)-2-(4-nitrobenzoyloxy)aniline
    NMR (DMSO-d$_6$, δ): 7.35–7.51 (3H, m), 7.70 (1H, m), 8.05 (2H, d, J=8.5 Hz), 8.26–8.41 (6H, m).
14) N-(4-Nitrobenzoyl)-2-phenylaniline
    NMR (CDCl$_3$, δ): 7.22–7.35 (2H, m), 7.39–7.58 (6H, m), 7.76 (2H, d, J=8.5 Hz), 8.00 (1H, br), 8.24 (2H, d, J=8.5 Hz), 8.48 (1H, d, J=8 Hz).
15) N-Cyclopentyl-N-(4-nitrobenzoyl)-p-anisidine
    NMR (CDCl$_3$, δ): 1.34–1.71 (6H, m), 1.91–2.12 (2H, m), 3.74 (3H, s), 4.86–5.17 (1H, m), 6.72 (2H, d, J=8 Hz), 6.92 (2H, d, J=8 Hz), 7.38 (2H, d, J=8 Hz), 8.00 (2H, d, J=8 Hz).
16) 2-Acetyl-N-(4-nitrobenzoyl)aniline
    NMR (CDCl$_3$, δ): 2.74 (3H, s), 7.23 (1H, dt, J=1, 8 Hz), 7.67 (1H, dt, J=1, 8 Hz), 8.00 (1H, dd, J=1, 8 Hz), 8.23 (2H, d, J=8.5 Hz), 8.39 (2H, d, J=8.5 Hz), 8.95 (1H, dd, J=1, 8 Hz).
17) 4-Nitro-N-(4-chlorophenyl)benzamide
    mp: 150–153° C.;
18) 4-Nitro-N-(3-methoxyphenyl)benzamide
    mp: 144–146° C.;
19) 4-Nitro-N-(4-methoxyphenyl)benzamide
    mp: 146–150° C.;
20) 4-Nitro-N-(3-chlorophenyl)benzamide
    mp: 159–164° C.;
21) 4-Nitro-N-(2-methylphenyl)benzamide
    mp: 155–158° C.;
22) 4-Nitro-N-benzyl-N-(2-methylphenyl)benzamide
    mp: 107–111° C.;
23) 4-Nitro-N-(2-trifluoromethylphenyl)benzamide
    mp: 126–128° C.; NMR (CDCl$_3$, δ): 7.35 (1H, t, J=6 Hz), 7.68 (1H, t, J=8 Hz), 7.70 (1H, t, J=10 Hz), 8.06 (2H, dt, J=1, 10 Hz), 8.16–8.24 (1H, br), 8.33–8.42 (3H, m).
24) N-Ethyl-N-(3-pentyl)-4-nitrobenzamido slightly yellow oil
25) 4-Nitro-N-(2,6-dimethylphenyl)benzamide
    mp: 192–195° C.;
26) N-Methyl-N-(4-tetrahydro-4H-pyranyl)-4-nitrobenzamide
    mp: 87–91° C.;
27) 3-Methoxy-4-nitro-N-(2-ethoxycarbonylphenyl)benzamide
    NMR (CDCl$_3$, δ): 1.44 (3H, t, J=7.5 Hz), 4.07 (3H, s), 4.43 (2H, q, J=7.5 Hz), 7.16 (1H, dd, J=7, 7 Hz), 7.60–7.67 (2H, m), 7.72 (1H, s), 7.95 (1H, d, J=7 Hz), 8.12 (1H, m), 8.87 (1H, d, J=7 Hz).
28) 4-Nitro-N-methyl-(2-cyano)phenylbenzamide
    NMR (CDCl$_3$, δ): 3.54 (3H, s), 7.22 (1H, m), 7.35 (1H, m), 7.46–7.65 (4H, m), 8.00–8.12 (2H, m).
29) 3-Methyl-4-nitro-N-methyl-N-[2-(3-phthalimidoprop-1-yloxy)phenyl]benzamide
    NMR (CDCl$_3$, δ): 2.21 (2H, m), 2.48 (3H, s), 3.39 (3H, s), 3.90–4.03 (4H, m), 6.76–6.83 (2H, m), 6.93 (1H, d, J=7 Hz), 7.10–7.26 (3H, m), 7.40 (1H, s), 7.67–7.76 (2H, m), 7.81–7.88 (2H, m).
30) 3-Methoxy-4-nitro-N-methyl-N-[2-(3-phthalimidoprop-1-yloxy)phenyl]benzamide
    NMR (CDCl$_3$, δ): 2.22 (2H, m), 3.38 (3H, s), 3.78 (3H, s), 3.91 (2H, t, J=7.5 Hz), 3.97 (2H, m), 6.78–6.85 (2H, m), 6.98 (1H, d, J=7.5 Hz), 7.10 (1H, s), 7.19 (1H, t, J=7.5 Hz), 7.61 (1H, d, J=7.5 Hz), 7.69–7.64 (2H, m), 7.80–7.86 (2H, m).
31) 4-Nitro-N-[2-[(E)-6-methoxycarbonyl-1-hexen-1-yl]phenyl]benzamide
    NMR (CDCl$_3$, δ): 1.53 (2H, m), 1.69 (2H, m), 2.22–2.37 (4H, m), 3.65 (3H, s), 6.13 (1H, dt, J=15, 7.5 Hz), 6.50 (1H, d, J=15 Hz), 7.20 (1H, t, J=7 Hz), 7.31 (1H, t, J=7 Hz), 7.41 (1H, d, J=7 Hz), 7.93–8.09 (3H, m), 8.33–8.40 (2H, m).
32) 4-Nitro-N-[2-[(Z)-6-methoxycarbonyl-1-hexen-1-yl]phenyl]benzamide
    NMR (CDCl$_3$, δ): 1.41 (2H, m), 1.57 (2H, m), 2.10 (2H, dt, J=7.7, 7.5 Hz), 2.20 (2H, t, J=7.5 Hz), 3.61 (3H, s), 5.97 (1H, dt, J=11, 7.5 Hz), 6.45 (1H, d, J=11 Hz), 7.19 (2H, m), 7.35 (1H, m), 8.00–8.07 (2H, m), 8.28–8.41 (2H, m).
33) 4-Nitro-N-[2-[N-(3-ethoxycarbonylprop-1-yl)oxyimino]methylphenyl]benzamide
    NMR (CDCl$_3$, δ): 1.25 (3H, t, J=7.5 Hz), 2.03 (2H, tt, J=7.5, 7.5 Hz), 2.43 (2H, t, J=7.5 Hz), 4.13 (2H, q, J=7.5 Hz), 4.27 (2H, t, J=7.5 Hz), 7.19 (1H, dt, J=1, 7 Hz), 7.31 (1H, dd, J=1, 7 Hz), 7.49 (1H, dt, J=1, 7 Hz), 8.19 (2H, d, J=8.5 Hz), 8.26 (1H, s), 8.38 (2H, d, J=8.5 Hz), 8.84 (1H, d, J=7 Hz).
34) 4-Nitro-N-[2-(5-ethoxycarbonylpent-1-ylthio)phenyl]benzamide NMR (CDCl$_3$, δ): 1.22 (3H, t, J=7.5 Hz), 1.34–1.47 (2H, m), 1.52–1.62 (4H, m), 2.21 (2H, t, J=7.5 Hz), 2.78 (2H, t, J=7.5 Hz), 4.10 (2H, q, J=7.5 Hz), 7.13 (1H, t, J=7 Hz), 7.41 (1H, t, J=7 Hz), 7.57 (1H, J=7 Hz), 8.10 (2H, d, J=8.5 Hz), 8.40 (2H, d, J=8.5 Hz), 8.56 (1H, d, J=7 Hz), 9.50 (1H, br).

35) 4-Nitro-N-[2-(3-ethoxycarbonylprop-1-yloxy)phenyl] benzamide

NMR (CDCl$_3$, δ): 1.17 t, J=7.5 Hz), 2.22 (2H, m), 2.50 (2H, t, J=7.5 Hz), 4.00 (2H, q, J=7.5 Hz), 4.14 (2H, J=7.5 Hz), 6.94 (1H, d, J=7 Hz), 7.00–7.15 (2H, m), 8.12 (2H, d, J=8.5 Hz), 8.36 (2H, d, J=8.5 Hz), 8.50 (1H, d, J=7 Hz), 8.69 (1H, s).

36) 4-Nitro-N-[2-(5-ethoxycarbonylpent-1-yloxy)pyridi-3-yl]benzamide

NMR (CDCl$_3$, δ): 1.23 (3H, t, J=7.5 Hz), 1.41 (2H, m), 1.69 (2H, m), 1.83 (2H, m), 2.31 (2H, t, J=7.5 Hz), 4.01 (2H, t, J=7.5 Hz), 4.12 (2H, q, J=7.5 Hz), 6.31 (1H, dd, J=7, 7 Hz), 7.05 (1H, dd, J=1, 7 Hz), 8.08 (2H, d, J=8.5 Hz), 8.33 (2H, d, J=8.5 Hz), 8.52 (1H, dd, J=1, 7 Hz), 9.31 (1H, s).

37) 4-Nitro-N-methyl-N-[3-(5-ethoxycarbonylpent-1-yloxy)pyrid-2-yl]benzamide

NMR (CDCl$_3$, δ): 1.25 (3H, t, J=7.5 Hz), 1.49 (2H, m), 1.64–1.82 (2H, m), 2.35 (2H, t, J=7.5 Hz), 3.43 (3H, s), 3.79 (2H, t, J=7.5 Hz), 4.19 (2H, q, J=7.5 Hz), 7.03 (1H, d, J=7 Hz), 7.12 (1H, m), 7.48 (2H, d, J=8.5 Hz), 7.95–8.02 (3H, m).

38) 3-Methyl-4-nitro-N-methyl-N-(4-chloro-2-benzyloxyphenyl)benzamide

NMR (CDCl$_3$, δ): 2.40 (3H, s), 3.35 (3H, s), 4.91 (1H, d, J=8.5 Hz), 5.09 (1H, d, J=8.5 Hz), 6.81–6.89 (2H, m), 6.96–7.10 (3H, m), 7.30–7.47 (5H, m), 7.67 (1H, d, J=7 Hz).

39) 4-Nitro-N-(2-benzyloxy-4-chlorophenyl)-N-methylbenzamide

NMR (CDCl$_3$, δ): 3.37 (3H, s), 4.92 (1H, d, J=10 Hz), 5.04 (1H, d, J=10 Hz), 6.80–6.92 (2H, m), 7.01 (1H, d, J=9 Hz), 7.28–7.50 (7H, m), 7.98 (2H, d, J=9 Hz).

40) 2-Chloro-4-nitro-N-(2-benzyloxy-4-chlorophenyl)-N-methylbenzamide

NMR (CDCl$_3$, δ): 3.39 (3H, s), 5.00–5.14 (2H, m), 6.79 (1H, d, J=8 Hz), 6.90 (3H, s), 7.09–7.20 (1H, m), 7.24 (1H, d, J=8 Hz), 7.33–7.52 (5H, m), 7.84 (1H, d, J=8 Hz), 8.06 (1H, s).

41) 2-Chloro-4-nitro-N-[2-(5-ethoxycarbonylpent-1-yloxy) phenyl]benzamide

NMR (CDCl$_3$, δ): 1.24 (3H, t, J=7 Hz), 1.42–1.56(2H, m), 1.62–1.76 (2H, m), 1.76–1.91 (2H, m), 2.30 (2H, t, J=7 Hz), 4.01–4.16 (4H, m), 6.92 (1H, d, J=9 Hz), 7.04 (1H, dd, J=9, 9 Hz), 7.13 (1H, dd, J=9, 9 Hz), 8.02 (1H, d, J=9 Hz), 8.25 (1H, d, J=9 Hz), 8.36 (1H, s), 8.51 (1H, d, J=9 Hz), 8.68 (1H, br s).

42) 3-Methoxy-4-nitro-N-[2-(5-ethoxycarbonylpent-1-yloxy)-4-methylphenyl]benzamide NMR (CDCl$_3$, δ): 1.23 (3H, t, J=7.5 Hz), 1.46–1.61 (2H, m), 1.62–1.79 (2H, m), 1.81–1.96 (2H, m), 2.31 (2H, t, J=7 Hz), 2.34 (3H, s), 4.04 (3H, s), 4.10 (2H, q, J=7 Hz), 6.73 (1H, s), 6.81 (1H, d, J=9 Hz), 7.38 (1H, d, J=9 Hz), 7.73 (1H, s), 7.96 (1H, d, J=9 Hz), 8.33 (1H, d, J=9 Hz), 8.54 (1H, s).

43) Ethyl 4-(4'-methylbiphenyl-2-carboxamido)-2-nitrobenzoate

NMR (CDCl$_3$, δ): 1.33 (3H, t, J=7 Hz), 2.42 (3H, s), 4.34 (2H, q, J=7 Hz), 7.16 (1H, br s), 7.24–7.40 (5H, m), 7.41–7.63 (4H, m), 7.67 (1H, d, J=9 Hz), 7.93 (1H, d, J=9 Hz).

44) Ethyl 3-chloro-4-(4'-methylbiphenyl-2-carboxamido)benzoate

NMR (CDCl$_3$, δ): 1.37 (3H, t, j=7 Hz), 2.35 (3H, s), 3.34 (2H, q, J=7 Hz), 7.19 (2H, d, J=8 Hz), 7.34 (2H, d, J=8 Hz), 7.41–7.62 (3H, m), 7.74 (1H, br s), 7.83–7.96 (3H, m), 8.63 (1H, br d, J=8 Hz).

45) 3-Methyl-4-nitro-N-(2-methylphenyl)benzamide
mp: 154–156° C.;

46) 3-Methoxy-4-nitro-N-(2-methylphenyl)benzamide
mp: 135–137° C.;

47) N-(2-Benzyloxy-4-chlorophenyl)-3-methoxy-N-methyl-4-nitrobenzamide

NMR (CDCl$_3$, δ): 3.37 (3H, s), 3.61 (3H, s), 4.89 (1H, d, J=11 Hz), 5.06 (1H, d, J=11 Hz), 6.80 (1H, d, J=9 Hz), 6.85–6.94 (2H, m), 7.01 (1H, s), 7.06 (1H, d, J=9 Hz), 7.29–7.47 (5H, m), 7.56 (1H, d, J=9 Hz).

48) Ethyl 4-(methylphenyl-2-carboxamido)-2-nitrobenzoate

NMR (CDCl$_3$, δ): 1.34 (3H, t, J=7 Hz), 2.49 (3H, s), 4.33 (2H, q, J=7 Hz), 7.19–7.53 (4H, m), 7.72–7.89 (2H, m), 8.04 (1H, br s), 8.19 (1H, br s).

Preparation 3

To a solution of 2-ethoxycarbonyl-N-(4-nitrobenzoyl) aniline (3.15 g) in N,N-dimethylformamide (30 ml) was added sodium hydride (60% in oil, 442 mg) and the solution was stirred at ambient temperature for 30 minutes. Iodomethane (1.56 g) was added to the solution and the mixture was stirred at ambient temperature for 4 hours. The solution was diluted with ethyl acetate and the solution was washed with successively with 1N hydrochloric acid, water and brine. The organic phase was dried over magnesium sulfate and the solvent was evaporated in vacuo to give an oil. The oil was solidified with diethyl ether to give 2-ethoxycarbonyl-N-methyl-N-(4-nitrobenzoyl)aniline (3.28 g) as a pale yellow powder.

NMR (CDCl$_3$, δ): 1.36 (3H, t, J=7 Hz), 3.44 (3H, s), 4.35 (2H, q, J=7 Hz), 7.20–7.52 (5H, m), 7.81 (1H, dd, J=8, 1.5 Hz), 7.98 (2H, d, J=8.5 Hz).

Preparation 4

The following compounds were obtained according to a similar manner to that of Preparation 3.

1) 2-Acetyl-N-methyl-N-(4-nitrobenzoyl)aniline

NMR (CDCl$_3$, δ): 2.37 (3H, s), 3.39 (3H, s), 7.20–7.50 (5H, m), 7.61 (1H, dd, J=1, 8 Hz), 7.96 (2H, d, J=8.5 Hz).

2) 2-[N-Methyl-N-(4-nitrobenzoyl)]aminopyridine

NMR (CDCl$_3$, δ): 3.95 (3H, s), 6.67 (1H, dt, J=1, 8 Hz), 7.60–7.71 (2H, m), 8.25 (2H, d, J=8.5 Hz), 8.39–8.51 (3H, m).

3) 2-Chloro-[N-methyl-N-(4-nitrobenzoyl)]aniline

NMR (CDCl$_3$, δ): 3.42 (3H, s), 7.08–7.25 (3H, m), 7.32–7.40 (1H, m), 7.50 (2H, d, J=8.5 Hz), 8.02 (2H, d, J=8.5 Hz).

4) 2-Isopropyl-[N-methyl-N-(4-nitrobenzoyl)aniline

NMR (CDCl$_3$, δ): 0.92 (3H, d, J=7 Hz), 1.20 (3H, d, J=7 Hz), 3.01 (1H, qq, J=7, 7 Hz), 3.45 (3H, s), 7.08–7.22 (2H, m), 7.06–7.29 (3H, m), 7.45 (2H, d, J=8.5 Hz), 8.00 (2H, d, J=8.5 Hz).

5) [N-Methyl-N-(4-nitrobenzoyl)]-o-anisidine

NMR (CDCl$_3$, δ): 3.39 (3H, s), 3.73 (3H, s), 6.76 (1H, dd, J=1, 8 Hz), 6.81 (1H, ddd, J=1, 8, 8 Hz), 7.05 (1H, dd, J=1, 8 Hz), 7.18 (1H, ddd, J=1, 8, 8 Hz), 7.45 (2H, d, J=8.5 Hz), 7.99 (1H, d, J=8.5 Hz).

6) 3-[N-Methyl-N-(4-nitrobenzoyl)]aminopyridine

NMR (CDCl$_3$, δ): 3.51 (3H, s), 7.24 (1H, dd, J=5.5, 9 Hz), 7.40 (1H, d, J=9 Hz), 7.42 (2H, d, J=8.5 Hz), 8.07 (2H, d, J=8.5 Hz), 8.33 (1H, s), 8.43 (1H, d, J=5.5 Hz).

7) 2-Methoxycarbonyl-3-[N-methyl-N-(4-nitrobenzoyl)]-aminothiophene

NMR (CDCl$_3$, δ): 3.41 (3H, s), 3.80 (3H, s), 6.98 (1H, d, J=7.5 Hz), 7.42–7.52 (3H, m), 8.03 (2H, d, J=8.5 Hz).

8) [N-Methyl-N-(4-nitrobenzoyl)]-2-(4-nitrobenzoyloxy) aniline

NMR (DMSO-d$_6$, δ): 3.33 (3H, s), 7.30–7.42 (3H, m), 7.50 (2H, d, J=8.5 Hz), 7.65 (1H, m), 8.11 (2H, d, J=8.5 Hz), 8.31 (2H, d, J=8.5 Hz), 8.50 (2H, d, J=8.5 Hz).

9) [N-Methyl-N-(4-nitrobenzoyl)]-2-phenylaniline

NMR (CDCl$_3$, δ): 3.53 (3H, s), 6.85–6.93 (4H, m), 7.19–7.45 (7H, m), 7.82 (2H, d, J=8.5 Hz).

Preparation 5

A mixture of N-methyl-N-(4-nitrobenzoyl)aniline (1.18 g) and iron powder (2.57 g) in a mixture of ethanol (30 ml) and acetic acid (6 ml) was stirred at 80° C. for 3 hours and the mixture was cooled to ambient temperature. The mixture was filtered through Celite and the filtrate was evaporated in vacuo. The residue was dissolved in chloroform and neutralized with saturated aqueous sodium hydrogen carbonate. The solution was filtered through Celite again and the organic phase of the filtrate was washed with brine, and dried over magnesium sulfate. The solvent was evaporated in vacuo and the residue was solidified with diethyl ether to give N-methyl-N-(4-aminobenzoyl)aniline (754 mg) as a pale yellow solid.

NMR (CDCl$_3$, δ): 3.44 (3H, s), 3.77 (2H, br), 6.40 (2H, d, J=8.5 Hz), 7.01–7.30 (7H, m).

Preparation 6

The following compounds were obtained according to a similar manner to that of Preparation 5.

1) N-Ethyl-N-(4-aminobenzoyl)aniline

NMR (CDCl$_3$, δ): 1.17 (3H, t, J=7 Hz), 3.72 (2H, br), 3.96 (2H, q, J=7 Hz), 6.39 (2H, d, J=8.5 Hz), 6.98–7.27 (7H, m).

2) 2-Ethoxycarbonyl-N-methyl-N-(4-aminobenzoyl)aniline

NMR (CDCl$_3$, δ): 1.34 (3H, t, J=7 Hz), 3.41 (3H, s), 3.25 (2H, br), 4.30 (2H, q, J=7 Hz), 6.37 (2H, d, J=8.5 Hz), 7.08 (2H, d, J=8.5 Hz), 7.19–7.30 (2H, m), 7.46 (1H, dt, J=1, 8 Hz), 7.77 (1H, d, J=8 Hz).

3) 2-[N-Methyl-N-(4-aminobenzoyl)]aminopyridine

NMR (CDCl$_3$, δ): 3.82 (3H, s), 3.92 (2H, br), 6.42 (1H, dt, J=1, 8 Hz), 6.76 (2H, d, J=8.5 Hz), 7.40–7.53 (2H, m), 8.13 (1H, d, J=8.5 Hz), 8.25 (1H, d, J=8 Hz).

4) 2-Chloro-N-methyl-N-(4-aminobenzoyl)aniline

NMR (CDCl$_3$, δ): 3.35 (3H, s), 3.76 (2H, br), 6.40 (2H, d, J=8.5 Hz), 7.02–7.19 (5H, m), 7.37 (1H, m).

5) N-Methyl-N-(4-aminobenzoyl)-p-toluidine

NMR (CDCl$_3$, δ): 2.28 (3H, s), 3.42 (3H, s), 3.77 (2H, br), 6.42 (2H, d, J=8.5 Hz), 6.93 (2H, d, J=8.5 Hz), 7.04 (2H, d, J=8.5 Hz), 7.15 (2H, d, J=8.5 Hz).

6) N-Methyl-N-(4-amino-2-chlorobenzoyl)aniline

NMR (CDCl$_3$, δ): 3.42 (3H, s), 3.73 (2H, br), 6.32 (1H, d, J=8 Hz), 6.48 (1H, s), 6.90 (1H, d, J=8 Hz), 7.01–7.25 (5H, m).

7) N-Methyl-N-(4-aminobenzoyl)-o-toluidine

NMR (CDCl$_3$, δ): 2.15 (3H, s), 3.34 (3H, s), 3.74 (2H, br), 6.37 (2H, d, J=8.5 Hz), 7.01–7.18 (6H, m).

8) 2-Isopropyl-[N-methyl-N-(4-aminobenzoyl)aniline

NMR (CDCl$_3$, δ): 0.87 (3H, d, J=7 Hz), 1.17 (3H, d, J=7 Hz), 3.00 (1H, qq, J=7, 7 Hz), 3.36 (3H, s), 3.73 (2H, br), 6.37 (2H, d, J=8.5 Hz), 7.10–7.28 (6H, m)

9) [N-Methyl-N-(4-aminobenzoyl)]-o-anisidine

NMR (CDCl$_3$, δ): 3.30 (3H, s), 3.70 (2H, br), 3.71 (3H, s), 6.38 (2H, d, J=8.5 Hz), 6.73–6.82 (2H, m), 7.00 (1H, dd, J=1, 8 Hz), 7.02–7.06 (3H, m).

10) 3-[N-Methyl-N-(4-aminobenzoyl)]aminopyridine

NMR (CDCl$_3$, δ): 3.50 (3H, s), 3.83 (2H, br), 6.42 (2H, d, J=8.5 Hz), 7.11 (2H, d, J=8.5 Hz), 7.20 (1H, d, J=6, 9 Hz), 7.38 (1H, m), 8.38 (12H, m).

11) 2-Methoxycarbonyl-3-[N-methyl-N-(4-aminobenzoyl)] aminothiophene

NMR (CDCl$_3$, δ): 3.37 (3H, s), 3.79 (2H, br), 3.80 (3H, s), 6.42 (2H, d, J=8.5 Hz), 6.84 (1H, d, J=5 Hz), 7.14 (2H, d, J=8.5 Hz), 7.37 (1H, d, J=5 Hz).

12) N-Methyl-N-(4-aminobenzoyl)-m-toluidine

NMR CDCl$_3$, δ): 2.27 (3H, s), 3.44 (3H, s), 3.76 (2H, br), 6.41 (2H, d, J=8.5 Hz), 6.80 (1H, d, J=8 Hz), 6.90 (1H, s), 6.95 (1H, d, J=8 Hz), 7.10 (1H, dd, J=8 Hz), 7.16 (2H, d, J=8.5 Hz).

13) N-Methyl-N-(4-aminobenzoyl)-2-benzoyloxyaniline

NMR (CDCl$_3$, δ): 3.37 (3H, s), 3.75 (2H, br), 6.90 (2H, d, J=8.5 Hz), 7.11–7.30 (6H, m), 7.50–7.70 (3H, m), 8.22 (2H, d, J=8.5 Hz).

14) N-Methyl-N-(4-aminobenzoyl)-2-phenylaniline

NMR (CDCl$_3$, δ): 3.31 (3H, s), 3.72 (2H, br), 6.28 (2H, d, J=8.5 Hz), 6.82 (2H, d, J=8.5 Hz), 7.09 (1H, m), 7.19–7.48 (8H, m).

15) 2-(3-Phthalimidopropyloxy)-[N-(4-aminobenzoyl)-N-methyl]aniline

NMR (CDCl$_3$, δ): 2.17 (2H, tt, J=7.5, 7.5 Hz), 3.32 (3H, s), 3.67 (2H, br), 3.81–4.02 (4H, m), 6.35 (2H, d, J=8.5 Hz), 6.71–6.80 (2H, m), 6.93–7.17 (4H, m), 7.62 (2H, m), 7.85 (2H, m).

16) 2-Acetyl-N-(4-aminobenzoyl)-N-methylaniline

NMR (CDCl$_3$, δ): 2.28 (3H, s), 3.44 (3H, s), 3.80 (2H, s), 6.37 (2H, br), 7.02 (2H, br), 7.28 (2H, d, J=8.5 Hz), 7.47 (2H, br t, J=8 Hz).

17) 4-Amino-N-methyl-N-[2-{3-(4-methyl-1-piperazinyl)-carbonylaminoprop-1-yloxy}phenyl]benzamide Rf: 0.06 (10% methanol in chloroform).

18) 4-Amino-N-methyl-N-(4-chlorophenyl)benzamide mp: 201–203° C.; NMR (CDCl$_3$, δ): 3.45 (3H, s), 3.76–3.85 (2H, br), 6.45 (2H, dd, J=1, 9 Hz), 7.00 (2H, dd, J=1, 9 Hz), 7.11 (2H, dd, J=1, 9 Hz), 7.20 (2H, dd, J=1, 9 Hz).

19) 4-Amino-N-methyl-N-(3-methoxyphenyl)benzamide

NMR (CDCl$_3$, δ): 3.45 (3H, s), 3.70 (3H, s), 6.32–6.46 (2H, m), 6.57–6.73 (3H, m), 7.08–7.25 (3H, m).

20) 4-Amino-N-methyl-N-(4-methoxyphenyl)benzamide mp: 195–200° C.; NMR (CDCl$_3$, δ): 3.44 (3H, s), 3.78 (3H, s), 6.43 (2H, dd, J=1, 9 Hz), 6.78 (2H, dd, J=1, 9 Hz), 6.96 (2H, dd, J=1, 9 Hz), 7.15 (2H, dd, J=1, 9 Hz).

21) 4-Amino-N-methyl-N-(3-chlorophenyl)benzamide

NMR (CDCl$_3$, δ): 3.48 (3H, s), 3.78–3.85 (2H, br), 6.35–6.50 (2H, m), 6.95–6.96 (1H, m), 7.10–7.21 (13H, m).

22) 4-Amino-N-ethoxycarbonylmethyl-N-(2-methylphenyl) benzamide

NMR (CDCl$_3$, δ): 1.29 (3H, t, J=7 Hz), 2.22 (3H, s), 3.70–3.85 (2H, br), 4.02 (1H, d, J=16 Hz), 4.22 (2H, q, J=7 Hz), 4.78 (1H, d, J=16 Hz), 6.38 (2H, d, J=8 Hz), 7.05–7.32 (6H, m).

23) 4-Amino-N-benzyl-N-(2-methylphenyl)benzamide

NMR (CDCl$_3$, δ): 1.88 (3H, s), 3.68–3.78 (2H, br), 4.70 (1H, d, J=14 Hz), 5.29 (1H, d, J=14 Hz), 6.36 (2H, d, J=9 Hz), 6.90–7.20 (11H, m).

24) 4-Amino-N-methyl-N-(2-trifluoromethylphenyl) benzamide

NMR (CDCl$_3$, δ): 3.38 (3H, s), 3.70–3.86 (2H, br), 6.30–6.58 (2H, br), 7.08–7.58 (5H, m), 7.69 (1H, d, J=7 Hz).

25) 4-Amino-3-methyl-N-methyl-N-(2-methylphenyl) benzamide mp: 139–144° C.;

26) N-Ethyl-N-(3-pentyl)-4-aminobenzamide mp: 132–135° C.;

27) 4-Amino-3-methoxy-N-methyl-N-(2-methylphenyl) benzamide

NMR (CDCl$_3$, δ): 2.20 (3H, s), 3.38 (3H, s), 3.62 (3H, s), 3.84–3.95 (2H, br), 6.40 (1H, d, J=9 Hz), 6.74–6.87(2H, br), 7.05–7.19 (4H, m).

28) 4-Amino-N-methyl-N-(2,6-dimethylphenyl)benzamide
mp: 158–160° C.;

29) N-Methyl-N-(4-tetrahydro-4H-pyranyl)-4-aminobenzamide
mp: 130–133° C.;

30) 4-Amino-N-methyl-N-(2-ethoxycarbonylmethoxyphenyl)benzamide
NMR (CDCl$_3$, δ): 1.30 (3H, t, J=8 Hz), 3.39 (3H, s), 3.68–3.72 (2H, br s), 4.26 (2H, q, J=8 Hz), 4.60 (2H, s), 6.40 (2H, d, J=8 Hz), 6.70 (1H, d, J=8 Hz), 6.80–6.86 (1H, m), 6.96 (1H, d, J=8 Hz), 7.10–7.16 (1H, m), 7.20 (2H, d, J=8 Hz).

31) 4-Amino-N-methyl-N-(2-methoxycarbonylmethylphenyl)benzamide
Rf: 0.41 (10% methanol in chloroform).

32) 4-Amino-N-methyl-N-[(2-ethoxycarbonylmethoxy-4-methyl)phenyl]benzamide
NMR (CDCl$_3$, δ): 1.32 (3H, t, J=8 Hz), 2.28 (3H, s), 3.36 (3H, s), 3.68–3.77 (2H, br s), 4.28 (2H, q, J=8 Hz), 4.60 (2H, s), 6.43 (2H, d, J=8 Hz), 6.50 (1H, s), 6.63 (1H, d, J=8 Hz), 6.86 (1H, d, J=8 Hz), 7.22 (2H, d, J=8 Hz).

33) 4-Amino-3-methoxy-N-methyl-N-(2-ethoxycarbonylmethoxyphenyl)benzamide
NMR (CDCl$_3$, δ): 1.29 (3H, t, J=8 Hz), 3.38 (3H, s), 3.67 (3H, s), 3.83–3.88 (2H, br), 4.26 (2H, q, J=8 Hz), 4.60 (2H, s).

34) 4-Amino-3-methoxy-N-methyl-N-[4-methyl-2-[3-(4-methyl-1-piperazinyl)carbonylaminoprop-1-yloxy]phenyl]benzamide
Rf: 0.06 (10% methanol in chloroform).

35) N-(2-Benzyloxy-4-methylphenyl)-N-methyl-4-aminobenzamide
NMR (CDCl$_3$, δ): 2.27 (3H, s), 3.33 (3H, s), 3.70 (2H, s), 4.91–5.10 (2H, m), 6.37 (2H, d, J=9 Hz), 6.63 (1H, d, J=9 Hz), 6.68 (1H, s), 6.91 (1H, d, J=9 Hz), 7.14 (2H, d, J=9 Hz), 7.27–7.43 (5H, m).

36) N-(2-Benzyloxy-5-methylphenyl)-N-methyl-4-aminobenzamide
NMR (CDCl$_3$, δ): 2.19 (3H, s), 3.34 (3H, s), 3.70 (2H, s), 6.37 (2H, d, J=9 Hz), 6.72 (1H, d, J=9 Hz), 6.85–6.95 (2H, m), 7.16 (2H, d, J=9 Hz), 7.24–7.40 (5H, m).

37) 4-Amino-N-(2-hydroxy-4-methylphenyl)-3-methoxy-N-methylbenzamide
NMR (CDCl$_3$, δ): 2.23 (3H, s), 3.26 (3H, s), 3.56 (3H, s), 6.42 (1H, d, J=9 Hz), 6.53 (1H, d, J=9 Hz), 6.63–6.82 (2H, m), 6.89 (1H, d, J=9 Hz).

38) 4-Amino-N-(2-hydroxyphenyl)-3-methoxy-N-methylbenzamide
NMR (CDCl$_3$, δ): 1.71 (1H, br s), 3.30 (3H, s), 3.56 (3H, s), 3.75–4.08 (2H, br s), 6.34 (1H, d, J=9 Hz), 6.61–6.80 (2H, m), 6.80–7.02 (3H, m), 7.1 (1H, dd, J=9, 9 Hz).

39) 4-Amino-N-(2-benzyloxy-4-chlorophenyl)-3-methoxy-N-methylbenzamide
NMR (CDCl$_3$, δ): 3.33 (3H, s), 3.56 (3H, s), 4.83–5.16 (2H, m), 6.38 (1H, d, J=9 Hz), 6.72 (1H, dd, J=9,2 Hz), 6.78–6.92 (3H, m), 7.01 (1H, d, J=9 Hz), 7.27–7.44 (5H, m).

40) 3-Methoxy-4-amino-N-methyl-N-(2-ethoxycarbonylphenyl)benzamide
NMR (CDCl$_3$, δ): 1.34 (3H, t, J=7.5 Hz), 3.41 (3H, s), 3.59 (3H, s), 3.88 (2H, s), 4.30 (2H, q, J=7.5 Hz), 6.38 (1H, d, J=7.5 Hz), 6.68–6.77 (2H, m), 7.20–7.29 (2H, m), 7.45 (1H, t, J=7.5 Hz), 7.78 (1H, d, J=7.5 Hz).

41) 4-Amino-N-methyl-N-(3-methyl-2-methoxycarbonyl)benzamide
NMR (CDCl$_3$, δ): 2.32 (3H, s), 3.33 (3H, s), 3.77 (2H, br s), 3.88 (3H, s), 6.40 (2H, d, J=8.5 Hz), 6.83 (1H, d, J=7.5 Hz), 7.07 (1H, d, J=7.5 Hz), 7.16 (1H, t, J=7.5 Hz), 7.23 (2H, d, J=8.5 Hz).

42) 4-Amino-N-methyl-N-[2-[3-(4-methylpiperazin-1-yl)carbonylamino-1-propyn-1-yl]phenyl]benzamide
NMR (CDCl$_3$, δ): 2.32 (3H, s), 2.47 (4H, t, J=6 Hz), 3.33 (3H, s), 3.60 (4H, t, J=6 Hz), 3.78 (2H, s), 4.24 (2H, m), 5.47 (1H, br t, J=6.5 Hz), 6.40 (2H, d, J=8.5 Hz), 7.11–7.32 (6H, m).

43) 4-Amino-N-methyl-(2-cyanophenyl)benzamide
NMR (CDCl$_3$, δ): 3.49 (3H, s), 3.82 (2H, s), 6.42 (2H, d, J=8.5 Hz), 7.11–7.20 (2H, m), 7.20–7.30 (2H, m), 7.48 (1H, t, J=7 Hz), 7.61 (1H, d, J=7 Hz).

44) 4-Amino-N-methyl-N-[2-[3-(4-dimethylaminopiperidin-1-yl)carbonylaminoprop-1-yloxy]phenyl]benzamide
MASS (m/z): 454 (M+1).

45) 4-Amino-3-methyl-N-[2-(3-phthalimidoprop-1-yloxy)phenyl]benzamide
NMR (CDCl$_3$, δ): 2.01 (3H, s), 2.20 (2H, m), 3.33 (3H, s), 3.63 (2H, s), 3.86–4.0 (4H, m), 6.32 (1H, d, J=7 Hz), 6.74–6.81 (2H, m), 6.90–6.98 (2H, m), 7.08–7.17 (2H, m), 7.66–7.72 (2H, m), 7.78–7.86 (2H, m).

46) 4-Amino-3-methoxy-N-methyl-N-[2-(3-phthalimidoprop-1-yloxy)phenyl]benzamide
NMR (CDCl$_3$, δ): 2.20 (2H, m), 3.32 (3H, s), 3.63 (3H, s), 3.81–4.02 (6H, m), 6.40 (1H, d, J=8 Hz), 6.77–6.82 (4H, m), 6.98 (1H, d, J=7.5 Hz), 7.12 (1H, t, J=7.5 Hz), 7.67–6.71 (2H, m), 6.80–6.84 (2H, m).

47) (E)-Methyl 7-(2-aminophenyl)-6-heptenoate
NMR (CDCl$_3$, δ): 1.52 (2H, m), 1.70 (2H, m), 2.26 (2H, dt, J=7.5, 7.5 Hz), 2.37 (2H, t, J=7.5 Hz), 3.68 (3H, s), 3.72 (2H, br), 6.04 (1H, dt, J=15, 7.5 Hz), 6.91 (1H, d, J=15 Hz), 6.67 (1H, d, J=7 Hz), 6.73 (1H, dd, J=7, 7 Hz), 7.04 (1H, dd, J=7, 7 Hz), 7.22 (1H, d, J=7 Hz).

48) (Z)-Methyl 7-(2-aminophenyl)-6-heptenoate
NMR (CDCl$_3$, δ): 1.45 (2H, m), 1.62 (2H, m), 2.17 (2H, dt, J=7.5, 7.5 Hz), 2.29 (2H, t, J=7.5 Hz), 3.65(3H, s), 3.66 (2H, br), 5.76 (1H, dt, J=11, 7.5 Hz), 6.30 (1H, d, J=11 Hz), 6.70 (1H, d, J=7 Hz), 7.74 (1H, d, J=7 Hz), 6.99–7.10 (2H, m).

49) 4-Amino-N-methyl-N-[2-[(E)-6-methoxycarbonyl-1-hexen-1-yl]phenyl]benzamide
NMR (CDCl$_3$, δ): 1.52 (2H, m), 1.69 (2H, m), 2.26 (2H, m), 2.35 (2H, t, J=7.5 Hz), 3.32 (3H, s), 3.66 (3H, s), 3.73 (2H, s), 6.18 (1H, dt, J=15, 7.5 Hz), 6.36 (2H, d, J=8.5 Hz), 6.49 (1H, d, J=15 Hz), 6.92 (1H, d, J=7 Hz), 7.03–7.20 (4H, m), 7.44 (7H, d).

50) 4-Amino-N-methyl-N-[2-[(Z)-6-methoxycarbonyl-1-hexen-1-yl]phenyl]benzamide
NMR (CDCl$_3$, δ): 1.39 (2H, m), 1.76 (2H, m), 2.01 (1H, m), 2.13 (1H, m), 2.30 (2H, t, J=7.5 Hz), 3.32 (3H, s), 3.66 (3H, s), 3.76 (2H, s), 5.70 (1H, dt, J=11, 7.5 Hz), 6.28–6.38 (3H, m), 7.03–7.24 (6H, m).

51) O-(3-Ethoxycarbonylprop-1-yl)-(2-amino)benzaldoxim
NMR (CDCl$_3$, δ): 1.27 (3H, t, J=7.5 Hz), 2.06 (2H, tt, J=7.5, 7.5 Hz), 2.45 (2H, t, J=7.5 Hz), 4.10–4.21 (4H, m), 5.50 (2H, s), 6.64–6.71 (2H, m), 7.07–7.18 (2H, m), 8.20 (1H, s).

52) 4-Amino-N-methyl-N-[2-[N-(3-ethoxycarbonylpropyl-1-yl)oxyimino]methylphenyl]benzamide
NMR (CDCl$_3$, δ): 1.27 (3H, t, J=7.5 Hz), 2.03 (2H, tt, J=7.5, 7.5 Hz), 2.43 (2H, t, J=7.5 Hz), 3.37 (3H, s), 3.77 (2H, s), 4.13 (2H, q, J=7.5 Hz), 4.20 (2H, t, J=7.5 Hz), 6.36 (1H, d, J=7 Hz), 7.00–7.11 (3H, m), 7.20–7.31 (2H, m), 7.74 (1H, d), 8.18 (1H, s).

53) 4-Amino-N-methyl-N-[2-(5-ethoxycarbonylpent-1-ylthio)phenyl]benzamide

NMR (CDCl₃, δ): 1.24 (3H, t, J=7.5 Hz), 1.50 (2H, m), 1.61–1.75 (4H, m), 2.31 (2H, t, J=7.5 Hz), 2.90 (2H, m), 3.30 (3H, s), 3.74 (2H, s), 4.13 (2H, q, J=7.5 Hz), 6.49 (2H, d, J=8.5 Hz), 6.92–7.05 (2H, m), 7.23–7.28 (4H, m).

54) 4-(4'-Methylbiphenyl-2-carboxamido)-N-methyl-N-[2-(3-ethoxycarbonylprop-1-yloxy)phenyl]benzamide NMR (CDCl₃, δ): 1.24 (3H, t, J=7.5 Hz), 2.10 (2H, m), 2.51 (2H, t, J=7.5 Hz), 3.31 (3H, s), 2.71 (2H, m), 3.97 (2H, br), 4.15 (2H, q, J=7.5 Hz), 5.40 (2H, d, J=8.5 Hz), 6.77–6.84 (2H, m), 7.01 (1H, d, J=7 Hz), 7.13 (1H, m), 7.17 (2H, d, J=8.5 Hz).

55) 2-(5-Ethoxycarbonylpent-1-yloxy)-3-aminopyridine

MASS (m/z): 253 (M+1).

56) 4-Amino-N-methyl-N-[2-(5-ethoxycarbonylpent-1-yloxy)pyrid-3-yl]benzamide

NMR (CDCl₃, δ): 1.24 (3H, t, 7.5 Hz), 1.30 (2H, m), 1.61–1.77 (4H, m), 2.30 (2H, t, J=7.5 Hz), 3.29 (3H, s), 3.81 (2H, s), 3.95 (2H, t, J=7.5 Hz), 4.11 (2H, q, J=7.5 Hz), 5.97 (1H, dd, J=7, 7 Hz), 6.44 (2H, d, J=8.5 Hz), 6.96 (2H, dd, J=1, 7 Hz), 7.13 (1H, dd, J=1, 7 Hz), 7.20 (2H, d, J=8.5 Hz).

57) 3-(5-Ethoxycarbonylpent-1-yloxy)-2-aminopyridine

NMR (CDCl₃, δ): 1.24 (3H, t, J=7.5 Hz), 1.52 (2H, m), 1.71 (2H, m), 1.85 (2H, m), 2.32 (2H, t, J=7.5 Hz), 3.94 (2H, t), 4.11 (2H, q, J=7.5 Hz), 4.63 (2H, br), 6.58 (1H, dd, J=7, 7.5 Hz), 6.88 (1H, dd, J=1, 7.5 Hz), 7.63 (1H, dd, J=1, 7 Hz).

58) 4-Amino-N-methyl-N-[3-(5-ethoxycarbonylpent-1-yloxy)pyrid-2-yl]benzamide

NMR (CDCl₃, δ): 1.25 (3H, t, J=7.5 Hz), 1.49 (2H, m), 1.64–1.82 (2H, m), 2.35 (2H, t, J=7.5 Hz), 3.43 (3H, s), 3.79 (2H, t, J=7.5 Hz), 4.19 (2H, q, J=7.5 Hz), 7.03 (1H, d, J=7 Hz), 7.12 (1H, m), 7.48 (2H, d, J=8.5 Hz), 7.95–8.02 (3H, m).

59) 3-Methyl-4-amino-N-methyl-N-(4-chloro-2-benzyloxyphenyl)benzamide

NMR (CDCl₃, δ): 1.98 (3H, s), 3.31 (3H, s), 3.69 (2H, br), 5.00 (2H, br), 6.31 (1H, d, J=7 Hz), 6.77–6.89 (3H, m), 6.96 (1H, d, J=7 Hz), 7.09 (1H, s), 7.38–7.40 (5H, m).

60) 4-Amino-N-methyl-N-[4-methyl-2-(5-methoxycarbonylpyrid-2-ylmethoxy)phenyl]benzamide NMR (CDCl₃, δ): 2.22 (3H, s), 3.30 (3H, s), 3.70 (2H, s), 3.98 (3H, s), 5.29 (3H, s), 6.38 (2H, d, J=8.5 Hz), 6.59 (1H, d, J=7 Hz), 6.73–6.82 (2H, m), 7.16 (2H, d, J=8.5 Hz), 7.28 (1H, m), 8.50 (1H, m), 9.10 (1H, m).

61) 4-Amino-N-methyl-N-[2-(5-methoxycarbonylpyrid-2-ylmethoxy)phenyl]benzamide

NMR (CDCl₃, δ): 3.31 (3H, s), 3.70 (2H, s), 3.98 (3H, s), 5.31 (2H, s), 6.39 (2H, d, J=8.5 Hz), 6.77 (1H, dd, J=7, 7 Hz), 6.93 (2H, d, J=8.5 Hz), 7.07–7.23 (4H, m), 8.49 (1H, m), 9.10 (1H, m).

62) 4-Amino-N-(2-benzyloxy-4-chlorophenyl)-N-methylbenzamide

NMR (CDCl₃, δ): 3.33 (3H, s), 3.75 (2H, br s), 4.92–5.10 (2H, m), 6.38 (2H, d, J=9 Hz), 6.79–6.90 (2H, m), 6.97 (1H, d, J=9 Hz), 7.10 (2H, d, J=9 Hz), 7.29–7.44 (5H, m).

63) 4-Amino-2-chloro-N-(2-benzyloxy-4-chlorophenyl)-N-methylbenzamide

NMR (CDCl₃, δ): 3.36 (3H, s), 3.71 (2H, br s), 5.07 (2H, br s), 6.24 (1H, dd, J=9, 2 Hz), 6.48 (1H, s), 6.76 (1H, dd, J=9, 2 Hz), 6.85 (2H, d, J=9 Hz), 7.06 (1H, d, J=9 Hz), 7.30–7.50 (5H, m)

64) 4-Amino-2-chloro-N-[2-(5-ethoxycarbonylpent-1-yloxy)phenyl]-N-methylbenzamide NMR (CDCl₃, δ): 1.25 (3H, t, J=7 Hz), 1.43–1.63 (2H, m), 1.63–1.79 (2H, m), 1.79–1.94 (2H, m), 2.35 (2H, t, J=7 Hz), 3.34 (3H, s), 3.64 (2H, br s), 3.98 (2H, t, J=7 Hz), 4.14 (2H, q, J=7 Hz), 6.23 (1H, dd, J=9, 2 Hz), 6.47 (1H, d, J=2 Hz), 6.66–6.81 (2H, m), 6.86 (1H, d, J=9 Hz), 7.03–7.14 (2H, m).

65) 4-Amino-3-methoxy-N-[2-(5-ethoxycarbonylpent-1-yloxy)-4-methylphenyl]-N-methylbenzamide NMR (CDCl₃, δ): 1.26 (3H, t, J=7 Hz), 1.41–1.55 (2H, m), 1.59–1.86 (4H, m), 2.26 (3H, s), 2.31 (2H, t, J=7 Hz), 3.29 (3H, s), 3.63 (3H, s), 3.75–4.01 (4H, m), 4.13 (2H, q, J=7 Hz), 6.41 (1H, d, J=9 Hz), 6.55–6.64 (2H, m), 6.77–6.89 (3H, m).

66) N-(2-Benzyloxy-4-methylphenyl)-N-methyl-4-aminobenzamide

NMR (CDCl₃, δ): 2.27 (3H, s), 3.33 (3H, s), 3.70 (2H, s), 4.91–5.10 (2H, m), 6.37 (2H, d, J=9 Hz), 6.63 (1H, d, J=9 Hz), 6.68 (1H, s), 6.91 (1H, d, J=9 Hz), 7.14 (2H, d, J=9 Hz), 7.27–7.43 (5H, m).

Preparation 7

A solution of p-anisidine (615 mg), cyclopentanone (420 mg) and acetic acid (2 ml) in methanol (30 ml) was cooled to 0° C., and sodium cyanoborohydride (315 mg) was added portionwise. The resulting solution was stirred at ambient temperature for 2 hours. The reaction mixture was then basified with 1N aqueous sodium hydroxide, and extracted with ethyl acetate. The organic extract was washed with brine, dried over sodium sulfate, and concentrated. The residue was purified by column chromatography (SiO₂ 30 g, diethyl ether:n-hexane=1:3) to give N-cyclopentyl-p-anisidine (530 mg).

NMR (CDCl₃, δ): 1.21–2.12 (8H, m), 3.74 (3H, s), 3.69–3.85 (1H, m), 6.57 (2H, d, J=8 Hz), 6.78 (2H, d, J=8 Hz), 7.04 (1H, br d, J=8 Hz).

Preparation 8

A solution of N-cyclopentyl-N-(4-nitrobenzoyl)-p-anisidine (1.0 g), 10% palladium on carbon (100 mg) and 2 drops of conc. hydrochloric acid in methanol (10 ml) was stirred under 3 atmospheric pressure of hydrogen at ambient temperature. After 4 hours, the reaction mixture was filtered through a bed of Celite, and concentrated to give N-(4-aminobenzoyl)-N-cyclopentyl-p-anisidine (870 mg), which was used directly for the next step without further purification.

Preparation 9

A solution of [N-methyl-N-(4-nitrobenzoyl)]-2-(4-nitrobenzoyloxy)aniline (1.76 g) in a mixture of methanol (20 ml) and 1N sodium hydroxide (10 ml) was stirred at ambient temperature for 5 hours and the mixture was extracted with chloroform. The chloroform solution was washed with water and brine, and dried over magnesium sulfate. The solvent was evaporated in vacuo to give an oil and the oil was purified by silica gel column (1% methanol in chloroform) to give [N-methyl-N-(4-nitrobenzoyl)]-2-hydroxyaniline (982 mg) as a white powder.

NMR (DMSO-d₆, δ): 3.23 (3H, s), 6.65 (1H, ddd, J=1, 8, 8 Hz), 6.77 (1H, dd, J=1, 8 Hz), 7.02 (1H, ddd, J=1, 8, 8 Hz), 7.13 (1H, dd, J=1, 8 Hz), 7.50 (2H, d, J=8.5 Hz), 8.02 (2H, d, J=8.5 Hz).

Preparation 10

To a mixture of [N-methyl-N-(4-nitrobenzoyl)]-2-hydroxyaniline (491 mg) and triethylamine (0.302 ml) in dichloromethane (20 ml) was added benzoyl chloride (0.202 ml) and the solution was stirred at ambient temperature for 4 hours. The solution was washed successively with 1N hydrochloric acid, saturated sodium hydrogen carbonate, water and brine, and dried over magnesium sulfate. The solvent was evaporated in vacuo and the residue was solidified with n-hexane to give [N-methyl-N-(4-nitrobenzoyl)]-2-benzoyloxyaniline (652 mg) as a pale yellow solid.

NMR (CDCl$_3$, δ): 3.42 (3H, s), 7.11–7.35 (4H, m), 7.49 (2H, d, J=8.5 Hz), 7.58 (2H, d, J=8.5 Hz), 7.70 (1H, d), 8.03 (2H, d, J=8.5 Hz), 8.13 (2H, d, J=8.5 Hz).

Preparation 11

To a solution of 2-hydroxy-[N-(4-nitrobenzoyl)-N-methyl]aniline (491 mg) in of N,N-dimethylformamide (20 ml) was added sodium hydride (60% in oil 72 mg). After being stirred at ambient temperature for 30 minutes, N-(3-bromopropyl)phthalimide (484 mg) was added to the solution and the mixture was stirred at ambient temperature for 4 hours. The mixture was diluted with ethyl acetate and the solution was washed successively with diluted hydrochloric acid, water and brine, dried over magnesium sulfate, and evaporated in vacuo to give an oil. The oil was purified by silica gel column (1% methanol in chloroform) to give 2-(3-phthalimidopropyloxy)-[N-(4-nitrobenzoyl)-N-methyl]aniline (713 mg) as a pale yellow solid.

NMR (CDCl$_3$, δ): 2.23 (2H, tt, J=7.5, 7.5 Hz), 3.40 (3H, s), 3.90–4.00 (4H, m), 6.79 (2H, t, J=8 Hz), 6.98 (1H, dd, J=1, 8 Hz), 6.98 (1H, dt, J=1, 8 Hz), 7.53 (2H, d, J=8.5 Hz), 7.73 (2H, m), 7.86 (2H, m), 8.01 (2H, d, J=8.5 Hz).

Preparation 12

To a solution of 6-amino-m-cresol (5.0 g) and triethylamine (10.3 g) in dichloromethane (150 ml) was added 4-nitrobenzoyl chloride (15.8 g) at ambient temperature. After 5 hours, the solid was filtered and washed with water and diethyl ether to give N,O-bis(4-nitrobenzoyl)-2-amino-5-methylphenol (12.5 g) as yellow crystal.

NMR (DMSO-d$_6$, δ): 2.37 (3H, s), 7.20 (1H, dd, J=9, 2 Hz), 7.28 (1H, d, J=2 Hz), 7.54 (1H, d, J=9 Hz), 8.04 (2H, d, J=9 Hz), 8.28 (4H, d, J=9 Hz), 8.36 (2H, d, J=9 Hz).

Preparation 13

The following compounds were obtained according to a similar manner to that of Preparation 12.
1) N,O-Bis(4-nitrobenzoyl)-2-aminophenethylalcohol NMR (DMSO-d$_6$, δ): 3.14 (2H, t, J=6 Hz), 4.53 (2H, t, J=6 Hz), 7.28–7.48 (4H, m), 8.10 (2H, d, J=8 Hz), 8.20 (2H, d, J=8 Hz), 8.30 (2H, d, J=8 Hz), 8.36 (2H, d, J=8 Hz).
2) 5-Methyl-N,O-bis(4-nitrobenzoyl)-2-aminophenol NMR (DMSO-d$_6$, δ): 2.38 (3H, s), 7.20 (1H, d, J=9 Hz), 7.28 (1H, s), 7.54 (1H, d, J=8 Hz), 8.04 (2H, d, J=9 Hz), 8.29 (4H, d, J=9 Hz), 8.37 (2H, d, J=9 Hz).
3) N,O-Bis(3-methoxy-4-nitrobenzoyl)-2-aminophenol NMR (DMSO-d$_6$, δ): 3.32 (3H, s), 3.86 (3H, s), 7.38–7.57 (6H, m), 7.70 (2H, d, J=11 Hz), 7.81–7.87 (1H, m), 7.96–8.04 (1H, m).
4) N,O-Bis(3-methoxy-4-nitrobenzoyl)-2-amino-5-methylphenol Rf: 0.63 (10% methanol in chloroform).
5) N-[2-(4-Nitrophenylcarbonyloxy)-5-methylphenyl]-4-nitrobenzamide NMR (DMSO-d$_6$, δ): 2.38 (3H, s), 7.18 (1H, dd, J=9, 2 Hz), 7.34 (1H, d, J=9 Hz), 7.50 (1H, d, J=2 Hz), 8.04 (2H, d, J=9 Hz), 8.30 (4H, d, J=9 Hz), 8.36 (2H, d, J=9 Hz).

Preparation 14

A solution of N-(2-benzyloxy-4-methylphenyl)-4-nitrobenzamide (4.7 g) in N,N-dimethylformamide (50 ml) was treated with sodium hydride (623 mg, 60% w/w in mineral oil) at 0° C. After 30 minutes, iodomethane (1.21 ml) was added, and the reaction mixture was stirred for 3 hours. The reaction was quenched with water and the mixture diluted with ethyl acetate. The organic phase was washed with water and brine. The organic solution was dried over magnesium sulfate and concentrated to give N-(2-benzyloxy-4-methylphenyl)-N-methyl-4-nitrobenzamide (4.6 g).

NMR (DMSO-d$_6$, δ): 2.21 (3H, s), 3.23 (3H, s), 5.00 (1H, d, J=12 Hz), 5.10 (1H, d, J=12 Hz), 6.67 (1H, d, J=9 Hz), 6.92 (1H, 5), 7.16 (1H, d, J=9 Hz), 7.32–7.47 (7H, m), 8.01 (2H, d, J=9 Hz):

Preparation 15

The following compounds were obtained according to a similar manner to that of Preparation 14.
1) N-(2-Benzyloxy-5-methylphenyl)-N-methyl-4-nitrobenzamide NMR (DMSO-d$_6$, δ): 2.15 (3H, s), 3.26 (3H, s), 4.96 (1H, d, J=11 Hz), 5.06 (1H, d, J=11 Hz), 6.91 (1H, d, J=9 Hz), 6.98 (1H, d, J=9 Hz), 7.14 (1H, s), 7.30–7.48 (7H, m), 8.03 (2H, d, J=9 Hz).
2) 2-Benzyloxy-4-chloro-N-tert-butoxycarbonyl-N-methylaniline NMR (CDCl$_3$, δ): 1.18–1.57 (9H, m), 3.12 (3H, s), 5.09 (2H, s), 6.86–7.24 (3H, m), 7.28–7.51 (5H, m).
3) 4-Nitro-N-methyl-N-(4-chlorophenyl)benzamide mp: 116–118° C.; NMR (CDCl$_3$, δ): 3.50 (3H, s), 7.00 (2H, d, J=9 Hz), 7.25 (2H, d, J=9 Hz), 7.46 (2H, d, J=10 Hz), 8.06 (2H, d, J=10 Hz).
4) 4-Nitro-N-methyl-N-(3-methoxyphenyl)benzamide mp: 83–87° C.; NMR (CDCl$_3$, δ): 3.50 (3H, s), 3.72 (3H, s), 6.58–6.63 (2H, m), 6.75 (1H, dd, J=1, 9 Hz), 7.16 (1H, dd, J=1, 9 Hz), 7.50 (2H, d, J=10 Hz), 8.04 (2H, d, J=10 Hz).
5) 4-Nitro-N-methyl-N-(4-methoxyphenyl)benzamide mp: 98–101° C.; NMR (CDCl$_3$, δ): 3.49 (3H, s), 3.75 (3H, s), 6.78 (2H, d, J=9 Hz), 6.95 (2H, d, J=9 Hz), 7.46 (2H, d, J=10 Hz), 8.03 (2H, d, J=10 Hz).
6) 4-Nitro-N-methyl-N-(3-chlorophenyl)benzamide NMR (CDCl$_3$, δ): 3.52 (3H, s), 6.83–6.92 (1H, m), 7.12 (1H, s), 7.15–7.20 (2H, m), 7.48 (2H, dd, J=1, 10 Hz), 8.09 (2H, dd, J=1, 10 Hz).
7) 4-Nitro-N-ethoxycarbonylmethyl-N-(2-methylphenyl)benzamide mp: 121–124° C.; NMR (CDCl$_3$, δ): 1.32 (3H, t, J=8 Hz), 2.27 (3H, s), 4.02 (1H, d, J=17 Hz), 4.27 (2H, q, J=8 Hz), 4.90 (1H, d, J=17 Hz), 7.03–7.18 (3H, m), 7.26 (1H, d, J=8 Hz), 7.48 (2H dd, J=1, 10 Hz), 8.02 (2H, dd, J=1, 10 Hz).
8) 4-Nitro-N-methyl-N-(2-trifluoromethylphenyl)benzamide mp: 105–107° C.;
9) 3-Methyl-4-nitro-N-methyl-N-(2-methylphenyl)benzamide mp: 75–77° C.;
10) 3-Methoxy-4-nitro-N-methyl-N-(2-methylphenyl)benzamide mp: 112–115° C.;
11) 4-Nitro-N-methyl-N-(2,6-dimethylphenyl)benzamide mp: 113–116° C.;
12) N-Methyl-N,O-bis(4-nitrobenzoyl)-2-aminophenethylalcohol NMR (CDCl$_3$, δ): 2.89 (1H, dt, J=7, 14 Hz), 3.07 (1H, dt, J=7, 1 Hz), 3.49 (3H, s), 4.56 (2H, q, J=7 Hz), 7.15–7.28 (4H, m), 7.44 (2H, d, J=9 Hz), 7.97 (2H, d, J=9 Hz), 8.15 (2H, d, J=8 Hz), 8.29 (2H, d, J=8 Hz).
13) 5-Methyl-N-methyl-N,O-bis(4-nitrobenzoyl)-2-aminophenol NMR (CDCl₃, δ): 2.37 (3H, s), 3.42 (3H, s), 6.99–7.11 (3H, m), 7.48 (2H, d, J=9 Hz), 8.06 (2H, d, J=9 Hz), 8.29 (2H, d, J=8 Hz), 8.42 (2H, d, J=8 Hz).

14) N,O-Bis(3-methoxy-4-nitrobenzoyl)-N-methyl-2-aminophenol

NMR (CDCl₃, δ): 3.45 (3H, s), 3.68 (3H, s), 4.07 (3H, s), 7.01–7.07 (2H, m), 7.17 (1H, d, J=8 Hz), 7.22–7.30 (2H, m), 7.35–7.40 (1H, m), 7.66 (1H, d, J=8 Hz), 7.77–7.84 (2H, m), 7.92 (1H, d, J=8 Hz).

15) N,O-Bis(3-methoxy-4-nitrobenzoyl)-N-methyl-2-amino-5-methylphenol

NMR (CDCl₃, δ): 2.39 (3H, s), 3.42 (3H, s), 3.71 (3H, s), 4.07 (3H, s), 6.99–7.09 (5H, m), 7.66 (1H, d, J=9 Hz), 7.75–7.81 (2H, m), 7.92 (1H, d, J=8 Hz).

16) 3-Methoxy-4-nitro-N-methyl-N-(2-ethoxycarbonylphenyl)benzamide

MASS (m/z): 359 (M+1).

17) 4-Nitro-N-methyl-N-[2-[(E)-6-methoxycarbonyl-1-hexen-1-yl]phenyl]benzamide

NMR (CDCl₃, δ): 1.53 (2H, m), 1.71 (2H, m), 2.24–2.40 (4H, m), 3.40 (3H, s), 3.69 (3H, s), 6.18 (1H, dt, J=15, 7.5 Hz), 6.44 (1H, d, J=15 Hz), 6.96 (1H, d, J=7 Hz), 7.09 (1H, t, J=7 Hz), 7.19 (1H, t, J=7 Hz), 7.38–7.45 (3H, m), 7.95–7.99 (2H, m).

18) 4-Nitro-N-methyl-N-[2-[(Z)-6-methoxycarbonyl-1-hexen-1-yl]phenyl]benzamide

NMR (CDCl₃, δ): 1.43 (2H, m), 1.61 (2H, m), 1.94 (1H, m), 2.11 (1H, m), 2.30 (2H, t, J=7.5 Hz), 3.40 (3H, s), 3.67 (3H, s), 5.80 (1H, dt, J=11, 7.5 Hz), 6.32 (1H, d, J=11 Hz), 7.05 (1H, d, J=7 Hz), 7.13–7.23 (3H, m), 7.41 (2H, d, J=8.5 Hz), 7.98 (2H, d, J=8.5 Hz).

19) 4-Nitro-N-methyl-N-[2-[N-(3-ethoxycarbonylprop-1-yl)oxyimino]methylphenyl]benzamide NMR (CDCl₃, δ): 1.26 (3H, t, J=7.5 Hz), 2.05 (2H, tt, J=7.5, 7.5 Hz), 2.44 (2H, t, J=7.5 Hz), 3.41 (3H, s), 4.15 (2H, q, J=7.5 Hz), 4.21 (2H, t, J=7.5 Hz), 7.08 (1H, dt, J=1, 7 Hz), 7.20–7.31 (2H, m), 7.38 (2H, d, J=8.5 Hz), 7.60 (1H, dd, J=1, 7 Hz), 7.99 (2H, d, J=8.5 Hz), 8.10 (1H, s).

20) 4-Nitro-N-methyl-N-[2-(5-ethoxycarbonylpent-1-ylthio)phenyl]benzamide

NMR (CDCl₃, δ): 1.27 (3H, t, J=7.5 Hz), 2.52 (2H, m), 1.63–1.77 (4H, m), 2.31 (2H, t, J=7.5 Hz), 2.90 (2H, m), 3.39 (3H, s), 4.13 (2H, q, J=7.5 Hz), 6.94–7.02 (2H, m), 7.11–7.22 (2H, m), 7.54 (2H, d, J=8.5 Hz), 8.00 (2H, d, J=8.5 Hz).

21) 4-Nitro-N-methyl-N-[2-(3-ethoxycarbonylprop-1-yloxy)phenyl]benzamide

NMR (CDCl₃, δ): 1.28 (3H, t, J=7.5 Hz), 2.23 (2H, m), 2.52 (2H, m), 3.37 (3H, s), 3.96 (2H, m), 4.16 (2H, q, J=7.5 Hz), 6.75–6.84 (2H, m), 7.01 (1H, d, J=7 Hz), 7.17 (1H, dd, J=7, 7 Hz), 7.46 (2H, d, J=8.5 Hz), 8.00 (2H, d, J=8.5 Hz).

22) 4-Nitro-N-methyl-N-[2-(5-ethoxycarbonylpent-1-yloxy)pyrid-3-yl]benzamide

NMR (CDCl₃, δ): 1.23 (3H, t, J=7.5 Hz), 1.30 (2H, m), 1.57–1.69 (4H, m), 2.29 (2H, t, J=7.5 Hz), 3.33 (3H, s), 3.88 (2H, t, J=7.5 Hz), 4.11 (2H, q, J=7.5 Hz), 6.01 (1H, dd, J=7, 7 Hz), 7.09 (1H, dd, J=1, 7 Hz), 7.18 (1H, dd, J=1, 7 Hz), 7.57 (2H, d, J=8.5 Hz), 8.08 (2H, d, J=8.5 Hz).

23) 2-Chloro-4-nitro-N-[2-(5-ethoxycarbonylpent-1-yloxy)phenyl]-N-methylbenzamide NMR (CDCl₃, δ): 1.26 (3H, t, J=7 Hz), 1.50–1.63 (2H, m), 1.69–1.81 (2H, m), 1.84–1.97 (2H, m), 2.37 (2H, t, J=7 Hz), 3.40 (3H, s), 3.94–4.06 (2H, m), 4.15 (2H, q, J=7 Hz), 6.70–6.81 (2H, m), 7.13 (1H, d, J=9 Hz), 7.16 (1H, d, J=9 Hz), 7.31 (1H, d, J=9 Hz), 7.87 (1H, d, J=9 Hz), 8.08 (1H, s).

24) 3-Methoxy-4-nitro-N-[2-(5-ethoxycarbonylpent-1-yloxy)-4-methylphenyl]-N-methylbenzamide NMR (CDCl₃, δ): 1.26 (3H, t, J=7 Hz), 1.43–1.59 (2H, m), 1.65–1.90 (4H, m), 2.27 (3H, s), 2.34 (2H, t, J=7 Hz), 3.33 (3H, s), 3.77 (3H, s), 3.82–3.99 (2H, m), 4.13 (2H, q, J=7 Hz), 6.59 (1H, d, J=9 Hz), 6.60 (1H, s), 6.86 (1H, d, J=9 Hz), 6.94 (1H, d, J=9 Hz), 7.06 (1H, s), 7.61 (1H, d, J=9 Hz).

25) 2-[5-(Ethoxycarbonyl)pent-1-yloxy]-N-methyl-N-tert-butoxycarbonylaniline

NMR (CDCl₃, δ): 1.25 (3H, t, J=7 Hz), 1.33 (9H, br s), 1.40–1.58 (2H, m), 1.58–1.86 (4H, m), 2.32 (2H, t, J=7 Hz), 3.12 (3H, s), 3.96 (2H, t, J=7 Hz), 4.13 (2H, q, J=7 Hz), 6.82–6.94 (2H, m), 7.03–7.23 (2H, m).

26) N-(2-Benzyloxy-4-methylphenyl)-N-methyl-4-nitrobenzamide

NMR (DMSO-d₆, δ): 2.21 (3H, s), 3.23 (3H, s), 5.00 (1H, d, J=12 Hz), 5.10 (1H, d, J=12 Hz), 6.67 (1H, d, J=9 Hz), 6.92 (1H, s), 7.16 (1H, d, J=9 Hz), 7.32–7.47 (7H, m), 8.01 (2H, d, J=9 Hz).

Preparation 16

To a suspension of N-[2-(4-nitrophenylcarbonyloxy)-4-methylphenyl]-4-nitrobenzamide (12.5 g) was added 1N sodium hydroxide (20 ml) at ambient temperature. After 3 hours, ethyl acetate (100 ml) and water (200 ml) was added to this solution and resulting solid was filtered and washed with water and diethyl ether to give N-(2-hydroxy-4-methylphenyl)-4-nitrobenzamide (3.9 g) as yellow crystal.

NMR (DMSO-d₆, δ): 2.24 (3H, s), 6.65 (1H, dd, J=9, 2 Hz), 6.74 (1H, d, J=2 Hz), 7.44 (1H, d, J=9 Hz), 8.18 (2H, d, J=9 Hz), 8.36 (2H, d, J=9 Hz), 9.50–9.90 (2H, m).

Preparation 17

The following compounds were obtained according to a similar manner to that of Preparation 16.

1) N-(2-Hydroxy-5-methylphenyl)-4-nitrobenzamide

NMR (DMSO-d₆, δ): 2.23 (3H, s), 6.81 (1H, d, J=9 Hz), 6.88 (1H, dd, J=9, 2 Hz), 7.44 (1H, d, J=2 Hz), 8.17 (2H, d, J=9 Hz), 8.35 (2H, d, J=9 Hz).

2) 4-Nitro-N-methyl-N-[2-(2-hydroxyethyl)phenyl]benzamide

NMR (CDCl₃, δ): 2.67 (1H, dt, J=6, 15 Hz), 2.85 (1H, dt, J=6, 15 Hz), 3.45 (3H, s), 3.90 (2H, t, J=6 Hz), 7.08 (1H, d, J=7 Hz), 7.14–7.28 (3H, m), 7.46 (2H, d, J=9 Hz), 7.98 (2H, d, J=9 Hz).

3) 5-Methyl-N-methyl-N-(4-nitrobenzoyl)-2-aminophenol

NMR (CDCl₃, δ): 2.22 (3H, s), 3.38 (3H, s), 5.83–5.86 (1H, br s), 6.56 (1H, dd, J=1, 9 Hz), 6.63 (1H, s), 6.78 (1H, d, J=9 Hz), 7.49 (2H, d, J=8 Hz), 8.00 (2H, dd, J=1, 8 Hz).

4) N-(3-Methoxy-4-nitrobenzoyl)-N-methyl-2-aminophenol

NMR (CDCl₃, δ): 3.23 (3H, s), 3.75 (3H, s), 6.66–6.72 (1H, m), 6.82 (1H, d, J=8 Hz), 6.97–7.13 (3H, m), 7.19 (1H, s), 7.70 (1H, d, J=8 Hz).

5) N-(3-Methoxy-4-nitrobenzoyl)-N-methyl-2-amino-5-methylphenol

NMR (CDCl₃, δ): 2.10 (3H, s), 3.18 (3H, s), 3.74 (3H, s), 6.35 (1H, d, J=8 Hz), 6.58 (1H, s), 6.87 (1H, d, J=8 Hz), 7.00 (1H, d, J=9 Hz), 7.26 (1H, s), 7.68 (1H, d, J=9 Hz).

6) N-(2-Hydroxy-4-methylphenyl)-4-nitrobenzamide

NMR (DMSO-d₆, δ): 2.24 (3H, s), 6.65 (1H, dd, J=9, 2 Hz), 6.74 (1H, d, J=2 Hz), 7.44 (1H, d, J=9 Hz), 8.18 (2H, d, J=9 Hz), 8.36 (2H, d, J=9 Hz), 9.50–9.90 (2H, m).

Preparation 18

The following compounds were obtained according to a similar manner to that of Preparation 11.

1) 4-Nitro-N-methyl-N-(2-ethoxycarbonylmethoxyphenyl)benzamide

NMR (CDCl$_3$, δ): 1.30 (3H, t, J=8 Hz), 3.42 (3H, s), 4.28 (2H, q, J=8 Hz), 4.66 (2H, d, J=3 Hz), 6.67 (1H, d, J=9 Hz), 6.81 (1H, t, J=8 Hz), 6.95 (1H, d, J=9 Hz), 7.16 (1H, t, J=8 Hz), 7.57 (2H, d, J=9 Hz), 8.00 (2H, d, J=9 Hz).

2) 4-Nitro-N-methyl-N-[(2-ethoxycarbonylmethoxy-4-methyl)phenyl]benzamide

NMR (CDCl$_3$, δ): 1.33 (3H, t, J=8 Hz), 2.27 (3H, s), 3.40 (3H, s), 4.30 (2H, q, J=8 Hz), 4.65 (2H, d, J=3 Hz), 6.47 (1H, s), 6.62 (1H, d, J=8 Hz), 6.83 (1H, d, J=8 Hz), 7.57 (2H, d, J=8 Hz), 8.01 (2H, d, J=8 Hz).

3) 3-Methoxy-4-nitro-N-methyl-N-(2-ethoxycarbonylmethoxyphenyl)benzamide

NMR (CDCl$_3$, δ): 1.30 (3H, t, J=8 Hz), 3.43 (3H, s), 3.82 (3H, s), 4.27 (2H, q, J=8 Hz), 4.66 (2H, d, J=7 Hz), 6.70 (1H, d, J=8 Hz), 6.81–6.88 (1H, m), 6.98 (1H, d, J=8 Hz), 7.02 (1H, d, J=8 Hz), 7.14–7.23 (2H, m), 7.60 (1H, d, J=8 Hz).

4) 4-Nitro-N-methyl-N-[2-(3-phthalimidoprop-1-yloxy)phenyl]benzamide

Rf: 0.18 (n-hexane:ethyl acetate=1:2).

5) 3-Methoxy-4-nitro-N-methyl-N-[4-methyl-2-(3-phthalimidoprop-1-yloxy)phenyl]benzamide NMR (CDCl$_3$, δ): 2.20 (2H, quint., J=7 Hz), 2.27 (3H, s), 3.36 (3H, s), 3.80 (3H, s), 3.88–3.98 (4H, m), 6.60 (1H, s), 6.62 (1H, d, J=8 Hz), 6.85 (1H, d, J=8 Hz), 6.98 (1H, dd, J=1, 9 Hz), 7.10 (1H, d, J=1 Hz), 7.60 (1H, d, J=9 Hz), 7.69–7.74 (2H, m), 7.82–7.87 (2H, m).

6) 2-(3-Ethoxycarbonylprop-1-yl)oxyaniline

NMR (CDCl$_3$, δ): 1.26 (3H, t, J=7.5 Hz), 2.15 (2H, tt, J=7.5, 7.5 Hz), 2.51 (2H, t, J=7.5 Hz), 3.79 (2H, br s), 4.04 (2H, t, J=7.5 Hz), 4.15 (2H, q, J=7.5 Hz), 6.65–6.82 (4H, m).

Preparation 19

To an ice bath cooled solution of 2-aminothiophenol (1.80 g) in N,N-dimethylformamide (35 ml) was added sodium hydride (60% in oil, 575 mg). After being stirred in an ice bath for 30 minutes, ethyl 6-bromohexanoate (3.21 g) was added and the mixture was stirred at ambient temperature for 3 hours. The mixture was diluted with ethyl acetate (100 ml) and the solution was washed with water and brine. The organic phase was dried over magnesium sulfate and the solvent was evaporated in vacuo to give an oil. The oil was purified by silica gel column (1% methanol in chloroform) to give 2-(5-ethoxycarbonylpent-1-yl)thioaniline (3.20 g) as a pale yellow amorphous.

NMR (CDCl$_3$, δ): 1.26 (3H, t, J=7.5 Hz), 1.35–1.47 (2H, m), 1.53–1.67 (4H, m), 2.28 (2H, t, J=7.5 Hz), 2.72 (2H, t, J=7.5 Hz), 4.12 (2H, q, J=7.5 Hz), 4.33 (2H, s), 6.65 (1H, d, J=7 Hz), 7.71 (1H, d, J=7 Hz), 7.10 (1H, t, J=7 Hz), 7.36 (1H, d, J=7 Hz).

Preparation 20

To a solution of N-(2-hydroxy-4-methylphenyl)-4-nitrobenzamide (3.8 g) in N,N-dimethylformamide (25 ml) was added potassium carbonate (3.85 g) and benzyl bromide (2.63 g). The reaction mixture was stirred at ambient temperature for 3 hours. The mixture was extracted with ethyl acetate and washed with water and brine. The organic solution was dried over magnesium sulfate. The solvent was removed by evaporation to give N-(2-benzyloxy-4-methylphenyl)-4-nitrobenzamide (4.8 g).

NMR (DMSO-d$_6$, δ): 2.32 (3H, s), 5.16 (3H, s), 6.82 (1H, d, J=9 Hz), 7.02 (1H, s), 7.24–7.40 (3H, m), 7.47 (3H, d, J=9 Hz), 8.16 (2H, d, J=9 Hz), 8.36 (2H, d, J=9 Hz), 9.88 (1H, s).

Preparation 21

The following compounds were obtained according to a similar manner to that of Preparation 20.

1) N-(2-Benzyloxy-5-methylphenyl)-4-nitrobenzamide

NMR (DMSO-d$_6$, δ): 2.26 (3H, s), 5.15 (2H, s), 6.97–7.08 (2H, m), 7.24–7.39 (3H, m), 7.46 (3H, d, J=9 Hz), 8.15 (2H, d, J=9 Hz), 8.36 (2H, d, J=9 Hz).

2) N-(2-Benzyloxy-4-methylphenyl)-4-nitrobenzamide

NMR (DMSO-d$_6$, δ): 2.32 (3H, s), 5.16 (3H, s), 6.82 (1H, d, J=9 Hz), 7.02 (1H, s), 7.24–7.40 (3H, m), 7.47 (3H, d, J=9 Hz), 8.16 (2H, d, J=9 Hz), 8.36 (2H, d, J=9 Hz), 9.88 (1H, s).

3) 2-[5-(Ethoxycarbonyl)pent-1-yloxy]-N-tert-butoxycarbonylaniline

NMR (CDCl$_3$, δ): 1.26 (3H, t, J=7 Hz), 1.43–1.59 (11H, m), 1.63–1.78 (2H, m), 1.78–1.92 (2H, m), 2.35 (2H, t, J=7 Hz), 4.01 (2H, t, J=7 Hz), 4.12 (2H, q, J=7 Hz), 6.77–6.86 (1H, m), 6.86–6.97 (2H, m), 7.03 (1H, br s), 7.99–8.10 (1H, m).

4) 4-Nitro-N-methyl-N-[4-methyl-2-(5-methoxycarbonylpyrid-2-ylmethoxy)phenyl]benzamide NMR (CDCl$_3$, δ): 2.24 (3H, s), 2.73 (3H, s), 3.99 (3H, s), 5.24 (1H, d, J=11 Hz), 5.31 (1H, d, J=11 Hz), 6.60 (1H, d, J=7 Hz), 6.69 (1H, s), 6.81 (1H, d, J=7 Hz), 7.23 (1H, s), 7.47 (2H, d, J=8.5 Hz), 7.99 (2H, d, J=8.5 Hz), 8.51 (1H, m), 9.12 (1H, m).

5) 4-Nitro-N-methyl-N-[2-(5-methoxycarbonylpyrid-2-ylmethoxy)phenyl]benzamide

NMR (CDCl$_3$, δ): 3.40 (3H, s), 3.99 (3H, s), 5.31 (2H, m), 6.80 (1H, dd, J=7, 7 Hz), 6.91 (1H, d, J=7 Hz), 6.98 (1H, d, J=7 Hz), 7.16 (1H, dd, J=7, 7 Hz), 7.28 (1H, s), 7.49 (2H, d, J=8.5 Hz), 7.99 (2H, d, J=8.5 Hz), 8.54 (1H, m), 9.12 (1H, m).

6) 3-(5-Ethoxycarbonylpent-1-yloxy)-2-nitropyridine

NMR (CDCl$_3$, δ): 1.25 (3H, t, J=7.5 Hz), 1.51 (2H, m), 1.70 (2H, m), 1.87 (2H, m), 2.31 (2H, t, J=7.5 Hz), 4.10 (2H, q, J=7.5 Hz), 4.75–7.53 (2H, m), 8.06 (1H, m).

7) 2-(5-Ethoxycarbonylpent-1-yloxy)-3-nitropyridine

NMR (CDCl$_3$, δ): 1.23 (3H, t, J=7.5 Hz), 1.40 (2H, m), 1.68 (2H, m), 1.82 (2H, m), 2.30 (2H, t, J=7.5 Hz), 4.10 (4H, m), 6.29 (1H, dd, J=7, 7 Hz), 7.18 (7H, dd, J=1 Hz), 8.30 (7H, dd, J=1 Hz).

8) O-(3-Ethoxycarbonylprop-1-yl)-(2-nitro)benzaldoxim

NMR (CDCl$_3$, δ): 1.25 (3H, t, J=7.5 Hz) 2.05 (2H, tt, J=7.5, 7.5 Hz), 2.43 (2H, t, J=7.5 Hz), 4.13 (2H, q, J=7.5 Hz), 4.24 (2H, t, J=7.5 Hz), 7.52 (1H, dt, J=1, 7 Hz), 7.62 (1H, dt, J=1, 7 Hz), 7.98 (1H, dd, J=1, 7 Hz), 8.04 (1H, dd, J=1, 7 Hz), 8.61 (1H, s).

9) 2-(5-Ethoxycarbonylpentyloxy)-[N-methyl-N-(4-nitrobenzoyl)]aniline

NMR (CDCl$_3$, δ): 1.26 (3H, t, J=7.5 Hz), 1.45–1.58 (2H, m), 1.67–1.76 (2H, m), 1.79–1.88 (2H, m), 2.34 (2H, t, J=7.5 Hz), 3.38 (3H, s), 3.84–4.00 (2H, m), 4.13 (2H, q, J=7.5 Hz), 6.72–6.82 (2H, m), 7.01 (1H, d, J=7 Hz), 7.17 (1H, t, J=7 Hz), 7.45 (2H, d, J=8.5 Hz), 7.98 (2H, d, J=8.5 Hz).

10) 3-Methoxy-4-nitro-N-[2-(6-chlorohex-1-yloxy)-4-methylphenyl]-N-methylbenzamide NMR (CDCl$_3$, δ): 1.41–1.61 (4H, m), 1.71–1.90 (4H, m), 2.27 (3H, s), 3.33 (3H, s), 3.56 (2H, t, J=7 Hz), 3.77 (3H, s), 3.82–3.98 (2H, m), 6.58–6.66 (2H, m), 6.85 (1H, d, J=9 Hz), 6.92 (1H, d, J=9 Hz), 7.06 (1H, s), 7.59 (1H, d, J=9 Hz).

Preparation 22

To a solution of 4-nitro-N-methyl-N-[2-(3-phthalimidoprop-1-yloxy)phenyl]benzamide (760 mg) in ethanol (15 ml) was added hydrazine hydrate (828 mg) and the solution was stirred at ambient temperature for 1 days. After evaporation in vacuo, the residue was diluted with ethyl acetate and then the organic solution was washed successively with saturated sodium bicarbonate aqueous solution and brine. Drying, filtering and removal of solvents afforded 4-nitro-N-methyl-N-[2-(3-aminoprop-1-yloxy) phenyl]benzamide (422 mg) as a yellow oil.

Rf: 0.06 (10% methanol in chloroform).

Preparation 23

The following compound was obtained according to a similar manner to that of Preparation 22. 3-Methoxy-4-nitro-N-methyl-N-[4-methyl-2-(3-aminoprop-1-yloxy)phenyl] benzamide Rf: 0.06 (10% methanol in chloroform).

Preparation 24

To a solution of 4-nitro-N-methyl-N-[2-(2-hydroxyethyl) phenyl]benzamide (686 mg) in N,N-dimethylformamide (12 ml) was added pyridinium dichromate (4.3 g) and the mixture was stirred at ambient temperature for 2 days. The mixture was diluted with water (80 ml) and the aqueous solution was extracted with ethyl acetate. The extract was washed with brine and dried over magnesium sulfate. Filtering and removal of solvents afforded a brown oil. To a solution of the brown oil in methanol (3 ml) and benzene (11 ml) was added trimethylsilyl diazomethane (1.7 ml) and the resulting solution was stirred at ambient temperature for 30 minutes. The mixture was evaporated in vacuo to give 4-nitro-N-methyl-N-(2-methoxycarbonylmethylphenyl) benzamide (517 mg) as a dark-green oil.

NMR (CDCl$_3$, δ): 3.42 and 3.45 (total 3H, s), 3.47–3.60 (2H, m), 3.72 and 3.88 (total 3H, s), 7.18–7.32 (3H, m), 7.37–7.48 (3H, m), 7.96–8.02 (2H, m).

Preparation 25

To an ice bath cooled mixture of 4-nitro-N-methyl-N-[2-[(E) and (Z)-6-methoxycarbonyl-1-hexen-1-yl]phenyl] benzamide (2.00 g) and nickel chloride hexahydrate (1.80 g) in a mixture of methanol (20 ml) and tetrahydrofuran (20 ml) was added sodium borohydride (954 mg) in small portions and the mixture was stirred in an ice bath for 1 hour. The solution was filtered through a bed of Celite and the filtrate was concentrated in vacuo. The residue was dissolved in ethyl acetate (100 ml) and the solution was washed with water and brine. The organic phase was dried over magnesium sulfate and the solvent was evaporated in vacuo to give an oil. The oil was purified by silica gel column (1% methanol in chloroform) to give 4-amino-N-methyl-N-[2-(6-methoxycarbonylhex-1-yl)phenyl]benzamide (1.28 g) as a pale yellow amorphous.

NMR (CDCl$_3$, δ): 1.24–1.30 (4H, m), 1.50–1.64 (4H, m), 2.28 (2H, t, J=7.5 Hz), 2.33 (1H, m), 2.48 (1H, m), 3.33 (3H, s), 3.65 (3H, s), 3.74 (2H, s), 6.34 (2H, d, J=8.5 Hz), 7.02–7.20 (6H, m).

Preparation 26

To a mixture of tetrahydro-4H-pyran-4-one (1.0 g) and methylamine (40% in methanol, 2.0 ml) in methanol (5 ml) was added sodium cyanoborohydride (0.62 g) at ambient temperature. The mixture was stirred overnight. The mixture was quenched by adding of water, and methanol was evaporated. The resulting mixture was extracted with chloroform, and then the organic layer was washed with brine. Drying and removal of solvents afforded 4-methylaminotetrahydro-4H-pyran (639 mg) as a slightly yellow oil.

Preoaration 27

To a solution of 2-methylaniline (1.0 g) and triethylamine (0.95 g) in N,N-dimethylformamide (15 ml) was added benzyl bromide (1.9 g) at ambient temperature and the mixture was stirred at ambient temperature overnight. The reaction mixture was diluted with ethyl acetate and it was washed with water and brine. Drying, filtering and the removal of solvents afforded a crude product. The crude product was chromatographed on silica gel (n-hexane:ethyl acetate=10:1) to give N-benzyl-2-methylaniline (795 mg) as a slightly yellow oil.

Preparation 28

2-Benzyloxy-4-chlorobenzoic acid (3.0 g) was heated under reflux in a mixture of benzene and t-butyl alcohol. Diphenylphosphoryl azide (3.14 g) and triethylamine (1.21 g) were added in one batch to the mixture and reflux was continued for a further 8 hours. Benzene was removed under reduced pressure and the residue taken up in ethyl acetate. An insoluble white solid was removed by filtration. The remaining organic filtrate was washed successively with diluted hydrochloric acid, water, saturated aqueous sodium hydrogen carbonate and brine. The organic layer was dried over magnesium sulfate and the solvent was evaporated to give 2-benzyloxy-4-chloro-N-tert-butoxycarbonylaniline (1.6 g).

NMR (CDCl$_3$, δ): 1.50 (9H, s), 5.08 (2H, s), 6.85–7.04 (3H, m), 7.31–7.49 (5H, m), 8.04 (1H, d, J=9 Hz).

Preparation 29

The following compounds were obtained according to a similar manner to that of Example 48.
1) 2-Benzyloxy-4-chloro-N-methylaniline
   NMR (CDCl$_3$, δ): 2.82 (3H, s), 5.03 (2H, s), 6.49 (1H, d, J=9 Hz), 6.81 (1H, d, J=2 Hz), 6.87 (1H, dd, J=9, 2 Hz), 7.31–7.46 (5H, m).
2) 2-[5-(Ethoxycarbonyl)pent-1-yloxy]-N-methylaniline
   NMR (CDCl$_3$, δ): 1.26 (3H, t, J=7 Hz), 1.43–1.57 (2H, m), 1.63–1.76 (2H, m), 1.76–1.88 (2H, m), 2.33 (2H, t, J=7 Hz), 2.86 (3H, s), 3.97 (2H, t, J=7 Hz), 4.13 (2H, q, J=7 Hz), 6.54–6.67 (2H, m), 6.73 (1H, d, J=9 Hz), 6.88 (1H, dd, J=9, 9 Hz).

Preparation 30

The following compounds were obtained according to a similar manner to that of Example 6.
1) 3-Chloro-4-(4'-methylbiphenyl-2-carboxamido)benzoic acid
   NMR (DMSO-d$_6$, δ): 2.32 (3H, s), 7.22 (2H, d, J=8 Hz), 7.37 (2H, d, J=8 Hz), 7.42–7.54 (2H, m), 7.54–7.67 (2H, m), 7.79–7.96 (3H, m).
2) 4-(Methylphenyl-2-carboxamido)-2-nitrobenzoic acid
   NMR (DMSO-d$_6$, δ): 2.41 (3H, s), 7.29–7.38 (2H, m), 7.44 (1H, dd, J=8, 8 Hz), 7.49–7.56 (1H, m), 7.89 (1H, d, J=8 Hz), 7.98 (1H, d, J=8 Hz), 8.36 (1H, s).
3) 4-(4'-Methylbiphenyl-2-carboxamido)-2-nitrobenzoic acid
   NMR (CDCl$_3$, δ): 2.40 (3H, s), 7.20–7.61 (9H, m), 7.73 (1H, d, J=9 Hz), 7.83 (1H, d, J=9 Hz).

Preparation 31

To a solution of 4-nitro-N-methyl-N-[2-(3-aminoprop-1-yloxy)phenyl]benzamide (422 mg) and triethylamine (130 mg) in dichloromethane (10 ml) was added phenyl chloroformate (201 mg) and the solution was stirred at 0° C. for 30 minutes. The reaction mixture was diluted with dichloromethane and then the organic solution was washed successively with 1N hydrochloric acid, saturated sodium bicarbonate aqueous solution and brine. Drying, filtering and removal of solvents afforded a crude product. The crude product was chromatographed on silica gel (eluent; 1% methanol in chloroform) to give 4-nitro-N-methyl-N-[2-(3-phenoxycarbonylaminoprop-1-yloxy)phenyl]benzamide (383 mg) as a slightly yellow oil.

NMR (CDCl$_3$, δ): 2.12 (2H, quint., J=7 Hz), 3.40 (3H, s), 3.50 (2H, q, J=7 Hz), 3.96–4.07 (2H, m), 5.22–5.28 (1H, br), 6.79–6.88 (2H, m), 7.01–7.23 (5H, m), 7.31–7.39 (2H, m), 7.48 (2H, d, J=8 Hz), 7.98 (2H, d, J=8 Hz).

Preparation 32

The following compounds were obtained according to a similar manner to that of Preparation 31.
1) 3-Methoxy-4-nitro-N-methyl-N-[4-methyl-2-(3-phenoxycarbonylaminoprop-1-yloxy)phenyl]benzamide NMR (CDCl$_3$, δ): 2.10 (2H, quint., J=6 Hz), 2.30 (3H, s), 3.37 (3H, s), 3.48 (2H, q, J=6 Hz), 3.78 (3H, s), 3.92–4.07 (2H, m), 5.23–5.30 (1H, br), 6.63–6.68 (2H, m), 6.90–6.99 (2H, m), 7.09–7.14 (3H, m), 7.17–7.23 (1H, m), 7.31–7.39 (2H, m), 7.60 (1H, d, J=8 Hz).
2) 4-Nitro-N-methyl-N-[2-(3-phenoxycarbonylamino-1-propyn-1-yl)phenyl]benzamide NMR (CDCl$_3$, δ): 3.47 (3H, s), 4.35 (2H, d, J=6.5 Hz), 5.55 (1H, br t, J=6.5 Hz), 7.10–7.28 (6H, m), 7.22–7.41 (3H, m), 7.54 (2H, d, J=8.5 Hz), 8.01 (2H, d, J=8.5 Hz).

Preparation 33

A mixture of 4-nitro-N-methyl-N-[2-(3-phenoxycarbonylaminoprop-1-yloxy)phenyl]benzamide (383 mg) and piperazine (256 mg) in N,N-dimethylformamide (8 ml) was stirred at 80° C. for 3 hours. The reaction mixture was diluted with ethyl acetate and then the organic solution was washed successively with saturated sodium bicarbonate aqueous solution and brine. Drying, filtering and removal of solvents afforded 4-nitro-N-methyl-N-[2-{3-(4-methyl-1-piperazinyl)carbonylaminoprop-1-yloxy}phenyl]benzamide (357 mg) as a slightly yellow oil.

NMR (CDCl$_3$, δ): 2.00–2.10 (2H, m), 2.31 (3H, s), 2.38–2.44 (4H, m), 3.37–3.45 (9H, m), 3.90–4.01 (2H, m), 4.69–4.75 (1H, m), 6.85–6.95 (1H, m), 7.00–7.25 (3H, m), 7.47 (2H, d, J=9 Hz), 8.00 (2H, d, J=9 Hz).

Preparation 34

The following compounds were obtained according to a similar manner to that of Preparation 33.
1) 3-Methoxy-4-nitro-N-methyl-N-[4-methyl-2-[3-(4-methyl-1-piperazinyl)carbonylaminoprop-1-yloxy]phenyl]benzamide NMR (CDCl$_3$, δ): 1.98–2.07 (2H, m), 2.28 (3H, s), 2.31 (3H, s), 2.38–2.42 (4H, m), 3.35 (3H, s), 3.37–3.46 (6H, m), 3.78 (3H, s), 3.88–4.00 (2H, m), 4.70–4.75 (1H, br), 6.80–6.84 (2H, m), 7.08 (1H, s), 7.20–7.26 (2H, m), 7.60 (1H, d, J=8 Hz).
2) 4-Nitro-N-methyl-N-[2-[3-(4-methylpiperazin-1-yl)carbonylamino-1-propyn-1-yl]phenyl]benzamide NMR (CDCl$_3$, δ): 2.32 (3H, s), 2.44 (4H, t, J=6 Hz), 3.41 (3H, s), 3.54 (4H, t, J=6 Hz), 4.32 (2H, m), 5.10 (1H, br t, J=6.5 Hz), 7.13–7.32 (4H, m), 7.55 (2H, d, J=8.5 Hz), 8.00 (2H, d, J=8.5 Hz).
3) 4-Nitro-N-methyl-N-[2-[3-(4-dimethylaminopiperidin-1-yl)carbonylaminoprop-1-yloxy]phenyl]benzamide MASS (m/z): 484 (M+1).

Preparation 35

The following compound was obtained according to a similar manner to that of Example 20.

3-(5-Ethoxycarbonylpent-1-yloxy)-2-methylaminopyridine

MASS (m/z): 267 (M+1).

EXAMPLE 1

To a solution of 2-(4-methylphenyl)benzoic acid (157 mg) dichloromethane (20 ml) were added oxalyl chloride (0.092 ml) and a few drop of N,N-dimethylformamide and the solution was stirred at ambient temperature for 2 hours. The solvent was evaporated in vacuo to give an acid chloride as an oil and the oil was added to a mixture of N-methyl-N-(4-aminobenzoyl)aniline (150 mg) and triethylamine (0.14 ml) in dichloromethane (20 ml). The mixture was stirred at ambient temperature for 2 hours and washed successively with 1N hydrochloric acid, water and brine, and dried over magnesium sulfate. The solvent was evaporated in vacuo to give an oil and the oil was subjected to silica gel column (30 g, 1% methanol in chloroform) to give an oil. The oil was solidified with diethyl ether to give 4-(4'-methylbiphenyl-2-carboxamido)-N-methyl-N-phenylbenzamide (230 mg).

NMR (CDCl$_3$, δ): 2.33 (3H, s), 3.46 (3H, s), 6.89–7.03 (5H, m), 7.11–7.56 (11H, m), 7.82 (1H, dd, J=1.5, 7.5 Hz).

EXAMPLE 2

The following compounds were obtained according to a similar manner to that of Example 1.
1) 4-(4'-Methylbiphenyl-2-carboxamido)-N-ethyl-N-phenylbenzamide NMR (CDCl$_3$, δ): 1.18 (3H, t, J=7 Hz), 2.32 (3H, s), 3.94 (2H, q, J=7 Hz), 6.84–7.02 (4H, m), 7.11–7.55 (13H, m), 7.72 (1H, dd, J=1.5, 8 Hz).
2) 4-(4'-Methylbiphenyl-2-carboxamido)-N-methyl-N-(2-ethoxycarbonylphenyl)benzamide NMR (CDCl$_3$, δ): 1.33 (3H, t, J=7 Hz), 2.32 (3H, s), 3.38 (3H, s), 4.28 (3H, q, J=7 Hz), 6.90 (2H, m), 7.05–7.56 (13H, m), 7.79 (2H, t, J=8 Hz).
3) 4-(4'-Methylbiphenyl-2-carboxamido)-N-methyl-N-(2-pyridyl)benzamide NMR (CDCl$_3$, δ): 2.39 (3H, s), 3.87 (3H, s), 6.50 (1H, dt, J=1, 7.5 Hz), 7.07 (1H, br), 7.17–7.27 (4H, m), 7.36 (2H, d, J=8.5 Hz), 7.43–7.58 (5H, m), 7.91 (1H, dd, J=1, 7 Hz), 8.18 (2H, d, J=8.5 Hz), 8.31 (1H, d, J=7.5 Hz).
4) 4-(4'-Methylbiphenyl-2-carboxamido)-N-methyl-N-(2-chlorophenyl)benzamide NMR (CDCl$_3$, δ): 2.35 (3H, s), 3.35 (3H, s), 6.88–7.56 (16H, m), 7.81 (1H, d, J=8 Hz).
5) 4-(4'-Methylbiphenyl-2-carboxamido)-N-methyl-N-(4-methylphenyl)benzamide NMR (CDCl$_3$, δ): 2.28 (3H, s), 2.33 (3H, s), 3.43 (3H, s), 6.86–6.96 (5H, m), 7.02 (2H, d, J=8.5 Hz), 7.17–7.55 (9H, m), 7.94 (1H, d, J=8 Hz).
6) 2-Chloro-4-(4'-methylbiphenyl-2-carboxamido)-N-methyl-N-phenylbenzamide NMR (CDCl$_3$, δ): 2.36 (3H, s), 3.47 (3H, s), 6.76–7.55 (16H, m), 7.80 (1H, d, J=8 Hz).
7) 4-(4'-Methylbiphenyl-2-carboxamido)-N-methyl-N-(2-methylphenyl)benzamide NMR (CDCl$_3$, δ): 2.16 (3H, s), 2.35 (3H, s), 3.31 (3H, s), 6.88–7.56 (16H, m), 7.82 (1H, d, J=8 Hz).
8) 4-(4'-Methylbiphenyl-2-carboxamido)-N-methyl-N-(2-isopropylphenyl)benzamide NMR (CDCl$_3$, δ): 0.82 (3H, d, J=7 Hz), 1.16 (3H, d, J=7 Hz), 2.37 (3H, s), 2.96 (1H, qq, J=7, 7 Hz), 3.38 (3H, s), 6.72–6.95 (2H, m), 7.07–7.55 (14H, m), 7.81 (1H, d, J=8 Hz).
9) 4-(4'-Methylbiphenyl-2-carboxamido)-N-methyl-N-(2-methoxyphenyl)benzamide NMR (CDCl₃, δ): 2.35 (3H, s), 3.32 (3H, s), 3.70 (3H, s), 6.78–6.93 (5H, m), 6.99 (1H, d, J=8 Hz), 7.12–7.20 (5H, m), 7.27–7.31 (2H, m), 7.37–7.54 (3H, m), 7.82 (1H, d, J=8 Hz).

10) 4-(4'-Methylbiphenyl-2-carboxamido)-N-methyl-N-(3-pyridyl)benzamide

NMR (CDCl₃, δ): 2.37 (3H, s), 3.46 (3H, s), 6.95–7.00 (3H, m), 7.14–7.55 (11H, m), 7.84 (1H, d, J=8 Hz), 8.31 (1H, d, J=3 Hz), 8.38 (1H, d, J=5.5 Hz).

11) 4-(4'-Methylbiphenyl-2-carboxamido)-N-methyl-N-[3-(2-methoxycarbonyl)thienyl]benzamide NMR (CDCl₃, δ): 2.37 (3H, s), 3.46 (3H, s), 3.79 (3H, s), 6.86 (1H, d, J=8 Hz), 6.95–7.02 (3H, m), 7.18–7.56 (10H, m), 7.83 (1H, dd, J=1, 8 Hz).

12) 4-(4'-Methylbiphenyl-2-carboxamido)-N-methyl-N-(3-methylphenyl)benzamide

NMR (CDCl₃, δ): 2.25 (3H, s), 2.34 (3H, s), 3.43 (3H, s), 6.77 (1H, d, J=8 Hz), 6.84–7.55 (15H, m), 7.82 (1H, dd, J=1, 8 Hz).

13) 4-(4'-Methylbiphenyl-2-carboxamido)-N-methyl-N-(2-benzoyloxyphenyl)benzamide NMR (CDCl₃, δ): 2.35 (3H, s), 3.37 (3H, s), 6.90–7.00 (3H, m), 7.14–7.71 (16H, m), 7.83 (1H, d, J=8 Hz), 8.11 (2H, d, J=8.5 Hz).

14) 4-(4'-Methylbiphenyl-2-carboxamido)-N-methyl-N-(2-nitrophenyl)benzamide

NMR (DMSO-d₆, δ): 2.28 (3H, s), 3.33 (3H, s), 7.01–7.18 (3H, m), 7.23–7.57 (11H, m), 7.68–7.95 (3H, m).

15) 4-(4'-Methylbiphenyl-2-carboxamido)-N-methyl-N-(2-phenylphenyl)benzamide

NMR (CDCl₃, δ): 2.37 (3H, s), 3.39 (3H, s), 6.70–6.97 (6H, m), 7.15–7.56 (15H, m), 7.82 (1H, d, J=8 Hz).

16) 4-(4'-Methylbiphenyl-2-carboxamido)-N-methyl-N-(2-allylphenyl)benzamide

NMR (CDCl₃, δ): 2.36 (3H, s), 3.08–3.40 (2H, m), 3.35 (3H, s), 5.05 (1H, d, J=15 Hz), 5.09 (1H, d, J=10 Hz), 5.66–5.90 (1H, m), 6.83–7.66 (16H, m), 7.80 (1H, d, J=8 Hz).

17) 4-(4'-Methylbiphenyl-2-carboxamido)-N-methyl-N-[2-(3-phthalimidopropyloxy)phenyl]benzamide NMR (CDCl₃, δ): 2.14 (2H, tt, J=7.5, 7.5 Hz), 2.30 (3H, s), 3.33 (3H, s), 3.84–3.99 (4H, m), 6.73–6.97 (6H, m), 7.08–7.55 (9H, m), 7.67 (2H, m), 7.79–7.86 (4H, m).

18) 4-(4'-Methylbiphenyl-2-carboxamido)-N-methyl-N-(2-acetylphenyl)benzamide

NMR (CDCl₃, δ): 2.20 (3H, s), 2.38 (3H, s), 3.41 (3H, s), 6.89 (2H, br), 7.04–7.54 (14H, m), 7.82 (1H, d, J=8 Hz).

19) 3-Methoxy-4-(4'-methylbiphenyl-2-carboxamido)-N-methyl-N-(2-ethoxycarbonylphenyl)benzamide NMR (CDCl₃, δ): 1.34 (3H, t, J=7.5 Hz), 3.41 (3H, s), 3.59 (3H, s), 3.88 (2H, s), 4.30 (2H, q, J=7.5 Hz), 6.38 (1H, d, J=7.5 Hz), 6.68–6.77 (2H, m), 7.20–7.29 (2H, m), 7.45 (1H, t, J=7.5 Hz), 7.78 (1H, d, J=7.5 Hz).

20) 4-(4'-Methylbiphenyl-2-carboxamido)-N-methyl-N-[(4-methyl-2-methoxycarbonyl)phenyl]benzamide NMR (CDCl₃, δ): 2.31 (3H, s), 2.37 (3H, s), 3.34 (3H, s), 3.90 (3H, s), 6.77 (1H, m), 6.86–6.98 (3H, m), 7.07–7.55 (10H, m), 7.83 (1H, d, J=7.5 Hz).

21) 4-(4'-Methylbiphenyl-2-carboxamido)-N-methyl-N-[2-[3-(4-methylpiperazin-1-yl)carbonylamino-(1-propyn-1-yl)]phenyl]benzamide NMR (CDCl₃, δ): 2.32 (3H, s), 2.39 (3H, s), 2.43 (4H, t, J=6 Hz), 3.36 (3H, s), 3.56 (4H, t, J=6 Hz), 4.26 (2H, m), 5.32 (1H, br t, J=6.5 Hz), 6.90–6.98 (3H, m), 7.10–7.32 (9H, m), 7.38–7.55 (3H, m), 7.82 (1H, d, J=7.5 Hz).

22) 4-(4'-Methylbiphenyl-2-carboxamido)-N-methyl-N-(2-cyanophenyl)benzamide

NMR (CDCl₃, δ): 2.38 (3H, s), 3.48 (3H, s), 6.95–7.00 (3H, m), 7.14–7.54 (11H, m), 7.60 (1H, d, J=7 Hz), 7.82 (1H, d, J=7 Hz).

23) 4-(4'-Methylbiphenyl-2-carboxamido)-N-methyl-N-[2-[3-(4-dimethylaminopiperidin-1-yl)carbonylaminoprop-1-yloxy]phenyl]benzamide NMR (CDCl₃, δ): 1.39 (2H, m), 1.73–1.83 (4H, m), 1.98 (2H, m), 2.25 (6H, s), 2.37 (3H, s), 2.74 (2H, m), 3.32 (3H, s), 3.36 (2H, m), 3.97 (2H, m), 4.86 (1H, br), 6.80–7.55 (15H, m), 7.80 (1H, d, J=7 Hz).

24) 4-(4'-Chlorobiphenyl-2-carboxamido)-N-methyl-N-[2-[3-(4-methylpiperazin-1-yl)carbonylaminoprop-1-yloxy]phenyl]benzamide NMR (CDCl₃, δ): 1.99 (2H, m), 2.28 (3H, s), 2.26 (4H, s), 3.33 (3H, s), 3.34–3.40 (6H, m), 3.93 (2H, m), 4.90 (1H, br), 6.79–6.92 (2H, m), 6.97–7.10 (4H, m), 7.14–7.57 (9H, m), 7.75 (1H, d, J=7 Hz).

25) 3-Methyl-4-(4'-methylbiphenyl-2-carboxamido)-N-methyl-N-[2-(3-phthalimidoprop-1-yloxy)phenyl]benzamide NMR (CDCl₃, δ): 1.42 (3H, s), 2.20 (2H, m), 2.34 (3H, s), 3.32 (3H, s), 3.86–4.02 (4H, m), 6.73–6.88 (2H, m), 7.06–7.54 (11H, m), 7.67–7.80 (2H, m), 7.88–7.95 (2H, m), 7.92 (1H, d, J=7 Hz).

26) 3-Methoxy-4-(4'-methylbiphenyl-2-carboxamido)-N-methyl-N-[2-(3-phthalimidoprop-1-yloxy)phenyl]benzamide NMR (CDCl₃, δ): 2.19 (2H, m), 2.22 (3H, s), 3.32 (3H, s), 3.40 (3H, s), 3.88–4.07 (5H, m), 6.77–6.95 (6H, m), 7.10–7.18 (3H, m), 7.26–7.53 (4H, m), 7.63–7.72 (2H, m), 7.76–7.82 (2H, m), 8.18 (1H, d, J=7 Hz).

27) 4-(4'-Methylbiphenyl-2-carboxamido)-N-methyl-N-[2-[(E)-6-methoxycarbonyl-1-hexen-1-yl]phenyl]benzamide NMR (CDCl₃, δ): 1.51 (2H, m), 1.67 (2H, m), 2.26 (2H, dt, J=7.5, 7.5 Hz), 2.33 (2H, t, J=7.5 Hz), 2.33 (3H, s), 3.31 (3H, s), 3.66 (3H, s), 6.13 (1H, dt, J=15, 7.5 Hz), 6.45 (1H, d, J=15 Hz), 6.85–6.93 (4H, m), 7.05 (1H, dd, J=7, 7 Hz), 7.10–7.17 (5H, m), 7.26 (2H, d, J=8.5 Hz), 7.33–7.52 (3H, m), 7.80 (1H, d, J=7 Hz).

28) 4-(4'-Methylbiphenyl-2-carboxamido)-N-methyl-N-[2-[(Z)-6-methoxycarbonyl-1-hexen-1-yl]phenyl]benzamide NMR (CDCl₃, δ): 1.36 (2H, m), 7.53 (2H, m), 1.90 (1H, m), 2.10 (1H, m), 2.28 (2H, t, J=7.5 Hz), 2.35 (3H, s), 3.32 (3H, s), 3.59 (3H, s), 5.69 (1H, dt, J=11, 7.5 Hz), 6.30 (1H, d, J=11 Hz), 6.90 (2H, d, J=8.5 Hz), 7.01–7.42 (12H, m), 7.50 (1H, t, J=7 Hz), 7.79 (1H, d, J=7 Hz).

29) 4-(4'-Methylbiphenyl-2-carboxamido)-N-methyl-N-[2-(6-methoxycarbonylhex-1-yl)phenyl]benzamide NMR (CDCl₃, δ): 1.25–1.39 (4H, m), 1.46–1.63 (4H, m), 2.26–2.27 (1H, m), 2.29 (2H, t, J=7.5 Hz), 2.37 (3H, s), 2.49 (1H, m), 2.36 (3H, s), 3.63 (3H, s), 6.92 (2H, d, J=8.5 Hz), 6.99–7.44 (12H, m), 7.51 (1H, t, J=7 Hz), 7.80 (1H, d, J=7 Hz).

30) 4-(40'-Methylbiphenyl-2-carboxamido)-N-methyl-N-[2-[N-(3-ethoxycarbonylprop-1-yl)oxyimino]methylphenyl]benzamide NMR (CDCl₃, δ): 1.24 (3H, t, J=7.5 Hz), 2.00 (2H, tt, J=7.5, 7.5 Hz), 2.33 (3H, s), 2.40 (2H, t, J=7.5 Hz), 3.34 (3H, s), 4.10 (2H, q, J=7.5 Hz), 4.18 (2H, t, J=7.5 Hz), 6.90–7.30 (11H, m), 7.35–7.51 (3H, m), 7.68 (1H, d, J=7 Hz), 7.79 (1H, d, J=7 Hz), 8.11 (1H, s).

31) 4-(4'-Methylbiphenyl-2-carboxamido)-N-methyl-[2-(5-ethoxycarbonylpent-1-ylthio)phenyl]benzamide NMR (CDCl₃, δ): 1.23 (3H, t, J=7.5 Hz), 1.48 (2H, m), 1.60–1.73 (4H, m), 2.30 (2H, t, J=7.5 Hz), 2.37 (3H, s), 2.89 (2H, m), 3.31 (3H, s), 4.10 (2H, q, J=7.5 Hz), 6.87–6.90 (4H, m), 4.12–7.19 (4H, m), 7.22–7.31 (4H, m), 7.36–7.52 (3H, m), 7.80 (1H, d, J=7 Hz).

32) 4-(4'-Methylbiphenyl-2-carboxamido)-N-methyl-N-[2-(3-ethoxycarbonylprop-1-yloxy)phenyl]benzamide NMR (CDCl₃, δ): 1.24 (3H, t, J=7.5 Hz), 2.09 (2H, m), 2.33 (3H, s), 2.49 (2H, t, J=7.5 Hz), 3.31 (3H, s), 3.96 (2H, m), 4.13 (2H, q, J=7.5 Hz), 6.74–6.81 (2H, m), 6.86–6.98 (4H, m), 7.10–7.21 (4H, m), 7.23–7.31 (2H, m), 7.35–7.53 (3H, m), 7.82 (1H, d, J=7 Hz).

33) 4-(4'-Methylbiphenyl-2-carboxamido)-N-methyl-N-[2-(5-ethoxycarbonylpent-1-yloxy)pyrid-3-yl]benzamide NMR (CDCl₃, δ): 1.20 (3H, t, J=7.5 Hz), 1.50 (2H, m), 1.57–1.73 (4H, m), 2.28 (2H, t, J=7.5 Hz), 2.36 (3H, s), 3.30 (3H, s), 3.91 (2H, t, J=7.5 Hz), 4.06 (2H, q, J=7.5 Hz), 5.98 (1H, dd, J=7, 7 Hz), 6.96–7.03 (3H, m), 7.07–7.14 (2H, m) 7.18 (2H, d, J=8.5 Hz), 7.23–7.31 (3H, m), 7.39–7.55 (3H, m), 7.82 (1H, d, J=7 Hz).

34) 4-(4'-Methylbiphenyl-2-carboxamido)-N-methyl-N-[3-(5-ethoxycarbonylpent-1-yloxy)pyrid-2-yl]benzamide NMR (CDCl₃, δ): 1.25 (3H, t, J=7.5 Hz), 1.42 (2H, m), 1.60–1.78 (4H, m), 2.33 (2H, m), 2.40 (3H, s), 3.40 (3H, s), 3.70 (2H, m), 4.12 (2H, q, J=7.5 Hz), 6.88–7.53 (13H, m), 7.81 (1H, d, J=7.5 Hz), 8.02 (1H, d, J=7 Hz).

35) 3-Methyl-4-(4'-methylbiphenyl-2-carboxamido)-N-methyl-N-(4-chloro-2-benzyloxyphenyl)benzamide NMR (CDCl₃, δ): 1.37 (3H, s), 2.34 (3H, s), 3.30 (3H, s), 4.97 (2H, m), 6.77–6.99 (5H, m), 7.02 (1H, s), 7.18 (2H, d, J=8.5 Hz), 7.29–7.54 (10H, m), 7.83 (1H, d, J=7 Hz), 7.99 (1H, d, J=7 Hz).

36) 4-(4-Methylbiphenyl-2-carboxamido)-N-methyl-N-[4-methyl-2-(5-methoxycarbonylpyrid-2-ylmethoxy)phenyl]benzamide NMR (CDCl₃, δ): 2.28 (3H, s), 2.47 (3H, s), 3.33 (3H, s), 3.99 (3H, s), 5.28 (2H, s), 6.58 (7H, d), 6.71–6.79 (2H, m), 6.85–6.94 (3H, m), 7.16–7.23 (4H, m), 7.31 (2H, d, J=8.5 Hz), 7.35–7.58 (3H, m), 7.82 (1H, d, J=7 Hz), 8.50 (1H, m), 9.11 (1H, m).

37) 4-(4'-Nitrobiphenyl-2-carboxamido)-N-methyl-N-[2-(5-methoxycarbonylpyrid-2-ylmethoxy)phenyl]benzamide NMR (CDCl₃, δ): 3.31 (3H, s), 3.98 (3H, s), 5.30 (2H, s), 6.78 (1H, dd, J=7, 7 Hz), 6.87–6.95 (2H, m), 7.03–7.27 (6H, m), 7.42 (1H, d, J=7 Hz), 7.48–7.63 (4H, m), 7.71 (1H, d, J=7 Hz), 9.21 (2H, d, J=8.5 Hz), 8.51 (1H, m), 9.10 (1H, m).

38) 3-Methoxy-4-(4'-nitrobiphenyl-2-carboxamido)-N-methyl-N-[4-methyl-2-[6-(4-methylpiperazin-1-yl)hex-1-yloxy]phenyl]benzamide NMR (CDCl₃, δ): 1.28–1.59 (8H, m), 1.69–1.88 (2H, m), 2.27 (6H, s), 2.27–2.65 (8H, m), 3.28 (3H, s), 3.50 (3H, s), 3.75–4.00 (2H, m), 6.51–6.66 (2H, m), 6.74–6.91 (3H, m), 7.42 (1H, d, J=9 Hz), 7.48–7.62 (4H, m), 7.67–7.80 (2H, m), 8.08 (1H, d, J=9 Hz), 8.19 (2H, d, J=9 Hz).

39) 4-(2-Phenylpyridine-3-carboxamido)-N-(4-chloro-2-benzyloxyphenyl)-N-methylbenzamide NMR (CDCl₃, δ): 3.30 (3H, s), 4.88–5.10 (2H, m), 6.77–7.03 (6H, m), 7.14 (2H, d, J=9 Hz), 7.30–7.47 (9H, m), 7.59–7.68 (2H, m), 8.14 (1H, d, J=9 Hz), 8.73–8.80 (1H, m).

40) 4-(4'-Methylbiphenyl-2-carboxamido)-N-[2-benzyloxy-4-chlorophenyl]-N-methylbenzamide NMR (CDCl₃, δ): 2.36 (3H, s), 3.32 (3H, s), 4.86–5.10 (2H, m), 6.77–6.99 (6H, m), 7.08–7.22 (4H, m), 7.23–7.56 (10H, m), 7.83 (1H, d, J=8 Hz).

41) 2-Chloro-4-(4'-methylbiphenyl-2-carboxamido)-N-[2-benzyloxy-4-chlorophenyl]-N-methylbenzamide NMR (CDCl₃, δ): 2.40 (3H, s), 3.34 (3H, s), 4.96–5.11 (2H, m), 6.69–6.99 (5H, m), 7.06 (1H, d, J=9 Hz), 7.14–7.59 (12H, m), 7.76–7.91 (1H, m).

42) 2-Chloro-4-(4'-methylbiphenyl-2-carboxamido)-N-[2-(5-ethoxycarbonylpent-1-yloxy)phenyl]-N-methylbenzamide NMR (CDCl₃, δ): 1.26 (3H, t, J=7 Hz), 1.45–1.60 (2H, m), 1.66–1.79 (2H, m), 1.79–1.94 (2H, m), 2.35 (2H, t, J=7 Hz), 2.36 (3H, s), 3.33 (3H, s), 3.96 (2H, t, J=7 Hz), 4.13 (2H, q, J=7 Hz), 6.65–6.79 (3H, m), 6.81–7.00 (3H, m), 7.00–7.56 (9H, m), 7.89 (1H, d, J=9 Hz).

43) 3-Methoxy-4-(2'-methylbiphenyl-2-carboxamido)-N-[2-(5-ethoxycarbonylpent-1-yloxy)-4-methylphenyl]-N-methylbenzamide NMR (CDCl₃, δ): 1.24 (3H, t, J=7 Hz), 1.40–1.56 (2H, m), 1.56–1.86 (4H, m), 2.12 (3H, s), 2.27 (3H, s), 2.32 (2H, t, J=7 Hz), 3.28 (3H, s), 3.46 (3H, s), 3.69–3.98 (2H, m), 4.12 (2H, q, J=7 Hz), 6.49–6.63 (2H, m), 6.70–6.88 (3H, m), 7.14–7.29 (4H, m), 7.40–7.56 (2H, m), 7.75 (1H, br s), 7.94 (1H, d, J=9 Hz), 8.16 (1H, br d, J=9 Hz).

44) 4-(2',4'-Dimethylbiphenyl-2-carboxamido)-3-methoxy-N-[2-(5-ethoxycarbonylpent-1-yloxy)-4-methylphenyl]-N-methylbenzamide NMR (CDCl₃, δ): 1.26 (3H, t, J=7 Hz), 1.41–1.56 (2H, m), 1.60–1.89 (4H, m), 2.06 (3H, s), 2.28 (3H, s), 2.33 (3H, s), 2.33 (2H, t, J=7 Hz), 3.29 (3H, s), 3.48 (3H, s), 3.73–3.99 (2H, m), 4.13 (2H, q, J=7 Hz), 6.49–6.54 (2H, m), 6.70–6.89 (3H, m), 6.98–7.08 (2H, m), 7.12 (1H, d, J=9 Hz), 7.21 (1H, d, J=9 Hz), 7.41–7.56 (2H, m), 7.81 (1H, s), 7.96 (1H, d, J=9 Hz), 8.19 (1H, d, J=9 Hz).

45) 3-Methoxy-4-(4'-nitrobiphenyl-2-carboxamido)-N-[2-(5-ethoxycarbonylpent-1-yloxy)-4-methylphenyl]-N-methylbenzamide NMR (CDCl₃, δ): 1.26 (3H, t, J=7 Hz), 1.41–1.57 (2H, m), 1.62–1.87 (4H, m), 2.30 (3H, s), 2.33 (2H, t, J=7 Hz), 3.29 (3H, s), 3.51 (3H, s), 3.75–3.99 (2H, m), 4.13 (2H, q, J=7 Hz), 6.52–6.65 (2H, m), 6.76–6.92 (3H, m), 7.42 (1H, d, J=8 Hz), 7.49–7.62 (4H, m), 7.70–7.80 (2H, m), 8.08 (1H, d, J=8 Hz), 8.19 (2H, d, J=8 Hz).

46) 4-(4'-Nitrobiphenyl-2-carboxamido)-N-(2-benzyloxy-4-methylphenyl)-N-methylbenzamide NMR (CDCl₃, δ): 2.28 (3H, s), 3.33 (3H, s), 4.93 (1H, d, J=11 Hz), 5.05 (1H, d, J=11 Hz), 6.63 (1H, d, J=9 Hz), 6.70 (1H, s), 6.88 (1H, d, J=9 Hz), 7.02–7.13 (3H, m), 7.17–7.28 (2H, m), 7.24–7.46 (5H, m), 7.46–7.65 (4H, m), 7.71 (1H, d, J=9 Hz), 8.21 (2H, d, J=9 Hz).

47) 4-(2-Prop-2-ylbenzamido)-N-methyl-N-[2-[3-(4-methylpiperazin-1-yl)carbonylaminoprop-1-yloxy]phenyl]benzamide NMR (CDCl₃, δ): 1.27 (6H, d, J=7 Hz), 2.02 (2H, m), 2.28 (3H, s), 2.36 (4H, m), 3.27–3.43 (7H, m), 3.33 (3H, s), 3.98 (2H, m), 4.88 (1H, br), 6.79–6.91 (2H, m), 7.02–7.23 (3H, m), 7.30–7.42 (6H, m), 7.52 (1H, m).

48) 4-(2-Methylbenzamido)-N-methyl-N-[2-[3-(4-methylpiperazin-1-yl)carbonylaminoprop-1-yloxy]phenyl]benzamide NMR (CDCl₃, δ): 2.01 (2H, m), 2.28 (3H, s), 2.34 (4H, m), 2.46 (3H, s), 3.30–3.40 (6H, m), 3.32 (3H, s), 3.96 (2H, m), 4.88 (1H, br), 6.81–6.90 (2H, m), 7.04–7.22 (3H, m), 7.31–7.45 (6H, m), 7.61 (1H, br).

49) 4-(2,3-Dimethylbenzamido)-N-methyl-N-[2-[3-(4-methylpiperazin-1-yl)carbonylaminoprop-1-yloxy]phenyl]benzamide NMR (CDCl₃, δ): 2.00 (2H, m), 2.27 (3H, s), 2.29 (3H, s), 2.32 (4H, m), 3.30 (3H, s), 3.35 (6H, m), 3.93 (2H, m), 4.97 (1H, br), 6.78–6.89 (2H, m), 7.05–7.48 (8H, m), 7.78 (1H, m).

50) 4-(1,2-Dimethylphenyl-3-carboxamido)-N-(2-benzyloxyphenyl)-N-methylbenzamide NMR (CDCl₃, δ): 2.29 (3H, s), 2.33 (3H, s), 3.37 (3H, s), 4.94–5.13 (2H, m), 6.78–6.93 (2H, m), 7.01–7.52 (15H, m).

51) 2-Chloro-4-(methylphenyl-2-carboxamido)-N-[2-(5-ethoxycarbonylpent-1-yloxy)phenyl]-N-methylbenzamide NMR (CDCl₃, δ): 1.26 (3H, t, J=7 Hz), 1.47–1.63 (2H, m), 1.66–1.80 (2H, m), 1.80–1.95 (2H, m), 2.35 (2H, t, J=7

Hz), 2.44 (3H, s), 3.34 (3H, s), 3.99 (2H, t, J=7 Hz), 4.13 (2H, q, J=7 Hz), 6.69–6.81 (2H, m), 7.02–7.42 (8H, m), 7.51 (1H, s), 7.67 (1H, s).

52) 4-(Methylphenyl-2-carboxamido)-N-(2-benzyloxy-4-chlorophenyl)-N-methylbenzamide NMR (CDCl$_3$, δ): 2.47 (3H, s), 3.34 (3H, s), 4.91–5.11 (2H, m), 6.83 (1H, d, J=9 Hz), 6.89 (1H, s), 6.98 (1H, d, J=9 Hz), 7.17–7.51 (13H, m);

53) 4-(4'-Methylbiphenyl-2-carboxamido)-N-methyl-N-[2-{3-(4-methyl-1-piperazinyl)carbonylaminoprop-1-yloxy}phenyl]benzamide NMR (CDCl$_3$, δ): 1.93–2.02 (2H, m), 2.28 (3H, s), 2.33–2.40 (7H, m), 3.33 (3H, s), 3.34–3.40 (6H, m), 3.87–3.98 (2H, br), 4.82–4.88 (1H, br), 6.80–6.96 (4H, m), 7.06–7.34 (8H, m), 7.38–7.56 (3H, m), 7.83 (1H, d, J=8 Hz).

54) 4-(4'-Methylbiphenyl)-2-carboxamido)-N-methyl-N-(4-chlorophenyl)benzamide mp: 153–155° C.; NMR (CDCl$_3$, δ): 2.39 (3H, s), 3.45 (3H, s), 6.90–7.00 (5H, m), 7.12–7.58 (10H, m), 7.85 (1H, dd, J=1, 9 Hz).

55) 4-(4'-Methylbiphenyl-2-carboxamido)-N-methyl-N-(3-methoxyphenyl)benzamide mp: 147–150° C.; NMR (CDCl$_3$, δ): 2.38 and 2.40 (total 3H, s), 3.47 (3H, s), 3.69 (3H, s), 6.51–6.64 (2H, m), 6.70 (1H, dd, J=1, 8 Hz), 6.88–7.00 (3H, m), 7.05–7.59 (9H, m), 7.83 (1H, dd, J=1, 9 Hz).

56) 4-(4'-Methylbiphenyl-2-carboxamido)-N-methyl-N-(4-methoxyphenyl)benzamide mp: 170–173° C.; NMR (CDCl$_3$, δ): 2.35 (3H, s), 3.41 (3H, s), 3.78 (3H, s), 6.75 (2H, d, J=9 Hz), 6.88–7.00 (5H, m), 7.14–7.58 (8H, m), 7.81 (1H, dd, J=1, 8 Hz).

57) 4-(4'-Methylbiphenyl-2-carboxamido)-N-methyl-N-(3-chlorophenyl)benzamide mp: 115–118° C.; NMR (CDCl$_3$, δ): 2.38 (3H, s), 3.45 (3H, s), 6.82–7.58 (15H, m), 7.83 (1H, dd, J=1, 9 Hz).

58) 4-(4'-Methylbiphenyl-2-carboxamido)-N-ethoxycarbonylmethyl-N-(2-methylphenyl)benzamide mp: 72–75° C.; NMR (CDCl$_3$, δ): 1.30 (3H, t, J=8 Hz), 2.22 (3H, s), 2.38 (3H, s), 4.00 (1H, d, J=17 Hz), 4.24 (2H, q, J=8 Hz), 4.82 (1H, d, J=17 Hz), 6.84–6.96 (3H, m), 7.05–7.58 (12H, m), 7.80 (1H, d, J=8 Hz).

59) 4-(4'-Methylbiphenyl-2-carboxamido)-N-benzyl-N-(2-methylphenyl)benzamide mp: 90–95° C.; NMR (CDCl$_3$, δ): 1.86 (3H, s), 2.36 and 2.41 (total 3H, s), 4.70 (1H, d, J=15 Hz), 5.28 (1H, d, J=15 Hz), 6.80–7.60 (20H, m), 7.80 (1H, d, J=6 Hz).

60) 4-(4'-Methylbiphenyl-2-carboxamido)-N-methyl-N-(2-trifluoromethylphenyl)benzamide mp: 90–93° C.; NMR (CDCl$_3$, δ): 2.38 (3H, s), 3.30–3.42 (3H, br s), 6.85–7.00 (2H, br), 7.10–7.55 (12H, m), 7.60–7.70 (1H, br d, J=8 Hz), 7.79–7.89 (1H, br d, J=8 Hz).

61) 3-Methyl-4-(4'-methylbiphenyl-2-carboxamido)-N-methyl-N-(2-methylphenyl)benzamide mp: 148–153° C.; NMR (CDCl$_3$, δ): 1.40 (3H, s), 2.19 (3H, s), 2.34 and 2.40 (total 3H, s), 3.35 (3H, s), 6.79 (1H, s), 6.88–7.57 (12H, m), 7.79 (1H, d, J=6 Hz), 7.90 (1H, d, J=9 Hz).

62) N-Ethyl-N-(3-pentyl)-4-(4'-methylbiphenyl-2-carboxamido)benzamide mp: 140–143° C.; NMR (CDCl$_3$, δ): 0.85 (6H, t, J=8 Hz), 0.90–1.05 (2H, br), 1.30 (3H, t, J=7 Hz), 1.38–1.60 (2H, m), 2.40 (3H, s), 3.15–3.52 (3H, m), 7.00 (1H, s), 7.10–7.60 (10H, m), 7.88 (1H, dd, J=1, 8 Hz).

63) 4-(4'-Methylbiphenyl-2-carboxamido)-3-methoxy-N-methyl-N-(2-methylphenyl)benzamide mp: 203–206° C.; NMR (CDCl$_3$, δ): 2.20 (3H, s), 2.35 (3H, s), 3.34 (3H, s), 3.36 (3H, s), 6.75–6.82 (2H, m), 7.00–7.34 (6H, m), 7.35–7.57 (4H, m), 7.68 (1H, s), 7.79 (1H, d, J=7 Hz), 8.18 (1H, d, J=10 Hz).

64) 4-(4'-Methylbiphenyl-2-carboxamido)-N-methyl-N-(2,6-dimethylphenyl)benzamide mp: 225–228° C.; NMR (CDCl$_3$, δ): 2.17 (6H, s), 2.36 (3H, s), 3.30 (3H, s), 6.85–7.58 (14H, m), 7.80 (1H, d, J=8 Hz).

65) N-Methyl-N-(4-tetrahydro-4H-pyranyl)-4-(4'-methylbiphenyl-2-carboxamido)benzamide mp: 178–182° C.; NMR (CDCl$_3$, δ): 1.56–1.75 (4H, br), 1.80–2.00 (2H, m), 2.40 (3H, s), 2.90 (3H, s), 3.30–3.60 (1H, br), 3.95–4.10 (2H, m), 7.05 (1H, s), 7.12–7.60 (10H, m), 7.88 (1H, d, J=8 Hz).

66) 4-(4'-Methylbiphenyl-2-carboxamido)-N-methyl-N-(2-ethoxycarbonylmethoxyphenyl)benzamide NMR (CDCl$_3$, δ): 1.29 (3H, t, J=8 Hz), 2.37 (3H, s), 3.38 (3H, s), 4.26 (2H, q, J=8 Hz), 4.60 (2H, s), 6.67 (1H, d, J=8 Hz), 6.78–6.97 (4H, m), 7.09–7.34 (7H, m), 7.36–7.55 (4H, m), 7.82 (1H, d, J=8 Hz).

67) 4-(4'-Methylbiphenyl-2-carboxamido)-N-methyl-N-(2-methoxycarbonylmethylphenyl)benzamide NMR (CDCl$_3$, δ): 2.37 (3H, s), 3.36 (3H, s), 3.40 (3H, s), 3.68 and 3.84 (total 2H, s), 6.90 (2H, d, J=8 Hz), 7.08–7.30 (11H, m), 7.37–7.52 (3H, m), 7.82 (1H, d, J=8 Hz).

68) 4-(4'-Methylbiphenyl-2-carboxamido)-N-methyl-N-[(2-ethoxycarbonylmethyl-4-methyl)phenyl]benzamide NMR (CDCl$_3$, δ): 1.30 (3H, t, J=8 Hz), 2.27 (3H, s), 2.37 (3H, s), 3.35 (3H, s), 4.26 (2H, q, J=8 Hz), 4.57 (2H, s), 6.47 (1H, s), 6.60 (1H, d, J=8 Hz), 6.78–6.96 (3H, m), 7.17–7.32 (7H, m), 7.36–7.55 (3H, m), 7.83 (1H, d, J=8 Hz).

69) 3-Methoxy-4-(4'-methylbiphenyl-2-carboxamido)-N-methyl-N-(2-ethoxycarbonylmethoxyphenyl)benzamide NMR (CDCl$_3$, δ): 1.28 (3H, t, J=7 Hz), 2.34 (3H, s), 3.39 (3H, s), 3.40 and 3.42 (total 3H, s), 4.20–4.29 (2H, m), 4.59 (2H, s), 6.69–6.93 (5H, m), 7.10–7.18 (3H, m), 7.26–7.31 (2H, m), 7.36–7.52 (3H, m), 7.67–7.69 (1H, br s), 7.79 (1H, d, J=8 Hz), 8.16–8.20 (1H, m).

70) 3-Methoxy-4-(4'-methylbiphenyl-2-carboxamido)-N-methyl-N-[4-methyl-2-[3-(4-methyl-1-piperazinyl)carbonylaminoprop-1-yloxy]phenyl]benzamide NMR (CDCl$_3$, δ): 1.95–2.02 (2H, m), 2.28 (3H, s), 2.30 (3H, s), 2.35–2.49 (7H, m), 3.25–3.45 (9H, m), 3.30 (3H, s), 3.80–3.98 (2H, m), 4.75–4.82 (1H, m), 6.60–6.92 (6H, m), 7.12–7.54 (8H, m), 7.80 (1H, d, J=8 Hz).

71) 4-(4'-Methylbiphenyl-2-carboxamido)-N-methyl-N-(2-benzyloxy-4-methylphenyl)benzamide NMR (CDCl$_3$, δ): 2.28 (3H, s), 2.36 (3H, s), 3.34 (3H, s), 4.94 (1H, d, J=11 Hz), 5.04 (1H, d, J=11 Hz), 6.62 (1H, d, J=9 Hz), 6.68 (1H, br s), 6.84–6.96 (4H, m), 7.17 (4H, d, J=9 Hz), 7.25–7.56 (10H, m), 7.84 (1H, d, J=9 Hz).

72) 4-(4'-Methylbiphenyl-2-carboxamido)-N-methyl-N-(2-benzyloxy-5-methylphenyl)benzamide NMR (CDCl$_3$, δ): 2.19 (3H, s), 2.35 (3H, s), 3.34 (3H, s), 4.89 (1H, d, J=11 Hz), 5.01 (1H, d, J=11 Hz), 6.73 (1H, d, J=9 Hz) 6.82–6.99 (5H, m), 7.14–7.24 (4H, m), 7.24–7.56 (10H, m), 7.83 (1H, d, J=9 Hz).

73) 4-(Biphenyl-2-carboxamido)-N-methyl-N-(2-benzyloxyphenyl)benzamide

NMR (CDCl$_3$, δ): 3.35 (3H, s), 4.95 (1H, br d, J=11 Hz), 5.06 (1H, br d, J=11 Hz), 6.76 (5H, m), 7.02 (1H, br d, J=9 Hz), 7.08–7.21 (3H, m), 7.27–7.58 (13H, m), 7.83 (1H, d, J=9 Hz).

74) 3-Methoxy-4-(4'-methylbiphenyl-2-carboxamido)-N-methyl-N-(2-hydroxy-4-methylphenyl)benzamide NMR (CDCl$_3$, δ): 2.22 (3H, s), 2.31 (3H, s), 3.30 (6H, s), 6.46–6.60 (1H, m), 6.64–6.82 (2H, m), 6.87–7.04 (2H, m), 7.12 (2H, d, J=9 Hz), 7.27 (2H, d, J=9 Hz), 7.34–7.46 (2H, m), 7.50 (1H, dd, J=9, 9 Hz), 7.70 (1H, br s), 7.78 (1H, d, J=9 Hz), 8.14–8.30 (1H, m).

75) 3-Methoxy-4-(4'-methylbiphenyl-2-carboxamido)-N-methyl-N-(2-hydroxyphenyl)benzamide NMR (CDCl$_3$, δ): 2.31 (3H, s), 3.34 (6H, br s), 7.64–7.06 (4H, m), 7.06–7.22 (3H, m), 7.22–7.33 (3H, m), 7.33–7.58 (3H, m), 7.69 (1H, br s), 7.79 (1H, d, J=9 Hz), 8.16–8.35 (1H, br s).

76) 4-(Biphenyl-2-carboxamido)-3-methoxy-N-methyl-N-(2-hydroxy-4-methylphenyl)benzamide NMR (CDCl$_3$, δ): 2.23 (3H, s), 3.22–3.46 (6H, m), 6.47–7.02 (5H, m), 7.25–7.58 (7H, m), 7.67 (1H, br s), 7.80 (1H, br d, J=9 Hz), 8.19 (1H, br d, J=9 Hz).

77) 3-Methoxy-4-(4'-methylbiphenyl-2-carboxamido)-N-methyl-N-(2-benzyloxy-4-chlorophenyl)benzamide NMR (CDCl$_3$, δ): 2.32 (3H, s), 3.28 (3H, s), 3.33 (3H, s), 4.78–5.12 (2H, m), 6.71–6.81 (2H, m), 6.81–6.91 (2H, m), 7.00 (1H, d, J=9 Hz), 7.14 (2H, d, J=9 Hz), 7.24–7.55 (10H, m), 7.69 (1H, s), 7.81 (1H, d, J=9 Hz), 8.19 (1H, d, J=9 Hz)

78) 4-(Methylphenyl-2-carboxamido)-N-methyl-N-(2-benzyloxy-4-methylphenyl)benzamide NMR (CDCl$_3$, δ): 2.26 (3H, s), 2.46 (3H, s), 3.34 (3H, s), 4.96 (1H, d, J=12 Hz), 5.06 (1H, d, J=12 Hz), 6.64 (1H, d, J=9 Hz), 6.71 (1H, s), 6.92 (1H, d, J=9 Hz), 7.14–7.57 (14H, m).

EXAMPLE 3

To a solution of N-(4-aminobenzoyl)-N-cyclopentyl-p-anisidine (870 mg) and pyridine (443 mg) in dichloromethane (20 ml) was added o-toluoyl chloride (868 mg) at 0° C. Then the mixture was stirred for 3 hours at ambient temperature. The reaction mixture was concentrated and diluted with ethyl acetate and the solution was washed with water, 1N-hydrochloric acid and brine. The organic layer was dried over magnesium sulfate and filtered. The filtrate was concentrated and purified by silica gel column chromatography (SiO$_2$ 20 g, ethyl acetate:n-hexane=1:2). The eluent was concentrated and triturated with diethyl ether to give N-cyclopentyl-N-[4-(2-methylbenzoylamino)benzoyl]-p-anisidine (750 mg).

NMR (CDCl$_3$, δ): 1.32–1.72 (6H, m), 1.88–2.08 (2H, m), 2.46 (3H, s), 3.76 (3H, s), 4.85–5.09 (1H, m), 6.77 (2H, d, J=8 Hz), 6.96 (2H, d, J=8 Hz), 7.17–7.53 (9H, m).

EXAMPLE 4

To a solution of 6-[2-(4-methylphenyl)benzoyl]aminonicotinic acid (333 mg) in dichloromethane (15 ml) were added oxalyl chloride (0.139 ml) and a few drop of N,N-dimethylformamide and the solution was stirred at ambient temperature for 2 hours. The solvent was evaporated in vacuo to give an acid chloride as an oil and the oil was added to a mixture of N-methyl-o-toluidine (121 mg) and triethylamine (0.168 mg) in dichloromethane (15 ml). The mixture was stirred at ambient temperature for 2 hours and washed successively with 1N hydrochloric acid, water and brine, and dried over magnesium sulfate. The solvent was evaporated in vacuo to give an oil and the oil was subjected to silica gel column (30 g, 1% methanol in chloroform) to give an oil. The oil was solidified with diethyl ether to give 2-(4'-methylbiphenyl-2-carboxamido)-N-methyl-N-(2-methylphenyl)-5-pyridinecarboxamide (112 mg).

NMR (CDCl$_3$, δ): 2.16 (3H, s), 2.29 (3H, s), 3.35 (3H, s), 6.98–7.27 (8H, m), 7.34–7.44 (2H, m), 7.48–7.57 (2H, m), 7.65 (1H, m), 7.88 (1H, s), 8.03 (2H, d, J=8.5 Hz).

EXAMPLE 5

To a mixture of 4-[2-(4-methylphenyl)benzoyl]-aminobenzoic acid (166 mg) and triethylamine (0.07 ml) in dichloromethane (10 ml) was added diphenylphosphoryl chloride (130 mg) and the solution was stirred at ambient temperature for 1 hour. To the resulting solution were added triethylamine (0.07 ml) and N-methylcyclohexylamine (56.6 mg) and the solution was stirred at ambient temperature for 4 hours. The solution was washed successively with 1N hydrochloric acid, saturated aqueous sodium hydrogen carbonate and brine, and dried over magnesium sulfate. The solvent was evaporated in vacuo to give an oil and the oil was subjected to silica gel column (10 g, 1% methanol in chloroform) to give 4-(4'-methylbiphenyl-2-carboxamido)-N-methyl-N-cyclohexylbenzamide (102 g) as a colorless amorphous.

NMR (CDCl$_3$, δ): 1.08–1.88 (7H, m), 1.64 (3H, s), 2.38 (3H, s), 2.75–2.97 (3H, s), 3.47 (1H, m), 7.02 (1H, s), 7.13–7.57 (9H, m), 7.90 (1H, dd, J=1, 8 Hz).

EXAMPLE 6

A solution of 4-(4'-methylbiphenyl-2-carboxamido)-N-methyl-N-(2-ethoxycarbonylphenyl)benzamide (500 mg) in a mixture of ethanol (20 ml) and 1N sodium hydroxide (2 ml) was heated at reflux for 4 hours and ethanol was evaporated in vacuo. Water (5 ml) was added to the residue and the aqueous solution was adjusted to pH 2 with 1N hydrochloric acid. The precipitate was filtered to give 4-(4'-methylbiphenyl-2-carboxamido)-N-methyl-N-(2-carboxyphenyl)benzamide (435 mg) as a white powder.

NMR (CDCl$_3$+CD$_3$OD, δ): 2.31 (3H, s), 3.41 (3H, s), 7.00 (2H, d, J=8.5 Hz), 7.08–7.55 (13H, m), 7.68 (1H, d, J=8 Hz), 7.83 (1H, d, J=8 Hz).

EXAMPLE 7

To a solution of 4-(4'-methylbiphenyl-2-carboxamido)-N-methyl-N-(2-benzoyloxyphenyl)benzamide (350 mg) in methanol (10 ml) was added potassium carbonate (89.5 mg) and the mixture was stirred at ambient temperature overnight. Chloroform was added to the mixture and the solution was washed with water and brine, and dried over magnesium sulfate. The solvent was evaporated in vacuo to give an oil and the oil was subjected to silica gel column (30 g, 1% methanol in chloroform) to give an oil. The oil was solidified with diethyl ether to give 4-(4'-methylbiphenyl-2-carboxamido)-N-methyl-N-(2-hydroxyphenyl)benzamide (228 mg) as a white powder.

NMR (CDCl$_3$, δ): 2.33 (3H, s), 3.32 (3H, s), 6.70–6.93 (4H, m), 7.05–7.28 (9H, m), 7.33–7.53 (4H, m), 7.83 (1H, d, J=8 Hz).

EXAMPLE 8

A mixture of 4-(4'-methylbiphenyl-2-carboxamido)-N-methyl-N-[2-(3-phthalimidopropyloxy)phenyl]benzamide (545 mg) and hydrazine hydrate (0.212 ml) in ethanol (20 ml) was refluxed for 4 hours. After removal of insoluble material, the filtrate was evaporated in vacuo to give an oil and the oil was subjected to a silica gel column (5% methanol in chloroform) to give 4-(4'-methylbiphenyl-2-carboxamido)-N-methyl-N-[2-(3-aminopropyloxy)phenyl]benzamide (425 mg).

NMR (CDCl$_3$, δ): 1.93 (2H, tt, J=7.5, 7.5 Hz), 2.34 (3H, s), 2.92 (2H, t, J=7.5 Hz), 3.31 (3H, s), 3.98 (2H, m), 6.73–6.83 (2H, m), 6.90–7.01 (4H, m), 7.09–7.54 (9H, m), 7.79 (2H, m).

EXAMPLE 9

To a solution of 4-(4'-methylbiphenyl-2-carboxamido)-N-methyl-N-(2-carboxyphenyl)benzamide (232 mg) in dichloromethane (10 ml) were added oxalyl chloride (0.069 ml) and a few drop of N,N-dimethylformamide and the solution was stirred at ambient temperature for 2 hours. Dichloromethane was evaporated in vacuo to give an acid chloride and conc. ammonia (5 ml) was added to the acid chloride. The mixture was stirred at ambient temperature for 1 hour and the precipitated solid was filtered. The solid was dissolved in chloroform and the solution was subjected to silica gel column (20 g, 2% methanol in chloroform). The product was solidified with diethyl ether to give 4-(4'-methylbiphenyl-2-carboxamido)-N-methyl-N-(2-carbamoylphenyl)benzamide (118 g) as a white powder.

NMR (CDCl$_3$, δ): 2.38 (3H, s), 3.73 (3H, s), 7.22–7.60 (16H, m), 7.78 (1H, m), 7.90 (1H, dd, J=1, 8 Hz), 8.39 (1H, dd, J=1, 8 Hz).

EXAMPLE 10

A mixture of 4-(4'-methylbiphenyl-2-carboxamido)-N-methyl-N-(2-carboxyphenyl)benzamide (232 mg), diphenylphosphoryl azide (151 mg), and triethylamine (0.084 ml) in benzene (10 ml) was refluxed for 5 hours and 1N hydrochloric acid (4 ml) was added to the solution. The mixture was refluxed for 4 hours and the mixture was washed with aqueous saturated sodium hydrogen carbonate and brine. The organic solution was dried over magnesium sulfate and the solvent was evaporated in vacuo to give crude oil. The oil was purified by silica gel column (10 g, 2% methanol in chloroform) and the product was solidified with diethyl ether to give 4-(4'-methylbiphenyl-2-carboxamido)-N-methyl-N-(2-aminophenyl)benzamide (120 mg).

NMR (CDCl$_3$, δ): 2.20 (3H, s), 3.34 (3H, s), 6.96–7.57 (17H, m), 9.05 (2H, br).

EXAMPLE 11

A solution of 4-(4'-methylbiphenyl-2-carboxamido)-N-methyl-N-(2-allylphenyl)benzamide (100 g) and 10% palladium on carbon (20 mg) in methanol (15 ml) was stirred under an atmospheric pressure of hydrogen at ambient temperature. After 3 hours, the reaction mixture was filtered through a bed of Celite, concentrated and then triturated from diethyl ether to give 4-(4'-methylbiphenyl-2-carboxamido)-N-methyl-N-(2-propylphenyl)benzamide (70 mg).

NMR (CDCl$_3$, δ): 0.95 (3H, t, J=7 Hz), 1.35–1.77 (2H, m), 2.22–2.61 (2H, m), 2.36 (3H, s), 3.37 (3H, s), 6.80–6.98 (3H, m), 6.99–7.60 (13H, m), 7.81 (1H, d, J=8 Hz).

EXAMPLE 12

A solution of 4-(4'-methylbiphenyl-2-carboxamido)-N-methyl-N-[2-(5-carboxy-1-pentenyl)phenyl]benzamide (150 mg) in ethanol (10 ml) was shaken under hydrogen atmosphere (3 atm.) in the presence of 10% palladium on carbon (50 mg) for 4 hours. The catalyst was filtered off and the filtrate was evaporated in vacuo and the residue was subjected to silica gel column (29% methanol in chloroform) to give 4-(4'-methylbiphenyl-2-carboxamido)-N-methyl-N-[2-(5-carboxypentyl)phenyl]benzamide (150 mg).

NMR (CDCl$_3$, δ): 1.28–1.46 (3H, m), 1.53–1.60 (3H, m), 2.25–2.68 (4H, m), 2.37 (3H, s), 3.34 (3H, s), 6.92 (2H, d, J=8.5 Hz), 7.02–7.52 (14H, m), 7.77 (1H, d, J=8 Hz).

EXAMPLE 13

To a solution of 4-(4'-methylbiphenyl-2-carboxamido)-N-methyl-N-(2-acetylphenyl)benzamide (200 mg) in methanol (15 ml) was added sodium borohydride (16.4 mg) and the solution was stirred at ambient temperature for 3 hours. Chloroform was added to the mixture and the solution was washed successively with water and brine, and dried over magnesium sulfate. The solvent was evaporated in vacuo to give a syrup and the crude product was purified by silica gel column (chloroform) to give 4-(4'-methylbiphenyl-2-carboxamido)-N-methyl-N-[2-(1-hydroxyethyl)phenyl]-benzamide (150 mg) as a white solid.

NMR (CDCl$_3$, δ): 1.12 (3H×⅓, d, J=7 Hz), 1.41 (3H×⅔, d, J=7 Hz), 2.35 (3H, s), 2.35 (3H×⅔, s), 3.42 (3H×⅓, s), 4.91 (1H, m), 6.84–6.95 (2H, m), 7.10–7.54 (14H, m), 7.82 (1H, d, J=8 Hz).

EXAMPLE 14

A solution of 4-(4'-methylbiphenyl-2-carboxamido)-N-methyl-N-(2-ethoxycarbonylphenyl)benzamide (493 mg) in tetrahydrofuran (20 ml) was cooled in an ice bath. Lithium aluminum hydride (1M solution in tetrahydrofuran, 2.5 ml) was added dropwise to the solution and the mixture was stirred at the same temperature for 2 hours. Water was slowly added to the solution and resulting mixture was acidified with 1N hydrochloric acid. The solution was extracted with chloroform and the organic solution was washed with water and brine, and dried over magnesium sulfate. The solvent was evaporated in vacuo and the residue was subjected to silica gel column (20 g, 2% methanol in chloroform). The product was solidified with diethyl ether to give 4-(4'-methylbiphenyl-2-carboxamido)-N-methyl-N-(2-hydroxymethylphenyl)benzamide (245 mg) as a white powder.

NMR (CDCl$_3$+CD$_3$OD, δ): 2.31 (3H, s), 3.35 (3H, s), 4.42 (1H, d, J=13 Hz), 4.57 (1H, d, J=13 Hz), 6.99–7.68 (17H, m).

EXAMPLE 15

A mixture of 4-(4'-methylbiphenyl-2-carboxamido)-N-methyl-N-(2-hydroxymethylphenyl)benzamide (100 mg) and acetic anhydride (34 mg) in pyridine (5 ml) was stirred at ambient temperature for 3 days and the solvent was evaporated in vacuo. The residue was dissolved in chloroform and the organic solution was washed successively with 1N hydrochloric acid, water and brine, and dried over magnesium sulfate. The solvent was evaporated in vacuo to give an oil and the oil was solidified with diethyl ether to give 4-(4'-methylbiphenyl-2-carboxamido)-N-methyl-N-(2-acetoxymethylphenyl)benzamide (105 mg) as a white powder.

NMR (CDCl$_3$, δ): 2.08 (3H, s), 2.34 (3H, s), 3.38 (3H, s), 4.92 (1H, d, J=12 Hz), 5.04 (1H, d, J=12 Hz), 6.87–6.97 (2H, m), 7.04–7.56 (14H, m), 7.82 (1H, d, J=8 Hz).

EXAMPLE 16

A mixture of 4-(4'-methylbiphenyl-2-carboxamido)-N-methyl-N-(2-hydroxymethylphenyl)benzamide (100 mg) and glutaric anhydride (50.7 mg) in pyridine (5 ml) was stirred at 90° C. for 10 hours and the solvent was evaporated in vacuo. The residue was dissolved in chloroform and washed successively with 1N hydrochloric acid, water and brine. The organic layer was dried over magnesium sulfate and the solvent was evaporated in vacuo to give an oil. The oil was purified by preparative thin layer chromatography to give 4-(4'-methylbiphenyl-2-carboxamido)-N-methyl-N-[2-(3-carboxypropionyloxymethyl)phenyl]benzamide (20 mg) as a white solid.

NMR (CDCl$_3$, δ): 1.93 (2H, tt, J=7, 7 Hz), 2.29–2.42 (7H, m), 3.35 (3H, s), 4.89 (1H, d, J=13 Hz), 5.04 (1H, d, J=13 Hz), 6.91 (2H, d, J=8.5 Hz), 7.05–7.54 (14H, m), 7.29 (1H, d, J=8 Hz).

EXAMPLE 17

A mixture of 4-(4'-methylbiphenyl-2-carboxamido)-N-methyl-N-(2-hydroxymethylphenyl)benzamide (225 mg) and magnesium dioxide (651 mg) in chloroform (10 ml) was refluxed for 3 hours and the solution was filtered through Celite. The filtrate was evaporated in vacuo to give a crude oil and the oil was subjected to silica gel column (1% methanol in chloroform). The product was solidified with diethyl ether to give 4-(4'-methylbiphenyl-2-carboxamido)-N-methyl-N-(2-formylphenyl)benzamide (209 mg) as a white powder.

NMR (CDCl$_3$, δ): 2.35 (3H, s), 3.47 (3H, s), 6.84–6.96 (2H, m), 7.06–7.60 (13H, m), 7.75–7.84 (2H, m), 10.8 (1H, s).

EXAMPLE 18

A mixture of 4-(4'-methylbiphenyl-2-carboxamido)-N-methyl-N-(2-formylphenyl)benzamide (150 mg), methylamine (38% in methanol, 0.5 ml) and 3 Å molecular sieves (500 mg) in methanol (10 ml) was stirred at ambient temperature overnight. Sodium borohydride (39 mg) was added to the solution and the mixture was stirred at ambient temperature for 4 hours. The mixture was diluted with chloroform and the solution was washed with saturated aqueous sodium hydrogen carbonate and brine. The organic phase was dried over magnesium sulfate and the solvent was evaporated in vacuo to give crude oil. The oil was purified by silica gel column (10 g, 2% methanol in chloroform) and the product was solidified with diethyl ether to give 4-(4'-methylbiphenyl-2-carboxamido)-N-methyl-N-(2-methylaminomethylphenyl)benzamide (160 mg) as a white powder.

NMR (CDCl$_3$, δ): 2.31 (3H, s), 2.37 (3H, s), 3.36 (3H, s), 3.49 (1H, d, J=14 Hz), 3.62 (1H, d, J=14 Hz), 6.83–6.96 (3H, m), 7.06–7.54 (13H, m), 7.82 (1H, d, J=8 Hz).

EXAMPLE 19

The following compound was obtained according to a similar manner to that of Example 18.

4-(4-Methylbiphenyl-2-carboxamido)-N-methyl-N-[2-(1-methylaminoethyl)phenyl]benzamide NMR (CDCl$_3$, δ): 1.36 (3H, d, J=7 Hz), 2.17 (3H, s), 2.32 (3H, s), 3.39 (3H, s), 3.77 (1H, q, J=7 Hz), 6.54–6.66 (2H, m), 6.83–7.57 (13H, m), 7.73–7.87 (2H, m).

EXAMPLE 20

To a solution of 4-(4'-methylbiphenyl-2-carboxamido)-N-methyl-N-(2-methylaminomethylphenyl)benzamide (154 mg) in a mixture of methanol (10 ml) and acetic acid (0.5 ml) were added aqueous formaldehyde (0.2 ml) and sodium cyanoborohydride (20.9 mg) and the solution was stirred at ambient temperature for 4 hours. The mixture was diluted with chloroform and the solution was washed with saturated aqueous sodium hydrogen carbonate and brine. The organic phase was dried over magnesium sulfate and the solvent was evaporated in vacuo to give crude oil. The oil was purified by silica gel column (10 g, 2% methanol in chloroform) and the product was solidified with diethyl ether to give 4-(4'-methylbiphenyl-2-carboxamido)-N-methyl-N-(2-dimethylaminomethylphenyl)benzamide (65 mg) as a white powder.

NMR (CDCl$_3$, δ): 2.16 (6H, s), 2.35 (3H, s), 3.08 (1H, d, J=14 Hz), 3.27 (1H, d, J=14 Hz), 3.38 (3H, s), 6.83–6.92 (3H, m), 7.05–7.57 (13H, m), 7.82 (1H, d, J=8 Hz).

EXAMPLE 21

The following compounds were obtained according to a similar manner to that of Example 20.

1) 4-(4'-Methylbiphenyl-2-carboxamido)-N-methyl-N-[2-(3-dimethylaminopropyloxy)phenyl]benzamide NMR (CDCl$_3$, δ): 1.95 (2H, tt, J=7.5, 7.5 Hz), 2.23 (6H, s), 2.33 (3H, s), 2.42 (2H, t, J=7.5 Hz), 3.32 (3H, s), 3.90–4.05 (4H, m), 6.72–6.98 (5H, m), 7.08–7.54 (10H, m), 7.82 (2H, d, J=8.5 Hz).

2) 4-(4'-Methylbiphenyl-2-carboxamido)-N-methyl-N-[2-(1-dimethylaminoethyl)phenyl]benzamide NMR (CDCl$_3$, δ): 0.51 (3H×⅔, d, J=7 Hz), 1.17 (3H×⅓, d, J=7 Hz), 2.08 (6H, s), 2.33 (3H, s), 2.99–3.23 (1H, m), 3.38 (3H×⅓, s), 3.40 (3H×⅔, s), 6.84–6.98 (4H, m), 7.15–7.56 (11H, m), 7.78 (2H, d, J=8.5 Hz).

EXAMPLE 22

The following compounds were obtained according to a similar manner to that of Example 4.

1) 6-(4'-Methylbiphenyl-2-carboxamido)-N-methyl-N-[2-(3-phthalimidoprop-1-yloxy)phenyl]nicotinamide NMR (CDCl$_3$, δ): 2.07 (2H, m), 2.32 (3H, s), 3.36 (3H, s), 3.85–3.97 (4H, m), 6.80 (2H, m), 6.96 (1H, d, J=7 Hz), 7.12–7.61 (10H, m), 7.68 (2H, m), 7.81 (2H, m), 7.98–8.11 (2H, m).

2) 2-Methoxy-4-(4'-methylbiphenyl-2-carboxamido)-N-methyl-N-[2-(3-phthalimidoprop-1-yloxy)phenyl]benzamide NMR (CDCl$_3$, δ): 2.23 (2H, m), 2.36 (3H, s), 3.38 (3H, s), 3.64 (3H, s), 3.84–4.01 (4H, m), 6.18 (1H, d, J=7 Hz), 6.64–7.55 (13H, m), 7.70–7.74 (2H, m), 7.80–7.88 (3H, m).

3) 3-Chloro-4-(4'-methylbiphenyl-2-carboxamido)-N-methyl-N-[2-(3-phthalimidoprop-1-yloxy)phenyl]benzamide NMR (CDCl$_3$, δ): 2.21 (2H, m), 2.33 (3H, s), 3.34 (3H, s), 3.86–4.03 (4H, m), 6.77–6.82 (2H, m), 6.95 (1H, m), 7.09–7.55 (11H, m), 7.68–7.72 (2H, m), 7.80–7.85 (3H, m).

4) 3-Chloro-4-(4'-methylbiphenyl-2-carboxamido)-N-[2-benzyloxy-4-chlorophenyl]-N-methylbenzamide NMR (CDCl$_3$, δ): 2.34 (3H, s), 3.31 (3H, s), 4.83–5.10 (2H, m), 6.80–6.93 (2H, m), 6.93–7.07 (2H, m), 7.14 (2H, d, J=8 Hz), 7.21–7.59 (12H, m), 7.79 (1H, d, J=8 Hz), 8.28 (1H, br d, J=8 Hz).

5) 2-Methoxy-4-(4'-methylbiphenyl-2-carboxamido)-N-[2-benzyloxy-4-chlorophenyl]-N-methylbenzamide NMR (CDCl$_3$, δ): 2.36 (3H, s), 3.32 (3H, s), 3.60 (3H, s), 4.96 (1H, d, J=10 Hz), 5.04 (1H, d, J=10 Hz), 6.20 (1H, d, J=9 Hz), 6.72 (1H, d, J=9 Hz), 6.78–6.92 (4H, m), 6.97 (1H, d, J=9 Hz), 7.15–7.56 (12H, m), 7.84 (1H, d, J=9 Hz).

6) 4-(4'-Methylbiphenyl-2-carboxamido)-2-nitro-N-[2-(5-ethoxycarbonylpent-1-yloxy)phenyl]-N-methylbenzamide NMR (CDCl$_3$, δ): 1.26 (3H, t, J=7 Hz), 1.42–1.62 (2H, m), 1.67–1.81 (2H, m), 1.81–1.97 (2H, m), 2.27–2.34 (2H, m), 2.39 (3H, s), 3.37 (3H, s), 3.96 (2H, t, J=7 Hz), 4.13 (2H, q, J=7 Hz), 6.69 (1H, dd, J=9, 9 Hz), 6.74 (1H, d, J=9 Hz), 6.94–7.63 (13H, m), 7.84 (1H, d, J=9 Hz).

7) 2-Methoxy-4-(methylphenyl-2-carboxamido)-N-(2-benzyloxy-4-chlorophenyl)-N-methylbenzamide NMR (CDCl$_3$, δ): 2.46 (3H, s), 3.33 (3H, s), 3.67 (3H, s), 4.99 (1H, d, J=10 Hz), 5.06 (1H, d, J=10 Hz), 6.68–6.79 (2H, m), 6.85 (1H, d, J=2 Hz), 6.95–7.06 (2H, m), 7.16–7.60 (11H, m).

8) 2-Methoxy-4-(methylphenyl-2-carboxamido)-N-[2-(5-ethoxycarbonylpent-1-yloxy)phenyl]-N-methylbenzamide NMR (CDCl$_3$, δ): 1.26 (3H, t, J=7 Hz), 1.46–1.62 (2H, m), 1.62–1.81 (2H, m), 1.81–1.96 (2H, m), 2.35 (2H, t, J=7

Hz), 2.44 (3H, s), 3.31 (3H, s), 3.70 (3H, s), 3.95 (2H, t, J=7 Hz), 4.12 (2H, q, J=7 Hz), 6.64–6.79 (3H, m), 6.97–7.45 (8H, m), 7.58 (1H, s).

9) 4-(Methylphenyl-2-carboxamido)-2-nitro-N-[2-(5-ethoxycarbonylpent-1-yloxy)phenyl]-N-methylbenzamide NMR (CDCl$_3$, δ): 1.26 (3H, t, J=7 Hz), 1.46–1.65 (2H, m), 1.67–1.82 (2H, m), 1.82–1.98 (2H, m), 2.37 (2H, t, J=7 Hz), 2.47 (3H, s), 3.35 (3H, s), 4.00 (2H, t, J=7 Hz), 4.13 (2H, q, J=7 Hz), 6.73 (1H, dd, J=9, 9 Hz), 6.79 (1H, d, J=9 Hz), 7.07–7.20 (2H, m), 7.20–7.49 (5H, m), 7.83 (1H, d, J=9 Hz), 8.03 (1H, br s), 8.11 (1H, br s).

EXAMPLE 23

The following compounds were obtained according to a similar manner to that of Example 6.

1) 3-Methoxy-4-(4'-methylbiphenyl-2-carboxamido)-N-methyl-N-(2-carbonylphenyl)benzamide NMR (CDCl$_3$, δ): 2.29 (3H, s), 3.33 (3H, s), 3.40 (3H, s), 6.68–6.88 (3H, m), 7.11 (2H, d, J=8.5 Hz), 7.18–7.51 (6H, m), 7.69 (1H, m), 7.80 (1H, d, J=7.5 Hz), 7.90 (1H, m), 8.18 (1H, m).

2) 4-(4'-Methylbiphenyl-2-carboxamido)-N-methyl-N-[2-[(E)-6-carboxy-1-hexen-1-yl]benzamide NMR (CDCl$_3$, δ): 1.53 (2H, m), 1.68 (2H, m), 2.25 (2H, m), 2.34 (3H, s), 2.36 (2H, t, J=7.5 Hz), 3.33 (3H, s), 6.13 (1H, dt, J=15, 7.5 Hz), 6.43 (1H, d, J=15 Hz), 6.75–7.42 (14H, m), 7.50 (1H, t, J=7 Hz), 7.80 (1H, d, J=7 Hz).

3) 4-(4'-Methylbiphenyl-2-carboxamido)-N-methyl-N-[2-[(Z)-6-carboxy-1-hexen-1-yl]phenyl]benzamide NMR (CDCl$_3$, δ): 1.25–1.39 (4H, m), 1.46–1.63 (4H, m), 2.26–2.27 (1H, m), 2.29 (2H, t, J=7.5 Hz), 2.37 (3H, s), 2.49 (1H, m), 2.36 (3H, s), 3.63 (3H, s), 6.92 (2H, d, J=8.5 Hz), 6.99–7.44 (12H, m), 7.51 (1H, t, J=7 Hz), 7.80 (1H, d, J=7 Hz).

4) 4-(4'-Methylbiphenyl-2-carboxamido)-N-methyl-N-[2-(6-carboxyhex-1-yl)phenyl]benzamide NMR (CDCl$_3$, δ): 1.27–1.90 (4H, m), 1.48–1.66 (4H, m), 2.30 (2H, m), 2.33 (3H, s), 2.47 (2H, m), 3.37 (3H, s), 6.87–6.96 (3H, m), 7.04–7.53 (12H, m), 7.80 (1H, d, J=7 Hz).

5) 4-(4'-Methylbiphenyl-2-carboxamido)-N-methyl-N-[2-[N-(3-carboxyprop-1-yl)oxyimino]methylphenyl]benzamide NMR (CDCl$_3$, δ): 2.02 (2H, tt, J=7.5, 7.5 Hz), 2.33 (3H, s), 2.46 (2H, t, J=7.5 Hz), 3.37 (3H, s), 4.19 (2H, t, J=7.5 Hz), 6.88–6.98 (3H, m), 7.02–7.29 (8H, m), 7.36–7.53 (3H, m), 7.76 (1H, d, J=7 Hz), 7.80 (1H, d, J=7 Hz), 8.10 (1H, s).

6) 4-(4'-Methylbiphenyl-2-carboxamido)-N-methyl-N-[2-(5-carboxypent-1-ylthio)phenyl]benzamide NMR (CDCl$_3$, δ): 1.50 (2H, m), 1.61–1.73 (4H, m), 2.33 (2H, m), 2.34 (3H, s), 2.88 (2H, m), 3.30 (3H, s), 6.86–6.99 (5H, m), 7.10–7.20 (4H, m), 7.22–7.30 (3H, m), 7.34–7.44 (2H, m), 7.49 (1H, dd, J=7, 7 Hz), 7.80 (1H, d, J=7 Hz).

7) 4-(4'-Methylbiphenyl-2-carboxamido)-N-methyl-N-[2-(5-carboxy-4-penten-1-ylcxy)phenyl]benzamide MASS (m/z): 549 (M+1).

8) 4-(4'-Methylbiphenyl-2-carboxamido)-N-methyl-N-[2-[N-(2-carboxyethyl)-N-(t-butoxycarbonyl)aminoethyloxy]phenyl]benzamide NMR (CDCl$_3$, δ): 1.44 (9H, s), 2.36 (3H, s), 2.63 (2H, m), 3.32 (3H, s), 3.42–3.43 (4H, m), 3.83 (1H, br), 4.06 (1H, br), 6.75–6.99 (4H, m), 7.03–7.11 (2H, m), 7.14–7.22 (4H, m), 7.28 (2H, d, J=8.5 Hz), 7.36–7.46 (2H, m), 7.51 (1H, dd, J=7, 7 Hz), 7.81 (2H, d, J=7 Hz).

9) 4-(4'-Methylbiphenyl-2-carboxamido)-N-methyl-N-[2-[2-(carboxymethoxyimino)ethoxy]phenyl]benzamide MASS (m/z): 552 (M+1).

10) 4-(4'-Methylbiphenyl-2-carboxamido)-N-methyl-N-[2-(4-carboxyphenylmethoxy)phenyl]benzamide NMR (CDCl$_3$, δ): 2.32 (3H, s), 3.39 (3H, s), 5.03 (2H, m), 6.80 (1H, d, J=7 Hz), 6.85–6.93 (3H, m), 7.10–7.21 (6H, m), 7.30 (2H, d, J=8.5 Hz), 7.34–7.52 (5H, m), 7.82 (1H, d, J=7 Hz), 8.11 (2H, d, J=8.5 Hz).

11) 4-(4'-Methylbiphenyl-2-carboxamido)-N-methyl-N-[2-(5-carboxypyrid-2-yl)methoxy]phenyl]benzamide NMR (CDCl$_3$, δ): 2.35 (3H, s), 3.37 (3H, s), 5.28 (2H, s), 6.78–7.02 (6H, m), 7.12–7.24 (5H, m), 7.30 (2H, d, J=8.5 Hz), 7.39–7.55 (3H, m), 7.81 (1H, d, J=7 Hz), 8.51 (1H, m), 9.15 (1H, m).

12) 4-(4'-Methylbiphenyl-2-carboxamido)-N-methyl-N-[2-(5-carboxypent-1-yloxy)pyrid-3-yl]benzamide NMR (CDCl$_3$, δ): 1.31 (2H, m), 1.61–1.79 (4H, m), 2.34 (2H, t, J=7.5 Hz), 2.37 (3H, s), 3.28 (3H, s), 3.96 (2H, br), 5.97 (1H, dd, J=7, 7 Hz), 6.94 (1H, d, J=7 Hz), 7.00 (2H, d, J=8.5 Hz), 7.13–7.31 (8H, m), 7.36–7.52 (3H, m), 7.81 (1H, d, J=7 Hz).

13) 4-(4'-Methylbiphenyl-2-carboxamido)-N-methyl-N-[3-(5-carboxypent-1-yloxy)pyrid-2-yl]benzamide NMR (CDCl$_3$, δ): 1.45 (2H, m), 1.63–1.75 (4H, m), 2.31–2.41 (2H, m), 2.32 (3H, s), 3.39 (2H, s), 3.72 (2H, m), 6.90–7.55 (13H, m), 7.81 (1H, d, J=7.5 Hz), 8.03 (1H, d, J=7 Hz).

14) 3-Methyl-4-(4'-methylbiphenyl-2-carboxamido)-N-methyl-N-[3-chloro-2-(5-carboxypenten-1-yloxy)phenyl]benzamide NMR (CDCl$_3$, δ): 1.41 (3H, s), 1.52 (2H, m), 1.67–1.85 (4H, m), 2.34 (3H, s), 3.90 (2H, m), 6.73–7.02 (5H, m), 7.09–7.18 (3H, m), 7.30–7.54 (5H, m), 7.83 (1H, d, J=7 Hz), 7.97 (1H, d, J=7 Hz).

15) 4-(4'-Methylbiphenyl-2-carboxamido)-N-methyl-N-[4-methyl-2-(5-carboxypyrid-2-ylmethoxy)phenyl]benzamide NMR (CDCl$_3$, δ): 2.29 (3H, s), 2.35 (3H, s), 3.22 (3H, s), 5.22 (2H, m), 6.61 (7H, d), 6.72 (1H, s), 7.83 (1H, d), 7.92 (2H, d, J=8.5 Hz), 7.02 (1H, s), 7.14–7.23 (4H, m), 7.28 (2H, d, J=8.5 Hz), 7.34–7.53 (3H, m), 7.81 (1H, d), 8.50 (1H, m), 9.13 (1H, m).

16) 4-(4'-Nitrobiphenyl-2-carboxamido)-N-methyl-N-[2-(5-carboxypyrid-2-ylmethoxy)phenyl]benzamide NMR (CDCl$_3$, δ): 3.31 (3H, s), 5.25 (2H, m), 6.80–6.99 (3H, m), 7.06–7.22 (4H, m), 7.34–7.54 (6H, m), 7.63 (2H, d, J=8.5 Hz), 8.14 (2H, d, J=8.5 Hz), 8.49 (1H, m), 9.09 (1H, m).

17) 4-(2-Phenylpyridlne-3-carboxamido)-N-[2-(5-carboxypent-1-yloxy)-4-chlorophenyl]-N-methylbenzamide NMR (CDCl$_3$, δ): 1.36–1.55 (2H, m), 1.56–1.82 (4H, m), 2.31 (2H, t, J=7 Hz), 3.28 (3H, s), 3.68–3.97 (2H, m), 6.73–6.86 (2H, m), 6.96 (1H, d, J=9 Hz), 7.18 (2H, d, J=9 Hz), 7.30–7.58 (6H, m), 7.72 (2H, d, J=9 Hz), 7.77–7.91 (1H, m), 8.44–8.54 (1H, m), 8.72–8.83 (1H, m).

18) 4-(4'-Methylbiphenyl-2-carboxamido)-N-[2-(5-carboxypent-1-yloxy)-4-chlorophenyl]-N-methylbenzamide NMR (CDCl$_3$, δ): 1.44–1.58 (2H, m), 1.63–1.86 (4H, m), 2.36 (3H, s), 2.38 (2H, t, J=7 Hz), 3.29 (3H, s), 3.76–3.97 (2H, m), 6.74–6.82 (2H, m), 6.87–7.02 (4H, m), 7.11–7.23 (4H, m), 7.29 (2H, d, J=9 Hz), 7.34–7.56 (3H, m), 7.76–7.85 (1H, m).

19) 3-Chloro-4-(4'-methylbiphenyl-2-carboxamido)-N-[2-(5-carboxypent-1-yloxy)-4-chlorophenyl]-N-methylbenzamide NMR (CDCl$_3$, δ): 1.46–1.60 (2H, m), 1.65–1.76 (4H, m), 2.36 (3H, s), 2.40 (2H, t, J=7 Hz), 3.28 and 3.33 (total 3H, s), 3.76–4.00 (2H, m), 6.75–6.86 (2H, m), 6.87–7.23 (4H, m), 7.24–7.37 (3H, m), 7.37–7.49 (2H, m), 7.49–7.61 (2H, m), 7.75–7.85 (1H, m), 8.18–8.36 (1H, m).

20) 2-Methoxy-4-(4'-methylbiphenyl-2-carboxamido)-N-[2-(5-carboxypent-1-yloxy)-4-chlorophenyl]-N-methylbenzamide NMR (CDCl$_3$, δ): 1.48–1.63 (2H, m), 1.64–1.90 (4H, m), 2.28–2.44 (5H, m), 3.25 and 3.29 (total 3H, s), 3.61 (3H, s), 3.75–3.94 (2H, m), 6.20–6.33 (1H, m), 6.62–6.74 (2H, m), 6.79 (1H, s), 6.86–7.33 (7H, m), 7.33–7.56 (3H, m), 7.77–7.86 (1H, m).

21) 2-Chloro-4-(4'-methylbiphenyl-2-carboxamido)-N-[2-(5-carboxypent-1-yloxy)-4-chlorophenyl]-N-methylbenzamide NMR (CDCl$_3$, δ): 1.48–1.64 (2H, m), 1.67–1.79 (2H, m), 1.79–1.93 (2H, m), 2.33–2.45 (5H, m), 3.30 and 3.34 (total 3H, s), 3.90–3.99 (2H, m), 6.66–7.56 (14H, m), 7.76–7.85 (1H, m).

22) 2-Chloro-4-(4'-methylbiphenyl-2-carboxamido)-N-[2-(5-carboxypent-1-yloxy)phenyl]-N-methylbenzamide NMR (CDCl$_3$, δ): 1.49–1.67 (2H, m), 1.67–1.97 (4H, m), 2.33–2.47 (5H, m), 3.34 (3H, s), 3.91–4.04 (2H, m), 6.66–6.82 (2H, m), 6.82–7.04 (4H, m), 7.05–7.59 (9H, m), 7.75–7.85 (1H, m).

23) 3-Methoxy-4-(2'-methylbiphenyl-2-carboxamido)-N-[2-(5-carboxypent-1-yloxy)-4-methylphenyl]-N-methylbenzamide NMR (CDCl$_3$, δ): 1.42–1.58 (2H, m), 1.63–1.83 (4H, m), 2.11 (3H, s), 2.27 (3H, s), 2.38 (2H, t, J=7 Hz), 3.30 (3H, s), 3.47 (3H, s), 3.70–3.96 (2H, m), 6.58 (2H, br s), 6.73–6.90 (3H, m), 7.14–7.28 (5H, m), 7.40–7.56 (2H, m), 7.77 (1H, s), 7.94 (1H, d, J=9 Hz), 8.15 (1H, d, J=9 Hz).

24) 4-(2',4'-Dimethylbiphenyl-2-carboxamido)-3-methyl-N-[2-(5-carboxypent-1-yloxy)-4-methylphenyl]-N-methylbenzamide NMR (CDCl$_3$, δ): 1.43–1.59 (2H, m), 1.64–1.86 (4H, m), 2.06 (3H, s), 2.26 (3H, s), 2.32 (3H, s), 2.39 (2H, t, J=7 Hz), 3.30 (3H, s), 3.47 (3H, s), 3.73–3.98 (2H, m), 6.59 (2H, br s), 6.74–6.92 (3H, m), 7.03 (2H, d, J=9 Hz), 7.11 (1H, d, J=9 Hz), 7.21 (1H, d, J=9 Hz), 7.39–7.54 (2H, m), 7.83 (1H, s), 7.96 (1H, d, J=9 Hz), 8.18 (1H, d, J=9 Hz).

25) 3-Methoxy-4-(4'-nitrobiphenyl-2-carboxamido)-N-[2-(5-carboxypent-1-yloxy)-4-methylphenyl]-N-methylbenzamide NMR (CDCl$_3$, δ): 1.43–1.57 (2H, m), 1.63–1.83 (4H, m), 2.30 (3H, s), 2.38 (2H, t, J=7 Hz), 3.30 (3H, s), 3.50 (3H, s), 3.71–3.97 (2H, m), 6.56–6.65 (2H, m), 6.81–6.93 (3H, m), 7.42 (1H, d, J=9 Hz), 7.48–7.62 (4H, m), 7.70–7.80 (2H, m), 8.09 (1H, d, J=9 Hz), 8.18 (2H, d, J=9 Hz).

26) 4-(4'-Aminobiphenyl-2-carboxamid)-N-[2-(5-carboxypent-1-yloxy)-4-methylphenyl]-N-methylbenzamide NMR (CDCl$_3$, δ): 1.45–1.59 (2H, m), 1.61–1.82 (4H, m), 2.26 (3H, s), 2.37 (2H, t, J=7 Hz), 3.28 (3H, s), 3.69–3.97 (2H, m), 6.51–6.64 (2H, m), 6.76 (2H, d, J=9 Hz), 6.84–7.08 (4H, m), 7.15–7.28 (4H, m), 7.31–7.52 (3H, m), 7.86 (1H, d, J=9 Hz).

27) 4-(4'-Methylbiphenyl-2-carboxamido)-2-nitro-N-[2-(5-carboxypent-1-yloxy)phenyl]-N-methylbenzamide NMR (CDCl$_3$, δ): 1.50–1.68 (2H, m), 1.68–1.82 (2H, m), 1.82–1.96 (2H, m), 2.34–2.48 (2H, m), 2.39 (3H, s), 3.36 (3H, s), 3.97 (2H, t, J=7 Hz), 6.70 (1H, dd, J=9, 9 Hz), 6.76 (1H, d, J=9 Hz), 7.02–7.64 (13H, m), 7.83 (1H, d, J=9 Hz).

28) 4-Methylphenyl-2-carboxamido)-N-methyl-N-[4-methyl-2-[5-(carboxypent-1-yloxy)phenyl]benzamide NMR (CDCl$_3$, δ): 1.44–1.59 (2H, m), 1.62–1.86 (4H, m), 2.28 (3H, s), 2.37 (2H, t, J=7 Hz), 2.45 (3H, s), 3.30 (3H, s), 3.76–3.98 (2H, m), 6.55–6.66 (2H, m), 6.91 (1H, d, J=9 Hz), 7.16–7.47 (8H, m), 7.67 (1H, br s).

29) 4-(4'-Methylbiphenyl-2-carboxamido)-N-methyl-N-[2-(5-carboxypentyloxy)phenyl]benzamide NMR (CDCl$_3$, δ): 1.46–1.61 (2H, m), 1.64–1.86 (4H, m), 2.36 (3H, s), 2.39 (2H, t, J=7 Hz), 3.32 (3H, s), 3.78–3.98 (2H, m), 6.74–6.84 (2H, m), 6.87–7.04 (4H, m), 7.11–7.24 (5H, m), 7.29 (2H, d, J=9 Hz), 7.34–7.56 (3H, m), 7.81 (1H, d, J=9 Hz).

30) 4-(4'-Methylbiphenyl-2-carboxamido)-N-methyl-N-(2-carboxymethoxyphenyl)benzamide NMR (DMSO-d$_6$, δ): 2.28 (3H, s), 3.22 (3H, s), 4.77 (2H, s), 6.76–6.82 (1H, m), 6.89–7.00 (2H, m), 7.10–7.36 (9H, m), 7.40–7.57 (4H, m).

31) 4-(4'-Methylbiphenyl-2-carboxamido)-N-methyl-N-(2-carboxymethylphenyl)benzamide NMR (CDCl$_3$, δ): 2.33 (3H, s), 3.30–3.42 (2H, m), 3.39 (3H, s), 6.90 (2H, d, J=8 Hz), 7.08–7.52 (14H, m), 6.69 and 7.74 (total 1H, d, J=8 Hz).

32) 4-(4'-Methylbiphenyl-2-carboxamido)-N-methyl-N-[(2-carboxymethoxy-4-methyl)phenyl]benzamide Rf: 0.06 (n-hexane:ethyl acetate=1:2).

33) 3-Methoxy-4-(4'-methylbiphenyl-2-carboxamido)-N-methyl-N-(2-carboxymethoxyphenyl)benzamide Rf: 0.09 (10% methanol in chloroform).

34) 4-(4'-Methylbiphenyl-2-carboxamido)-N-methyl-N-[2-(4-carboxybutoxy)phenyl]benzamide NMR (CDCl$_3$, δ): 1.73–1.88 (4H, m), 2.84 (3H, s), 2.92 (2H, t, J-7 Hz), 3.31 (3H, s), 3.75–3.98 (2H, m), 6.76 (1H, d, J=9 Hz), 6.81 (1H, d, J=9 Hz), 6.92 (2H, br d, J=9 Hz), 7.02 (2H, br d, J=9 Hz), 7.09–7.23 (4H, m), 7.23–7.32 (2H, m), 7.33–7.53 (3H, m), 7.79 (1H, d, J=9 Hz).

35) 4-(4'-Methylbiphenyl-2-carboxamido)-N-methyl-N-[2-(3-carboxypropoxy)phenyl]benzamide NMR (CDCl$_3$, δ): 1.99–2.16 (2H, m), 2.34 (3H, s), 2.52 (3H, t, J=7 Hz), 3.33 (3H, s), 3.78–4.03 (2H, m), 6.72–6.86 (2H, m), 6.86–7.06 (4H, m), 7.09–7.32 (7H, m), 7.33–7.45 (2H, m), 7.46–7.64 (1H, m), 7.78 (1H, d, J=9 Hz).

36) 4-(4'-Methylbiphenyl-2-carboxamido)-N-methyl-N-[2-(7-carboxyheptyloxy)phenyl]benzamide NMR (CDCl$_3$, δ): 1.31–1.53 (6H, m), 1.58–1.71 (2H, m), 1.71–1.83 (2H, m), 2.35 (2H, t, J=7 Hz), 2.36 (3H, s), 3.30 (3H, s), 3.78–3.97 (2H, m), 6.72–6.83 (2H, m), 6.87–7.06 (4H, m), 7.09–7.24 (5H, m), 7.28 (2H, d, J=9 Hz), 7.34–7.56 (3H, m), 7.79 (1H, d, J=9 Hz).

37) 4-(4'-Methylbiphenyl-2-carboxamido)-N-methyl-N-[2-(5-carboxypentyloxy)-4-methylphenyl]benzamide NMR (CDCl$_3$, δ): 1.46–1.61 (2H, m), 1.64–1.87 (4H, m), 2.30 (3H, s), 2.38 (3H, s), 2.36–2.46 (2H, m), 3.31 (3H, s), 3.77–3.99 (2H, m), 4.12–4.80 (1H, br s), 6.60 (2H, br s), 6.86 (1H, d, J=9 Hz), 6.90–7.04 (3H, m), 7.13–7.26 (4H, m), 7.31 (2H, d, J=9 Hz), 7.36–7.56 (3H, m), 7.82 (1H, d, J=9 Hz).

38) 4-(4'-Methylbiphenyl-2-carboxamido)-N-methyl-N-[2-(5-carboxypentyloxy)-5-methylphenyl]benzamide NMR (CDCl$_3$, δ): 1.43–1.56 (2H, m), 1.62–1.83 (4H, m), 2.17 (3H, s), 2.36 (3H, s), 2.37 (2H, t, J=7 Hz), 3.30 (3H, s), 3.71–3.94 (2H, m), 6.66 (1H, d, J=9 Hz), 6.82 (1H, s), 6.87–7.00 (4H, m), 7.14–7.25 (16H, m), 7.29 (2H, d, J=9 Hz), 7.35–7.46 (2H, m), 7.51 (1H, dd, J=9, 9 Hz), 7.81 (1H, d, J=9 Hz).

39) 4-(4'-Methylbiphenyl-2-carboxamido)-N-methyl-N-[2-(6-carboxyhexyloxy)phenyl]benzamide NMR (CDCl$_3$, δ): 1.37–1.56 (4H, m), 1.61–1.84 (4H, m), 2.36 (3H, s), 2.37 (2H, t, J=7 Hz), 3.33 (3H, s), 3.76–3.99 (2H, m), 6.74–6.83 (2H, m), 6.87–7.03 (4H, m), 7.10–7.24 (5H, m), 7.29 (2H, d, J=9 Hz), 7.34–7.56 (3H, m), 7.81 (1H, d, J=9 Hz).

40) 3-Methoxy-4-(4'-methylbiphenyl-2-carboxamido)-N-methyl-N-[2-(5-carboxypentyloxy)-4-methylphenyl]benzamide NMR (CDCl₃, δ): 1.42–1.60 (2H, m), 1.61–1.95 (4H, m), 2.28 (3H, s), 2.34 (3H, s), 2.31–2.45 (2H, m), 3.30 (3H, s), 3.43 (3H, s), 3.74–3.98 (2H, m), 6.60 (2H, br d, J=9 Hz), 6.76–6.94 (3H, m), 7.15 (2H, d, J=9 Hz), 7.24–7.33 (2H, m), 7.34–7.55 (3H, m), 7.69 (1H, s), 7.79 (1H, d, J=9 Hz), 8.16 (1H, d, J=9 Hz).

41) 4-(Biphenyl-2-carboxamido)-N-methyl-N-[2-(5-carboxypentyloxy)phenyl]benzamide NMR (CDCl₃, δ): 1.40–1.61 (2H, m), 1.61–1.94 (4H, m), 2.32–2.46 (2H, m), 3.32 (3H, s), 3.76–3.98 (2H, m), 6.72–6.84 (2H, m), 6.84–7.04 (4H, m), 7.09–7.24 (3H, m), 7.30–7.58 (8H, m), 7.82 (1H, d, J=9 Hz).

42) 3-Methoxy-4-(4'-methylbiphenyl-2-carboxamido)-N-methyl-N-[2-(5-carboxypentyloxy)phenyl]benzamide NMR (CDCl₃, δ): 1.42–1.60 (2H, m), 1.61–1.89 (4H, m), 2.33 (3H, s), 2.31–2.44 (2H, m), 3.32 (3H, s), 3.39 (3H, s), 3.76–4.00 (2H, m), 6.73–6.90 (4H, m), 6.99 (1H, d, J=9 Hz), 7.09–7.20 (3H, m), 7.28 (2H, d, J=9 Hz), 7.34–7.54 (3H, m), 7.69 (1H, s), 7.80 (1H, d, J=9 Hz), 8.17 (1H, d, J=9 Hz).

43) 4-(Biphenyl-2-carboxamido)-3-methoxy-N-methyl-N-[2-(5-carboxypentyloxy)-4-methylphenyl]benzamide NMR (CDCl₃, δ): 1.44–1.59 (2H, m), 1.65–1.85 (4H, m), 2.28 (3H, s), 2.38 (2H, t, J=7 Hz), 3.30 (3H, s), 3.41 (3H, s), 3.73–3.86 (1H, m), 3.86–3.98 (1H, m), 6.55–6.63 (2H, m), 6.77–6.89 (3H, m), 7.24–7.57 (8H, m), 7.66 (1H, s), 7.80 (1H, d, J=9 Hz), 8.14 (1H, d, J=9 Hz).

44) 3-Methoxy-4-(4'-methylbiphenyl-2-carboxamido)-N-methyl-N-[2-(5-carboxypentyloxy)-4-chlorophenyl]benzamide NMR (CDCl₃, δ): 1.45–1.59 (2H, m), 1.65–1.86 (4H, m), 2.32 and 2.33 (total 3H, s), 2.38 (2H, t, J=7 Hz), 3.29 and 3.32 (total 3H, s), 3.40 and 3.42 (total 3H, s), 3.77–3.99 (2H, m), 6.74–7.03 (5H, m), 7.10–7.18 (2H, m), 7.24–7.32 (2H, m), 7.35–7.54 (3H, m), 7.69 (1H, br d, J=9 Hz), 7.80 (1H, dd, J=9, 9 Hz), 8.13–8.24 (1H, m).

45) 4-(2-Methylphenylbenzamido)-N-methyl-N-[4-chloro-2-(5-carboxypyrid-2-ylmethyloxy)phenyl]benzamide NMR (CDCl₃, δ): 2.33 (3H, s), 3.13 (3H, s), 3.60 (3H, s), 5.32 (1H, d, J=11 Hz), 5.43 (1H, d, J=11 Hz), 6.85 (1H, m), 6.97–7.06 (3H, m), 7.14 (1H, d, J=7 Hz), 7.20–7.47 (5H, m), 8.52 (1H, m), 9.06 (1H, m).

46) 4-(1,2-Dimethylphenyl-3-carboxamido)-N-[2-(5-carboxypent-1-yloxy)phenyl]-N-methylbenzamide NMR (CDCl₃, δ): 1.45–1.60 (2H, m), 1.63–1.87 (4H, m), 2.29 (3H, s), 2.30 (3H, s), 2.36 (2H, t, J=7 Hz), 3.33 (3H, s), 3.77–4.00 (2H, m), 6.75–6.86 (2H, m), 6.96–7.47 (10H, m), 7.64 (1H, br s).

47) 2-Methoxy-4-(methylphenyl-2-carboxamido)-N-[2-(5-carboxypent-1-yloxy)-4-chlorophenyl]-N-methylbenzamide NMR (CDCl₃, δ): 1.48–1.66 (2H, m), 1.66–1.94 (4H, m), 2.26–2.54 (5H, m), 3.27 and 3.31 (total 3H, s), 3.70 (3H, br s), 3.83–4.00 (2H, m), 6.64–6.84 (3H, m), 6.89–7.14 (3H, m), 7.14–7.49 (5H, m), 7.64–7.80 (1H, m).

48) 2-Chloro-4-(methylphenyl-2-carboxamido)-N-[2-(5-carboxypent-1-yloxy)phenyl]-N-methylbenzamide NMR (CDCl₃, δ): 1.49–1.66 (2H, m), 1.66–1.80 (2H, m), 1.80–1.96 (2H, m), 2.38 (2H, t, J=7 Hz), 2.43 (3H, s), 3.34 (3H, s), 3.98 (2H, t, J=7 Hz), 6.68–6.81 (2H, m), 7.00–7.41 (8H, m), 7.51 (1H, br s), 7.80 (1H, br s).

49) 2-Methoxy-4-(methylphenyl-2-carboxamido)-N-[2-(5-carboxypent-1-yloxy)phenyl]-N-methylbenzamide NMR (CDCl₃, δ): 1.48–1.94 (6H, m), 2.39 (2H, t, J=7 Hz), 2.44 (3H, br s), 3.29 (3H, s), 3.68 (3H, br s), 3.84–4.04 (2H, m), 6.63–6.82 (3H, m), 6.96–7.44 (8H, m), 7.75 (1H, br s).

50) 4-(Methylphenyl-2-carboxamido)-2-nitro-N-[2-(5-carboxypent-1-yloxy)phenyl]-N-methylbenzamide NMR (CDCl₃, δ): 1.44–1.66 (2H, m), 1.67–1.80 (2H, m), 1.80–1.96 (2H, m), 2.38 (2H, t, J=7 Hz), 2.44 (3H, s), 3.33 (3H, s), 3.98 (2H, t, J=7 Hz), 6.71 (1H, dd, J=9, 9 Hz), 6.78 (1H, d, J=9 Hz), 7.04–7.46 (8H, m), 7.80 (1H, br d, J=9 Hz), 8.06 (1H, br s), 8.39 (1H, br s).

51) 4-(Methylphenyl-2-carboxamido)-N-[2-(5-carboxypent-1-yloxy)-4-chlorophenyl]-N-methylbenzamide NMR (CDCl₃, δ): 1.44–1.60 (2H, m), 1.63–1.87 (4H, m), 2.37 (2H, t, J=7 Hz), 2.44 and 2.47 (total 3H, s), 3.29 and 3.33 (total 3H, s), 3.75–4.00 (2H, m), 6.75–6.86 (2H, m), 6.92–7.07 (1H, m), 7.07–7.51 (9H, m), 7.59–7.76 (1H, m).

52) 4-(4'-Methylbiphenyl-2-carboxamido)-N-carboxymethyl-N-(2-methylphenyl)benzamide mp: 189–192° C.; NMR (CDCl₃, δ): 2.20 (3H, s), 2.37 (3H, s), 4.13 (1H, d, J=16 Hz), 4.80 (1H, d, J=16 Hz), 6.85–6.96 (3H, m), 7.08–7.58 (12H, m), 7.80 (1H, d, J=9 Hz).

EXAMPLE 24

A suspension of 4-(4'-methylbiphenyl-2-carboxamido)-N-methyl-N-[2-(5-phthalimidopentyloxy)phenyl]benzamide (1.1 g) in ethanol (20 ml) was stirred rapidly and treated with hydrazine hydrate (844 mg). The mixture was stirred at 60° C. for 3 hours. After cooling, the reaction mixture was diluted with diethyl ether and filtered through Celite. The Celite was washed with diethyl ether, and the filtrate was concentrated. The residual milky oil was again dissolved in diethyl ether, filtered through Celite, washed with diethyl ether, and concentrated to give 4-(4'-methylbiphenyl-2-carboxamido)-N-methyl-N-[2-(5-aminopentyloxy)phenyl]benzamide NMR (CDC₃, δ): 1.42–1.59 (3H, m), 1.71–1.87 (2H, m), 1.92–2.11 (3H, m), 2.36 (3H, s), 2.72 (2H, t, J=7 Hz), 3.32 (3H, s), 3.77–4.00 (2H, m), 6.73–6.84 (2H, m), 6.86–7.05 (4H, m), 7.08–7.24 (5H, m), 7.28 (2H, d, J=9 Hz), 7.34–7.56 (3H, m), 7.80 (1H, d, J=9 Hz).

EXAMPLE 25

The following compounds were obtained according to a similar manner to that of Example 24.

1) 4-(4'-Methylbiphenyl-2-carboxamido)-N-methyl-N-[2-(4-aminobutoxy)phenyl]benzamide NMR (CDCl₃, δ): 1.56–1.82 (4H, m), 2.30 (3H, s), 2.40–2.86 (4H, m), 3.27 (3H, s), 3.70–3.96 (2H, m), 6.68–6.86 (2H, m), 6.89–7.52 (16H, m), 7.69 (1H, d, J=9 Hz).

2) 4-(4'-Methylbiphenyl-2-carboxamido)-N-methyl-N-[2-(3-aminoprop-1-yloxy)phenyl]benzamide Rf: 0.09 (10% methanol in chloroform).

3) 6-(4'-Methylbiphenyl-2-carboxamido)-N-methyl-N-[2-(3-aminoprop-1-yloxy)phenyl]nicotinamide NMR (CDCl₃, δ): 2.03 (2H, m), 2.30 (3H, s), 3.00 (2H, m), 3.30 (3H, s), 3.97 (2H, m), 6.77–6.86 (2H, m), 7.03 (1H, d, J=7 Hz), 7.10–7.18 (3H, m), 7.24 (2H, d, J=8.5 Hz), 7.34–7.42 (2H, m), 7.50 (1H, t, J=7 Hz), 7.57–7.68 (2H, m), 7.92–8.10 (2H, m).

4) 3-Methyl-4-(4'-methylbiphenyl-2-carboxamido)-N-methyl-N-[2-(3-aminoprop-1-yloxy)phenyl]benzamide NMR (CDCl₃, δ): 1.41 (3H, s), 1.92 (2H, m), 2.34 (3H, s), 2.91 (2H, t, J=7.5 Hz), 3.31 (3H, s), 3.96 (1H, m), 4.03 (1H, m), 6.74–6.84 (3H, m), 6.94–7.02 (2H, m), 7.10–7.19 (4H, m), 7.20–7.55 (4H, m), 7.81 (1H, d, J=7 Hz), 7.93 (1H, d, J=7 Hz).

5) 3-Methoxy-4-(4'-methylbiphenyl-2-carboxamido)-N-methyl-N-[2-(3-aminoprop-1-yloxy)phenyl]benzamide NMR (CDCl₃, δ): 1.96 (2H, m), 2.33 (3H, s), 2.93 (2H, t, J=7.5 Hz), 3.33 (3H, s), 3.41 (3H, s), 3.97 (1H, m), 4.08

(1H, m), 6.78–6.90 (4H, m), 7.00 (1H, d, J=7 Hz), 7.12–7.20 (3H, m), 7.29 (1H, m), 7.38–7.54 (3H, m), 7.67 (1H, s), 7.80 (1H, d, J=7 Hz), 8.20 (1H, d, J=7 Hz).

6) 2-Methoxy-4-(4'-methylbiphenyl-2-carboxamido)-N-methyl-N-[2-(3-aminoprop-1-yloxy)phenyl]benzamide NMR (CDCl$_3$, δ): 1.99 (2H, m), 2.35 (3H, s), 2.94 (2H, t, J=7.5 Hz), 3.36 (3H, s), 3.96 (1H, m), 4.08 (1H, m), 3.64 (3H, s), 3.84–4.01 (4H, m), 6.18 (1H, d, J=7 Hz), 6.64–7.55 (13H, m), 7.82 (1H, d, J=7 Hz).

7) 3-Chloro-4-(4'-methylbiphenyl)-2-carboxamido)-N-methyl-N-[2-(3-aminoprop-1-yloxy)phenyl]benzamide NMR (CDCl$_3$, δ): 1.93 (2H, m), 2.35 (3H, s), 2.90 (2H, t, J=7.5 Hz), 3.32 (3H, s), 3.95 (1H, m), 4.04 (1H, m), 6.83 (2H, d, J=8.5 Hz), 6.98–7.57 (11H, m), 7.79 (1H, d, J=7 Hz), 8.27 (1H, m).

EXAMPLE 26

To a solution of 4-(4'-methylbiphenyl-2-carboxamido)-N-methyl-N-(2-carboxymethoxyphenyl)benzamide (295 mg), N-methylpiperazine (60 mg) and 1-hydroxybenzotriazole hydrate (97 mg) in N,N-dimethylformamide (5 ml) was added N-ethyl-N'-(3-dimethylaminopropyl)carbodiimide hydrochloride (137 mg) at 0° C. and the mixture was stirred at ambient temperature for 15 hours. The resulting mixture was diluted with ethyl acetate and then the organic layer was washed successively with saturated sodium bicarbonate aqueous solution and brine. Drying, filtering and removal of solvents afforded a crude product. The crude product was chromatographed on silica gel (eluent; 3% methanol in chloroform) to give 4-(4'-methylbiphenyl-2-carboxamido)-N-methyl-N-[2-(4-methyl-1-piperazinyl)carbonylmethoxyphenyl]benzamide (213 mg) as a white powder.

NMR (CDCl$_3$, δ): 2.31 (3H, s), 2.36 (3H, s), 2.30–2.46 (4H, br), 3.37 (3H, s), 3.52–3.70 (4H, m), 4.60 (2H, d, J=9 Hz), 6.80–7.00 (6H, m), 7.12–7.32 (6H, m), 7.36–7.55 (3H, m), 7.83 (1H, d, J=8 Hz).

EXAMPLE 27

The following compounds were obtained according to a similar manner to that of Example 26.

1) 4-(4'-Methylbiphenyl-2-carboxamido)-N-methyl-N-[2-(4-methyl-1-piperazinyl)carbonylmethylphenyl]benzamide NMR (CDCl$_3$, δ): 2.23–2.33 (4H, m), 2.28 (3H, s), 2.38 (3H, s), 3.13–3.18 (1H, m), 3.27–3.39 (4H, m), 3.37 (3H, s), 3.59–3.66 (1H, m), 6.89–6.97 (2H, m), 7.10–7.53 (13H, m), 7.82 (1H, d, J=8 Hz).

2) 4-(4'-Methylbiphenyl-2-carboxamido)-N-methyl-N-[{2-(4-methyl-1-piperazinyl)carbonylmethoxy-4-methyl}phenyl]benzamide NMR (CDCl$_3$, δ): 2.28 (3H, s), 2.31 (3H, s), 2.34–2.46 (4H, m), 2.37 (3H, s), 3.34 (3H, s), 3.54–3.68 (4H, m), 4.59 (2H, d, J=8 Hz), 6.60–6.66 (2H, br s), 6.84 (1H, d, J=8 Hz), 6.87–6.98 (3H, m), 7.17–7.23 (4H, m), 7.25–7.33 (2H, m), 7.37–7.56 (3H, m), 7.82 (1H, d, J=8 Hz).

3) 3-Methoxy-4-(4'-methylbiphenyl-2-carboxamido)-N-methyl-N-[2-(4-methyl-1-piperazinyl)carbonylmethoxyphenyl]benzamide NMR (CDCl$_3$, δ): 2.30 (3H, s), 2.36 (3H, s), 2.37–2.46 (4H, br), 3.38 (3H, s), 3.42 (3H, s), 3.52–3.58 (2H, br), 3.60–3.68 (2H, br), 4.58–4.63 (2H, br), 6.80–6.88 (4H, m), 6.95–7.02 (1H, m), 7.12–7.20 (3H, m), 7.26–7.32 (2H, m), 7.36–7.54 (3H, m), 7.68–7.72 (1H, br s), 7.79 (1H, d, J=8 Hz), 8.17–8.22 (1H, m).

4) 4-(4'-Methylbiphenyl-2-carboxamido)-N-methyl-N-[2-{(4-dimethylamino-1-piperidinyl)carbonylmethoxy}-phenyl]benzamide Rf: 0.16 (chloroform:methanol:acetic acid=8:2:1).

5) 4-(4'-Methylbiphenyl-2-carboxamido)-N-methyl-N-[2-[4-(4-methylpiperazine-1-carbonylamino)butoxy]phenyl]benzamide NMR (CDCl$_3$, δ): 1.60–1.86 (4H, m), 2.29 (3H, s), 2.36 (3H, s), 2.33–2.43 (4H, m), 3.20–3.35 (2H, m), 3.32 (3H, s), 3.35–3.46 (4H, m), 3.72–3.84 (1H, m), 3.84–3.96 (1H, m), 4.84 (1H, br s), 6.72–7.01 (5H, m), 7.02–7.33 (8H, m), 7.36–7.57 (3H, m), 7.81 (1H, d, J=9 Hz).

6) 4-(4'-Methylbiphenyl-2-carboxamido)-N-methyl-N-[2-[5-(4-methylpiperazin-1-yl)carbonylpentyloxy]phenyl]benzamide NMR (CDCl$_3$, δ): 1.40–1.59 (2H, m), 1.60–1.91 (4H, m), 2.30 (3H, s), 2.26–2.45 (6H, m), 2.35 (3H, s), 3.31 (3H, s), 3.49 (2H, t, J=6 Hz), 3.60 (2H, t, J=6 Hz), 3.76–4.01 (2H, m), 6.72–6.84 (2H, m), 6.88–7.06 (4H, m), 7.08–7.57 (10H, m), 7.80 (1H, d, J=9 Hz).

7) 4-(4'-Methylbiphenyl-2-carboxamido)-N-methyl-N-[2-[4-(4-methylpiperazin-1-yl)carbonylbutoxy]phenyl]benzamide NMR (CDCl$_3$, δ): 1.72–1.90 (4H, m), 2.29 (3H, s), 2.35 (3H, s), 2.32–2.47 (6H, m), 3.30 (3H, s), 3.46–3.53 (2H, m), 3.68–3.76 (2H, m), 3.80–3.99 (2H, m), 6.78 (2H, d, J=9 Hz), 6.87–7.00 (4H, m), 7.08–7.22 (5H, m), 7.27 (2H, d, J=9 Hz), 7.33–7.60 (3H, m), 7.80 (1H, d, J=9 Hz).

8) 4-(4'-Methylbiphenyl-2-carboxamido)-N-methyl-N-[2-[3-(4-methylpiperazin-1-yl)carbonylpropoxy]phenyl]benzamide NMR (CDCl$_3$, δ): 2.04–2.18 (2H, m), 2.30 (3H, s), 2.36 (3H, s), 2.34–2.36 (4H, m), 2.50 (2H, t, J=7 Hz), 3.32 (3H, s), 3.45–3.54 (2H, m), 3.59–3.70 (2H, m), 3.86–4.06 (2H, m), 6.81 (2H, d, J=9 Hz), 6.86–6.97 (3H, m), 7.00 (1H, d, J=9 Hz), 7.09–7.23 (5H, m), 7.28 (2H, d, J=9 Hz), 7.33–7.56 (3H, m), 7.79 (1H, d, J=9 Hz).

9) 4-(4'-Methylbiphenyl-2-carboxamido)-N-methyl-N-[4-methyl-2-[5-(4-methylpiperazin-1-yl)carbonylpentyloxy]phenyl]benzamide NMR (CDCl$_3$, δ): 1.43–1.56 (2H, m), 1.61–1.87 (4H, m), 2.27 (3H, s), 2.30 (3H, s), 2.36 (3H, s), 2.23–2.43 (6H, m), 3.29 (3H, s), 3.48 (2H, dd, J=7, 7 Hz), 3.61 (2H, dd, J=7, 7 Hz), 3.73–3.85 (1H, m), 3.85–3.96 (1H, m), 6.57 (1H, d, J=9 Hz), 6.59 (1H, s), 6.83 (1H, d, J=9 Hz), 6.94 (2H, d, J=9 Hz), 7.02 (1H, s), 7.14–7.24 (4H, m), 7.30 (2H, d, J=9 Hz), 7.36–7.67 (3H, m), 7.81 (1H, d, J=9 Hz).

10) 4-(4'-Methylbiphenyl-2-carboxamido)-N-methyl-N-[5-methyl-2-[5-(4-methylpiperazin-1-yl)-carbonylpentyloxy]phenyl]benzamide NMR (CDCl$_3$, δ): 1.40–1.55 (2H, m), 1.59–1.83 (4H, m), 2.16 (3H, s), 2.30 (3H, s), 2.36 (3H, s), 2.28–2.44 (6H, m), 3.31 (3H, s), 3.48 (2H, dd, J=6, 6 Hz), 3.60 (2H, dd, J=6, 6 Hz), 3.67–3.80 (1H, m), 3.80–3.95 (1H, m), 6.66 (1H, d, J=9 Hz), 6.80 (1H, s), 6.89–6.99 (3H, m), 7.02 (1H, s), 7.14–7.24 (4H, m), 7.30 (2H, d, J=9 Hz), 7.34–7.56 (3H, m), 7.81 (1H, d, J=9 Hz).

11) 4-(4'-Methylbiphenyl-2-carboxamido)-N-methyl-N-[2-[6-(4-methylpiperazin-1-yl)carbonyihexyloxy]phenyl]benzamide NMR (CDCl$_3$, δ): 1.34–1.53 (4H, m), 1.56–1.70 (2H, m), 1.70–1.82 (2H, m), 2.28 (3H, s), 2.35 (3H, s), 2.26–2.42 (6H, m), 3.32 (3H, s), 3.46 (2H, dd, J=6, 6 Hz), 3.57 (2H, dd, J=6, 6 Hz), 3.76–4.00 (2H, m), 6.73–6.82 (2H, m), 6.92–7.01 (3H, m), 7.08–7.24 (6H, m), 7.29 (2H, d, J=9 Hz), 7.34–7.46 (2H, m), 7.50 (1H, dd, J=9, 9 Hz), 7.79 (1H, d, J=9 Hz).

12) 3-Methoxy-4-(4'-methylbiphenyl-2-carboxamido)-N-methyl-N-[4-methyl-2-[5-(4-methylpiperazin-1-yl)carbonylpentyloxy]phenyl]benzamide NMR (CDCl₃, δ): 1.45–1.58 (2H, m), 1.62–1.88 (4H, m), 2.28 (3H, s), 2.30 (3H, s), 2.33 (3H, s), 2.26–2.43 (6H, m), 3.30 (3H, s), 3.42 (3H, s), 3.48 (2H, dd, J=7, 7 Hz), 3.63 (2H, dd, J=7, 7 Hz), 3.78–4.01 (2H, m), 6.52–6.64 (2H, m), 6.76–6.87 (3H, m), 7.13 (2H, d, J=9 Hz), 7.28 (2H, d, J=9 Hz), 7.34–7.55 (3H, m), 7.69 (1H, s), 7.80 (1H, d, J=9 Hz), 8.16 (1H, d, J=9 Hz).

13) 4-(4'-Methylbiphenyl-2-carboxamido)-N-methyl-N-[2-4-[1-(t-butoxycarbonyl)piperidine-4-carbonylamino]butoxyphenyl]benzamide NMR (CDCl₃, δ): 1.44 (9H, s), 1.53–1.84 (8H, m), 2.18–2.37 (1H, m), 2.35 (3H, s), 2.60–2.81 (2H, m), 3.19–3.36 (2H, m), 3.32 (3H, s), 3.71–3.96 (2H, m), 4.02–4.19 (2H, m), 5.94–6.06 (1H, m), 6.70–7.04 (5H, m), 7.06–7.33 (8H, m), 7.34–7.56 (3H, m), 7.80 (1H, d, J=9 Hz).

14) 4-(Biphenyl-2-carboxamido)-N-methyl-N-[2-[5-(4-methylpiperazin-1-yl)carbonylpentyloxy]phenyl]benzamide NMR (CDCl₃, δ): 1.42–1.56 (2H, m), 1.59–1.87 (4H, m), 2.29 (3H, s), 2.26–2.44 (6H, m), 3.31 (3H, s), 3.48 (2H, dd, J=7, 7 Hz), 3.60 (2H, dd, J=7, 7 Hz), 3.73–4.00 (2H, m), 6.72–6.83 (2H, m), 6.86–7.03 (4H, m), 7.08–7.22 (3H, m), 7.29–7.61 (8H, m), 7.82 (1H, d, J=9 Hz).

15) 3-Methoxy-4-(4'-methylbiphenyl-2-carboxamido)-N-methyl-N-[2-[5-(4-methylpiperazin-1-yl)carbonylpentyloxy]phenyl]benzamide NMR (CDCl₃, δ): 1.44–1.58 (2H, m), 1.61–1.90 (4H, m), 2.30 (3H, s), 2.34 (3H, s), 2.25–2.45 (6H, m), 3.33 (3H, s), 3.38 (3H, s), 3.49 (2H, dd, J=7, 7 Hz), 3.64 (2H, dd, J=7, 7 Hz), 3.78–4.02 (2H, m), 6.72–6.89 (4H, m), 6.94 (1H, d, J=9 Hz), 7.08–7.18 (3H, m), 7.27 (2H, d, J=9 Hz), 7.34–7.54 (3H, m), 7.67 (1H, s), 7.78 (1H, d, J=9 Hz), 8.18 (1H, d, J=9 Hz).

16) 4-(4'-Methylbiphenyl-2-carboxamido)-N-methyl-N-[4-methyl-2-[5-(piperazin-1-yl)carbonylpentyloxy]phenyl]benzamide NMR (CDCl₃, δ): 1.42–1.87 (6H, m), 2.27 (3H, s), 2.30–2.38 (2H, m), 2.36 (3H, s), 2.77–2.90 (4H, m), 3.29 (3H, s), 3.44 (2H, dd, J=7, 7 Hz), 3.57 (2H, dd, J=7, 7 Hz), 3.74–3.96 (2H, m), 6.52–6.62 (2H, m), 6.82 (1H, d, J=9 Hz), 6.89–7.01 (3H, m), 7.14–7.23 (4H, m), 7.30 (2H, d, J=9 Hz), 7.34–7.56 (3H, m), 7.81 (1H, d, J=9 Hz).

17) 4-(Biphenyl-2-carboxamido)-3-methoxy-N-methyl-N-[2-[5-(4-methylpiperazin-1-yl)carbonylpentyloxy]phenyl]benzamide NMR (CDCl₃, δ): 1.44–1.58 (2H, m), 1.58–1.86 (4H, m), 2.27 (3H, s), 2.29 (3H, s), 2.29–2.44 (6H, m), 3.29 (3H, s), 3.40 (3H, s), 3.49 (2H, dd, J=7, 7 Hz), 3.64 (2H, dd, J=7, 7 Hz), 3.76–4.01 (2H, m), 6.52–6.64 (2H, m), 6.76–6.87 (3H, m), 7.23–7.57 (8H, m), 7.65 (1H, s), 7.80 (1H, d, J=9 Hz), 8.16 (1H, d, J=9 Hz).

18) 3-Methoxy-4-(4'-methylbiphenyl-2-carboxamido)-N-methyl-N-[4-chloro-2-[5-(4-methylpiperazin-1-yl)carbonylpentyloxy]phenyl]benzamide NMR (CDCl₃, δ): 1.42–1.59 (2H, m), 1.61–1.92 (4H, m), 2.23–2.47 (12H, m), 3.28 and 3.32 (total 3H, s), 3.37 and 3.41 (total 3H, s), 3.43–3.53 (2H, m), 3.57–3.69 (2H, m), 3.76–4.03 (2H, m), 6.69–6.98 (5H, m), 7.06–7.19 (2H, m), 7.21–7.33 (2H, m), 7.33–7.55 (3H, m), 7.68 (1H, br d, J=9 Hz), 7.79 (1H, dd, J=9, 9 Hz), 8.20 (1H, dd, J=9, 9 Hz).

19) 4-(2-Methylbenzamido)-N-methyl-N-[4-chloro-2-[5-(4-methylpiperazin-1-yl)pyrid-2-ylmethoxy]phenyl]benzamide NMR (CDCl₃, δ): 2.33 (1H, s), 2.42–2.53 (4H, m), 2.47 (3H, s), 3.31 (3H, s), 3.54 (2H, m), 3.37 (3H, s), 4.00 (2H, m), 5.27 (2H, m), 6.69 (1H, d, J=7 Hz), 6.84 (1H, dd, J=1, 7 Hz), 6.94–6.99 (2H, m), 7.08 (7H, d), 7.20–7.27 (2H, m), 7.33–7.48 (3H, m), 7.53 (1H, s), 8.00 (1H, m), 8.59 (1H, m).

20) 4-(1,2-Dimethylphenyl-3-carboxamido)-N-methyl-N-[2-[5-(4-methylpiperazin-1-ylcarbonyl)pent-1-yloxy]phenyl]benzamide NMR (CDCl₃, δ): 1.43–1.59 (2H, m), 1.61–1.74 (2H, m), 1.74–1.88 (2H, m), 2.24–2.42 (6H, m), 2.30 (6H, s), 2.33 (3H, s), 3.34 (3H, s), 3.43–3.52 (2H, m), 3.52–3.62 (2H, m), 3.76–4.00 (2H, m), 6.76–6.86 (2H, m), 7.01 (1H, d, J=9 Hz), 7.08–7.28 (4H, m), 7.33 (2H, d, J=9 Hz), 7.43 (2H, d, J=9 Hz), 7.59 (1H, s).

21) 2-Methoxy-4-(methylphenyl-2-carboxamido)-N-[4-chloro-2-[5-(4-methylpiperazin-1-ylcarbonyl)pent-1-yloxy]phenyl]-N-methylbenzamide NMR (CDCl₃, δ): 1.45–1.63 (2H, m), 1.63–1.95 (4H, m), 2.24–2.56 (12H, m), 3.28 and 3.32 (total 3H, s), 3.41–3.53 (2H, m), 3.53–3.64 (2H, m), 3.71 (3H, br s), 3.83–4.03 (2H, m), 6.64–6.82 (3H, m), 6.90–7.14 (3H, m), 7.14–7.47 (4H, m), 7.61–7.75 (1H, m).

22) 2-Chloro-4-(methylphenyl-2-carboxamido)-N-methyl-N-[2-[5-(4-methylpiperazin-1-ylcarbonyl)pent-1-yloxy]phenyl]benzamide NMR (CDCl₃, δ): 1.46–1.63 (2H, m), 1.63–1.96 (4H, m), 2.25–2.47 (6H, m), 2.30 (3H, s), 2.44 (3H, s), 3.33 (3H, s), 3.41–3.52 (2H, m), 3.52–3.63 (2H, m), 3.98 (2H, t, J=7 Hz), 6.68–6.80 (2H, m), 7.00–7.42 (8H, m), 7.56 (1H, s), 7.88 (1H, s).

23) 2-Methoxy-4-(methylphenyl-2-carboxamido)-N-methyl-N-[2-[5-(4-methylpiperazin-1-ylcarbonyl)pent-1-yloxy]phenyl]benzamide NMR (CDCl₃, δ): 1.48–1.66 (2H, m), 1.66–1.96 (4H, m), 2.24–2.52 (6H, m), 2.31 (3H, s), 2.47 (3H, s), 3.34 (3H, s), 3.42–3.54 (2H, m), 3.54–3.65 (2H, m), 3.71 (3H, br s), 3.85–4.03 (2H, m), 6.62–6.80 (3H, m), 6.95–7.46 (8H, m), 7.64 (1H, br s).

24) 4-(Methylphenyl-2-carboxamido)-2-nitro-N-methyl-N-[2-[5-(4-methylpiperazin-1-ylcarbonyl)pent-1-yloxy]phenyl]benzamide NMR (CDCl₃, δ): 1.46–1.83 (4H, m), 1.83–2.00 (2H, m), 2.24–2.51 (6H, m), 2.31 (3H, s), 2.47 (3H, s), 3.35 (3H, s), 3.42–3.63 (4H, m), 3.90–4.06 (2H, m), 6.67–6.82 (2H, m), 7.06–7.49 (7H, m), 7.84 (1H, d, J=9 Hz), 8.18 (1H, br s), 8.27 (1H, br s).

25) 4-(Methylphenyl-2-carboxamido)-N-[4-chloro-2-[5-(4-methylpiperazin-1-ylcarbonyl)pent-1-yloxy]phenyl]-N-methylbenzamide NMR (CDCl₃, δ): 1.40–1.58 (2H, m), 1.59–1.89 (4H, m), 2.31 (3H, s), 2.23–2.42 (6H, m), 2.46 and 2.48 (total 3H, s), 3.31 and 3.36 (total 3H, s), 3.42–3.52 (2H, m), 3.52–3.63 (2H, m), 3.75–4.01 (2H, m), 6.75–6.86 (2H, m), 6.91–7.05 (1H, m), 7.08–7.52 (8H, m), 7.63–7.73 (1H, m).

26) 3-Methoxy-4-(4'-methylbiphenyl-2-carboxamido)-N-methyl-N-[2-(4-methylpiperazin-1-yl)carbonylphenyl]benzamide NMR (CDCl₃, δ): 2.16–2.55 (10H, m), 3.18–3.57 (8H, m), 3.83 (2H, m), 7.02–7.52 (11H, m), 7.61–7.85 (3H, m), 8.30 (1H, m).

27) 3-Methoxy-4-(4'-methylbiphenyl-2-carboxamido)-N-methyl-N-[2-(4-dimethylaminopiperid-1-yl)carbonylphenyl]benzamide NMR (CDCl₃, δ): 2.17–2.40 (13H, m), 3.20–3.80 (10H, m), 7.07–7.50 (11H, m), 7.60–7.86 (3H, m), 8.30 (1H, m).

28) 4-(4'-Methylbiphenyl-2-carboxamido)-N-methyl-N-[2-[(Z)-6-(4-methylpiperazin-1-yl)carbonyl-1-hexen-1-yl]phenyl]benzamide NMR (CDCl₃, δ): 1.46 (2H, m), 1.80 (1H, m), 2.09 (1H, m), 2.22–2.34 (6H, m), 2.28 (3H, s), 2.33 (3H, s), 3.33 (3H, s), 3.43 (2H, m), 3.49 (2H, m), 5.64 (1H, dt, J=11, 7.5 Hz), 6.76 (1H, d, J=11 Hz), 6.98 (2H, d, J=8.5 Hz), 7.06–7.41 (11H, m), 7.48 (1H, t, J=7 Hz), 7.57 (1H, s), 7.74 (1H, d, J=7 Hz).

29) 4-(4'-Methylbiphenyl-2-carboxamido)-N-methyl-N-[2-[(E)-6-(4-methylpiperazin-1-yl)carbonyl-1-hexen-1-yl]phenyl]benzamide NMR (CDCl$_3$, δ): 1.52 (2H, m), 1.64 (2H, m), 2.20–2.41 (8H, m), 2.27 (3H, s), 2.31 (3H, s), 3.32 (3H, s), 3.48 (2H, m), 3.58 (2H, m), 6.11 (1H, dt, J=15, 7.5 Hz), 6.42 (1H, d, J=15 Hz), 6.90–6.98 (3H, m), 7.04–7.52 (12H, m), 7.80 (1H, d, J=7.5 Hz).

30) 4-(4'-Methylbiphenyl-2-carboxamido)-N-methyl-N-[2-[6-(4-methylpiperazin-1-yl)carbonylhex-1-yl]phenyl]benzamide NMR (CDCl$_3$, δ): 1.18–1.33 (4H, m), 1.42–1.56 (4H, m), 2.23–2.44 (8H, m), 2.28 (3H, s), 2.33 (3H, s), 3.36 (3H, s), 3.42–3.50 (4H, m), 6.99 (2H, d, J=8.5 Hz), 7.11–7.42 (12H, m), 7.50 (1H, t, J=7 Hz), 7.77 (1H, d, J=7 Hz).

31) 4-(4'-Methylbiphenyl-2-carboxamido)-N-methyl-N-[2-[N-[(4-methylpiperazin-1-yl)carbonylprop-1-yl]oxyimino]methylphenyl]benzamide NMR (CDCl$_3$, δ): 1.98 (2H, m), 2.29 (3H, s), 2.30–2.44 (6H, m), 2.36 (3H, s), 3.39 (3H, s), 3.48 (2H, m), 3.54 (2H, m), 4.18 (2H, t, J=7.5 Hz), 6.95 (2H, m), 7.03–7.30 (9H, m), 7.36–7.53 (3H, m), 7.68 (2H, d, J=7 Hz), 7.79 (1H, d, J=7 Hz), 8.08 (1H, s).

32) 4-(4'-Methylbiphenyl-2-carboxamido)-N-methyl-N-[2-[5-(4-methylpiperazin-1-yl)carbonylpent-1-ylthio]phenyl]benzamide NMR (CDCl$_3$, δ): 1.48 (2H, m), 1.55–1.72 (4H, m), 2.27–2.40 (6H, m), 2.19 (3H, s), 2.33 (3H, s), 2.85 (2H, m), 3.31 (3H, s), 3.46 (2H, m), 3.53 (2H, m), 6.92–7.02 (4H, m), 7.11–7.18 (4H, m), 7.21–7.30 (4H, m), 7.34–7.42 (2H, m).

33) 4-(4'-Methylbiphenyl-2-carboxamido)-N-methyl-N-[2-[5-(4-methylpiperazin-1-yl)carbonylpenten-1-yloxy]phenyl]benzamide NMR (CDCl$_3$, δ): 1.91 (2H, m), 2.28 (3H, s), 2.32 (3H, s), 2.32–2.42 (6H, m), 3.33 (3H, s), 3.51 (2H, m), 3.62 (2H, m), 3.70–4.00 (2H, m), 6.28 (1H, d, J=15 Hz), 6.73–6.86 (2H, m), 6.90–7.02 (2H, m), 7.07–7.21 (4H, m), 7.29 (2H, d, J=8.5 Hz), 7.36–7.56 (4H, m), 7.62–7.70 (2H, m), 7.78 (1H, d, J=7 Hz).

34) 4-(4'-Methylbiphenyl-2-carboxamido)-N-methyl-N-[2-[N-[2-(4-methylpiperazin-1-yl)carbonylethyl]-N-(t-butoxycarbonyl)aminoethoxy]phenyl]benzamide MASS (m/z): 734 (M+1).

35) 4-(4'-Methylbiphenyl-2-carboxamido)-N-methyl-N-[2-[2-((4-methylpiperazin-1-yl)carbonylmethoxyimino)ethoxy]phenyl]benzamide NMR (CDCl$_3$, δ): 2.28 (1.5H, s), 2.30 (1.5H, s), 2.33 (3H, s), 2.33–2.45 (4H, m), 3.33 (1.5H, s), 3.35 (1.5H, s), 3.43–3.69 (4H, m), 4.44–4.86 (4H, m), 6.71–6.98 (5H, m), 7.03–7.22 (5H, m), 7.30 (2H, d, J=8.5 Hz), 7.34–7.54 (4H, m), 7.80 (1H, m).

36) 4-(4'-Methylbiphenyl-2-carboxamido)-N-methyl-N-[2-[4-(4-methylpiperazin-1-yl)carbonylphenyl]methoxy]phenyl]benzamide NMR (CDCl$_3$, δ): 2.31 (3H, s), 2.33 (3H, s), 2.33–2.53 (4H, m), 3.36 (3H, s), 3.47 (2H, m), 4.80 (2H, m), 5.00 (2H, m), 6.83 (2H, d, J=8.5 Hz), 6.85–6.93 (2H, m), 6.98 (1H, s), 7.04 (1H, d, J=7 Hz), 7.11–7.19 (5H, m), 7.26–7.54 (7H, m), 7.81 (7H, d).

37) 4-(4'-Methylbiphenyl-2-carboxamido)-N-methyl-N-[2-[5-(4-methylpiperazin-1-yl)carbonylpyrid-2-ylmethoxy]phenyl]benzamide NMR (CDCl$_3$, δ): 2.33 (3H, s), 2.36 (3H, s), 2.38–2.55 (4H, m), 3.34 (4H, s), 3.51 (2H, m), 3.80 (2H, m), 5.28 (2H, s), 6.78 (1H, dd, J=7, 7 Hz), 6.87–7.00 (5H, m), 7.11–7.21 (5H, m), 7.29 (2H, d, J=8.5 Hz), 7.28–7.54 (3H, m), 7.82 (1H, d, J=7 Hz), 8.00 (1H, d, J=7 Hz), 8.55 (1H, s).

38) 4-(4'-Methylbiphenyl-2-carboxamido)-N-methyl-N-[2-[5-(4-methylpiperazin-1-yl)carbonylpent-1-yloxy]pyrid-3-yl]benzamide NMR (CDCl$_3$, δ): 1.27 (2H, m), 1.54–1.72 (4H, m), 2.22–2.37 (6H, m), 2.27 (3H, s), 2.35 (3H s), 3.31 (3H, s), 3.22 (2H, m), 3.50 (2H, m), 3.90 (2H, m), 5.98 (1H, dd, J=7, 7 Hz), 6.99 (1H, d, J=7 Hz), 7.08 (2H, d, J=8.5 Hz), 7.12–7.20 (3H, m), 7.26–7.31 (3H, m), 7.38–7.53 (4H, m), 7.78 (1H, d, J=7 Hz).

39) 4-(4'-Methylbiphenyl-2-carboxamido)-N-methyl-N-[3-[5-(4-methylpiperazin-1-yl)carbonylpent-1-yloxy]pyrid-2-yl]benzamide NMR (CDCl$_3$, δ): 1.42 (2H, m), 1.56–1.78 (4H, m), 2.30 (3H, s), 2.30–2.44 (6H, m), 2.36 (3H, s), 3.40 (3H, s), 3.48 (2H, m), 3.58 (2H, m), 3.68 (2H, m), 6.90–7.56 (13H, m), 7.81 (1H, d, J=7.5 Hz), 8.02 (1H, d, J=7 Hz).

40) 3-Methyl-4-(4'-methylbiphenyl-2-carboxamido)-N-methyl-N-[4-chloro-2-[5-(4-methylpiperazin-1-yl)carbonylpenten-1-yloxy)phenyl]benzamide NMR (CDCl$_3$, δ): 1.41 (3H, s), 1.51 (2H, m), 1.69 (2H, m), 1.81 (2H, m), 2.29 (3H, s), 2.29–2.44 (6H, m), 2.35 (3H, s), 3.27 (3H, s), 3.49 (2H, m), 3.61 (2H, m), 3.88 (2H, m), 6.71–7.00 (5H, m), 7.10 (1H, s), 7.18 (2H, d, J=8.5 Hz), 7.09–7.54 (5H, m), 7.83 (7H, d), 7.99 (1H, d, J=7 Hz).

41) 4-(4'-Methylbiphenyl-2-carboxamido)-N-methyl-N-[4-methyl-2-[5-(4-methylpiperazin-1-yl)pyrid-2-ylmethoxy]phenyl]benzamide NMR (CDCl$_3$, δ): 2.28 (3H, s), 2.33 (3H, s), 2.37 (3H, s), 2.39–2.53 (4H, m), 3.30 (3H, s), 3.50 (2H, m), 3.80 (2H, m), 5.22 (2H, s), 6.56 (1H, d, J=7 Hz), 6.70–6.80 (2H, m), 6.88–6.94 (3H, m), 7.13–7.21 (4H, m), 7.29 (2H, d, J=8.5 Hz), 7.36–7.53 (3H, m), 7.82 (1H, d, J=7 Hz), 7.99 (1H, m), 8.58 (1H, m).

42) 4-(4'-Nitrobiphenyl-2-carboxamido)-N-methyl-N-[2-[5-(4-methylpiperazin-1-ylcarbonyl)pyrid-2-ylmethoxy]phenyl]benzamide NMR (CDCl$_3$, δ): 2.32 (3H, s), 2.42 (2H, m), 2.50 (2H, m), 3.31 (3H, s), 3.50 (2H, m), 3.79 (2H, m), 5.27 (2H, s), 6.80 (1H, dd, J=7, 7 Hz), 6.89 (1H, d, J=7 Hz), 6.99 (1H, d, J=7 Hz), 7.07 (2H, d, J=8.5 Hz), 7.14–7.30 (4H, m), 7.41 (1H, d, J=7 Hz), 7.46–7.61 (4H, m), 7.70 (1H, d, J=7 Hz), 7.97 (1H, m), 8.20 (2H, d, J=8.5 Hz), 8.52 (1H, m).

43) 4-(2-Phenylpyridine-3-carboxamido)-N-[4-chloro-2-[5-(4-methylpiperazin-1-ylcarbonyl)pent-1-yloxy]phenyl]-N-methylbenzamide NMR (CDCl$_3$, δ): 1.33–1.51 (2H, m), 1.51–1.83 (4H, m), 2.25–2.43 (6H, m), 2.30 (3H, s), 3.29 (3H, s), 3.41–3.50 (2H, m), 3.50–3.59 (2H, m), 3.59–3.76 (1H, m), 3.76–3.96 (1H, m), 6.73–6.83 (2H, m), 6.93 (1H, d, J=8 Hz), 7.01 (2H, d, J=8 Hz), 7.18 (2H, d, J=8 Hz), 7.33–7.45 (5H, m), 7.59–7.68 (2H, m), 8.11 (1H, d, J=8 Hz), 8.75–8.80 (1H, m).

44) 4-(4'-Methylbiphenyl-2-carboxamido)-N-[4-chloro-2-[5-(4-methylpiperazin-1-ylcarbonyl)pent-1-yloxy]phenyl]-N-methylbenzamide NMR (CDCl$_3$, δ): 1.41–1.56 (2H, m), 1.60–1.86 (4H, m), 2.23–2.43 (6H, m), 2.30 (3H, s), 2.36 (3H, s), 3.27 (3H, s), 3.43–3.53 (2H, m), 3.54–3.64 (2H, m), 3.70–3.99 (2H, m), 6.73–6.82 (2H, m), 6.83–7.05 (4H, m), 7.10–7.23 (4H, m), 7.29 (2H, d, J=9 Hz), 7.34–7.56 (3H, m), 7.82 (1H, d, J=9 Hz).

45) 4-(4'-Methylbiphenyl-2-carboxamido)-N-[4-chloro-2-[5-[N-(2-diethylaminoethyl)-N-methylcarbonyl]pent-1-yloxy]phenyl]-N-methylbenzamide NMR (CDCl$_3$, δ): 1.00 (3H, t, J=7 Hz), 1.02 (3H, t, J=7 Hz), 1.40–1.56 (2H, m), 1.60–1.89 (4H, m), 2.25–2.40 (2H, m), 2.36 (3H, s), 2.46–2.62 (6H, m), 2.91 and 3.03 (total 3H, s), 3.26 (3H, s), 3.34 (1H, t, J=6 Hz), 3.43 (1H, t, J=6 Hz), 3.72–3.98 (2H, m), 6.70–6.80 (2H, m), 6.80–7.06 (4H, m), 7.06–7.23 (4H, m), 7.29 (2H, d, J=8 Hz), 7.33–7.56 (3H, m), 7.81 (1H, d, J=8 Hz).

46) 4-(4'-Methylbiphenyl-2-carboxamido)-N-[4-chloro-2-[5-(4-methylhomopiperazin-1-ylcarbonyl)pent-1-yloxy]phenyl]-N-methylbenzamide NMR (CDCl₃, δ): 1.39–1.56 (2H, m), 1.61–2.01 (6H, m), 2.27–2.40 (8H, m), 2.48–2.67 (4H, m), 3.28 (3H, s), 3.48–3.68 (4H, m), 3.73–4.00 (2H, m), 6.73–6.83 (2H, m), 6.83–7.08 (4H, m), 7.09–7.34 (6H, m), 7.34–7.56 (3H, m), 7.82 (1H, d, J=8 Hz).

47) 3-Chloro-4-(4'-methylbiphenyl-2-carboxamido)-N-[4-chloro-2-[5-(4-methylpiperazin-1-ylcarbonyl)pent-1-yloxy]phenyl]-N-methylbenzamide NMR (CDCl₃, δ): 1.43–1.60 (2H, m), 1.64–1.94 (4H, m), 2.27–2.46 (6H, m), 2.31 (3H, s), 2.35 (3H, s), 3.28 and 3.32 (total 3H, s), 3.43–3.53 (2H, m), 3.59–3.68 (2H, m), 3.77–4.00 (2H, m), 6.74–7.23 (6H, m), 7.24–7.36 (3H, m), 7.37–7.49 (2H, m), 7.49–7.60 (2H, m), 7.75–7.85 (1H, m), 8.19–8.36 (1H, m).

48) 2-Methoxy-4-(4'-methylbiphenyl-2-carboxamido)-N-[4-chloro-2-[5-[(4-methylpiperazin-1-ylcarbonyl)pent-1-yloxy]phenyl]-N-methylbenzamide NMR (CDCl₃, δ): 1.44–1.63 (2H, m), 1.63–1.93 (4H, m), 2.26–2.45 (12H, m), 3.28 and 3.51 (total 3H, s), 3.44–3.55 (2H, m), 3.56–3.67 (2H, m), 3.62 (3H, s), 3.78–4.03 (2H, m), 6.18–6.33 (1H, m), 6.60–6.76 (2H, m), 6.80–7.58 (11H, m), 7.81 (1H, dd, J=8, 8 Hz).

49) 2-Chloro-4-(4'-methylbiphenyl-2-carboxamido)-N-[4-chloro-2-[5-(4-methylpiperazin-1-ylcarbonyl)pent-1-yloxy]phenyl]-N-methylbenzamide NMR (CDCl₃, δ): 1.46–1.63 (2H, m), 1.63–1.80 (2H, m), 1.80–1.96 (2H, m), 2.26–2.46 (6H, m), 2.32 (3H, s), 2.38 (3H, s), 3.30 and 3.35 (total 3H, s), 3.43–3.53 (2H, m), 3.56–3.68 (2H, m), 3.87–4.01 (2H, m), 6.66–7.57 (14H, m), 7.74–7.86 (1H, m).

50) 2-Chloro-4-(4'-methylbiphenyl-2-carboxamido)-N-[2-[5-(4-methylpiperazin-1-ylcarbonyl)pent-1-yloxy]phenyl]-N-methylbenzamide NMR (CDCl₃, δ): 1.46–1.63 (2H, m), 1.63–1.79 (2H, m), 1.79–1.94 (2H, m), 2.26–2.47 (6H, m), 2.31 (3H, s), 2.37 (3H, s), 3.34 (3H, s), 3.43–3.54 (2H, m), 3.57–3.66 (2H, m), 3.96 (2H, t, J=7 Hz), 6.64–6.79 (2H, m), 6.79–7.01 (4H, m), 7.01–7.56 (9H, m), 7.79 (1H, d, J=9 Hz).

51) 3-Methoxy-4-(2'-methylbiphenyl-2-carboxamido)-N-[4-methyl-2-[5-(4-methylpiperazin-1-ylcarbonyl)pent-1-yloxy]phenyl]-N-methylbenzamide NMR (CDCl₃, δ): 1.41–1.57 (2H, m), 1.60–1.88 (4H, m), 2.10 (3H, br s), 2.24 (3H, s), 2.30 (3H, s), 2.21–2.43 (6H, m), 3.30 (3H, s), 3.38–3.52 (5H, m), 3.56–3.68 (2H, m), 3.73–3.98 (2H, m), 6.47–6.63 (2H, m), 6.69–6.85 (3H, m), 7.13–7.28 (5H, m), 7.41–7.56 (2H, m), 7.74 (1H, br s), 7.94 (1H, d, J=9 Hz), 8.16 (1H, br d, J=9 Hz).

52) 4-(2',4'-Dimethylbiphenyl-2-carboxamido)-3-methoxy-N-[4-methyl-2-[5-(4-methylpiperazin-1-ylcarbonyl)pent-1-yloxy]phenyl]-N-methylbenzamide NMR (CDCl₃, δ): 1.41–1.58 (2H, m), 1.58–1.87 (4H, m), 2.06 (3H, s), 2.20–2.43 (15H, m), 3.28 (3H, s), 3.39–3.53 (5H, m), 3.57–3.67 (2H, m), 3.72–3.99 (2H, m), 6.49–6.63 (2H, m), 6.70–6.86 (3H, m), 6.95–7.06 (2H, m), 7.10 (1H, d, J=9 Hz), 7.20 (1H, d, J=9 Hz), 7.37–7.54 (2H, m), 7.81 (1H, s), 7.96 (1H, d, J=9 Hz), 8.18 (1H, d, J=9 Hz).

53) 3-Methoxy-4-(4'-nitrobiphenyl-2-carboxamido)-N-[4-methyl-2-[5-(4-methylpiperazin-1-ylcarbonyl)pent-1-yloxy]phenyl]-N-methylbenzamide NMR (CDCl₃, δ): 1.45–1.58 (2H, m), 1.62–1.87 (4H, m), 2.26–2.43 (6H, m), 2.27 (3H, s), 2.29 (3H, s), 3.31 (3H, s), 3.45–3.54 (2H, m), 3.50 (3H, s), 3.59–3.67 (2H, m), 3.76–3.99 (2H, m), 6.55–6.65 (2H, m), 6.76–6.91 (3H, m), 7.42 (1H, d, J=9 Hz), 7.48–7.62 (4H, m), 7.70–7.80 (2H, m), 8.09 (1H, br d, J=9 Hz), 8.20 (2H, d, J=9 Hz).

54) 3-Methoxy-4-(4'-nitrobiphenyl-2-carboxamido)-N-[2-[5-(4-dimethylaminopiperidin-1-ylcarbonyl)pent-1-yloxy]-4-methylphenyl]-N-methylbenzamide NMR (CDCl₃, δ): 1.29–1.57 (4H, m), 1.61–1.96 (6H, m), 2.29 (9H, s), 2.25–2.41 (3H, m), 2.49–2.63 (1H, m), 2.92–3.08 (1H, m), 3.30 (3H, s), 3.49 (3H, s), 3.75–3.99 (3H, m), 4.56–4.68 (1H, m), 6.53–6.66 (2H, m), 6.76–6.90 (3H, m), 7.41 (1H, d, J=9 Hz), 7.48–7.52 (4H, m), 7.69–7.79 (2H, m), 8.07 (1H, d, J=9 Hz), 8.19 (2H, d, J=9 Hz).

55) 3-Methoxy-4-(4'-nitrobiphenyl-2-carboxamido)-N-[4-methyl-2-[5-[4-(4-pyridylpiperazin)-1-ylcarbonyl]pent-1-yloxy]phenyl]-N-methylbenzamide NMR (CDCl₃, δ): 1.45–1.87 (6H, m), 2.29 (3H, s), 2.39 (2H, t, J=7 Hz), 3.30 (3H, s), 3.28–3.41 (4H, m), 3.50 (3H, s), 3.58–3.67 (2H, m), 3.72–3.80 (2H, m), 3.80–4.01 (2H, m), 6.53–6.67 (4H, m), 6.76–6.91 (3H, m), 7.42 (1H, d, J=9 m), 7.49–7.61 (4H, m), 7.67–7.78 (2H, m), 8.08 (1H, d, J=9 Hz), 8.17 (2H, d, J=9 Hz), 8.27 (2H, d, J=9 Hz).

56) 4-(4'-Aminobiphenyl-2-carboxamido)-N-methyl-N-[4-methyl-2-]5-[(4-methylpiperazin-1-ylcarbonyl)pent-1-yloxy]phenyl]benzamide NMR (CDCl₃, δ): 1.42–1.56 (2H, m), 1.60–1.84 (4H, m), 2.26 (3H, s), 2.30 (3H, s), 2.28–2.43 (6H, m), 3.28 (3H, s), 3.48 (2H, dd, J=6, 6 Hz), 3.61 (2H, dd, J=6, 6 Hz), 3.71–3.97 (4H, m), 6.53–6.60 (2H, m), 6.67 (2H, d, J=9 Hz), 6.83 (1H, d, J=9 Hz), 6.94–7.02 (2H, br d, J=9 Hz), 7.06 (1H, br s), 7.15–7.25 (3H, m), 7.31–7.42 (2H, m), 7.43–7.52 (1H, m), 7.82 (1H, d, J=9 Hz).

57) 4-(4'-Methylbiphenyl-2-carboxamido)-2-nitro-N-[2-[5-(4-methylpiperazin-1-ylcarbonyl)pent-1-yloxy]phenyl]-N-methylbenzamide NMR (CDCl₃, δ): 1.48–1.63 (2H, m), 1.64–1.80 (2H, m), 1.81–1.97 (2H, m), 2.27–2.47 (9H, m), 2.32 (3H, s), 3.36 (3H, s), 3.44–3.56 (2H, m), 3.57–3.66 (2H, m), 3.89–4.00 (2H, m), 6.69 (1H, dd, J=9, 9 Hz), 6.75 (1H, d, J=9 Hz), 7.03–7.61 (13H, m), 7.83 (1H, d, J=9 Hz).

58) 4-(Methylphenyl-2-carboxamido)-N-methyl-N-[4-methyl-2-[5-(4-methylpiperazin-1-yl)carbonylpent-1-yloxy]phenyl]benzamide NMR (CDCl₃₁ δ) 1.42–1.57 (2H, m), 1.58–1.87 (4H, m), 2.28 (3H, s), 2.29 (3H, s), 2.30–2.42 (6H, m), 2.47 (3H, s), 3.33 (3H, s), 3.47 (2H, dd, J=6, 6 Hz), 3.57 (2H, dd, J=6, 6 Hz), 3.74–3.99 (2H, m), 6.56–6.64 (2H, m), 6.88 (1H, d, J=9 Hz), 7.17–7.47 (8H, m), 7.66 (1H, s).

59) 4-(4'-Methylbiphenyl-2-carboxamido)-N-dimethylaminocarbonylmethyl-N-(2-methylphenyl)benzamide mp: 110–115° C.; NMR (CDCl₃, δ): 2.23 (3H, s), 2.37 (3H, s), 3.00 (3H, s), 3.06 (3H, s), 3.92 (1H, d, J=15 Hz), 5.10 (1H, d, J=15 Hz), 6.88 (3H, d, J=10 Hz), 7.04–7.56 (12H, m), 7.80 (1H, d, J=6 Hz).

EXAMPLE 28

The following compounds were obtained by reacting the compounds, which were prepared according to a similar manner to that of Example 26, with hydrogen chloride.

1) 3-Methoxy-4-(4'-methylbiphenyl- 2-carboxamido)-N-methyl-N-[4-methyl-2-[5-[4-(2-(2-hydroxyethoxy)ethyl)piperazin-1-ylcarbonyl]pent-1-yloxy]phenyl]benzamide hydrochloride NMR (DMSO-d₆, δ): 1.36–1.50 (2H, m), 1.50–1.64 (2H, m), 1.64–1.80 (2H, m), 2.23 (3H, s), 2.30 (3H, s), 2.38 (2H, t, J=7 Hz), 2.84–3.68 (18H, m), 3.73–4.11 (5H, m), 4.33–4.47 (1H, m), 6.63 (1H, d, J=8 Hz), 6.74–6.79 (3H, m), 7.00 (1H, d, J=8 Hz), 7.16 (2H, d, J=8 Hz), 7.28 (2H, d, J=8 Hz), 7.35–7.49 (2H, m), 7.50–7.61 (2H, m), 7.70 (1H, d, J=8 Hz), 8.91 (1H, s).

2) 3-Methoxy-4-(4'-methylbiphenyl-2-carboxamido)-N-methyl-N-[4-methyl-2-[5-[4-(4-pyridyl)piperazin-1-ylcarbonyl]pent-1-yloxy]phenyl]benzamide dihydrochloride NMR (DMSO-$d_6$, δ): 1.38–1.53 (2H, m), 1.53–1.66 (2H, m), 1.66–1.80 (2H, m), 2.23 (3H, s), 2.30 (3H, s), 2.38 (2H, t, J=7 Hz), 3.16 (3H, s), 3.46 (3H, s), 3.53–3.77 (8H, m), 3.78–4.01 (2H, m), 6.64 (1H, d, J=8 Hz), 6.74–6.88 (3H, m), 7.00 (1H, d, J=8 Hz), 7.14 (4H, dd, J=8, 8 Hz), 7.26 (2H, d, J=8 Hz), 7.33–7.45 (2H, m), 7.53 (2H, dd, J=8, 8 Hz), 7.69 (1H, d, J=8 Hz), 8.23 (2H, d, J=8 Hz), 8.89 (1H, s).

3) 3-Methoxy-4-(4'-methylbiphenyl-2-carboxamido)-N-methyl-N-[4-methyl-2-[5-(2-morpholinoethylcarbamoyl)-pent-1-yloxy]phenyl]benzamide hydrochloride NMR (DMSO-$d_6$, δ): 1.34–1.47 (2H, m), 1.52–1.66 (2H, m), 1.66–1.78 (2H, m), 2.14 (2H, t, J=7 Hz), 2.23 (3H, s), 2.31 (3H, s), 2.98–3.21 (4H, m), 3.18 (3H, s), 3.38–3.53 (7H, m), 3.67–4.02 (6H, m), 6.65 (1H, d, J=9 Hz), 6.76–6.87 (3H, m), 7.01 (1H, d, H=9 Hz), 7.17 (2H, d, J=9 Hz), 7.29 (2H, d, J=9 Hz), 7.36–7.48 (2H, m), 7.48–7.60 (2H, m), 7.70 (1H, d, J=9 Hz), 8.14–8.24 (1H, m), 8.92 (1H, s).

4) 3-Methoxy-4-(4'-methylbiphenyl-2-carboxamido)-N-methyl-N-[4-methyl-2-[5-(2-pyridylmethylcarbamoyl)-pent-1-yloxy]phenyl]benzamide hydrochloride NMR (DMSO-$d_6$, δ): 1.34–1.47 (2H, m), 1.51–1.77 (4H, m), 2.16–2.33 (2H, m), 2.23 (1H, s), 2.28 (3H, s), 3.14 (3H, s), 3.46 (3H, s), 3.76–4.01 (2H, m), 4.55 (2H, d, J=6 Hz), 6.63 (1H, d, J=9 Hz), 6.74–6.88 (3H, m), 6.99 (1H, d, J=9 Hz), 7.15 (2H d, J=9 Hz), 7.28 (2H, d, J=9 Hz), 7.34–7.47 (2H, m), 7.47–7.60 (2H, m), 7.65–7.83 (3H, m), 8.33 (1H, dd, J=9, 9 Hz), 8.68–8.78 (2H, m), 8.89 (1H, s).

5) 3-Methoxy-4-(4'-methylbiphenyl-2-carboxamido)-N-methyl-N-[4-methyl-2-[5-[4-(pyrrolidinocarbonylmethyl)piperazin-1-ylcarbonyl]pent-1-yloxy]phenyl]benzamide dihydrochloride NMR (DMSO-$d_6$, δ): 1.36–1.65 (4H, m), 1.65–1.98 (6H, m), 2.24 (3H, s), 2.30 (3H, s), 2.33–2.45 (2H, m), 2.90–4.50 (22H, m), 6.64 (1H, d, J=8 Hz), 6.73–6.83 (3H, m), 7.02 (1H, d, J=8 Hz), 7.17 (2H, d, J=8 Hz), 7.29 (2H, d, J=8 Hz), 7.35–7.50 (2H, m), 7.50–7.63 (2H, m), 7.71 (1H, d, J=8 Hz), 8.91 (1H, s).

6) 4-(4'-Methylbiphenyl-2-carboxamido)-N-methyl-N-[2-[7-(4-methylpiperazin-1-yl)carboxyheptyloxy]phenyl]-benzamide hydrochloride NMR (CDCl$_3$, δ): 1.38–1.55 (6H, m), 1.55–1.69 (2H, m), 1.69–1.89 (2H, m), 1.86 (3H, s), 2.35 (3H, s), 2.24–2.38 (2H, m), 2.61–2.90 (4H, m), 3.29 (3H, s), 3.23–3.49 (2H, m), 3.75–4.01 (4H, m), 6.78 (2H, br d, J=9 Hz), 6.90–7.04 (3H, m), 7.11–7.34 (7H, m), 7.35–7.56 (3H, m), 7.77 (1H, d, J=9 Hz).

EXAMPLE 29

A solution of 4-(4'-methylbiphenyl-2-carboxamido)-N-methyl-N-(2-benzyloxy-4-methylphenyl)benzamide (2.2 g), 10% palladium hydroxide (220 mg) in methanol (50 ml) was stirred under atmospheric pressure of hydrogen at ambient temperature. After 5 hours, the reaction mixture was filtered through a bed of Celite, and then concentrated to give 4-(4'-methylbiphenyl-2-carboxamido)-N-methyl-N-[2-hydroxy-4-methylphenyl]benzamide (1.71 g).

NMR (DMSO-$d_6$, δ): 2.16 (3H, s), 2.27 (3H, s), 3.15 (3H, s), 6.47 (1H, d, J=9 Hz), 6.61 (1H, s), 6.83 (1H, d, J=9 Hz), 7.10–7.24 (4H, m), 7.24–7.38 (4H, m), 7.43 (2H, d, J=9, 9 Hz), 7.47–7.58 (2H, m), 9.71 (1H, br s).

EXAMPLE 30

The following compounds were obtained according to a similar manner to that of Example 29.

1) 4-(4'-Methylbiphenyl-2-carboxamido)-N-methyl-N-(2-hydroxy-5-methylphenyl)benzamide NMR (DMSO-$d_6$, δ): 2.08 (3H, s), 2.27 (3H, s), 3.16 (3H, s), 6.68 (1H, d, J=9 Hz), 6.77–6.88 (2H, m), 7.10–7.68 (12H, m), 9.56 (1H, s).

2) 4-(Biphenyl-2-carboxamido)-N-methyl-N-(2-hydroxyphenyl)benzamide

NMR (DMSO-$d_6$, δ): 3.17 (3H, s), 6.66 (1H, dd, J=9, 9 Hz), 6.81 (1H, d, J=9 Hz), 6.97 (1H, d, J=9 Hz), 7.03 (1H, dd, J=9, 9 Hz), 7.17 (2H, d, J=9 Hz), 7.23–7.61 (11H, m), 9.88 (1H, br s).

3) 3-Methoxy-4-(4'-methylbiphenyl-2-carboxamido)-N-methyl-N-(4-chloro-2-hydroxyphenyl)benzamide NMR (CDCl$_3$, δ): 2.31 (3H, s), 3.28 (3H, s), 3.33 (3H, s), 6.62–6.80 (2H, m), 6.87–7.01 (2H, m), 7.04–7.17 (3H, m), 7.21–7.30 (2H, m), 7.33–7.46 (2H, m), 7.50 (1H, dd, J=9, 9 Hz), 7.64–7.83 (2H, m), 8.13–8.28 (1H, m).

4) 3-Chloro-4-(4'-methylbiphenyl-2-carboxamido)-N-[4-chloro-2-hydroxyphenyl]-N-methylbenzamide NMR (CDCl$_3$, δ): 2.32 (3H, s), 3.29 and 3.33 (total 3H, s), 6.61–8.34 (15H, m).

5) 2-Methoxy-4-(4'-methylbiphenyl-2-carboxamido)-N-[4-chloro-2-hydroxyphenyl]-N-methylbenzamide NMR (DMSO-$d_6$, δ): 2.28 (3H, s), 3.13 and 3.16 (total 3H, s), 3.54 (3H, s), 6.51–6.69 (1H, m), 6.70–6.80 (1H, m), 6.86–7.06 (3H, m), 7.06–7.23 (3H, m), 7.24–7.32 (2H, m), 7.37–7.59 (4H, m).

6) 2-Chloro-4-(4'-methylbiphenyl-2-carboxamido)-N-(4-chloro-2-hydroxyphenyl]-N-methylbenzamide NMR (CDCl$_3$, δ): 2.36 and 2.42 (total 3H, s), 3.20–3.41 (3H, m), 6.63–7.94 (15H, m).

7) 4-(4'-Methylbiphenyl-2-carboxamido)-N-[4-chloro-2-hydroxyphenyl]-N-methylbenzamide NMR (DMSO-$d_6$, δ): 2.28 (3H, s), 3.15 (3H, s), 6.73 (1H, d, J=8 Hz), 6.83 (1H, s), 7.04 (1H, d, J=8 Hz), 7.10–7.23 (4H, m), 7.24–7.58 (9H, m).

8) 4-(2-Phenylpyridine-3-carboxamido)-N-(4-chloro-2-hydroxyphenyl)-N-methylbenzamide NMR (DMSO-$d_6$, δ): 3.15 (3H, s), 6.73 (1H, dd, J=8, 2 Hz), 6.82 (1H, d, J=2 Hz), 7.04 (1H, d, J=8 Hz), 7.20 (2H, d, J=8 Hz), 7.28–7.44 (6H, m), 7.44–7.53 (1H, m), 7.57–7.68 (2H, m), 7.98 (1H, dd, J=8, 2 Hz), 8.70–8.79 (1H, m).

9) 4-(Methylphenyl-2-carboxamido)-N-methyl-N-(2-hydroxy-4-methylphenyl)benzamide NMR (DMSO-$d_6$, δ): 2.14 (3H, s), 2.33 (3H, s), 3.16 (3H, s), 3.22–3.43 (2H, br s), 6.47 (1H, d, J=9 Hz), 6.63 (1H, s), 6.84 (1H, d, J=9 Hz), 7.19–7.33 (4H, m), 7.34–7.44 (2H, m), 7.53 (2H, d, J=9 Hz).

10) 3-Methyl-4-(4'-methylbiphenyl-2-carboxamido)-N-methyl-N-(4-chloro-2-hydroxyphenyl)benzamide NMR (CDCl$_3$, δ): 1.43 (3H, s), 2.33 (3H, s), 3.27 (3H, s), 6.60–7.20 (7H, m), 7.28–7.55 (5H, m), 7.74–7.95 (3H, m).

11) 4-(1,2-Dimethylphenyl-3-carboxamido)-N-(2-hydroxyphenyl)-N-methylbenzamide

NMR (DMSO-$d_6$, δ): 2.20 (3H, s), 2.27 (3H, s), 3.20 (3H, s), 6.67 (1H, dd, J=8, 8 Hz), 6.81 (1H, d, J=8 Hz), 6.96–7.07 (2H, m), 7.08–7.30 (5H, m), 7.53 (2H, d, J=8 Hz), 9.86 (1H, s).

12) 2-Methoxy-4-(methylphenyl-2-carboxamido)-N-(4-chloro-2-hydroxyphenyl)-N-methylbenzamide NMR (CDCl$_3$, δ): 2.35 and 2.49 (total 3H, s), 3.18 and 3.26 (total 3H, s), 3.65 and 3.92 (total 3H, br s), 6.52–6.67 (1H, m), 6.67–7.69 (10H, m).

13) 4-(Methylphenyl-2-carboxamido)-N-(4-chloro-2-hydroxyphenyl)-N-methylbenzamide NMR (CDCl$_3$, δ): 2.33 (3H, br s), 3.24 and 3.30 (total 3H, br s), 3.47 (1H, s), 6.58–7.56 (11H, m), 8.20–8.36 (1H, m).

EXAMPLE 31

To a solution of 4'-methylbiphenyl-2-carboxamido-N-methyl-N-(2-hydroxyphenyl)benzamide (263 mg) in N,N-dimethylformamide (15 ml) was added potassium carbonate (250 mg), ethyl 6-bromohexanoate (161 mg) and sodium iodide (cat.) at 60° C. The reaction mixture was stirred at same temperature for 13 hours. The reaction mixture was cooled in an ice bath and quenched with 1N hydrochloric acid (4 ml) and water (20 ml). The mixture was extracted with ethyl acetate. The organic phase was washed with water and brine. The organic solution was dried over magnesium sulfate. The solvent was removed by evaporation to give 4-(4'-methylbiphenyl-2-carboxamido)-N-methyl-N-[2-(5-ethoxycarbonylpentyloxy)phenyl]benzamide (380 mg).

NMR (CDCl$_3$, δ): 1.26 (3H, t, J=7 Hz), 1.33–1.56 (2H, m), 1.61–1.89 (4H, m), 2.32 (2H, t, J=7 Hz), 2.35 (3H, s), 3.32 (3H, s), 3.79–3.99 (2H, m), 4.12 (2H, q, J=7 Hz), 6.79 (2H, d, J=9 Hz), 6.87–7.00 (4H, m), 7.09–7.24 (5H, m), 7.29 (2H, d, J=9 Hz), 7.35–7.56 (3H, m), 7.81 (1H, br d, J=9 Hz).

EXAMPLE 32

The following compounds were obtained according to a similar manner to that of Example 31.

1) 4-(4'-Methylbiphenyl-2-carboxamido)-N-methyl-N-[2-(3-ethoxycarbonylpropoxy)phenyl]benzamide NMR (CDCl$_3$, δ): 1.26 (3H, t, J=7 Hz), 2.08(2H, t, J=7 Hz), 2.35 (3H, s), 2.50 (2H, t, J=7 Hz), 3.32 (3H, s), 3.84–4.02 (2H, m), 4.14 (2H, q, J=7 Hz), 6.80 (2H, d, J=9 Hz), 6.86–7.00 (4H, m), 7.09–7.23 (5H, m), 7.28 (2H, d, J=9 Hz), 7.34–7.56 (3H, m), 7.81 (1H, d, J=9 Hz).

2) 4-(4'-Methylbiphenyl-2-carboxamido)-N-methyl-N-[2-(5-chloropentyloxy)phenyl]benzamide NMR (CDCl$_3$, δ): 1.55–1.69 (2H, m), 1.76–1.94 (4H, m), 2.36 (3H, s), 3.33 (3H, s), 3.57 (2H, t, J=7 Hz), 3.81–4.00 (2H, m), 6.75–6.84 (2H, m), 6.86–7.03 (4H, m), 7.10–7.25 (5H, m), 7.30 (2H, d, J=9 Hz), 7.35–7.56 (3H, m), 7.83 (1H, d, J=9 Hz).

3) 4-(4'-Methylbiphenyl-2-carboxamido)-N-methyl-N-[2-(4-hydroxybutoxy)phenyl]benzamide NMR (CDCl$_3$, δ): 1.63–1.94 (4H, m), 2.36 (3H, s), 3.32 (3H, s), 3.44–3.76 (2H, m), 3.81–4.01 (2H, m), 6.74–6.86 (2H, m), 6.88–7.07 (4H, m), 7.10–7.26(5H, m), 7.29 (2H, d, J=9 Hz) 7.35–7.56 (3H, m), 7.81 (1H, d, J=9 Hz).

4) 4-(4'-Methylbiphenyl-2-carboxamido)-N-methyl-N-[2-(5-ethoxycarbonylpentyloxy)-4-methylphenyl]benzamide NMR (CDCl$_3$, δ): 1.26 (3H, t, J=7 Hz), 1.41–1.55 (2H, m), 1.61–1.84 (4H, m), 2.28 (3H, s), 2.34 (2H, t, J=7 Hz), 2.36 (3H, s), 3.29 (3H, s), 3.76–3.97 (2H, m), 4.12 (2H, q, J=7 Hz), 6.54–6.62 (2H, m), 6.82 (1H, d, J=9 Hz), 6.86–6.99 (3H, m), 7.14–7.23 (4H, m), 7.30 (2H, d, J=9 Hz), 7.35–7.56 (3H, m), 7.82 (1H, d, J=9 Hz).

5) 4-(4'-Methylbiphenyl-2-carboxamido)-N-methyl-N-[2-(5-ethoxycarbonylpentyloxy)-5-methylphenyl]benzamide NMR (CDCl$_3$, δ): 1.25 (3H, t, J=7 Hz), 1.38–1.54 (2H, m), 1.60–1.82 (4H, m), 2.16(3H, s), 2.32 (2H, t, J=7 Hz), 2.36 (3H, s), 3.29 (3H, s), 3.70–3.94 (2H, m), 4.12 (2H, q, J=7 Hz), 6.66(1H, d, J=9 Hz), 6.79 (1H, s), 6.86–7.00 (4H, m), 7.13–7.25 (4H, m), 7.30 (2H, d, J=9 Hz), 7.34–7.55 (3H, m), 7.81 (1H, d, J=9 Hz).

6) 3-Methoxy-4-(4'-methylbiphenyl-2-carboxamido)-N-methyl-N-[2-(5-ethoxycarbonylpentyloxy)-4-methylphenyl]benzamide NMR (CDCl$_3$, δ): 1.26 (3H, t, J=7 Hz), 1.40–1.58 (2H, m), 1.59–1.94 (4H, m), 2.28 (3H, s), 2.34 (3H, s), 2.25–2.38 (2H, m), 3.29 (3H, s), 3.43 (3H, s), 3.76–3.99 (2H, m), 4.12 (2H, q, J=7 Hz), 6.52–6.66 (2H, m), 6.74–6.90 (3H, m), 7.14 (2H, d, J=9 Hz), 7.23–7.34 (2H, m), 7.35–7.56 (3H, m), 7.69 (1H, s), 7.80 (1H, d, J=9 Hz), 8.17 (1H, d, J=9 Hz).

7) 4-(Biphenyl-2-carboxamido)-N-methyl-N-[2-(5-ethoxycarbonylpentyloxy)phenyl]benzamide NMR (CDCl$_3$, δ): 1.26 (3H, t, J=7 Hz), 1.38–1.56 (2H, m), 1.56–1.93 (4H, m), 2.33 (2H, t, J=7 Hz), 3.31 (3H, s), 3.75–3.99 (2H, m), 4.11 (2H, q, J=7 Hz), 6.71–6.82 (2H, m), 6.82–6.99 (4H, m), 7.07–7.24 (3H, m), 7.30–7.57 (8H, m), 7.82 (1H, d, J=9 Hz).

8) 4-(4'-Methylbiphenyl-2-carboxamido)-N-methyl-N-[2-(4-ethoxycarbonylbutoxy)phenyl]benzamide NMR (CDCl$_3$, δ): 1.25 (3H, t, J=7 Hz), 1.58–1.96 (4H, m), 2.35 (3H, s), 2.28–2.42 (2H, m), 3.32 (3H, s), 3.77–4.00 (2H, m), 4.14 (2H, q, J=7 Hz), 6.78 (2H, br d, J=9 Hz), 6.84–7.02 (4H, m), 7.06–7.32 (7H, m), 7.33–7.56 (3H, m), 7.81 (1H, br s, J=9 Hz).

9) 4-(4'-Methylbiphenyl-2-carboxamido)-N-methyl-N-[2-(7-methoxycarbonylheptyloxy)phenyl]benzamide NMR (CDCl$_3$, δ): 1.29–1.53 (6H, m), 1.54–1.69 (2H, m), 1.70–1.83 (2H, m), 2.30 (2H, t, J=7 Hz), 2.35 (3H, s), 3.31 (3H, s), 3.64 (3H, s), 3.78–3.97 (2H, m), 6.71–6.83 (2H, m), 6.86–7.04 (4H, m), 7.07–7.22 (5H, m), 7.29 (2H, d, J=9 Hz), 7.33–7.56 (3H, m), 7.81 (1H, d, J=9 Hz).

10) 3-Methoxy-4-(4'-methylbiphenyl-2-carboxamido-N-methyl-N-[2-(5-ethoxycarbonylpentyloxy)phenyl]benzamide NMR (CDCl$_3$, δ): 1.24 (3H, t, J=7 Hz), 1.32–1.94 (6H, m), 2.33 (3H, s), 2.26–2.38 (2H, m), 3.32 (3H, s), 3.38 (3H, s), 3.77–4.01 (2H, m), 4.12 (2H, q, J=7 Hz), 6.70–6.87 (4H, m), 6.94 (1H, br d J=9 Hz), 7.05–7.19 (3H, m), 7.27 (2H, br d, J=9 Hz), 7.32–7.53 (3H, m), 7.67 (1H, br s), 7.79 (1H, d, J=9 Hz), 8.17 (1H, br d, J=9 Hz).

11) 4-(Biphenyl-2-carboxamido)-3-methoxy-N-methyl-N-[2-(5-ethoxycarbonylpentyloxy)-4-methylphenyl]benzamide NMR (CDCl$_3$, δ): 1.26 (3H, t, J=7 Hz), 1.42–1.56 (2H, m), 1.60–1.86 (4H, m), 2.28 (3H, s), 2.33 (2H, t, J=7 Hz), 3.29 (3H, s), 3.41 (3H, q), 3.76–3.99 (2H, m), 4.13 (2H, q, J=7 Hz), 6.52–6.65 (2H, m), 6.76–6.88 (3H, m), 7.23–7.57 (8H, m), 7.65 (1H, br s), 7.81 (1H, d, J=9 Hz), 8.16 (1H, d, J=9 Hz).

12) 3-Methoxy-4-(4'-methylbphenyl-2-carboxainido)-N-methyl-N-[4-chloro-2-(-ethoxycarbonylpentyloxy)-phenyl]benzamide NMR (CDCl$_3$, δ): 1.26 (3H, t, J=7 Hz), 1.43–1.56 (2H, m), 1.62–1.87 (4H, m), 2.27–2.36 (5H, m), 3.27 and 3.32 (total 3H, s), 3.39 and 3.42 (total 3H, s), 3.78–4.00 (2H, m), 4.13 (2H, q, J=7 Hz), 6.72–6.97 (5H, m), 7.08–7.18 (2H m), 7.25–7.33 (2H, m), 7.34–7.55 (3H, m), 7.68 (1H, br d, J=9 Hz), 7.79 (1H, dd, J=9, 9 Hz), 8.13–8.26 (1H, m)

13) 4-(4'-Methylbiphenyl-2-carboxamido)-N-methyl-N-[2-(4-phthalimidobutoxy)phenyl]benzamide NMR (CDCl$_3$, δ): 1.53–1.96 (4H, m), 2.34 (3H, s), 3.31 (3H, s), 3.66–3.80 (2H, m), 3.83–4.04 (2H, m), 6.73–6.83 (2H, m), 6.85–7.00 (4H, m), 7.07–7.24 (5H, m), 7.29 (2H, d, J=9 Hz), 7.34–7.56 (3H, m), 7.66–7.77 (2H, m), 7.77–7.89 (3H, m).

14) 4-(4'-Methylbiphenyl-2-carboxamido)-N-methyl-N-[2-(3-phthalimidoprop-1-yloxy)phenyl]benzamide NMR (CDCl$_3$, δ): 2.19 (2H, quint., J=6 Hz), 2.35 (3H, s), 3.35 (3H, s), 3.86–3.98 (4H, m), 6.75–6.85 (7H, m), 7.10–7.34 (6H, m), 7.38–7.55 (3H, m), 7.68–7.88 (5H, m).

15) 4-(4'-Methylbiphenyl-2-carboxamido)-N-methyl-N-[2-(3-hydroxypropoxy)phenyl]benzamide NMR (CDCl₃, δ): 2.00 (2H, t, J=7 Hz), 2.36 (3H, s), 3.32 (3H, s), 3.76–3.86 (2H, m), 3.88–4.14 (2H, m), 6.76–7.06 (5H, m), 7.11–7.34 (8H, m), 7.34–7.56 (3H, m), 7.81 (1H, d, J=9 Hz).

16) 4-(4-Methylbiphenyl-2-carboxamido)-N-methyl-N-[2-(4-methoxycarbonylphenylmethoxy)phenyl]benzamide NMR (CDCl₃, δ): 2.34 (3H, s), 3.38 (3H, s), 3.91 (3H, s), 4.91–5.13 (2H, m), 6.78 (1H, s, J=7 Hz), 6.82–6.92 (3H, m), 7.07–7.19 (6H, m), 7.27–7.54 (7H, m), 7.82 (1H, d, J=7 Hz), 8.02 (2H, d, J=8.5 Hz).

17) 4-(4'-Methylbiphenyl-2-carboxamido)-N-methyl-N-[2-(5-methoxycarbonylpyrid-2-ylmethoxy)phenyl]benzamide NMR (CDCl₃, δ): 2.34 (3H, s), 3.32 (3H, s), 3.99 (3H, s), 5.30 (2H, s), 6.78 (1H, dd, J=7, 7 Hz), 7.85–7.94 (5H, m), 7.10–7.23 (5H, m), 7.30 (2H, d, J=8.5 Hz), 7.36–7.54 (5H, m), 7.83 (1H, d, J=7 Hz), 8.50 (1H, m), 9.10 (1H, m).

18) 4-(4'-Methylbiphenyl-2-carboxamido)-N-methyl-N-[2-[4-(4-t-butoxycarbonylpiperazin-1-yl)-sulfonylphenylmethoxy]phenyl]benzamide NMR (CDCl₃, δ): 1.40 (9H, s), 2.32 (3H, s), 2.91–3.02 (4H, m), 3.37 (3H, s), 3.96–3.53 (4H, m), 5.06 (2H, m), 6.80 (1H, d, J=7 Hz), 6.87–6.94 (3H, m), 7.11–7.20 (6H, m), 7.24–7.51 (7H, m), 7.72 (2H, d, J=8.5 Hz), 7.82 (1H, d, J=7 Hz).

19) 3-Methyl-4-(4'-methylbiphenyl-2-carboxamido)-N-methyl-N-[3-chloro-2-(5-ethoxycarbonylpenten-1-yloxy)phenyl]benzamide NMR (CDCl₃, δ): 1.23 (3H, t, J=7.5 Hz), 1.42 (3H, s), 1.48 (2H, m), 1.70 (2H, m), 1.79 (2H, m), 2.31 (2H, t, J=7.5 Hz), 2.35 (3H, s), 3.26 (3H, s), 3.88 (2H, m), 4.12 (2H, q, J=7.5 Hz), 6.71–7.00 (4H, m), 7.09 (1H, s), 7.28 (2H, d, J=8.5 Hz), 7.29–7.53 (5H, m), 7.82 (1H, d, J=7 Hz), 7.98 (2H, d, J=7 Hz).

20) 4-(4'-Methylbiphenyl-2-carboxamido)-N-[4-chloro-2-(5-ethoxycarbonylpent-1-yloxy)phenyl]-N-methylbenzamide NMR (CDCl₃, δ): 1.26 (3H, t, J=7 Hz), 1.40–1.55 (2H, m), 1.61–1.87 (4H, m), 2.27–2.40 (5H, m), 3.28 and 3.31 (total 3H, s), 3.75–3.98 (2H, m), 4.11 (2H, q, J=7 Hz), 6.72–6.80 (2H, m), 6.84–7.00 (4H, m), 7.09–7.24 (4H, m), 7.30 (2H, d, J=9 Hz), 7.34–7.56 (3H, m), 7.78–7.87 (1H, m).

21) 3-Chloro-4-(4'-methylbiphenyl-2-carboxamido)-N-[4-chloro-2-(5-ethoxycarbonylpent-1-yloxy)phenyl]-N-methylbenzamide NMR (CDCl₃, δ): 1.26 (3H, t, J=7 Hz), 1.40–1.57 (2H, m), 1.63–1.88 (4H, m), 2.27–2.42 (5H, m), 3.28 and 3.32 (total 3H, s), 3.77–4.00 (2H, m), 4.13 (2H, q, J=7 Hz), 6.75–6.85 (2H, m), 6.85–7.36 (7H, m), 7.36–7.50 (2H, m), 7.50–7.60 (2H, m), 7.75–7.84 (1H, m), 8.21–8.36 (1H, m).

22) 2-Methoxy-4-(4'-methylbiphenyl-2-carboxamido)-N-[4-chloro-2-(5-ethoxycarbonylpent-1-yloxy)phenyl]-N-methylbenzamide NMR (CDCl₃, δ): 1.26 (3H, t, J=7 Hz), 1.44–1.60 (2H, m), 1.65–1.93 (4H, m), 2.26–2.43 (5H, m), 3.29 and 3.33 (total 3H, s), 3.64 (3H, s), 3.80–3.98 (2H, m), 4.13 (2H, q, J=7 Hz), 6.16–6.28 (1H, m), 6.60–6.76 (2H, m), 6.80–7.12 (4H, m), 7.13–7.24 (2H, m), 7.24–7.33 (2H, m), 7.33–7.56 (3H, m), 7.78–7.87 (1H, m).

23) 2-Chloro-4-(4'-methylbiphenyl-2-carboxamido)-N-[4-chloro-2-(5-ethoxycarbonylpent-1-yloxy)phenyl]-N-methylbenzamide NMR (CDCl₃, δ): 1.20–1.32 (3H, m), 1.45–1.63 (2H, m), 1.63–1.96 (4H, m), 2.28–2.46 (5H, m), 3.23–3.37 (3H, m), 3.88–4.00 (2H, m), 4.07–4.20 (2H, m), 6.66–7.60 (14H, m), 7.76–7.86 (1H, m).

24) 4-(4'-Aminobiphenyl-2-carboxamido)-N-[2-(5-ethoxycarbonylpent-1-yloxy)-4-methylphenyl]-N-methylbenzamide NMR (CDCl₃, δ): 1.26 (3H, t, J=7 Hz), 1.39–1.56 (2H, m), 1.59–1.87 (4H, m), 2.27 (3H, s), 2.31 (2H, t, J=7 Hz), 3.28 (3H, s), 3.72–3.97 (4H, m), 4.12 (2H, q, J=7 Hz), 6.51–6.61 (2H, m), 6.68 (2H, d, J=9 Hz), 6.82 (1H, d, J=9 Hz), 6.92–7.08 (3H, m), 7.14–7.29 (4H, m), 7.32–7.42 (2H, m), 7.47 (1H, dd, J=9, 9 Hz), 7.81 (1H, d, J=9 Hz).

25) 4-(Methylphenyl-2-carboxamido)-N-methyl-N-[4-methyl-2-[5-(ethoxycarbonylpent-1-yloxy)phenyl]benzamide NMR (CDCl₃, δ): 1.24 (3H, t, J=7 Hz), 1.39–1.57 (2H, m), 1.61–1.88 (4H, m), 2.26 (3H, s), 2.34 (2H, t, J=7 Hz), 2.45 (3H, s), 3.31 (3H, s), 3.77–3.98 (2H, m), 4.10 (2H, q, J=7 Hz), 6.52–6.66 (2H, m), 6.86 (1H, d, J=9 Hz), 7.16–7.50 (8H, m), 7.58 (1H, br s).

26) 4-(2-Phenylpyridine-3-carboxamido)-N-[4-chloro-2-(5-ethoxycarbonylpent-1-yloxy)phenyl]-N-methylbenzamide NMR (CDCl₃, δ): 1.26 (3H, t, J=7 Hz), 1.39–1.63 (2H, m), 1.61–1.85 (4H, m), 2.33 (2H, t, J=7 Hz), 3.29 (3H, s), 3.73–3.97 (2H, m), 4.10 (2H, q, J=7 Hz), 6.74–6.81 (2H, m), 6.89 (1H, d, J=9 Hz), 6.97 (2H, d, J=9 Hz), 7.06 (1H, s), 7.18 (2H, d, J=9 Hz), 7.34–7.46 (4H, m), 7.59–7.68 (2H, m), 8.16 (1H, d, J=9 Hz), 8.76–8.82 (1H, m).

27) 4-(2-Methylbenzamido)-N-methyl-N-[4-chloro-2-(5-methoxycarbonylpyrid-2-ylmethoxy)phenyl]benzamide NMR (CDCl₃, δ): 2.47 (3H, s), 3.32 (3H, s), 3.76 (3H, s), 3.99 (3H, s), 5.30 (2H, s), 6.67–6.76 (2H, m), 6.90 (1H, m), 6.99 (1H, d, J=7 Hz), 7.10 (1H, d, J=7 Hz), 7.20–7.48 (6H, m), 8.53 (1H, m), 9.13 (1H, m).

28) 4-(1,2-Dimethylphenyl-3-carboxamido)-N-[2-(5-ethoxycarbonylpent-1-yloxy)phenyl]-N-methylbenzamide NMR (CDCl₃, δ): 1.26 (3H, t, J=7 Hz), 1.44–1.58 (2H, m), 1.58–1.89 (4H, m), 2.25–2.39 (8H, m), 3.33 (3H, s), 3.80–4.01 (2H, m), 4.11 (2H, q, J=7 Hz), 6.74–6.86 (2H, m), 7.00 (1H, d, J=8 Hz), 7.04–7.55 (9H, m).

29) 4-(Methylphenyl-2-carboxamido)-N-[4-chloro-2-(5-ethoxycarbonylpent-1-yloxy)phenyl]-N-methylbenzamide NMR (CDCl₃, δ): 1.25 (3H, t, J=7 Hz), 1.40–1.58 (2H, m), 1.58–1.91 (4H, m), 2.33 (2H, t, J=7 Hz), 2.45 and 2.46 (total 3H, s), 3.30 and 3.34 (total 3H, s), 3.77–3.99 (2H, m), 4.11 (2H, q, J=7 Hz), 6.75–6.85 (2H, m), 6.88–7.04 (1H, m), 7.10–7.66 (9H, m).

EXAMPLE 33

To a mixture of 4-(4'-methylbiphenyl-2-carboxamido)-N-methyl-N-[2-(2-hydroxyiminoethoxy)phenyl]benzamide (255 mg) and potassium carbonate (78.5 mg) in N,N-dimethylformamide (10 ml) was added ethyl bromoacetate (94.9 mg) and the mixture was stirred at ambient temperature for 5 hours. The mixture was diluted with ethyl acetate (30 ml) and the solution was washed with water and brine. The organic phase was dried over magnesium sulfate and the solvent was evaporated in vacuo to give an oil. The oil was purified by silica gel column (chloroform) to give 4-(4'-methylbiphenyl-2-carboxamido)-N-methyl-N-[2-[2-(ethoxycarbonylmethoxyimino)ethoxy]phenyl]benzamide (245 mg) as a colorless amorphous.

NMR (CDCl₃, δ): 1.29 (3H, m), 2.34 (3H, s), 3.28–3.90 (3H, m), 4.21 (2H, m), 4.45–4.87 (4H, m), 6.65–6.97 (6H, m), 7.02–7.23 (5H, m), 7.28 (2H, d, J=8.5 Hz), 7.34–7.53 (3H, m), 7.82 (1H, d, J=7 Hz).

EXAMPLE 34

1) To a solution of 4'-methylbiphenyl-2-carboxamido-N-methyl-N-(2-hydroxyphenyl)benzamide (750 mg) in N,N-dimethylformamide (35 ml) was added potassium carbonate (1.42 g), 1,4-dibromobutane (1.11 g). The reaction mixture was stirred at 60° C. for 3 hours and to this mixture containing 4'-methylbiphenyl-2-carboxamido-N-methyl-N-[2-(4-bromobutoxy)phenyl]benzamide was added 1-methylpiperazine (1.03 g) and stirring was continued additional 15 hours. The mixture was extracted with ethyl acetate and washed with water and brine. The organic solution was dried over sodium sulfate. The solvent was removed by evaporation and purified by silica gel column chromatography (SiO$_2$; 35 g, 5% methanol in dichloromethane) to give 4-(4'-methylbiphenyl-2-carboxamido)-N-methyl-N-[2-[4-(4-methylpiperazin-1-yl)butoxy]phenyl]benzamide.

2) The obtained compound was reacted with hydrogen chloride to give 4-(4'-methylbiphenyl-2-carboxamido)-N-methyl-N-[2-[4-(4-methylpiperazin-1-yl)butoxy]phenyl]benzamide dihydrochloride (480 mg).

NMR (CDCl$_3$, δ): 1.72–1.95 (2H, m), 1.95–2.12 (2H, m), 2.35 (3H, s), 2.88 (3H, s), 3.09–3.33 (2H, m), 3.31 (3H, s), 3.52–4.19 (10H, m), 6.70 (1H, d, J=9 Hz), 6.86–7.55 (15H, m), 7.76 (1H, br d, J=9 Hz).

EXAMPLE 35

The following compound was obtained according to a similar manner to that of Example 34–1).

4-(4'-Methylbiphenyl-2-carboxamido)-N-methyl-N-[2-[6-(4-methylpiperazin-1-yl)hexyloxy]phenyl]benzamide NMR (CDCl$_3$, δ): 1.31–1.61 (6H, m), 1.72–1.86 (2H, m), 2.29 (3H, s), 2.36 (2H, t, J=7 Hz), 2.37 (3H, s), 2.38–2.66 (8H, m), 3.32 (3H, s), 3.80–4.00 (2H, m), 6.73–6.84 (2H, m), 6.88–7.00 (4H, m), 7.11–7.24 (5H, m), 7.30 (2H, d, J=9 Hz), 7.35–7.56 (3H, m), 7.82 (1H, d, J=9 Hz).

EXAMPLE 36

The following compound was obtained according to a similar manner to that of Example 34.

4-(4'-Methylbiphenyl-2-carboxamido)-N-methyl-N-[2-[8-(4-methylpiperazin-1-yl)octyloxy]phenyl]benzamide dihydrochloride NMR (CDCl$_3$, δ): 1.19–1.56 (8H, m), 1.56–1.95 (4H, m), 2.36 (3H, s), 2.88 (3H, s), 2.90 (2H, t, J=7 Hz), 2.95–3.14 (2H, m), 3.31 (3H, s), 3.42–3.70 (4H, m), 3.70–4.11 (4H, m), 6.72–6.86 (2H, m), 6.95–7.07 (3H, m), 7.09–7.58 (11H, m), 7.79 (1H, d, J=9 Hz).

EXAMPLE 37

To a solution of 4-(1,2-dimethylphenyl-3-carboxamido)-N-(2-hydroxyphenyl)-N-methylbenzamide (710 mg) in N,N-dimethylformamide (25 ml) was added potassium carbonate (786 mg), 1-bromo-6-chlorohexane (757 mg). The reaction mixture was stirred at 70° C. for 12 hours and to this mixture was added 1-methylpiperazine (1.1 g) and catalytic amount of sodium iodide and stirring was continued additional 16 hours. The mixture was extracted with ethyl acetate and washed with water and brine. The organic solution was dried over sodium sulfate. The solvent was removed by evaporation and purified by silica gel column chromatography (SiO$_2$; 40 g, 5% methanol in chloroform) to give 4-(1,2-dimethylphenyl-3-carboxamido)-N-methyl-N-[2-[6-(4-methylpiperazinyl)hex-1-yloxy]phenyl]benzamide (200 mg) as amorphous.

NMR (CDCl$_3$, δ): 1.30–1.60 (4H, m), 1.72–1.94 (2H, m), 2.18–2.66 (19H, m), 3.34 (3H, s), 3.83–4.00 (2H, m), 6.76–6.87 (2H, m), 6.99 (1H, d, J=9 Hz), 7.07–7.53 (9H, m).

EXAMPLE 38

To a solution of 4-(4'-methylbiphenyl-2-carboxamido)-N-methyl-N-[2-(3-bromopropoxy)phenyl]benzamide (520 mg) in N,N-dimethylformamide (15 ml) was added potassium carbonate (386 mg) and 1-methylpiperazine (280 mg) at ambient temperature. The reaction mixture was stirred at 60° C. for 12 hours. The reaction mixture was cooled and extracted with ethyl acetate and washed with water, saturated sodium hydrogen carbonate and brine. The organic solution was dried over sodium sulfate. The solvent was removed by evaporation and subjected to silica gel column chromatography (SiO$_2$; 30 g, 10% methanol in chloroform) to give 4-(4'-methylbiphenyl-2-carboxamido)-N-methyl-N-[2-[3-(4-methylpiperazin-1-yl)propoxy]phenyl]benzamide (180 mg).

NMR (CDCl$_3$, δ): 1.86–2.08 (2H, m), 2.29 (3H, s), 2.36 (3H, s), 2.39–2.67 (10H, m), 3.31 (3H, s), 3.82–4.07 (2H, m), 6.71–7.02 (5H, m), 7.06–7.56 (11H, m), 7.81 (1H, d, J=9 Hz).

EXAMPLE 39

The following compounds were obtained according to a similar manner to that of Example 38.

1) 4-(4'-Methylbiphenyl-2-carboxamido)-N-methyl-N-[2-[5-(4-methylpiperazin-1-yl)pentyloxy]phenyl]benzamide NMR (CDCl$_3$, δ): 1.41–1.63 (4H, m), 1.74–1.86 (2H, m), 2.32 (3H, s), 2.36 (3H, s), 2.20–2.65 (10H, m), 3.32 (3H, s), 3.78–4.00 (2H, m), 6.72–6.82 (2H, m), 6.86–6.98 (4H, m), 7.09–7.22 (5H, m), 7.29 (2H, d, J=9 Hz), 7.34–7.56 (3H, m), 7.82 (1H, d, J=9 Hz).

2) 3-Methoxy-4-(4'-methylbiphenyl-2-carboxamido)-N-methyl-N-[4-chloro-2-[6-(4-methylpiperazin-1-yl)hex-1-yloxy]phenyl]benzamide dihydrochloride NMR (CDCl$_3$, δ): 1.41–1.58 (4H, m), 1.72–1.83 (2H, m), 1.83–1.97 (2H, m), 2.34 and 2.35 (total 3H, s), 2.88 (3H, s), 3.06–3.16 (2H, m), 3.28 and 3.32 (total 3H, s), 3.39 and 3.43 (total 3H, s), 3.46–4.14 (10H, m), 6.74–7.05 (5H, m), 7.11–7.19 (2H, m), 7.25–7.31 (2H, m), 7.35–7.56 (3H, m), 7.67–7.75 (1H, m), 7.75–7.84 (1H, m), 8.13–8.24 (1H, m).

3) 3-Methoxy-4-nitro-N-[2-[6-(4-methylpiperazin-1-yl)hex-1-yloxy]-4-methylphenyl]-N-methylbenzamide NMR (CDCl$_3$, δ): 1.32–1.62 (6H, m), 1.70–1.90 (4H, m), 2.28 (3H, s), 2.29 (3H, s), 2.35 (2H, t, J=7 Hz), 2.22–2.70 (6H, m), 3.34 (3H, s), 3.77 (3H, s), 3.81–3.98 (2H, m), 6.55–6.65 (2H, m), 6.86 (1H, d, J=9 Hz), 6.94 (1H, d, J=9 Hz), 7.06 (1H, s), 7.61 (1H, d, J=9 Hz).

EXAMPLE 40

To a solution of 4-(4'-methylbiphenyl-2-carboxamido)-N-methyl-N-[2-(5-chloropentyloxy)phenyl]benzamide (800 mg) in N,N-dimethylformamide (15 ml) was added Potassium phthalimide (821 mg) and sodium iodide (cat.) at ambient temperature. The reaction mixture was stirred at 80° C. for 18 hours. The reaction mixture was cooled and extracted with ethyl acetate and washed with water and brine. The organic solution was dried over magnesium sulfate. The solvent was removed by evaporation and subjected to silica gel column chromatography (SiO$_2$; 50 g, 0.5% methanol in chloroform) to give 4-(4'-methylbiphenyl-2-carboxamido)-N-methyl-N-[2-(5-phthalimidopentyloxy)phenyl]benzamide (1.1 g).

NMR (CDCl$_3$, δ): 1.43–1.56 (2H, m), 1.67–1.89 (4H, m), 2.35 (3H, s), 3.29 (3H, s), 3.70 (2H, t, J=7 Hz), 3.79–3.96 (2H, m), 6.74–6.84 (2H, m), 6.88–7.04 (4H, m), 7.09–7.24 (4H, m), 7.29 (2H, d, J=9 Hz), 7.34–7.55 (3H, m), 7.66–7.92 (5H, m).

EXAMPLE 41

A solution of 4-(4'-methylbiphenyl-2-carboxamido)-N-methyl-N-[2-(5-aminopentyloxy)phenyl]benzamide (750 mg) in dichloromethane (30 ml) was treated with pyridine (681 mg) and phenyl chloroformate (675 mg). After 18 hours, the solvent was removed and the residue was dissolved in ethyl acetate, washed with 1N hydrochloric acid, water, saturated sodium hydrogen carbonate solution and brine, dried over sodium sulfate, concentrated, and purified by silica gel column chromatography (SiO$_2$; 50 g, 1% methanol in dichloromethane) to give 4-(4'-methylbiphenyl-2-carboxamido)-N-methyl-N-[2-(5-phenoxycarbonylaminopentyloxy)phenyl]benzamide (590 mg).

NMR (CDCl$_3$, δ): 1.45–1.72 (4H, m), 1.73–1.88 (2H, m), 2.36 (3H, s), 3.23–3.39 (2H, m), 3.33 (3H, s), 3.79–4.00 (2H, m), 5.44–5.51 (1H, m), 6.74–6.87 (2H, m), 6.88–6.99 (3H, m), 7.01–7.56 (16H, m), 7.82 (1H, d, J=9 Hz).

EXAMPLE 42

The following compounds were obtained according to a similar manner to that of Example 41.

1) 4-(4'-Methylbiphenyl-2-carboxamido)-N-methyl-N-[2-(3-phenoxycarbonylaminoprop-1-yloxy)phenyl]benzamide NMR (CDCl$_3$, δ): 2.05 (2H, quint., J=6 Hz), 2.36 (3H, s), 3.36 (3H, s), 3.43 (2H, q, J=6 Hz), 3.85–4.06 (2H, m), 5.32–5.40 (1H, br), 6.80–6.96 (4H, m), 7.05–7.55 (17H, m), 7.80 (1H, d, J=8 Hz).

2) 4-(4'-Methylbiphenyl-2-carboxamido)-N-methyl-N-[2-(4-phenoxycarbonylaminobutoxy)phenyl]benzamide NMR (CDCl$_3$, δ): 1.66–1.91 (4H, m), 2.34 (3H, s), 3.25–3.40 (2H, m), 3.34 (3H, s), 3.77–4.00 (2H, m), 5.36 (1H, br t, J=7 Hz), 6.72–7.00 (5H, m), 7.00–7.56 (16H, m), 7.81 (1H, d, J=9 Hz).

3) 6-(4'-Methylbiphenyl-2-carboxamido)-N-methyl-N-[2-[3-(phenoxycarbonylamino)prop-1-yloxy]phenyl]nicotinamide MASS (m/z): 615 (M+1).

4) 3-Methyl-4-(4'-methylbiphenyl-2-carboxamido)-N-methyl-N-[2-(3-phenoxycarbonylaminoprop-1-yloxy)phenyl]benzamide NMR (CDCl$_3$, δ): 1.45 (3H, s), 2.04 (2H, m), 2.34 (3H, s), 3.35 (3H, s), 3.42 (2H, m), 3.92 (1H, m), 4.03 (1H, m), 5.42 (1H, br), 6.80–6.92 (3H, m), 7.03–7.54 (15, m), 7.83 (1H, d, J=7 Hz), 7.91 (1H, m).

5) 3-Methoxy-4-(4'-methylbiphenyl-2-carboxamido)-N-methyl-N-[2-(3-phenoxycarbonylaminoprop-1-yloxy)phenyl]benzamide NMR (CDCl$_3$, δ): 2.06 (2H, m), 2.32 (3H, s), 3.31–3.48 (2H, m), 3.35 (3H, s), 3.40 (3H, s), 3.90 (1H, m), 4.04 (1H, m), 5.33 (1H, br), 6.79–6.90 (4H, m), 7.03–7.21 (6H, m), 7.27–7.53 (7H, m), 7.68 (1H, s), 7.79 (1H, d, J=7 Hz), 8.20 (1H, m).

6) 2-Methoxy-4-(4'-methylbiphenyl-2-carboxamido)-N-methyl-N-[2-(3-phenoxycarbonylaminoprop-1-yloxy)phenyl]benzamide NMR (CDCl$_3$, δ): 2.13 (2H, m), 2.36 (3H, s), 3.36 (3H, s), 3.61 (2H, m), 3.63 (3H, s), 4.02 (2H, m), 5.41 (1H, br), 6.22 (1H, d, J=7 Hz), 6.70–6.78 (2H, m), 6.82 (1H, s), 6.94–7.53 (15H, m), 7.82 (1H, d, J=7 Hz).

7) 3-Chloro-4-(4'-methylbiphenyl-2-carboxamido)-N-methyl-N-[2-(3-phenoxycarbonylaminoprop-1-yloxy)phenyl]benzamide NMR (CDCl$_3$, δ): 2.07 (2H, m), 2.33 (3H, s), 3.35 (3H, s), 3.45 (2H, m), 3.92 (1H, m), 4.03 (1H, m), 5.30 (1H, br), 6.80–6.90 (2H, m), 7.02–7.53 (16H, m), 7.78 (1H, d, J=7 Hz), 8.28 (1H, m).

EXAMPLE 43

To a solution of 4-(4'-methylbiphenyl-2-carboxamido)-N-methyl-N-[2-(5-phenoxycarbonylaminopentyloxy)phenyl] benzamide (290 mg) in N,N-dimethylformamide (15 ml) was added 1-methylpiperazine (271 mg) at ambient temperature. The reaction mixture was stirred at 80° C. for 10 hours. The reaction mixture was cooled and extracted with ethyl acetate and washed with saturated sodium hydrogen carbonate and brine. The organic solution was dried over sodium sulfate. The solvent was removed by evaporation and subjected to silica gel column chromatography (SiO$_2$; 30 g, 5% methanol in chloroform) to give 4-(4'-methylbiphenyl-2-carboxamido)-N-methyl-N-[2-[5-(4-methylpiperazin-1-carbonylamino)pentyloxy]phenyl]benzamide (190 mg).

NMR (CDCl$_3$, δ): 1.37–1.66 (4H, m), 1.68–1.83 (2H, m), 2.26 (3H, s), 2.29–2.39 (4H, m), 2.34 (3H, s), 3.11–3.29 (2H, m), 3.32 (3H, s), 3.33–3.43 (4H, br t, J=7 Hz), 3.76–3.96 (2H, m), 5.00 (1H, br t, J=7 Hz), 6.76 (1H, d, J=9 Hz), 6.83 (1H, dd, J=9, 9 Hz), 6.96 (2H, br d, J=9 Hz), 7.02–7.33 (9H, m), 7.35–7.56 (3H, m), 7.78 (1H, d, J=9 Hz).

EXAMPLE 44

The following compounds were obtained according to a similar manner to that of Example 43.

1) 4-(4'-Methyibiphenyl-2-carboxamido)-N-methyl-N-[2-{3-(N,N-dimethylhydrazino)carbonylaminoprop-1-yloxy}phenyl]benzamide NMR (CDCl$_3$, δ): 1.95–2.05 (2H, m), 2.35 (3H, s), 2.88 (6H, s), 3.33 (3H, s), 3.34–3.42 (2H, m), 3.85–4.02 (2H, m), 6.80–7.06 (6H, m), 7.15–7.32 (6H, m), 7.38–7.56 (4H, m), 7.82 (1H, d, J=8 Hz).

2) 6-(4'-Methylbiphenyl-2-carboxamido)-N-methyl-N-[2-[3-(4-methylpiperazin-1-yl)carbonylaminoprop-1-yloxy]phenyl]nicotinamide NMR (CDCl$_3$, δ): 1.98 (2H, m), 2.29 (3H, s), 2.33 (3H, s), 2.39 (4H, m), 3.34 (3H, s), 3.34–3.40 (6H, m), 3.92 (2H, m), 4.77 (1H, br), 6.76–6.90 (2H, m), 7.08 (1H, d, J=7 Hz), 7.12–7.20 (2H, m), 7.24–7.29 (2H, m), 7.38–7.45 (2H, m), 7.48–7.77 (4H, m), 7.97–8.10 (2H, m).

3) 3-Methyl-4-(4'-methylbiphenyl-2-carboxamido)-N-methyl-N-[2-[3-(4-methylpiperazin-1-yl)carbonylaminoprop-1-yloxy]phenyl]benzamide NMR (CDCl$_3$, δ): 1.42 (3H, s), 1.92 (2H, m), 2.20 (3H, s), 2.27 (4H, m), 2.32 (3H, s), 3.25 (3H, s), 3.37–3.42 (6H, m), 3.89 (2H, m), 5.21 (1H, br), 6.73–7.83 (2H, m), 6.95–7.18 (6H, m), 7.25–7.50 (4H, m), 7.70–7.82 (2H, m).

4) 3-Methoxy-4-(4'-methylbiphenyl-2-carboxamido)-N-methyl-N-[2-[3-(4-methylpiperazin-1-yl)-carbonylaminoprop-1-yloxy]phenyl]benzamide NMR (CDCl$_3$, δ): 2.00 (2H, m), 2.27 (3H, s), 2.35 (3H, s), 2.37 (4H, m), 3.33 (3H, s), 3.34 (3H, s), 3.34–3.41 (6H, m), 3.93 (2H, m), 4.82 (1H, br), 6.80–6.92 (3H, m), 7.05–7.55 (10H, m), 7.70 (1H, s), 7.80 (1H, d, J=7 Hz).

5) 2-Methoxy-4-(4'-methylbiphenyl-2-carboxamido)-N-methyl-N-[2-[3-(4-methylpiperazin-1-yl)-carbonylaminoprop-1-yloxy]phenyl]benzamide NMR (CDCl$_3$, δ): 2.02 (2H, m), 2.23 (3H, s), 2.31 (3H, s), 2.34 (4H, m), 3.28 (3H, s), 2.32–2.42 (6H, m), 3.55 (3H, s), 3.97 (2H, m), 5.13 (1H, br), 6.30 (1H, d, J=7 Hz), 6.63–6.73 (2H, m), 6.80 (1H, s), 6.90–7.52 (9H, m), 7.73 (1H, d, J=7 Hz), 7.94 (1H, s).

6) 3-Chloro-4-(4'-methylbiphenyl-2-carboxamido)-N-methyl-N-[2-[3-(4-methylpiperazin-1-yl)carbonylaminoprop-1-yloxy]benzamide NMR (CDCl$_3$, δ): 2.00 (2H, m), 2.30 (3H, s), 2.37 (3H, s), 2.39 (4H, m), 3.32 (3H, s), 3.35–3.41 (6H, m), 3.83–4.01 (2H, m), 4.83 (1H, br), 6.80–6.90 (2H, m), 7.02–7.57 (11H, m), 7.80 (1H, d, J=7 Hz), 8.28 (1H, m).

EXAMPLE 45

The following compound was obtained according to similar manners to those of Example 41 and 43.

4-(4'-Methylbiphenyl-2-carboxamido)-N-methyl-N-[2-[3-[1-methyl-4-piperidyloxycarbonylamino)propoxy]phenyl]benzamide NMR (CDCl$_3$, δ): 1.63–1.79 (2H, m), 1.86–2.06 (4H, m), 2.21–2.40 (2H, m), 2.30 (3H, s), 2.35 (3H, s), 2.68 (2H, br s), 3.33 (3H, s), 3.27–3.40 (2H, m), 3.81–4.06 (2H, m), 4.68 (1H, br s), 5.03 (1H, br s), 6.75–7.07 (6H, m), 7.10–7.25 (5H, m), 7.29 (2H, d, J=9 Hz), 7.35–7.66 (3H, m), 7.81 (1H, d, J=9 Hz).

EXAMPLE 46

A solution of 4-(4'-methylbiphenyl-2-carboxamido)-N-methyl-N-[2-(3-hydroxypropoxy)phenyl]benzamide (300 mg) in dichloromethane (15 ml) was treated with pyridine (95.8 mg) and p-nitrophenyl chloroformate (183 mg). After 4.5 hours, 1-methylpiperazine (303 mg) was added to the reaction mixture and stirred for a further 1 hour at ambient temperature. After concentration, the residue was dissolved in ethyl acetate and washed with saturated sodium hydrogen carbonate solution and brine, dried over sodium sulfate, concentrated, and purified by silica gel column chromatography (SiO$_2$; 30 g, 3% methanol in dichloromethane) to give 4-(4'-methylbiphenyl-2-carboxamido)-N-methyl-N-[2-[3-(4-methylpiperazin-1-carbonyloxy)propoxy]phenyl]benzamide (200 mg) as white amorphous.

NMR (CDCl$_3$, δ): 2.06–2.17 (2H, m), 2.30 (3H, s), 2.36 (3H, s), 2.33–2.42 (4H, m), 3.33 (3H, s), 3.48 (4H, br t, J=7 Hz), 3.86–4.06 (2H, m), 4.26 (2H, t, J=7 Hz), 6.76–7.02 (6H, m), 7.10–7.33 (7H, m), 7.35–7.56 (3H, m), 7.82 (1H, d, J=9 Hz).

EXAMPLE 47

The following compounds were obtained according to a similar manner to that of Example 46.
1) 4-(4'-Methylbiphenyl-2-carboxamido)-N-methyl-N-[2-[2-(N,N-dimethylamino)ethylcarbamoyloxy]phenyl]benzamide NMR (CDCl$_3$, δ): 2.28 (6H, s), 2.35 (3H, s), 2.22–2.34 (2H, m), 2.47 (2H, t, J=7 Hz), 3.35 (3H, s), 3.26–3.39 (2H, m), 5.66 (1H, m), 6.86–7.33 (13H, m), 7.33–7.56 (3H, m), 7.80 (1H, d, J=9 Hz).
2) 4-(4'-Methylbiphenyl-2-carboxamido)-N-methyl-N-[2-[4-(4-methylpiperazin-1-carbonyloxy)butoxy]phenyl]benzamide NMR (CDCl$_3$, δ): 1.74–1.93 (4H, br s), 2.29 (3H, s), 2.34 (3H, s), 2.31–2.50 (4H, m), 3.32 (3H, s), 3.39–3.62 (4H, m), 3.78–4.00 (2H, m), 4.13 (2H, br t, J=7 Hz), 6.74–6.84 (2H, m), 6.86–7.01 (4H, m), 7.06–7.34 (6H, m), 7.34–7.56 (3H, m), 7.81 (1H, br d, J=9 Hz).

EXAMPLE 48

To a solution of 4-(4'-methylbiphenyl-2-carboxamido)-N-methyl-N-[2-[4-[1-(t-butoxycarbonyl)piperidine-4-carbonylamino]butoxy]phenyl]benzamide (440 mg) in dichloromethane (15 ml) was added trifluoroacetic acid (1 ml) at 0° C. The reaction mixture was allowed to warm to ambient temperature and stirred for 2 hours. The solution was evaporated to remove excess trifluoroacetic acid. The residue was diluted with dichloromethane and washed with saturated sodium hydrogen carbonate and brine. The organic layer was dried over sodium sulfate, concentrated, and purified by silica gel column chromatography (SiO$_2$; 20 g, 1% ammonia solution (28%)–10% methanol in dichloromethane) to give 4-(4'-methylbiphenyl-2-carboxamido)-N-methyl-N-[2-[4-(piperidine-4-carbonylamino)butoxyphenyl]benzamide (310 mg).

NMR (CDCl$_3$, δ): 1.50–1.90 (8H, m), 2.17–2.37 (1H, m), 2.34 (3H, s), 2.59 (2H, dd, J=11, 11 Hz), 3.08 (2H, br d, J=11 Hz), 3.31 (3H, s), 3.19–3.39 (2H, m), 3.73–3.97 (2H, m), 5.94 (1H, br s), 6.71–7.34 (13H, m), 7.34–7.57 (3H, m), 7.80 (1H, d, J=9 Hz).

EXAMPLE 49

The following compounds were obtained according to a similar manner to that of Example 48.
1) 4-(4'-Methylbiphenyl-2-carboxamido)-N-methyl-N-[2-[2-(4-methylpiperazin-1-yl)carbonylethyl]aminoethoxy]phenyl]benzamide NMR (CDCl$_3$, δ): 2.28 (3H, s), 2.32–2.41 (4H, m), 2.37 (3H, s), 2.56 (2H, t, J=7.5 Hz), 3.00 (2H, t, J=7.5 Hz), 3.03 (2H, m), 3.32 (3H, s), 3.47 (2H, m), 3.59 (2H, m), 3.91 (1H, br), 4.06 (1H, br), 6.78–6.94 (2H, m), 6.89–7.02 (4H, m), 7.10–7.22 (4H, m), 7.28 (2H, d, J=8.5 Hz), 7.37–7.54 (3H, m), 7.82 (1H, d, J=7 Hz).
2) 4-(4'-Methylbiphenyl-2-carboxamido)-N-methyl-N-[2-[4-(piperazin-1-yl)sulfonylphenylmethoxy]phenyl]benzamide NMR (CDCl$_3$, δ): 2.32 (3H, s), 2.88–3.01 (8H, m), 3.37 (3H, s), 5.03 (2H, m), 7.80 (1H, d, J=7 Hz), 7.86–7.92 (3H, m), 7.10–7.20 (7H, m), 7.26–7.54 (7H, m), 7.75 (2H, d, J=8.5 Hz), 7.81 (1H, d, J=7 Hz).

EXAMPLE 50

A solution of 3-methoxy-4-(4'-nitrobiphenyl-2-carboxamido)-N-[4-methyl-2-[5-(4-methylpiperazin-1-ylcarbonyl)pent-1-yloxy]phenyl]-N-methylbenzamide (910 mg), 20% palladium hydroxide (200 mg) in methanol (30 ml) was stirred under atmospheric pressure of hydrogen at ambient temperature. After 5 hours, the reaction mixture was filtered through a bed of Celite, and the solvent was removed by evaporation and the crude product was purified by silica gel column chromatography (SiO$_2$; 30 g, 5% methanol in chloroform) to give free product. To a solution of this product (810 mg) in ethanol (20 ml) was added 1N hydrochloric acid (2.39 ml) and stirred at ambient temperature for 10 minutes. The solvent was removed to give 4-(4'-aminobiphenyl-2-carboxamido)-3-methoxy-N-[4-methyl-2-[5-(4-methylpiperazin-1-ylcarbonyl)pent-1-yloxy]phenyl]-N-methylbenzamide dihydrochloride as amorphous.

NMR (DMSO-d$_6$, δ): 1.37–1.50 (2H, m), 1.50–1.64 (2H, m), 1.67–1.80 (2H, m), 2.24 (3H, s), 2.38 (2H, t, J=7 Hz), 2.74 (3H, s), 2.80–3.50 (4H, m), 3.17 (3H, s), 3.54 (3H, s), 3.73–4.55 (6H, m), 6.63 (1H, d, J=9 Hz), 6.81 (3H, br s), 6.96–7.04 (1H, m), 7.30 (2H, d, J=9 Hz), 7.38–7.71 (7H, m), 9.16 (1H, s).

EXAMPLE 51

The following compounds were obtained according to a similar manner to that of Example 50.
1) 4-(4'-Aminobiphenyl-2-carboxamido)-3-methoxy-N-[2-[5-(4-dimethylaminopiperidin-1-ylcarbonyl)pent-1-yloxy]-4-methylphenyl]-N-methylbenzamide NMR (CDCl$_3$, δ): 1.33–2.08 (10H, m), 2.27 (3H, s), 2.30–2.45 (8H, m), 2.45–2.66 (1H, m), 2.94–3.08 (1H, m), 3.29 (3H, s), 3.46 (3H, s), 3.70–4.01 (4H, m), 4.60–4.75 (11H, m), 6.50–6.67 (4H, m), 6.72–6.89 (3H, m), 7.18 (2H, d, J=9 Hz), 7.30–7.41 (2H, m), 7.42–7.52 (1H, m), 7.71–7.82 (2H, m), 8.16 (1H, d, J=9 Hz).
2) 4-(4'-Aminobiphenyl-2-carboxamido)-3-methoxy-N-[4-methyl-2-[5-[4-(4-pyridyl)piperazin-1-ylcarbonyl]pent-1-yloxy]phenyl]-N-methylbenzamide NMR (CDCl$_3$, δ): 1.46–1.61 (2H, m), 1.65–1.91 (6H, m), 2.27 (3H, s), 2.40 (2H, t, J=7 Hz), 3.31 (3H, s), 3.30–3.41

(4H, m), 3.47 (3H, s), 3.56–3.68 (2H, m), 3.70–3.80 (2H, m), 3.80–4.01 (2H, m), 6.52–6.67 (6H, m), 6.74–6.84 (2H, m), 6.86 (1H, s), 7.17 (2H, d, J=9 Hz), 7.33–7.40 (2H, m), 7.43–7.51 (1H, m), 7.72–7.81 (2H, m), 8.17 (1H, br d, J=9 Hz), 8.27 (2H, d, J=9 Hz).

3) 4-(4'-Aminobiphenyl-2-carboxamido)-3-methoxy-N-[2-(5-carboxypent-1-yloxy)-4-methylphenyl]-N-methylbenzamide NMR (CDCl$_3$, δ): 1.45–1.58 (2H, m), 1.60–1.84 (4H, m), 2.27 (3H, s), 2.35 (2H, t, J=7 Hz), 3.29 (3H, s), 3.44 (3H, s), 3.70–3.84 (1H, m), 3.85–3.98 (1H, m), 6.54–6.63 (2H, m), 6.66 (2H, d, J=9 Hz), 6.80–6.90 (3H, m), 7.20 (2H, d, J=9 Hz), 7.30–7.41 (2H, m), 7.42–7.51 (1H, m), 7.73–7.86 (2H, m), 8.17 (1H, br d, J=9 Hz).

4) 4-(4'-Aminobiphenyl-2-carboxamido)-3-methoxy-N-methyl-N-[4-methyl-2-[6-(4-methylpiperazin-1-yl)hex-1-yloxy]phenyl]benzamide NMR (CDCl$_3$, δ): 1.30–1.65 (5H, m), 1.69–1.84 (2H, m), 2.25 (3H, s), 2.36 (3H, s), 2.30–2.84 (15H, m), 3.29 (3H, s), 3.47 (3H, s), 3.66–4.02 (4H, m), 6.50–6.67 (4H, m), 6.79 (2H, d, J=9 Hz), 6.87 (1H, s), 7.17 (2H, d, J=9 Hz), 7.36 (2H, dd, J=9, 9 Hz), 7.47 (1H, dd, J=9, 9 Hz), 7.70–7.82 (2H, m), 8.17 (1H, d).

5) 2-Ainino-4-(4'-methylbiphenyl-2-carboxamido)-N-[2-[5-(4-methylpiperazin-1-ylcarbonyl)pent-1-yloxy]phenyl]-N-methylbenzamide NMR (CDCl$_3$, δ): 1.40–1.57 (2H, m), 1.57–1.76 (2H, m), 1.76–1.91 (2H, m), 2.29 (3H, s), 2.35 (3H, s), 2.24–2.43 (6H, m), 3.29 (3H, s), 3.40–3.53 (2H, m), 3.53–3.66 (2H, m), 3.82 (2H, t, J=7 Hz), 4.77 (2H, br s), 5.76 (1H, br d, J=9 Hz), 6.63 (1H, br d, J=9 Hz), 6.71–6.86 (4H, m), 6.96 (1H, d, J=9 Hz), 7.06–7.54 (8H, m), 7.76 (1H, d, J=9 Hz).

6) 2-Amino-4-(methylphenyl-2-carboxamido)-N-methyl-N-[2-[5-(4-methylpiperazin-1-ylcarbonyl)pent-1-yloxy]phenyl]benzamide NMR (CDCl$_3$, δ): 1.42–1.58 (2H, m), 1.59–1.77 (2H, m), 1.78–1.84 (2H, m), 2.28 (3H, s), 2.26–2.43 (6H, m), 2.46 (3H, s), 3.33 (3H, s), 3.41–3.52 (2H, m), 3.54–3.66 (2H, m), 3.96 (2H, t, J=7 Hz), 4.90 (2H, br s), 6.33 (1H, br d, J=9 Hz), 6.81 (3H, dd, J=9, 9 Hz), 7.01 (1H, d, J=9 Hz), 7.08–7.44 (8H, m).

EXAMPLE 52

A solution of 4-(4'-nitrobiphenyl-2-carboxamido)-N-(2-benzyloxy-4-methylphenyl)-N-methylbenzamide (430 mg), 20% palladium hydroxide (80 mg) in methanol (20 ml) and 1,4-dioxane (30 ml) was stirred under atmospheric pressure of hydrogen at 30° C. After 5 hours, the reaction mixture was filtered through a bed of Celite, and the solvent was removed by evaporation and the crude product was purified by silica gel column chromatography (SiO$_2$; 30 g, 3% methanol in chloroform) to give 4-(4'-aminobiphenyl-2-carboxamido)-N-(2-hydroxy-4-methylphenyl)-N-methylbenzamide (350 mg) as amorphous.

NMR (CDCl$_3$, δ): 2.20 (3H, s), 3.31 (3H, s), 3.63–3.89 (2H, br s), 6.40–6.84 (5H, m), 6.85–7.04 (2H, m), 7.05–7.31 (5H, m), 7.31–7.40 (2H, m), 7.48 (1H, dd, J=9, 9 Hz), 7.64–7.78 (1H, m).

EXAMPLE 53

A mixture of 4-(4'-nitrobiphenyl-2-carboxamido)-N-methyl-N-[2-[5-(4-methylpiperazin-1-ylcarbonyl)pyrid-2-ylmethoxy]phenyl]benzamide (300 mg) and iron powder (122 mg) in a mixture of ethanol (10 ml) and acetic acid (1 ml) was refluxed for 3 hours and the mixture was evaporated in vacuo. The residue was stirred in a mixture of chloroform (20 ml) and saturated aqueous sodium hydrogen carbonate (20 ml) at ambient temperature for 30 minutes and the mixture was filtered through a bed of Celite. The organic phase of the filtrate was separated and washed with brine. The organic solution was dried over magnesium sulfate and the solvent was evaporated in vacuo to give a syrup. The crude product was purified by silica gel column (chloroform:methanol:conc. ammonia=10:1:0.1) to give 4-(4'-aminobiphenyl-2-carboxamido)-N-methyl-N-[2-[5-(4-methylpiperazin-1-ylcarbonyl)pyrid-2-ylmethoxy]phenyl]benzamide (157 mg) as a pale yellow amorphous.

NMR (CDCl$_3$, δ): 2.32 (3H, s), 2.42 (2H, m), 2.50 (2H, m), 3.33 (3H, s), 3.50 (2H, m), 3.71–3.95 (4H, m), 5.28 (3H, s), 6.63 (2H, d, J=8.5 Hz), 6.87 (1H, dd, J=7, 7 Hz), 6.87–7.01 (4H, m), 7.11–7.28 (5H, m), 7.32–7.50 (3H, m), 7.79 (1H, d, J=7 Hz), 7.97 (1H, m), 8.55 (1H, m).

EXAMPLE 54

To an ice bath cooled solution of (4-carboxybutyl)triphenylphosphonium bromide (371 mg) in N,N-dimethylacetamide (15 ml) was added potassium t-butoxide (188 mg) and the mixture was stirred at the same temperature for 30 minutes. To the resulting mixture was added 4-(4'-methylbiphenyl-2-carboxamido)-N-methyl-N-(2-formylphenyl)benzamide (250 mg) and the mixture was stirred in an ice bath for 3 hours. The mixture was diluted with ethyl acetate (40 ml) and the solution was washed successively with 1N hydrochloric acid (30 ml), water (20 ml) and brine (20 ml). The organic phase was dried over magnesium sulfate and the solvent was evaporated in vacuo to give an oil. The crude oil was purified by silica gel column (1% methanol in chloroform) to give 4-(4'-methylbiphenyl-2-carboxamido)-N-methyl-N-[2-(5-carboxypenten-1-yl)phenyl]benzamide (201 mg) as a colorless amorphous.

MASS (m/z): 533 (M+1).

EXAMPLE 55

A mixture of 4-(4'-methylbiphenyl-2-carboxamido)-N-methyl-N-[2-(3-formylprop-1-yloxy)phenyl]benzamide (507 mg) and (carbethoxymethylene)triphenylphosphorane (418 mg) in tetrahydrofuran (20 ml) was stirred at ambient temperature overnight and the solvent was evaporated in vacuo. The oily residue was purified by silica gel column (chloroform) to give 4-(4'-methylbiphenyl-2-carboxamido)-N-methyl-N-[2-(5-ethoxycarbonyl-4-penten-1-yloxy)phenyl]benzamide (435 mg) as a colorless amorphous.

NMR (CDCl$_3$, δ): 1.26 (3H, t, J=7.5 Hz), 1.93 (2H, m), 2.35 (3H, s), 2.39 (2H, m), 3.31 (3H, s), 3.77–3.97 (2H, m), 4.16 (2H, q, J=7.5 Hz), 5.84 (1H, dt, J=15, 1 Hz), 6.73–6.82 (2H, m), 6.88–7.01 (4H, m), 7.10–7.21 (4H, m), 7.29 (2H, d, J=8.5 Hz), 7.33–7.55 (4H, m), 7.82 (1H, d, J=7 Hz).

EXAMPLE 56

The following compound was obtained according to a similar manner to that of Preparation 11.

4-(4'-Methylbiphenyl-2-carboxamido)-N-methyl-N-[2-(2-acetoxyethoxy)phenyl]benzamide NMR (CDCl$_3$, δ): 2.06 (3H, s), 2.35 (3H, s), 3.33 (3H, s), 4.10 (2H, m), 4.39 (2H, m), 6.78–6.99 (6H, m), 7.10–7.29 (6H, m), 7.36–7.53 (3H, m), 7.82 (1H, d, J=7 Hz).

EXAMPLE 57

A mixture of 4-(4'-methylbiphenyl-2-carboxamido)-N-methyl-N-[2-(2-acetoxyethoxy)phenyl]benzamide and potassium carbonate (129 mg) in methanol (15 ml) was stirred at ambient temperature for 2 hours and the mixture was diluted with ethyl acetate (30 ml). The solution was washed with water and brine and the organic solution was dried over magnesium sulfate and the solvent was evaporated in vacuo to give 4-(4'-methylbiphenyl-2-carboxamido)-N-methyl-N-[2-(2-hydroxyethoxy)phenyl] benzamide (450 mg) as an oil.

NMR (CDCl$_3$, δ): 2.34 (3H, s), 3.32 (3H, s), 3.88 (2H, m), 3.99 (2H, m), 6.77–6.99 (4H, m), 7.08–7.30 (8H, m), 7.38 (1H, m), 7.43 (1H, d, J=7 Hz), 7.52 (1H, d, J=7 Hz), 7.82 (1H, d, J=7 Hz).

EXAMPLE 58

A solution of 4-(4'-methylbiphenyl-2-carboxamido)-N-methyl-N-[2-(6-methoxycarbonyl-5-hexenyloxy)phenyl] benzamide (360 mg) and nickel chloride hexahydrate (594 mg) in methanol (15 ml) and tetrahydrofuran (15 ml) was treated at 0° C. with sodium borohydride (283 mg) and stirred at 0° C. for 4 hours. The reaction mixture was diluted with tetrahydrofuran and filtered through a bed of Celite and then concentrated. The residue was diluted with ethyl acetate and washed with water and brine. The organic layer was dried over magnesium sulfate, concentrated to give 4-(4'-methylbiphenyl-2-carboxamido)-N-methyl-N-[2-(6-methoxycarbonylhexyloxy)phenyl]benzamide (340 mg).

NMR (CDCl$_3$, δ): 1.32–1.54 (4H, m), 1.60–1.85 (4H, m), 2.33 (2H, t, J=7 Hz), 2.36 (3H, s), 3.33 (3H, s), 3.65 (3H, s), 3.79–3.99 (2H, m), 6.76 (1H, d, J=9 Hz), 6.79 (1H, d, J=9 Hz), 6.86–7.00 (4H, m), 7.10–7.23 (5H, m), 7.30 (2H, d, J=9 Hz), 7.34–7.56 (3H, m), 7.82 (1H, d, J=9 Hz).

EXAMPLE 59

To an ice cooled mixture of 4-(4'-methylbiphenyl-2-carboxamido)-N-methyl-N-[2-[3-(4-methylpiperazin-1-yl) carbonylamino-(1-propyn-1-yl)]phenyl]benzamide (250 mg) and nickel chloride hexahydrate (297 mg) in a mixture of tetrahydrofuran (5 ml) and methanol (5 ml) was added sodium borohydride in small portions and the mixture was stirred at the same temperature for 1 hour. The mixture was filtered through bed of Celite and the filtrate was evaporated in vacuo. The residue was dissolved in chloroform (20 ml) and washed with water and brine. The organic solution was dried over magnesium sulfate and the solvent was evaporated in vacuo to give a syrup. The residue was solidified with diethyl ether to give 4-(4'-methylbiphenyl-2-carboxamido)-N-methyl-N-[2-[3-(4-methylpiperazin-1-ylcarbonyl)aminoprop-1-yl]phenyl]benzamide (75.0 mg) as a powder.

NMR (CDCl$_3$, δ): 2.12–2.56 (8H, m), 2.27 (3H, s), 2.36 (3H, s), 3.00–3.38 (6H, m), 3.40 (3H, s), 6.84–6.93 (2H, m), 7.10–7.57 (13H, m), 7.80 (1H, d, J=7.5 Hz).

EXAMPLE 60

A solution of 4-(4'-methylbiphenyl-2-carboxamido-N-methyl-N-[2-(4-ethoxycarbonylbutoxy)phenyl]benzamide (1.26 g) and dry tetrahydrofuran (30 ml) was cooled to 0° C., and lithium aluminum hydride (93.5 mg) was added. The reaction mixture was maintained at 0° C. for 1 hour, and then was quenched by adding 1N hydrochloric acid. The resulting mixture was filtered through a bed of Celite, diluted with ethyl acetate, washed with brine, dried over magnesium sulfate, and concentrated to give 4-(4'-methylbiphenyl-2-carboxamido)-N-methyl-N-[2-(5-hydroxypentyloxy) phenyl]benzamide (1.18 g).

NMR (CDCl$_3$, δ): 1.45–1.70 (4H, m), 1.72–1.86 (2H, m), 2.36 (3H, s), 3.32 (3H, s), 3.67 (2H, t, J=7 Hz), 3.76–3.99 (2H, m), 6.74–6.84 (2H, m), 6.87–7.06 (4H, m), 7.09–7.24 (5H, m), 7.28 (2H, d, J=9 Hz), 7.34–7.46 (2H, m), 7.51 (1H, dd, J=9, 9 Hz), 7.80 (1H, d, J=9 Hz).

EXAMPLE 61

The following compound was obtained according to a similar manner to that of Example 60.

4-(4'-Methylbiphenyl-2-carboxamido)-N-methyl-N-[2-(4-hydroxymethylphenylmethoxy)phenyl]benzamide NMR (CDCl$_3$, δ): 2.33 (3H, s), 3.34 (3H, s), 4.80 (1H, d, J=6 Hz), 5.30 (2H, m), 6.76–7.00 (6H, m), 7.07–7.19 (5H, m), 7.24–7.53 (8H, m), 7.81 (1H, d, J=7 Hz).

EXAMPLE 62

To a solution of 4-(4'-methylbiphenyl-2-carboxamido)-N-ethoxycarbonylmethyl-N-(2-methylphenyl)benzamide (100 mg) in ethanol (5 ml) was added sodium borohydride (37 mg) at 0° C. and the mixture was stirred for 2 hours at ambient temperature. Since the reaction was not completed and it was so slow, sodium borohydride (220 mg) was added to the mixture at 0° C. and stirred overnight. The reaction mixture was neutralized with 1N hydrochloric acid and diluted with ethyl acetate. The organic layer was washed with brine and dried over magnesium sulfate. Filtering and the removal of solvents afforded 4-(4'-methylbiphenyl-2-carboxamido)-N-(2-hydroxyethyl)-N-(2-methylphenyl) benzamide (70 mg) as a colorless prisms.

mp: 115–118° C.; NMR (CDCl$_3$, δ): 2.20 (3H, s), 2.38 (3H, s), 3.68–3.90 (4H, m), 4.08–4.30 (1H, m), 6.90 (3H, d, J=6 Hz), 7.10–7.58 (12H, m), 7.80 (1H, d, J=7 Hz).

EXAMPLE 63

The following compound was obtained according to a similar manner to that of Example 17.

4-(4'-Methylbiphenyl-2-carboxamido)-N-methyl-N-[2-(4-formylphenylmethoxy)phenyl]benzamide This compound was used for further reaction without purification.

EXAMPLE 64

To a solution of oxalyl chloride (174 mg) in dichloromethane (15 ml) was added dimethyl sulfoxide (107 mg) at −78° C. and the solution was stirred at the same temperature for 10 minutes. A solution of 4-(4'-methylbiphenyl-2-carboxamido)-N-methyl-N-[2-(2-hydroxyethoxy)phenyl] benzamide (440 mg) in dichloromethane (5 ml) was added to the mixture at −78° C. After being stirred at −78° C. for 20 minutes, triethylamine (0.51 ml) was added to the mixture at the same temperature and the cooling bath was removed. The mixture was stirred at ambient temperature for 3 hours and the solution was washed successively with 1N hydrochloric acid, water and brine. The organic solution was dried over magnesium sulfate and the solvent was evaporated in vacuo to give 4-(4'-methylbiphenyl-2-carboxamido)-N-methyl-N-[2-(formylmethoxy)phenyl] benzamide (420 mg) as an amorphous.

NMR (CDCl$_3$, δ): 2.35 (3H, s), 3.39 (3H, s), 5.30 (2H, s), 6.61 (1H, d, J=7 Hz), 7.86–6.97 (3H, m), 7.10–7.31 (8H, m), 7.37–7.54 (3H, m), 7.82 (1H, d, J=7 Hz), 9.56 (1H, s).

EXAMPLE 65

To a mixture of 4-(4'-methylbiphenyl-2-carboxamido)-N-methyl-N-[2-(formylmethoxy)phenyl]benzamide (400 mg)

and 4-methyl-1-(N-methylamino)methylcarbonylpiperazine (143 mg) in a mixture of methanol (15 ml) and acetic acid (0.5 ml) was added sodium cyanoborohydride (52.4 mg) and the mixture was stirred at ambient temperature for 4 hours. The solution was diluted with ethyl acetate (30 ml) and washed successively with saturated aqueous sodium hydrogen carbonate, water and brine. The organic solution was dried over magnesium sulfate and the solvent was evaporated in vacuo. The residue was purified by silica gel column (chloroform:methanol:conc. ammonia=10:1:0.1) to give 4-(4'-methylbiphenyl-2-carboxamido)-N-methyl-N-[2-[2-[N-methyl-N-(4-methylpiperazin-1-yl)carbonylmethylamino]ethoxy]phenyl]benzamide (310 mg) as a colorless amorphous.

NMR (CDCl$_3$, δ): 2.27 (3H, s), 2.30–2.38 (4H, m), 2.36 (3H, s), 2.43 (3H, s), 2.90 (2H, m), 3.28–3.32 (2H, m), 3.31 (3H, s), 3.55 (2H, m), 3.60 (2H, m), 3.89 (1H, m), 4.07 (1H, m), 6.78 (2H, m), 6.86–6.98 (4H, m), 7.10–7.30 (5H, m), 7.37–7.53 (4H, m), 7.82 (1H, d, J=7 Hz).

EXAMPLE 66

The following compound was obtained according to a similar manner to that of Example 65.

4-(4'-Methylbiphenyl-2-carboxamido)-N-methyl-N-[2-[4-(4-methylpiperazin-1-yl)methylphenylmethoxy]phenyl]benzamide NMR (CDCl$_3$, δ): 2.19 (3H, s), 2.34 (3H, s), 2.39–2.60 (8H, m), 3.35 (3H, s), 3.50 (2H, s), 4.98 (2H, m), 6.77–6.91 (5H, m), 7.00 (1H, d), 7.10–7.20 (5H, m), 7.25–7.53 (8H, m), 7.82 (1H, d, J=7 Hz).

EXAMPLE 67

The following compound was obtained according to similar manners to those of Examples 64 and 65.

4-(4'-Methylbiphenyl-2-carboxamido)-N-methyl-N-[2-[2-(2-methoxycarbonylethyl)aminoethoxy]phenyl]benzamide NMR (CDCl$_3$, δ): 2.35 (3H, s), 2.53 (2H, t, J=7.5 Hz), 2.97 (2H, t, J=7.5 Hz), 2.99 (2H, m), 3.32 (3H, s), 3.68 (3H, s), 3.90–4.02 (2H, m), 6.75–6.83 (2H, m), 6.88–7.01 (4H, m), 7.10–7.24 (4H, m), 7.30 (2H, d, J=8.5 Hz), 7.36–7.53 (3H, m), 7.80 (1H, d, J=7 Hz).

EXAMPLE 68

The following compound was obtained according to similar manners to those of Examples 64 and 55.

4-(4'-Methylbiphenyl-2-carboxamido)-N-methyl-N-[2-(6-methoxycarbonyl-5-hexenyloxy)phenyl]benzamide NMR (CDCl$_3$, δ): 1.55–1.70 (2H, m), 1.73–1.86 (2H, m), 2.28 (2H, dt, J=7, 7 Hz), 2.36 (3H, s), 3.33 (3H, s), 3.73 (3H, s), 3.78–3.99 (2H, m), 5.86 (1H, d, J=15 Hz), 6.78 (1H, d, J=9 Hz), 6.81 (1H, d, J=9 Hz), 6.88–7.04 (5H, m), 7.10–7.23 (4H, m), 7.30 (2H, d, J=9 Hz), 7.34–7.56 (3H, m), 7.82 (1H, d, J=9 Hz).

EXAMPLE 69

To a solution of 4-(4'-methylbiphenyl-2-carboxamido)-N-methyl-N-[2-(3-ethoxycarbonylprop-1-yloxy)phenyl]benzamide (1.10 g) in dichloromethane (20 ml) was added dropwise a solution of diisobutylaluminum hydride in toluene (1.5 M solution, 2 ml) at −78° C. and the mixture was stirred at the same temperature for 2 hours. The reaction was quenched with addition of water and the resulting mixture was warmed to ambient temperature. The mixture was extracted with dichloromethane and the organic phase was washed successively with 1N hydrochloric acid, water and brine. The organic solution was dried over magnesium sulfate and the solvent was evaporated in vacuo to give 4-(4'-methylbiphenyl-2-carboxamido)-N-methyl-N-[2-(3-formylprop-1-yloxy)phenyl]benzamide (987 mg) as a syrup. The unstable aldehyde was immediately used for next step.

EXAMPLE 70

To a solution of oxalyl chloride (127 mg) in dichloromethane (20 ml) was added dimethyl sulfoxide (78 mg) at −78° C. and the solution was stirred at the same temperature for 10 minutes. A solution of 4-(4'-methylbiphenyl-2-carboxamido)-N-methyl-N-[2-(2-hydroxyethoxy)phenyl]benzamide (400 mg) in dichloromethane (5 ml) was added to the mixture at −78° C. After being stirred at −78° C. for 20 minutes, triethylamine (0.50 ml) was added to the mixture at the same temperature and the cooling bath was removed. The mixture was stirred at ambient temperature for 3 hours and the solution was washed successively with 1N hydrochloric acid, water and brine. The organic solution was dried over magnesium sulfate and the solvent was evaporated in vacuo to give 4-(4'-methylbiphenyl-2-carboxamido)-N-methyl-N-[2-(formylmethyloxy)phenyl]benzamide (399 mg) as an amorphous. To a mixture of the crude obtained aldehyde (399 mg) and hydroxylamine hydrochloride (174 mg) in ethanol (20 ml) was added potassium carbonate (173 mg) in water (2 ml) and the solution was stirred at ambient temperature for 2 hours. The mixture was diluted with ethyl acetate (30 ml) and the solution was washed with water and brine. The organic phase was dried over magnesium sulfate and the solvent was evaporated in vacuo to give 4-(4'-methylbiphenyl-2-carboxamido)-N-methyl-N-[2-(2-hydroxyiminoethoxy)phenyl]benzamide (288 mg) as an amorphous.

NMR (CDCl$_3$, δ): 2.34 (3H, s), 3.34 (1.5H, s), 3.36 (1.5H, s), 4.52 (0.5H, br), 4.73 (0.5H, br), 6.78–6.95 (6H, m), 7.05–7.21 (7H, m), 7.28 (2H, d, J=8.5 Hz), 7.36–7.53 (3H, m), 7.80 (1H, d, J=7 Hz).

EXAMPLE 71

The following compounds were obtained according to a similar manner to that of Example 20.

1) 4-(4'-Methylbiphenyl-2-carboxamido)-N-methyl-N-[2-[2-[N-[2-(4-methylpiperazin-1-yl)carbonylethyl]-N-methylaminoethoxy]phenyl]benzamide NMR (CDCl$_3$, δ): 2.11 (1.5H, s), 2.16 (1.5H, s), 2.28 (1.5H, s), 2.30 (1.5H, s), 2.30–2.40 (4H, m), 2.61 (2H, t, J=7.5 Hz), 3.30 (1.5H, s), 3.32 (1.5H, s), 3.39–3.87 (9H, m), 4.03 (1H, m), 6.74–7.01 (4H, m), 7.06 (1H, d, J=7 Hz), 7.12–7.20 (5H, m), 7.30 (2H, d, J=8.5 Hz), 7.37–7.53 (3H, m), 7.79 (1H, m).

2) 4-(4'-Methylbiphenyl-2-carboxamido)-N-methyl-N-[2-[4-(4-methylpiperazin-1-yl)sulfonylphenylmethoxy]phenyl]benzamide NMR (CDCl$_3$, δ): 2.23 (3H, s), 2.32 (3H, s), 2.41–2.50 (4H, m), 2.97–3.08 (4H, m), 3.38 (3H, s), 5.03 (2H, m), 6.78 (1H, d, J=7 Hz), 7.86–7.93 (3H, m), 7.11–7.22 (6H, m), 7.31 (2H, d, J=8.5 Hz), 7.37–7.53 (5H, m), 7.76 (2H, d, J=8.5 Hz), 7.84 (1H, d, J=7 Hz).

EXAMPLE 72

To a solution of 4-(4'-aminobiphenyl-2-carboxamido)-3-methoxy-N-[2-[5-(4-dimethylaminopiperidin-1-ylcarbonyl)pent-1-yloxy]-4-methylphenyl]-N-methylbenzamide (180 mg) and 37% formalin (3 ml) in methanol (20 ml) and acetic acid (0.5 ml) was added sodium cyanoborohydride (80 mg) at ambient temperature. The mixture was stirred at same temperature for 3 hours and quenched with saturated sodium hydrogen carbonate. The mixture was extracted with ethyl acetate and washed with saturated sodium hydrogen carbonate, brine and dried over sodium sulfate. The solvent was removed by evaporation and the crude product was purified by preparative thin layer chromatography (10% methanol in chloroform) to give free product. To a solution of this product (120 mg) in ethanol (10 ml) was added 1N hydrochloric acid (0.33 ml) and stirred at ambient temperature for 10 minutes. The solvent was removed to give 4-(4'-dimethylaminobiphenyl-2-carboxamido)-3-methoxy-N-[2-[5-(4-dimethylaminopiperidin-1-ylcarbonyl)pent-1-yloxy]-4-methylphenyl]-N-methylbenzamide dihydrochloride (130 mg) as amorphous.

NMR (DMSO-$d_6$, δ): 1.25–2.10 (10H, m), 2.26 (3H, s), 2.20–2.40 (2H, m), 2.63 (3H, s), 2.64 (3H, s), 2.99 (6H, s), 3.16 (3H, s), 3.20–3.50 (2H, m), 3.49 (3H, s), 3.50–4.10 (4H, m), 4.47–4.60 (1H, m), 6.64 (1H, d, J=9 Hz), 6.74–6.90 (3H, m), 7.01 (1H, d, J=9 Hz), 7.04–7.25 (1H, m), 7.31–7.48 (4H, m), 7.49–7.62 (2H, m), 7.68–7.78 (1H, m), 8.96 (1H, br s).

EXAMPLE 73

A mixture of 4-(4'-methylbiphenyl-2-carboxamido)-N-methyl-N-(2-cyanophenyl)benzamide (350 mg) and trimethyltin azide (453 mg) in xylene (15 ml) heated at 120° C. for 2 days and cooled to ambient temperature. The solution was directly applied to silica gel column (the column was pre-packed with chloroform as a solvent). The column was eluted with 2% methanol in chloroform and the solvent was evaporated in vacuo. The residue was solidified with diethyl ether to give 4-(4'-methylbiphenyl-2-carboxamido)-N-methyl-N-[2-(tetrazol-5-yl)phenyl]benzamide (233 mg) as a white powder.

NMR (DMSO-$d_6$, δ): 2.28 (3H, s), 3.19 (3H, s), 6.93 (2H, d, J=8.5 Hz), 7.10–7.53 (13H, m), 7.74 (1H, d, J=7 Hz).

EXAMPLE 74

A mixture of 4-(4'-methylbiphenyl-2-carboxamido)-N-methyl-N-[2-[5-(4-methylpiperazin-1-yl)carbonylpent-1-ylthio]phenyl]benzamide (500 mg) and m-chloroperbenzoic acid (133 mg) in dichloromethane (20 ml) was stirred in an ice bath for 2 hours and the solution was washed successively with saturated aqueous sodium hydrogen carbonate, water and brine. The organic solution was dried over magnesium sulfate and the solvent was evaporated in vacuo to give a syrup. The crude product was solidified with diethyl ether to give 4-(4'-methylbiphenyl-2-carboxamido)-N-methyl-N-[2-[5-(4-methylpiperazin-1-yl)carbonylpent-1-ylsulfinyl]phenyl]benzamide (423 mg) as a white powder.

MASS (m/z): 665 (M+1).

EXAMPLE 75

A mixture of 4-(4'-methylbiphenyl-2-carboxamido)-N-methyl-N-[2-[5-(4-methylpiperazin-1-yl)carbonylpent-1-ylthio]phenyl]benzamide (500 mg) and m-chloroperbenzoic acid (332 mg) in dichloromethane (20 ml) was stirred at ambient temperature for 4 hours and the solution was washed successively with saturated aqueous sodium hydrogen carbonate, water and brine. The organic solution was dried over magnesium sulfate and the solvent was evaporated in vacuo to give a syrup. The crude product was solidified with diethyl ether to give 4-(4'-methylbiphenyl-2-carboxamido)-N-methyl-N-[2-[5-(4-methylpiperazin-1-yl)carbonylpent-1-ylsulfonyl]phenyl]benzamide (455 mg) as a white powder.

MASS (m/z): 681 (M+1).

EXAMPLE 76

A mixture of 4-(4'-methylbiphenyl-2-carboxamido)-N-methyl-N-[2-[2-(2-methoxycarbonylethyl)aminoethoxy]phenyl]benzamide (409 mg), di-tert-butyl dicarbonate (189 mg) and triethylamine (87.8 mg) in dichloromethane (20 ml) was stirred in an ice bath for 6 hours and the mixture was washed successively with 1N hydrochloric acid, water and brine. The organic solution was dried over magnesium sulfate and the solvent was evaporated in vacuo to give 4-(4'-methylbiphenyl-2-carboxamido)-N-methyl-N-[2-[2-[N-(2-methoxycarbonylethyl)-N-(t-butoxycarbonyl)amino]ethyloxy]phenyl]benzamide (450 mg) as a colorless amorphous.

NMR (CDCl$_3$, δ): 1.44 (9H, s), 2.35 (3H, s), 2.58 (2H, m), 3.31 (3H, s), 3.68 (2H, t, J=7.5 Hz), 3.66 (2H, m), 3.82–5.13 (2H, m), 6.76–7.02 (6H, m), 7.11–7.22 (4H, m), 7.28 (2H, d, J=8.5 Hz), 7.35–7.53 (3H, m), 7.81 (1H, d, J=7 Hz).

EXAMPLE 77

To a solution of 4-(4'-methylbiphenyl-2-carboxamido)-N-methyl-N-[2-(3-hydroxypropoxy)phenyl]benzamide (520 mg) in dichloromethane (20 ml) was added triphenylphosphine (827 mg) and carbon tetrabromide (1.39 g) at ambient temperature. The mixture was stirred for 2 hours and diluted with ethyl acetate and washed successively with saturated sodium hydrogen carbonate and brine, and dried over magnesium sulfate. The solid was removed and the solvent was removed by evaporation to give crude product. The crude material was subjected to a silica gel column chromatography (SiO$_2$; 50 g, 0.5% methanol in chloroform) to give 4-(4'-methylbiphenyl-2-carboxamido)-N-methyl-N-[2-(3-bromopropoxy)phenyl]benzamide (540 mg) as white amorphous.

NMR (CDCl$_3$, δ): 2.24–2.33 (2H, m), 2.36 (3H, s), 3.33 (3H, s), 3.59 (2H, t, J=7 Hz), 3.93–4.17 (2H, m), 6.78–6.96 (5H, m), 7.02 (1H, br d, J=9 Hz), 7.12–7.24 (4H, m), 7.30 (2H, d, J=9 Hz), 7.35–7.56 (3H, m), 7.82 (1H, d, J=9 Hz).

EXAMPLE 78

A solution of 4-(4'-methylbiphenyl-2-carboxamido)-N-methyl-N-[4-methyl-2-[5-(piperazin-1-yl)carbonylpentyloxy]phenyl]benzamide (150 mg) in dichloromethane (15 ml) was treated with pyridine (0.04 ml) and trifluoroacetic anhydride (0.04 ml) at 0° C. After 30 minutes, the mixture was allowed to warm to ambient temperature and stirred for 1.5 hours. The reaction mixture was diluted with ethyl acetate and washed with water, saturated sodium bicarbonate solution and brine, dried over magnesium sulfate, concentrated, and purified by column chromatography (SiO$_2$; 30 g, ethyl acetate:n-hexane=1:1) to give 4-(4'-methylbiphenyl-2-carboxamido)-N-methyl-N-[4-methyl-2-[5-(4-trifluoroacetylpiperazin-1-yl)carbonylpentyloxy]phenyl]benzamide (80 mg).

NMR (CDCl$_3$, δ): 1.46–1.59 (2H, m), 1.64–1.86 (4H, m), 2.27 (3H, s), 2.36 (3H, s), 2.32–2.43 (2H, m), 3.28 (3H, s), 3.48–3.74 (8H, m), 3.74–3.9 (2H, m), 6.54–6.63 (2H, m), 6.84 (1H, d, J=9 Hz), 6.94 (3H, br d, J=9 Hz), 7.18 (4H, br d, J=9 Hz), 7.29 (2H, d, J=9 Hz), 7.34–7.56 (3H, m), 7.81 (1H, d, J=9 Hz).

What is claimed is:

1. A compound of the formula:

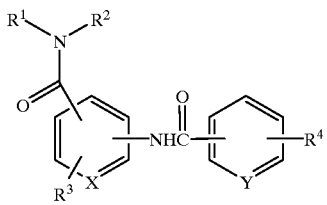
(I)

wherein
- R¹ is aryl or haloaryl, each of which is substituted with lower alkoxy substituted with N-(lower alkyl)-piperazinylcarbonyl, esterified carboxy or carboxy; or pyridyl, or thienyl, each of which is optionally substituted with esterified carboxy;
- R² is lower alkyl optionally substituted with hydroxy, aryl or acyl; or cyclo(lower)alkyl;
- R³ is hydrogen, halogen, lower alkyl, lower alkoxy, nitro or amino;
- R⁴ is lower alkyl, or optionally substituted aryl;
- X is CH; and
- Y is CH;

or a pharmaceutically acceptable salt thereof.

2. The compound of claim 1, wherein
- R² is lower alkyl or cyclo(lower)alkyl;
- R³ is hydrogen, halogen or lower alkoxy; and
- R⁴ is lower alkyl, or aryl optionally substituted with halogen, nitro, amino or lower alkylamino.

3. The compound of claim 1, wherein
- R¹ is aryl or haloaryl, each of which is substituted with lower alkoxy substituted with N-(lower alkyl)-piperazinylcarbonyl, esterified carboxy or carboxy;
- R² is lower alkyl; and
- R⁴ is aryl optionally substituted with amino.

4. The compound of claim 3, wherein
- R³ is hydrogen or lower alkoxy.

5. A process for preparing a compound of the formula (I):

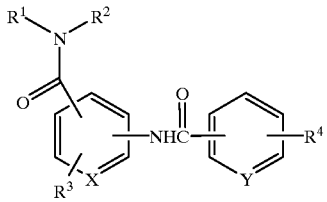
(I)

wherein
- R¹ is aryl or haloaryl, each of which is substituted with lower alkoxy substituted with N-(lower alkyl)-piperazinylcarbonyl, esterified carboxy or carboxy; or pyridyl, or thienyl, each of which are optionally substituted with esterified carboxy;
- R² is lower alkyl optionally substituted with hydroxy, aryl or acyl; or cyclo(lower)alkyl;
- R³ is hydrogen, halogen, lower alkyl, lower alkoxy, nitro or amino;
- R⁴ is lower alkyl; or optionally substituted aryl;
- X is CH; and
- Y is CH;

or a pharmaceutically acceptable salt thereof, which comprises, 1) reacting a compound of the formula (II):

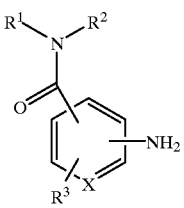
(II)

or a salt thereof with a compound of the formula (III):

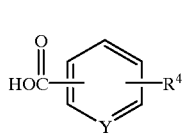
(III)

or a reactive compound thereof at the carboxy group or a salt thereof to provide a compound of the formula (I):

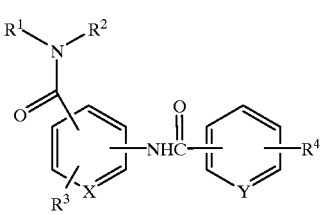
(I)

or a salt thereof, or 2) reacting a compound of the formula (IV):

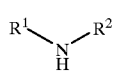
(IV)

or a salt thereof with a compound of the formula (IV):

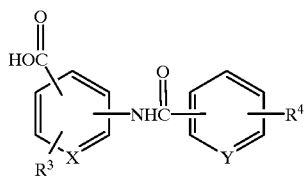
(V)

or a reactive compound thereof at the carboxy group or a salt thereof to provide a compound of the formula (I):

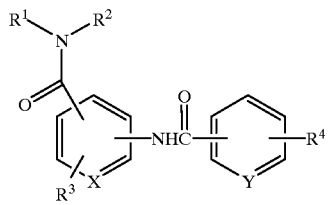

(I)

or a salt thereof, or 3) subjecting a compound of the formula (Ia):

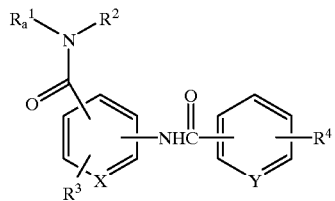

(Ia)

or a salt thereof to a deesterification reaction to provide a compound of the formula (Ib):

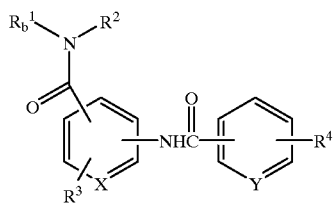

(Ib)

or a salt thereof, and wherein in the above formulas, $R_a^1$ and $R_b^1$ are each independently as defined above for $R^1$; and further wherein $R_a^1$ contains ester groups, and $R_b^1$ has said ester groups removed by said deesterification reaction; or 4) subjecting a compound of the formula (Ic):

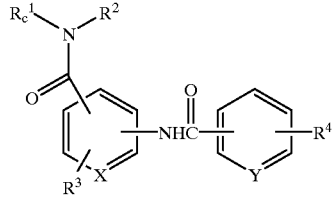

(Ic)

or salt thereof to deacylation reaction to provide a compound of the formula (Id):

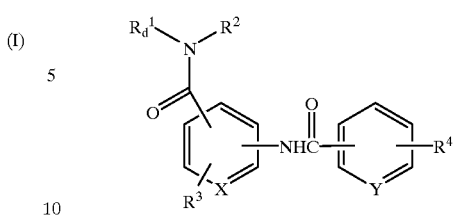

(Id)

or a salt, thereof, and wherein in the above formulas, $R_c^1$ and $R_d^1$ are each independently as defined above for $R^1$, wherein $R_c^1$ contains an ester group, and $R_d^1$ has said ester group removed by said deacylation reaction;

5) subjecting a compound of the formula (Ie):

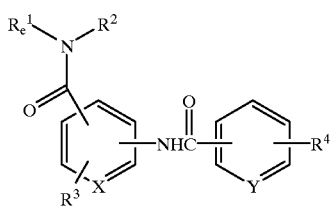

(Ie)

or a salt thereof to an elimination reaction of the N-protective group to provide a compound of the formula (If):

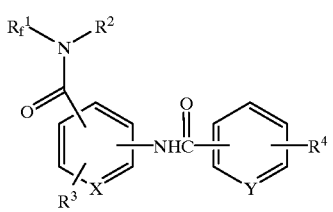

(If)

or a salt thereof, and wherein in the above formulas, $R_e^1$ and $R_f^1$ are each independently as defined above for $R^1$, and further wherein $R_e^1$ contains a protected amino group, and $R_f^1$ has said protecting group removed by said elimination reaction;

6) reacting a compound of the formula (Ib):

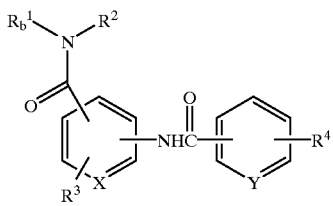

(Ib)

or a reactive compound thereof at the carboxy group or a salt thereof with an amine or its salt to provide a compound of the formula (Ig):

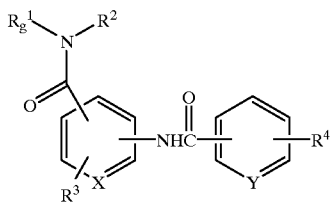

(Ig)

or a salt thereof, and wherein in the above formulas,
$R_b^1$ and $R_g^1$ are each independently as defined for $R^1$, further wherein
$R_b^1$ contains a carboxy group, and $R_g^1$ contains a carbamoyl group corresponding to said carboxy group of $R_b^1$; or 7) reacting a compound of the formula (Ih):

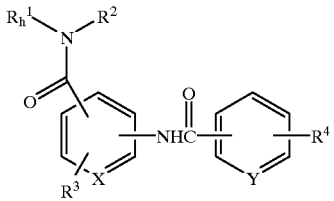

(Ih)

or a reactive compound thereof at the carboxy group or a salt thereof with an azide compound and then reacting the resultant product with an acid to provide a compound of the formula (Ii):

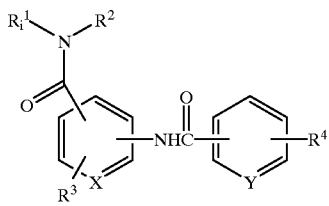

(Ii)

or a salt thereof, and wherein in the above formulas,
$R_h^1$ and $R_i^1$ are each independently as defined above for $R^1$, further wherein
$R_h^1$ contains a carboxy group, and and $R_i^1$ contains an amino group corresponding to said carboxy group of $R_h^1$; or 8) subjecting a compound of the formula (Ij):

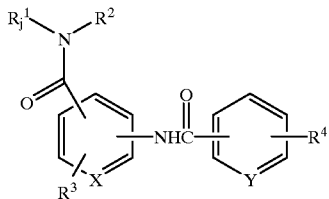

(Ij)

or a salt thereof to reduction to provide a compound of the formula:

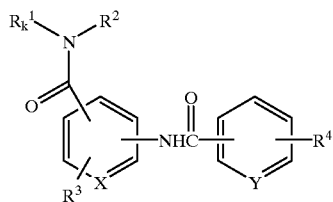

(Ik)

or a salt thereof, and wherein in the above formulas,
$R_j^1$ and $R_k^1$ are each independently as defined above for $R^1$, and further wherein
$R_j^1$ contains unsaturated aliphatic groups, and $R_k^1$ contains saturated aliphatic groups corresponding thereto; or 9) reacting a compound of the formula (Il):

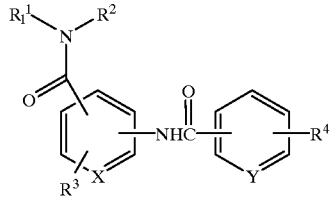

(Il)

or a salt thereof with a reducing agent to provide a compound of the formula (Im):

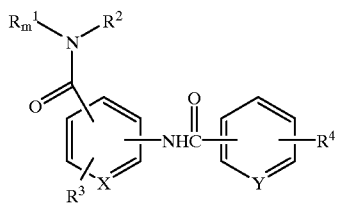

(Im)

or a salt thereof, and wherein in the above formulas,
$R_l^1$ and $R_m^1$ are each independently as defined above for $R^1$, and further wherein
$R_l^1$ contains esterified carboxy, and $R_m^1$ contains hydroxymethyl corresponding thereto; or 10) reacting a compound of the formula:

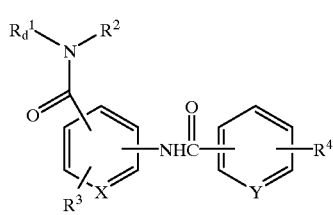

(Id)

or a salt thereof with an acylating agent to provide a compound of the formula (Ic):

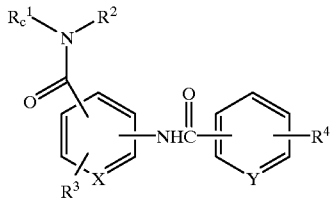

(Ic)

or a salt thereof, and wherein in the above formulas, $R_c^1$ and $R_d^1$ are each independently as defined above; or 11) subjecting a compound of the formula:

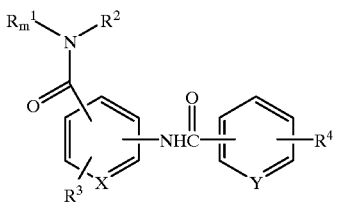

(Im)

or a salt thereof to oxidation reaction to provide a compound of the formula (In):

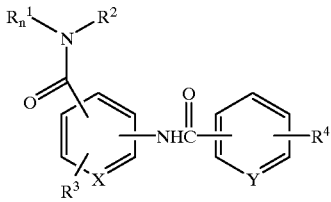

(In)

or a salt thereof, and wherein in the above formulas, $R_m^1$ and $R_n^1$ are each independently as defined above for $R^1$, wherein $R_m^1$ is as define above, and $R_n^1$ is substituted with alkanoyl or formyl groups; or 12) reacting a compound of the formula (In):

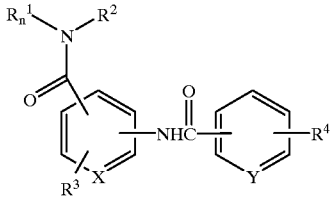

(In)

or a salt thereof with mono or di(lower)alkylamine, N-acyl(lower)alkyl-N-lower alkylamine, or a salt thereof in the presence of a reducing agent to provide a compound of the formula (Io):

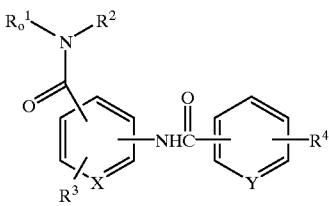

(Io)

or a salt thereof, in the above formulas,
$R_n^1$ and $R_o^1$ are each independently as defined above for $R^1$, and further wherein
$R_o^1$ further contains substituent groups comprising (lower alkyl)amino (lower)alkyl, N-acyl (lower) alkylamino; or 13) reacting a compound of the formula (Ip):

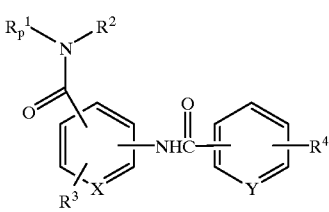

(Ip)

or a salt thereof with lower alkanal to provide a compound of the formula (Iq):

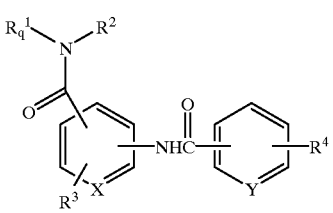

(Iq)

or a salt thereof, and wherein in the above formulas,
$R_p^1$ and $R_q^1$ are each independently as defined above for $R^1$, and further wherein
$R_p^1$ contains an amino group, and $R_q^1$ contains a corresponding alkylated amino group; or 14) subjecting a compound of the formula:

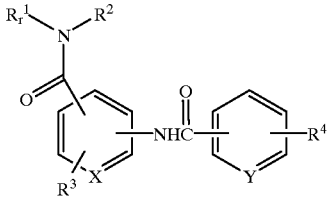

(Ir)

or a salt thereof to catalytic reduction to provide a compound of the formula (Is):

(Is)

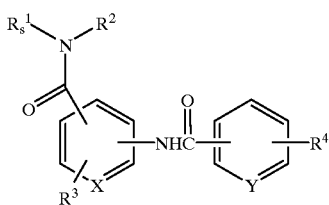

or a salt thereof, in the above formulas,
$R_r^1$ and $R_s^1$ are each independently as defined above for $R^1$, and further wherein
$R_r^1$ contains a methoxy group, and $R_s^1$ contains a corresponding hydroxy group;
15) reacting a compound of the formula (Is):

(Is)

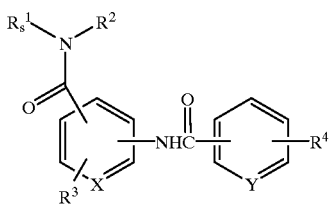

or a salt thereof with a compound of the formula (VI):

$Z^1-R^5$          (VI)

or a salt thereof to provide a compound of the formula (It):

(It)

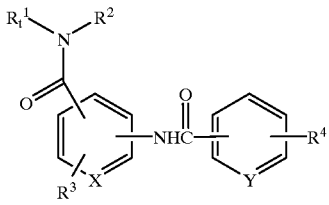

or a salt thereof, and wherein in the above formulas,
$R_s^1$ is as defined above;
$Z^1$ is an acid residue; and
$R_t^1$ is as defined for $R_s^1$, except that hydroxy groups of $R_t^1$ are converted to alkoxy groups, which are optionally substituted; or
16) reacting a compound of the formula:

(Iu)

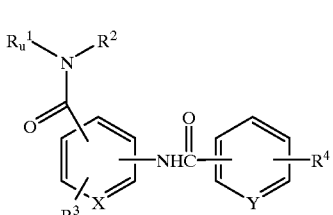

or a salt thereof with a compound of the formula:

$Z^2-R^6$          (VIII)

to provide a compound of the formula (Iw):

(Iv)

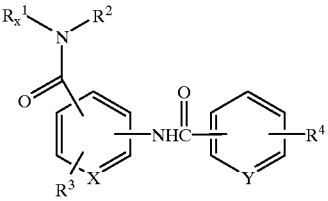

or a salt thereof, and wherein in the above formulas,
$R^6$ is lower alkyl substituted with acyl;
$Z^2$ is an acid residue; and
$R_u^1$ contains alkoxy substituted with acyl, and
$R_v^1$ contains alkoxy substituted with acyl(lower)alkyloxyimino; or (Iw)

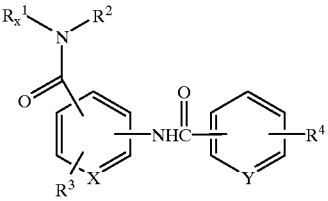

17) reacting a compound of the formula:
or a salt thereof with an amine or potassium phthalimide to provide a compound of the formula:

(Ix)

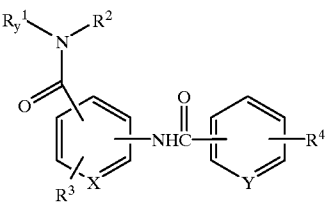

or a salt thereof, wherein in the above formulas,
$R_w^1$ and $R_x^1$ are as defined above for $R^1$, wherein
$R_w^1$ contains alkoxy substituted with halogen, and
$R_x^1$ contains alkoxy substituted with amino, lower alkylamino or, phthalimido at a corresponding position.
18) reacting a compound of the formula:

(Iy)

or a salt thereof with an acylating agent to provide a compound of the formula:

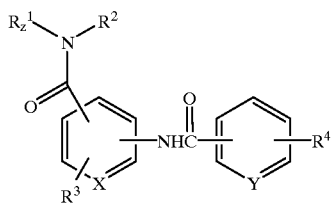

(Iz)

or a salt thereof, wherein in the above formulas,
$R_y^1$ and $R_z^1$ are as defined above for $R^1$, wherein $R_y^1$ contains an amino group, and $R_z^1$ contains an acylated amino at a corresponding position; or 19) reacting a compound of the formula:

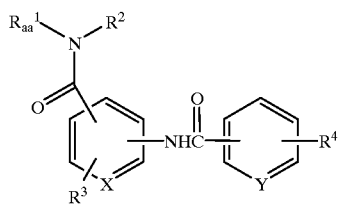

(I-1)

or a salt thereof with or lower alkylhydrazine to provide a compound of the formula:

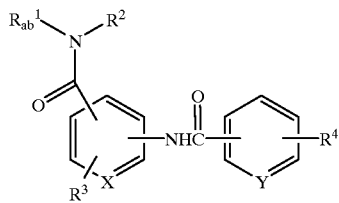

(I-2)

or a salt thereof, wherein in the above formulas,
$R_{aa}^1$ and $R_{ab}^1$ are as defined above for $R_1$, and further wherein $R_{aa}^1$ contains an aryloxycarbonylamino substituent, and $R_{ab}^1$ contains an alkylhydrazinocarbonylamino substituent in a corresponding position; or 20) reacting a compound of the formula:

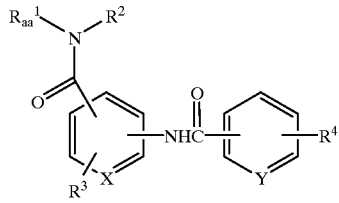

(I-1)

or a salt thereof with heterocyclic compound substituted with hydroxy to provide a compound of the formula:

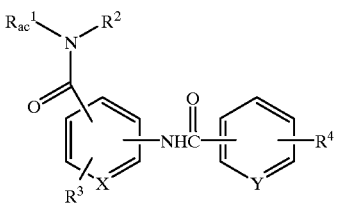

(I-3)

or a salt thereof, and wherein in the above formulas,
$R_{aa}^1$ is as defined above, and $R_{ac}^1$ contains a lower alkyl substituent substituted with heterocyclicoxycarbonylamino, or alkoxy substitued with heterocyclicoxycarbonylamino; or 21) reacting a compound of the formula:

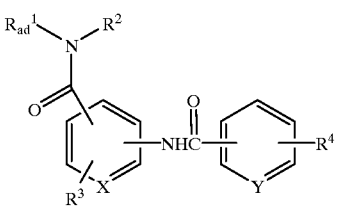

(I-4)

or a salt thereof with an N-containing heterocyclic compound or lower alkylamino(lower)alkylamine to provide a compound of the formula:

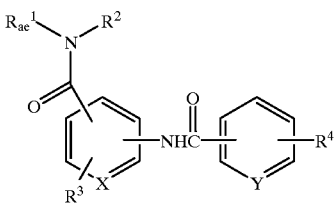

(I-5)

or a salt thereof, and wherein in the above formulas,
$R_{ad}^1$ and $R_{ae}^1$ are as defined above for $R^1$, and further wherein $R_{ad}^1$ contains an aryloxycarbonyloxy substituent, and $R_{ae}^1$ contains heterocyclic carbonyloxy at a corresponding position;

22) subjecting a compound of the formula:

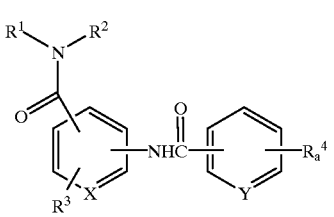

(I-6)

or a salt thereof to reduction to provide a compound of the formula:

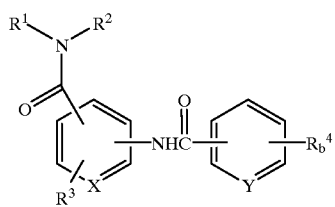

(I-7)

or a salt thereof, and wherein in the above formulas,
$R_a^4$ is aryl substituted with nitro; and
$R_b^4$ is aryl substituted with amino; or
23) subjecting a compound of the formula:

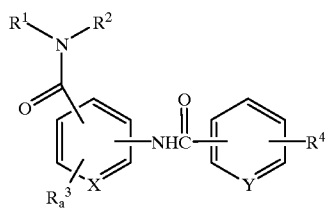

(I-8)

or a salt thereof to reduction to provide a compound of the formula:

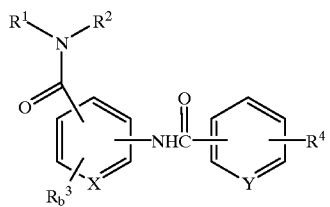

(I-9)

or a salt thereof, wherein in the above formulas,
$R_a^3$ is nitro; and
$R_b^3$ is amino; or
24) reacting a compound of the formula:

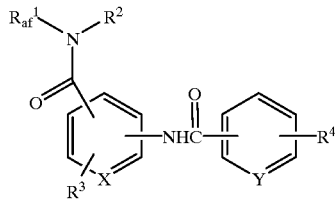

(I-10)

or a salt thereof with a compound of the formula:

B—CH$_2$—R$^7$   (VIII)

or a reactive compound thereof to provide a compound of the formula:

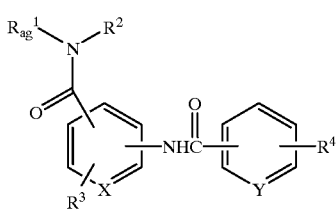

(I-11)

or a salt thereof, wherein in the above formulas,
$R_f^1$ is lower alkyl, aryl, haloaryl, cyclo(lower)alkyl or a heterocyclic group, each of which is substituted with fornyl; lower alkyl substituted with formyl; or lower alkoxy substituted with formyl;
B is carboxy, esterified carboxy, di-esterified phosphono or triphenylphosphonium salt;
$R^7$ is lower alkyl optionally substituted with acyl; and
$R_g^1$ is lower alkyl, aryl, haloaryl, cyclo(lower)alkyl or a heterocyclic group, each of which is substituted with lower alkenyl optionally substituted with acyl; lower alkenyloxy optionally substituted with acyl; or
25) reacting a compound of the formula:

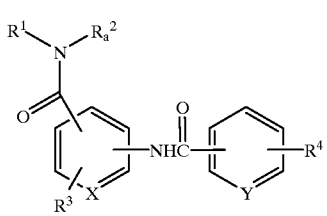

(I-12)

or a salt thereof with a reducing agent to provide a compound of the formula:

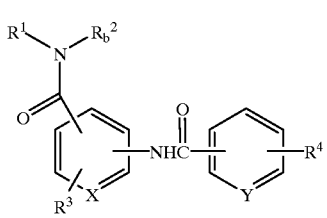

(I-13)

or a salt thereof, wherein in the above formulas,
$R_a^2$ is lower alkyl substituted with carboxy or esterified carboxy; and
$R_b^2$ is lower alkyl substituted with hydroxy; or 26) reacting a compound of the formula:

(I-14)

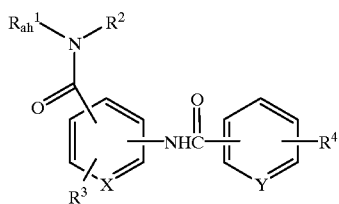

or a salt thereof with a reducing agent to provide a compound of the formula:

(I-15)

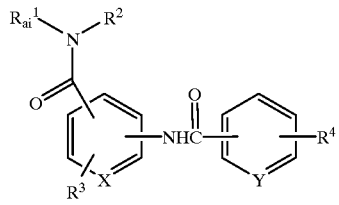

or a salt thereof, wherein in the above formulas;
$R_a^1$ and $R_b^1$ are as defined above for $R^1$, and further wherein $R_a^1$ contains a lower alkyl or alkoxy group substituted with esterified carboxy; and $R_b^1$ contains a corresponding lower alkyl or alkoxy group substituted with formyl;

27) reacting a compound of the formula:

(I-16)

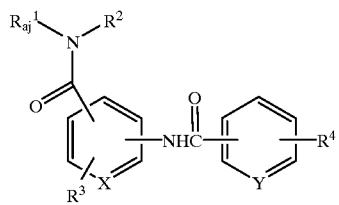

or a salt thereof with hydroxylamine or its salt to provide a compound of the formula:

(I-17)

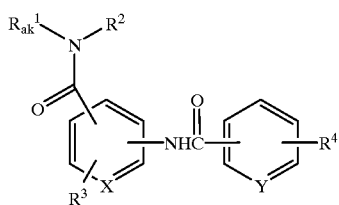

or a salt thereof, in the above formulas,
$R_{aj}^1$ and $R_{ak}^1$ are as defined above for $R^1$, and further wherein $R_{aj}^1$ contains an alkoxy group substituted with formyl, and $R_{ak}^1$ contains a corresponding alkoxy group substituted with hydroxyimino;

28) reacting a compound of the formula:

(I-7)

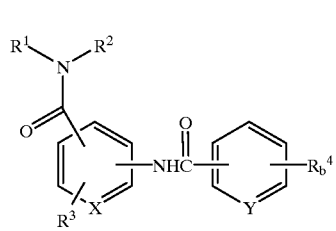

or a salt thereof with lower alkanal to provide a compound of the formula:

(I-18)

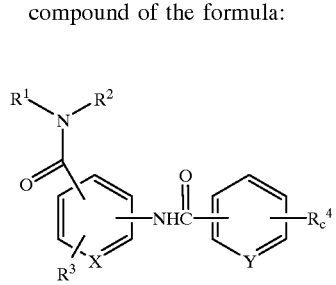

or a salt thereof, in the above formulas,
$R_c^4$ is aryl substituted with lower alkylamino; or 29) reacting a compound of the formula:

(I-19)

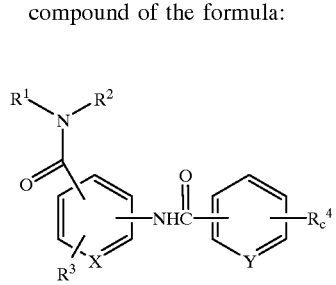

or a salt thereof with an azide compound to provide a compound of the formula:

(I-20)

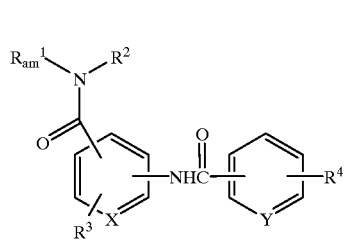

or a salt thereof, wherein in the above formulas,
$R_{al}^1$ and $R_{am}^1$ are as defined above for $R^1$, and further wherein $R_{al}^1$ contains a cyano substituent, and $R_{am}^1$ contains a tetrazolyl substituent at a corresponding position; or 30) subjecting a compound of the formula:

(I-21)

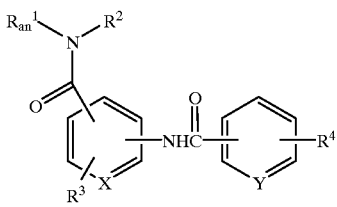

or a salt thereof with an oxidizing agent to provide a compound of the formula:

(I-22)

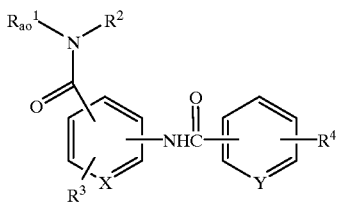

or a salt thereof, wherein in the above formulas, $R_{an}^1$ and $R_{ao}^1$ are as defined above for $R^1$, and further wherein $R_{an}^1$ contains a lower alkythio substituted with acyl, and $R_{ao}^1$ contains a lower alkylsulfinyl or lowr alkylsulfonyl substituted with acyl at a corresponding position; or, 31) subjecting a compound of the formula:

(I-23)

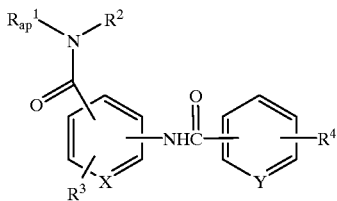

or a salt thereof to introduction reaction of N-protective group to provide a compound of the formula:

(I-24)

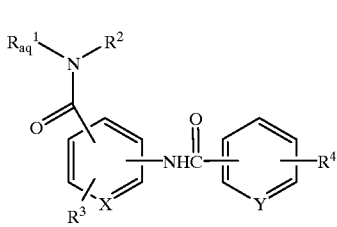

or a salt thereof, wherein in the above formulas, $R_{ap}^1$ and $R_{aq}^1$ are as defined above for $R^1$, and further wherein $R_{ap}^1$ contains alkoxy substituted with acyl(lower) alkylamino, and $R_{aq}^1$ contains alkoxy substituted with N-protected-acyl(lower) alkylamino at a corresponding position; or 32) reacting a compound of the formula:

(I-25)

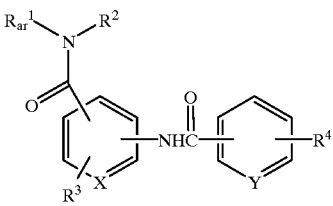

or a salt thereof with a halogenating agent to provide a compound of the formula:

(I-26)

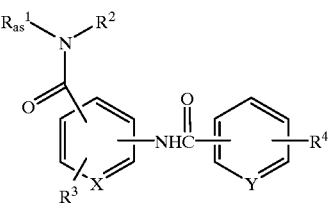

or a salt thereof, wherein in the above formulas, $R_{ar}^1$ and $R_{as}^1$ are as defined above for $R^1$, and further wherein $R_{ar}^1$ contains alkyl or alkoxy substituted with hydroxy, and $R_{as}^1$ contains lower alkyl or alkoxy substituted with halogen, or 33) reacting a compound of the formula:

(I-27)

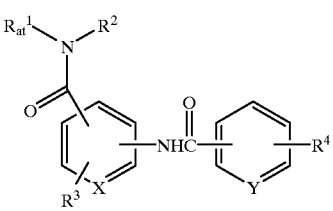

or a salt thereof with an acylating agent to provide a compound of the formula:

(I-28)

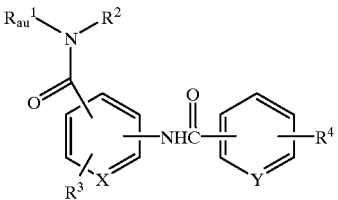

or a salt thereof, wherein in the above formulas, $R_{at}^1$ and $R_{au}^1$ are as defined above for $R^1$, and further wherein $R^{at1}$ contains alkoxy substituted with piperazinylcarbonyl, and $R_{au}^1$ contains alkoxy substituted with acylpiperazinylcarbonyl; or 34) subjecting a compound of the formula:

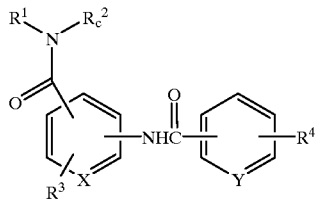

(I-29)

or a salt thereof to deesterification reaction to provide a compound of the formula:

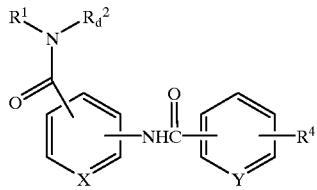

(I-30)

or a salt thereof, wherein in the above formulas,
$R^2$ is lower alkyl substituted with esterified carboxy; and
$R^2$ is lower alkyl substituted with carboxy; or
35) reacting a compound of the formula:

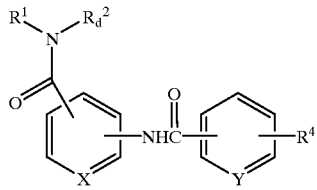

(I-30)

or its reactive compound thereof at the carboxy group or a salt thereof with an amine or a salt thereof to provide a compound of the formula:

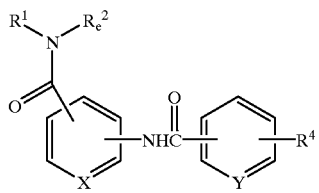

(I-31)

or a salt thereof, wherein in the above formulas,
$R_d^2$ is lower alkyl substituted with carboxy;
$R_e^2$ is lower alkyl substituted with substituted or unsubstituted N-containing heterocycliccarbonyl; carbamoyl; or substituted or unsubstituted lower alkylcarbamoyl.

6. A pharmaceutical composition comprising one or more compounds of claim 1, as an active ingredient, and a pharmaceutically acceptable carrier.

7. A method of therapeutically treating hypertension, heart failure, renal insufficiency, edema, ascites, vasopressin parasecretion syndrome, hepatocirrhosis, hyponatremia, hypokalemia, diabetes, circulation disorder, celebrovascular disease, Meniere's syndrome or motion sickness in a mammal, which comprises administering an effective amount of one or more compounds of claim 1 to a mammal in need thereof.

8. The method of claim 7, wherein said mammal is a human.

* * * * *